(12) United States Patent
Toida et al.

(10) Patent No.: US 11,130,724 B2
(45) Date of Patent: Sep. 28, 2021

(54) COMPOUND, RESIN, COMPOSITION, RESIST PATTERN FORMATION METHOD, AND CIRCUIT PATTERN FORMATION METHOD

(71) Applicant: Mitsubishi Gas Chemical Company, Inc., Tokyo (JP)

(72) Inventors: Takumi Toida, Hiratsuka (JP); Takashi Sato, Hiratsuka (JP); Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 198 days.

(21) Appl. No.: 16/065,714

(22) PCT Filed: Dec. 26, 2016

(86) PCT No.: PCT/JP2016/088737
§ 371 (c)(1),
(2) Date: Jun. 22, 2018

(87) PCT Pub. No.: WO2017/111165
PCT Pub. Date: Jun. 29, 2017

(65) Prior Publication Data
US 2019/0010108 A1 Jan. 10, 2019

(30) Foreign Application Priority Data

Dec. 25, 2015 (JP) .............................. JP2015-254433

(51) Int. Cl.
*G03F 7/11* (2006.01)
*G03F 7/039* (2006.01)
(Continued)

(52) U.S. Cl.
CPC .............. *C07C 39/14* (2013.01); *C07C 39/15* (2013.01); *C08G 8/02* (2013.01); *C08L 61/16* (2013.01);
(Continued)

(58) Field of Classification Search
CPC .. C08L 61/16; C08L 2312/00; C08L 2203/16; C07C 39/15; C07C 39/14;
(Continued)

(56) References Cited

U.S. PATENT DOCUMENTS 4,108,665 A 8/1978 Gutman
4,536,465 A * 8/1985 Uehara .................. G03F 7/0236
430/165

(Continued)

FOREIGN PATENT DOCUMENTS

CN 1853141 A 10/2006
CN 1942825 A 4/2007
(Continued)

OTHER PUBLICATIONS

Machine transal;tion of JP 05-001127 (Jan. 1993).*
Machine translation of JP62-289536 (1987).*
T. Nakayama et al., "A New Three-Component Photoresist Based on Calix[4]resorcinarene Derivative, a Cross-linker, and a Photoacid Generator", Bull. Chem. Soc. Jpn., 71, 2979-2984 (1998), The Chemical Society of Japan.
(Continued)

*Primary Examiner* — Martin J Angebranndt
(74) *Attorney, Agent, or Firm* — Fitch, Even, Tabin & Flannery LLP

(57) ABSTRACT

The present invention employs a compound represented by the following formula (0):

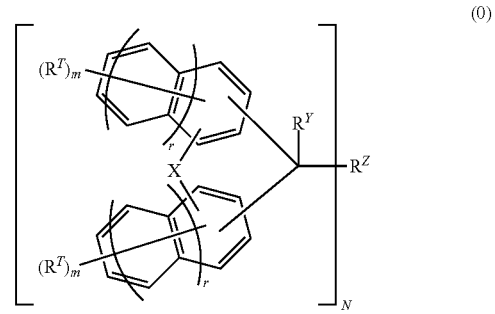

wherein $R^Y$ is a linear, branched, or cyclic alkyl group of 1 to 30 carbon atoms or an aryl group of 6 to 30 carbon atoms;
$R^Z$ is an N-valent group of 1 to 60 carbon atoms or a single bond;
each $R^T$ is independently an alkyl group of 1 to 30 carbon atoms optionally having a substituent, an aryl group of 6 to 40 carbon atoms optionally having a substituent, an alkenyl group of 2 to 30 carbon atoms optionally having a substituent, an alkoxy group of 1 to 30 carbon atoms optionally having a substituent, a halogen atom, a nitro group, an amino group, a cyano group, a thiol group, a hydroxy group, or a group in which a hydrogen atom of a hydroxy group is replaced with an acid dissociation group, wherein the alkyl group, the alkenyl group, and the aryl group each optionally contain an ether bond, a ketone bond, or an ester bond, wherein at least one $R^T$ is a hydroxy group or a group in which a hydrogen atom of a hydroxy group is replaced with an acid dissociation group;
X is an oxygen atom, a sulfur atom, or not a crosslink; each m is independently an integer of 0 to 9, wherein at least one m is an integer of 1 to 9;
N is an integer of 1 to 4, wherein when N is an integer of 2 or larger, N structural formulas within the parentheses [ ] are the same or different; and
each r is independently an integer of 0 to 2.

18 Claims, No Drawings

(51) Int. Cl.
*G03F 7/038* (2006.01)
*G03F 7/09* (2006.01)
*G03F 7/20* (2006.01)
*C07C 39/14* (2006.01)
*C07C 39/15* (2006.01)
*C08L 61/16* (2006.01)
*C08G 8/02* (2006.01)
*G03F 7/023* (2006.01)
*G03F 7/34* (2006.01)

(52) U.S. Cl.
CPC .............. *G03F 7/023* (2013.01); *G03F 7/038* (2013.01); *G03F 7/039* (2013.01); *G03F 7/091* (2013.01); *G03F 7/094* (2013.01); *G03F 7/11* (2013.01); *G03F 7/2002* (2013.01); *G03F 7/343* (2013.01); *C08L 2203/16* (2013.01); *C08L 2312/00* (2013.01)

(58) Field of Classification Search
CPC .......... G03F 7/094; G03F 7/039; G03F 7/038; G03F 7/343; G03F 7/023; G03F 7/11; G03F 7/20; G03F 7/2002; G03F 7/091; C08G 8/02
See application file for complete search history.

(56) References Cited

U.S. PATENT DOCUMENTS

| | | | | |
|---|---|---|---|---|
| 5,210,003 | A * | 5/1993 | Schadeli | C07D 309/10 430/270.1 |
| 5,310,619 | A * | 5/1994 | Crivello | G03F 7/0045 430/270.1 |
| 5,645,969 | A * | 7/1997 | Matsuo | G03F 7/0236 430/165 |
| 5,856,561 | A * | 1/1999 | Nagata | C07C 69/734 560/57 |
| 6,835,786 | B2 | 12/2004 | Ishii et al. | |
| 2003/0211421 | A1* | 11/2003 | Hanabata | C07C 43/313 430/285.1 |
| 2005/0074695 | A1 | 4/2005 | Nakamura | |
| 2005/0081789 | A1 | 4/2005 | Kato | |
| 2005/0255712 | A1 | 11/2005 | Kato et al. | |
| 2007/0172759 | A1 | 7/2007 | Ogihara | |
| 2008/0153031 | A1 | 6/2008 | Echigo et al. | |
| 2010/0047709 | A1 | 2/2010 | Echigo | |
| 2010/0316950 | A1* | 12/2010 | Oguro | G03F 7/094 430/270.1 |
| 2012/0220805 | A1* | 8/2012 | Yoshitomo | C07C 37/20 568/720 |
| 2013/0004896 | A1* | 1/2013 | Echigo | C07C 43/196 430/286.1 |
| 2014/0246641 | A1 | 9/2014 | Jameson, III et al. | |
| 2014/0248561 | A1 | 9/2014 | Echigo et al. | |
| 2015/0037735 | A1 | 2/2015 | Yang et al. | |
| 2015/0090691 | A1* | 4/2015 | Echigo | C07D 311/96 216/49 |
| 2015/0184018 | A1 | 7/2015 | Endo et al. | |
| 2015/0368224 | A1 | 12/2015 | Echigo | |
| 2015/0376157 | A1 | 12/2015 | Echigo et al. | |
| 2015/0376158 | A1* | 12/2015 | Echigo | H01L 21/31116 430/323 |
| 2017/0073288 | A1* | 3/2017 | Makinoshima | G03F 7/327 |
| 2017/0075220 | A1 | 3/2017 | Sato | |
| 2019/0278180 | A1* | 9/2019 | Echigo | H05K 3/0023 |
| 2019/0359756 | A1* | 11/2019 | Echigo | C07D 311/78 |

FOREIGN PATENT DOCUMENTS

| | | |
|---|---|---|
| CN | 103733136 A | 4/2014 |
| DE | 4405108 * | 8/1994 |
| EP | 1666970 A1 | 6/2006 |
| EP | 2660257 A1 | 11/2013 |
| EP | 2743770 A1 | 6/2014 |
| EP | 3118183 | 1/2017 |
| EP | 3118684 | 1/2017 |
| EP | 3395845 | 10/2018 |
| GN | 101889247 A | 11/2010 |
| JP | 61-138614 * | 6/1986 |
| JP | S62-289536 A | 12/1987 |
| JP | 05-01127 * | 1/1993 |
| JP | 1994-202320 A | 7/1994 |
| JP | 2002-334869 A | 11/2002 |
| JP | 2004-046222 A | 2/2004 |
| JP | 2004-177668 A | 6/2004 |
| JP | 2004-271838 A | 9/2004 |
| JP | 2005222573 | 8/2005 |
| JP | 2005-250434 A | 9/2005 |
| JP | 2005-326838 A | 11/2005 |
| JP | 2007-206371 A | 8/2007 |
| JP | 2007199653 | 8/2007 |
| JP | 2007-226170 A | 9/2007 |
| JP | 2007-226204 A | 9/2007 |
| JP | 2008-145539 A | 6/2008 |
| JP | 2008-208312 A | 9/2008 |
| JP | 2009-173623 A | 8/2009 |
| JP | 2010-138393 A | 6/2010 |
| JP | 2012-047832 A | 3/2012 |
| JP | 2014073986 | 4/2014 |
| JP | 2014-106263 A | 6/2014 |
| JP | 2015-514691 A | 5/2015 |
| JP | 2015-174877 A | 10/2015 |
| JP | 2016012061 | 1/2016 |
| JP | 2017088675 | 5/2017 |
| KR | 10-2009-0090866 A | 8/2009 |
| TW | I390347 B | 3/2013 |
| TW | 201321362 A1 | 6/2013 |
| TW | 201500351 A | 1/2015 |
| WO | 2004/066377 A1 | 8/2004 |
| WO | 2013/024778 A1 | 2/2013 |
| WO | 2013/024779 A1 | 2/2013 |
| WO | 2013024779 * | 2/2013 |
| WO | 2014/030579 A1 | 2/2014 |
| WO | 2014/123032 A1 | 8/2014 |
| WO | 2014123005 | 8/2014 |
| WO | 2014123102 * | 8/2014 |
| WO | 2014/137485 A1 | 9/2014 |
| WO | 2015137485 | 9/2015 |
| WO | 2015137486 * | 9/2015 |
| WO | 2015165786 | 11/2015 |
| WO | 2017111165 | 6/2017 |

OTHER PUBLICATIONS

Shinji Okazaki et al., "New Trends of Photoresists", CMC Publishing Co., Ltd., Sep. 2009, pp. 211-259.
Brzezinski, Bogumil et al., "A cyclic cation-bonded system with large cation polarizabilities due to collective cation motion in salts of bis[3,3'-(2,2'-dihydroxybiphenyl)]methane," Journal of Molecular Structure, 1999, vol. 476, pp. 69-72.
Printing Technology Practical Manual, Printing and Printing Equipment Industries Association of China, Nov. 1991, p. 1550.

* cited by examiner

COMPOUND, RESIN, COMPOSITION, RESIST PATTERN FORMATION METHOD, AND CIRCUIT PATTERN FORMATION METHOD

CROSS-REFERENCE TO RELATED APPLICATIONS

This application is a U.S. national phase application filed under 35 U.S.C. § 371 of International Application PCT/JP2016/088737, filed Dec. 26, 2016, designating the United States, which claims priority from Japanese Application Number 2015-254433, filed Dec. 25, 2015.

Field of the Invention

The present invention relates to a compound and a resin having a specific structure, and a composition comprising the compound and/or the resin. The present invention also relates to pattern formation methods (a resist pattern formation method and a circuit pattern formation method) using the composition.

Background of the Invention

In the production of semiconductor devices, fine processing is practiced by lithography using photoresist materials. In recent years, further miniaturization based on pattern rules has been demanded along with increase in the integration and speed of LSI. The light source for lithography used upon forming resist patterns has been shifted to ArF excimer laser (193 nm) having a shorter wavelength from KrF excimer laser (248 nm). The introduction of extreme ultraviolet (EUV, 13.5 nm) is also expected.

However, because conventional polymer-based resist materials have a molecular weight as large as about 10,000 to 100,000 and also wide molecular weight distribution, in lithography using such a polymer-based resist material, roughness occurs on a pattern surface; the pattern dimension becomes difficult to be controlled; and there is a limitation in miniaturization.

Accordingly, various low molecular weight resist materials have been proposed so far in order to provide resist patterns having higher resolution. The low molecular weight resist materials are expected to provide resist patterns having high resolution and small roughness, because of their small molecular sizes.

Various materials are currently known as such low molecular resist materials. For example, an alkaline development type negative type radiation-sensitive composition (see, for example, Patent Literature 1 and Patent Literature 2) using a low molecular weight polynuclear polyphenolic compound as a main component has been suggested; and as a candidate of a low molecular weight resist material having high heat resistance, an alkaline development type negative type radiation-sensitive composition (see, for example, Patent Literature 3 and Non Patent Literature 1) using a low molecular weight cyclic polyphenolic compound as a main component has been suggested as well. Also, as a base compound of a resist material, a polyphenol compound is known to be capable of imparting high heat resistance despite a low molecular weight and useful for improving the resolution and roughness of a resist pattern (see, for example, Non Patent Literature 2).

The present inventors have proposed a resist composition containing a compound having a specific structure and an organic solvent (see Patent Literature 4) as a material that is excellent in etching resistance and is also soluble in a solvent and applicable to a wet process.

Also, the light source for lithography used upon forming resist patterns has been shifted to ArF excimer laser (193 nm) having a shorter wavelength from KrF excimer laser (248 nm). However, as the miniaturization of resist patterns proceeds, the problem of resolution or the problem of collapse of resist patterns after development arises. Therefore, resists have been desired to have a thinner film. However, if resists merely have a thinner film, it is difficult to obtain the film thicknesses of resist patterns sufficient for substrate processing. Therefore, there has been a need for a process of preparing a resist underlayer film between a resist and a semiconductor substrate to be processed, and imparting functions as a mask for substrate processing to this resist underlayer film in addition to a resist pattern.

Various resist underlayer films for such a process are currently known. For example, in order to achieve a resist underlayer film for lithography having the selectivity of a dry etching rate close to that of resists, unlike conventional resist underlayer films having a fast etching rate, an underlayer film forming material for a multilayer resist process containing a resin component having at least a substituent that generates a sulfonic acid residue by eliminating a terminal group under application of predetermined energy, and a solvent has been suggested (see Patent Literature 5). Also, in order to achieve a resist underlayer film for lithography having the selectivity of a dry etching rate smaller than that of resists, a resist underlayer film material comprising a polymer having a specific repeat unit has been suggested (see Patent Literature 6). Furthermore, in order to achieve a resist underlayer film for lithography having the selectivity of a dry etching rate smaller than that of semiconductor substrates, a resist underlayer film material comprising a polymer prepared by copolymerizing a repeat unit of an acenaphthylene and a repeat unit having a substituted or unsubstituted hydroxy group has been suggested (see Patent Literature 7).

Meanwhile, as materials having high etching resistance for this kind of resist underlayer film, amorphous carbon underlayer films formed by CVD using methane gas, ethane gas, acetylene gas, or the like as a raw material are well known. However, resist underlayer film materials that can form resist underlayer films by a wet process such as spin coating or screen printing have been demanded from the viewpoint of a process.

The present inventors have proposed an underlayer film forming composition for lithography containing a compound having a specific structure and an organic solvent (see Patent Literature 8) as a material that is excellent in etching resistance, has high heat resistance, and is soluble in a solvent and applicable to a wet process.

As for methods for forming an intermediate layer used in the formation of a resist underlayer film in a three-layer process, for example, a method for forming a silicon nitride film (see Patent Literature 9) and a CVD formation method for a silicon nitride film (see Patent Literature 10) are known. Also, as intermediate layer materials for a three-layer process, materials comprising a silsesquioxane-based silicon compound are known (see Patent Literature 11 and Patent Literature 12).

Various compositions have been further proposed as optical component forming compositions. Examples thereof include acrylic resins (see Patent Literatures 13 and 14).

CITATION LIST

Patent Literature

Patent Literature 1: Japanese Patent Laid-Open No. 2005-326838
Patent Literature 2: Japanese Patent Laid-Open No. 2008-145539
Patent Literature 3: Japanese Patent Laid-Open No. 2009-173623
Patent Literature 4: International Publication No. WO 2013/024778
Patent Literature 5: Japanese Patent Laid-Open No. 2004-177668
Patent Literature 6: Japanese Patent Laid-Open No. 2004-271838
Patent Literature 7: Japanese Patent Laid-Open No. 2005-250434
Patent Literature 8: International Publication No. WO 2013/024779
Patent Literature 9: Japanese Patent Laid-Open No. 2002-334869
Patent Literature 10: International Publication No. WO 2004/066377
Patent Literature 11: Japanese Patent Laid-Open No. 2007-226170
Patent Literature 12: Japanese Patent Laid-Open No. 2007-226204
Patent Literature 13: Japanese Patent Laid-Open No. 2010-138393
Patent Literature 14: Japanese Patent Laid-Open No. 2015-174877

Non Patent Literature

Non Patent Literature 1: T. Nakayama, M. Nomura, K. Haga, M. Ueda: Bull. Chem. Soc. Jpn., 71, 2979 (1998)
Non Patent Literature 2: Shinji Okazaki et al., "New Trends of Photoresists", CMC Publishing Co., Ltd., September 2009, pp. 211-259

SUMMARY OF INVENTION

As mentioned above, a large number of film forming compositions for lithography for resist purposes and film forming compositions for lithography for underlayer film purposes have heretofore been suggested. However, none of these compositions not only have high solvent solubility that permits application of a wet process such as spin coating or screen printing but achieve both of heat resistance and etching resistance at high dimensions. Thus, the development of novel materials is required.

Also, a large number of compositions for optical members have heretofore been suggested. However, none of these compositions achieve all of heat resistance, transparency, and refractive index at high dimensions. Thus, the development of novel materials is required.

The present invention has been made to solve the problems mentioned above. An object of the present invention is to provide a compound, a resin, and a composition (e.g., a composition for use in film formation for lithography or optical component formation) that are applicable to a wet process and are useful for forming a photoresist and an underlayer film for photoresists excellent in heat resistance, solubility, and etching resistance, and pattern formation methods (a resist pattern formation method and a circuit pattern formation method) using the composition.

The inventors have, as a result of devoted examinations to solve the above problems, found out that use of a compound or a resin having a specific structure can solve the above problems, and reached the present invention.

More specifically, the present invention is as follows.

[1]

A compound represented by the following formula (0):

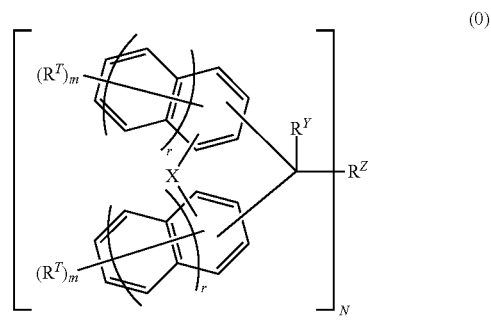

(0)

wherein $R^Y$ is a linear, branched, or cyclic alkyl group of 1 to 30 carbon atoms or an aryl group of 6 to 30 carbon atoms;

$R^Z$ is an N-valent group of 1 to 60 carbon atoms or a single bond;

each $R^T$ is independently an alkyl group of 1 to 30 carbon atoms optionally having a substituent, an aryl group of 6 to 40 carbon atoms optionally having a substituent, an alkenyl group of 2 to 30 carbon atoms optionally having a substituent, an alkoxy group of 1 to 30 carbon atoms optionally having a substituent, a halogen atom, a nitro group, an amino group, a cyano group, a thiol group, a hydroxy group, or a group in which a hydrogen atom of a hydroxy group is replaced with an acid dissociation group, wherein the alkyl group, the alkenyl group, and the aryl group each optionally contain an ether bond, a ketone bond, or an ester bond, wherein at least one $R^T$ is a hydroxy group or a group in which a hydrogen atom of a hydroxy group is replaced with an acid dissociation group;

X is an oxygen atom, a sulfur atom, or not a crosslink;

each m is independently an integer of 0 to 9, wherein at least one m is an integer of 1 to 9;

N is an integer of 1 to 4, wherein when N is an integer of 2 or larger, N structural formulas within the parentheses [ ] are the same or different; and each r is independently an integer of 0 to 2.

[2]

The compound according to [1], wherein the compound represented by the above formula (0) is a compound represented by the following formula (1):

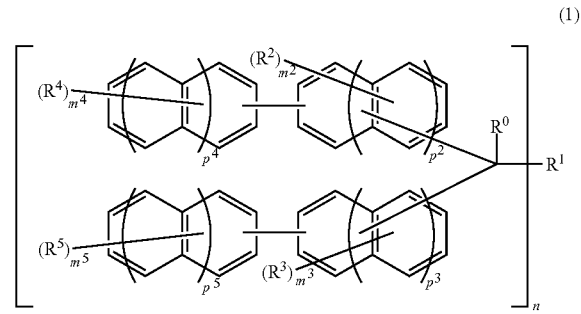

(1)

wherein $R^0$ is as defined in the above $R^Y$;

$R^1$ is an n-valent group of 1 to 60 carbon atoms or a single bond;

$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;

$m^2$ and $m^3$ are each independently an integer of 0 to 8;

$m^4$ and $m^5$ are each independently an integer of 0 to 9, provided that $m^2$, $m^3$, $m^4$, and $m^5$ are not 0 at the same time;

n is as defined in the above N, wherein when n is an integer of 2 or larger, n structural formulas within the parentheses [ ] are the same or different; and $p^2$ to $p^5$ are as defined in the above r.

[3]

The compound according to [1], wherein the compound represented by the above formula (0) is a compound represented by the following formula (2):

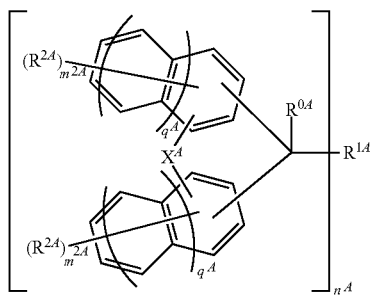

(2)

wherein $R^{0A}$ is as defined in the above $R^Y$;

$R^{1A}$ is an $n^A$-valent group of 1 to 60 carbon atoms or a single bond;

each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is as defined in the above N, wherein when $n^A$ is an integer of 2 or larger, $n^A$ structural formulas within the parentheses [ ] are the same or different;

$X^A$ is an oxygen atom, a sulfur atom, or not a crosslink;

each $m^{2A}$ is independently an integer of 0 to 7, provided that at least one $m^{2A}$ is an integer of 1 to 7; and each $q^A$ is independently 0 or 1.

[4]

The compound according to [2], wherein the compound represented by the above formula (1) is a compound represented by the following formula (1-1):

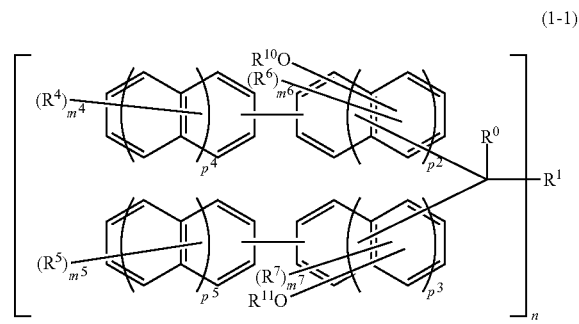

(1-1)

wherein $R^0$, $R^1$, $R^4$, $R^5$, n, $p^2$ to $p^5$, $m^4$, and $m^5$ are as defined above;

$R^6$ and $R^7$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group;

$R^{10}$ and $R^{11}$ are each independently a hydrogen atom or an acid dissociation group; and $m^6$ and $m^7$ are each independently an integer of 0 to 7, provided that $m^4$, $m^5$, $m^6$, and $m^7$ are not 0 at the same time.

[5]

The compound according to [4], wherein the compound represented by the above formula (1-1) is a compound represented by the following formula (1-2):

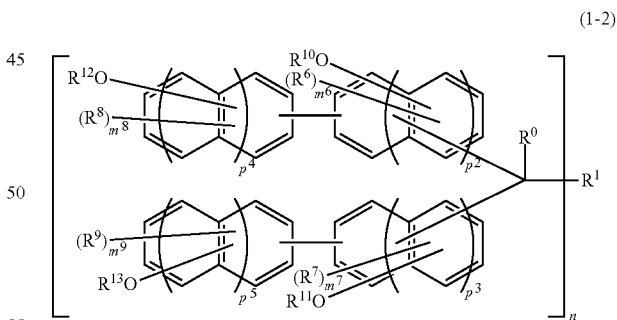

(1-2)

wherein $R^0$, $R^1$, $R^6$, $R^7$, $R^{10}$, $R^{11}$, n, $p^2$ to $p^5$, $m^6$, and $m^7$ are as defined above;

$R^8$ and $R^9$ are as defined in the above $R^6$ and $R^7$;

$R^{12}$ and $R^{13}$ are as defined in the above $R^{10}$ and $R^{11}$; and $m^8$ and $m^9$ are each independently an integer of 0 to 8, provided that $m^6$, $m^7$, $m^8$, and $m^9$ are not 0 at the same time.

[6]
The compound according to [3], wherein the compound represented by the above formula (2) is a compound represented by the following formula (2-1):

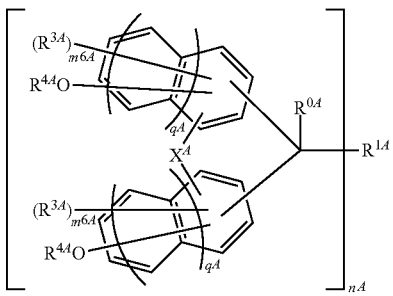

(2-1)

wherein $R^{0A}$, $R^{1A}$, $n^A$, $q^A$, and $X^A$ are as defined in the description of the above formula (2);
each $R^{3A}$ is independently a halogen atom, a linear, branched, or cyclic alkyl group of 1 to 30 carbon atoms, an aryl group of 6 to 30 carbon atoms, or an alkenyl group of 2 to 30 carbon atoms;
each $R^{4A}$ is independently a hydrogen atom or an acid dissociation group; and
each $m^{6A}$ is independently an integer of 0 to 5.

[7]
A resin obtained with the compound according to [1] as a monomer.

[8]
The resin according to [7], wherein the resin has a structure represented by the following formula (3):

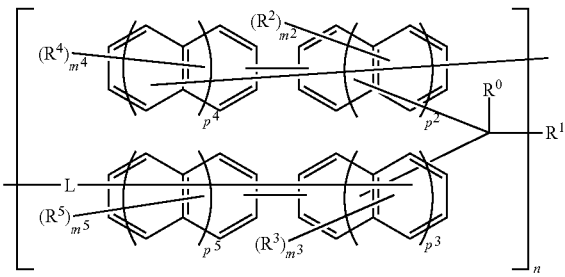

(3)

wherein L is a linear or branched alkylene group of 1 to 30 carbon atoms or a single bond;
$R^0$ is as defined in the above $R^Y$;
$R^1$ is an n-valent group of 1 to 60 carbon atoms or a single bond;
$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;
$m^2$ and $m^3$ are each independently an integer of 0 to 8;
$m^4$ and $m^5$ are each independently an integer of 0 to 9, provided that $m^2$, $m^3$, $m^4$, and $m^5$ are not 0 at the same time;
n is as defined in the above N, wherein when n is an integer of 2 or larger, n structural formulas within the parentheses [ ] are the same or different; and
$p^2$ to $p^5$ are as defined in the above r.

[9]
The resin according to [7], wherein the resin has a structure represented by the following formula (4):

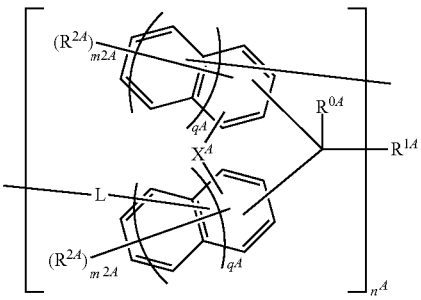

(4)

wherein L is a linear or branched alkylene group of 1 to 30 carbon atoms or a single bond;
$R^{0A}$ is as defined in the above $R^Y$;
$R^{1A}$ is an $n^A$-valent group of 1 to 60 carbon atoms or a single bond;
each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;
$n^A$ is as defined in the above N, wherein when $n^A$ is an integer of 2 or larger, $n^A$ structural formulas within the parentheses [ ] are the same or different;
$X^A$ is an oxygen atom, a sulfur atom, or not a crosslink;
each $m^{2A}$ is independently an integer of 0 to 7, provided that at least one $m^{2A}$ is an integer of 1 to 6; and
each $q^A$ is independently 0 or 1.

[10]
A composition comprising one or more selected from the group consisting of the compound according to any of [1] to [6] and the resin according to any of [7] to [9].

[11]
The composition according to [10], further comprising a solvent.

[12]
The composition according to [10] or [11], further comprising an acid generating agent.

[13]
The composition according to any of [10] to [12], further comprising an acid crosslinking agent.

[14]
The composition according to any of [10] to [13], wherein the composition is used in film formation for lithography.

[15]
The composition according to any of [10] to [13], wherein the composition is used in optical component formation.

[16]
A method for forming a resist pattern, comprising the steps of: forming a photoresist layer on a substrate using the composition according to [14]; and then irradiating a predetermined region of the photoresist layer with radiation for development.

[17]

A method for forming a resist pattern, comprising the steps of: forming an underlayer film on a substrate using the composition according to [14]; forming at least one photoresist layer on the underlayer film; and then irradiating a predetermined region of the photoresist layer with radiation for development.

[18]

A method for forming a circuit pattern, comprising the steps of: forming an underlayer film on a substrate using the composition according to [14]; forming an intermediate layer film on the underlayer film using a resist intermediate layer film material; forming at least one photoresist layer on the intermediate layer film; then irradiating a predetermined region of the photoresist layer with radiation for development, thereby forming a resist pattern; and then etching the intermediate layer film with the resist pattern as a mask, etching the underlayer film with the obtained intermediate layer film pattern as an etching mask, and etching the substrate with the obtained underlayer film pattern as an etching mask, thereby forming a pattern on the substrate.

The present invention can provide a compound, a resin, and a composition (e.g., a composition for use in film formation for lithography or optical component formation) that are applicable to a wet process and are useful for forming a photoresist and an underlayer film for photoresists excellent in heat resistance, solubility, and etching resistance, and pattern formation methods (a resist pattern formation method and a circuit pattern formation method) using the composition.

DESCRIPTION OF EMBODIMENTS

As mentioned later, the compound and the resin of the present embodiment have high solubility in a safe solvent and have good heat resistance and etching resistance. The resist composition of the present embodiment imparts a good shape to a resist pattern.

Also, the compound and the resin of the present embodiment are applicable to a wet process and can achieve a compound, a resin, and a film forming composition for lithography useful for forming a photoresist underlayer film excellent in heat resistance and etching resistance. Furthermore, this film forming composition for lithography employs the compound or the resin having high heat resistance and also high solvent solubility and having a specific structure and can therefore form a resist and an underlayer film that is prevented from deteriorating during high temperature baking and is also excellent in etching resistance against oxygen plasma etching or the like. In addition, the underlayer film thus formed is also excellent in adhesiveness to a resist layer and can therefore form an excellent resist pattern. Moreover, the composition of the present embodiment has high refractive index and is prevented from being stained by heat treatment in a wide range from a low temperature to a high temperature. Therefore, the composition is also useful as various optical component forming compositions.

Hereinafter, embodiments of the present invention will be described. The embodiments described below are given merely for illustrating the present invention. The present invention is not limited only by these embodiments.

The compound of the present embodiment is represented by the following formula (0):

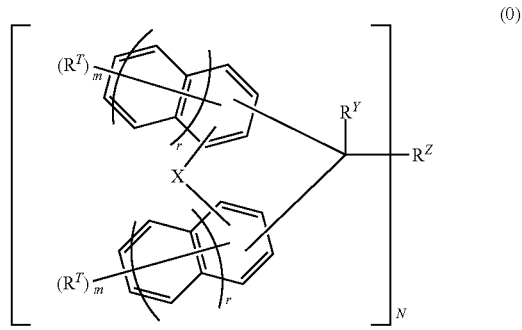

wherein $R^Y$ is a linear, branched, or cyclic alkyl group of 1 to 30 carbon atoms or an aryl group of 6 to 30 carbon atoms;

$R^Z$ is an N-valent group of 1 to 60 carbon atoms or a single bond;

each $R^T$ is independently an alkyl group of 1 to 30 carbon atoms optionally having a substituent, an aryl group of 6 to 40 carbon atoms optionally having a substituent, an alkenyl group of 2 to 30 carbon atoms optionally having a substituent, an alkoxy group of 1 to 30 carbon atoms optionally having a substituent, a halogen atom, a nitro group, an amino group, a cyano group, a thiol group, a hydroxy group, or a group in which a hydrogen atom of a hydroxy group is replaced with an acid dissociation group, wherein the alkyl group, the alkenyl group, and the aryl group each optionally contain an ether bond, a ketone bond, or an ester bond, wherein at least one $R^T$ is a hydroxy group or a group in which a hydrogen atom of a hydroxy group is replaced with an acid dissociation group;

X is an oxygen atom, a sulfur atom, or not a crosslink;

each m is independently an integer of 0 to 9, wherein at least one m is an integer of 1 to 9;

N is an integer of 1 to 4, wherein when N is an integer of 2 or larger, N structural formulas within the parentheses [ ] are the same or different; and each r is independently an integer of 0 to 2.

The "alkyl group of 6 to 30 carbon atoms optionally having a substituent" is not particularly limited, but may be an unsubstituted methyl group, ethyl group, n-propyl group, i-propyl group, n-butyl group, i-butyl group, t-butyl group, cyclopropyl group, cyclobutyl group, or the like or may be a methyl group, an ethyl group, a n-propyl group, an i-propyl group, a n-butyl group, an i-butyl group, a t-butyl group, a cyclopropyl group, a cyclobutyl group, or the like having a substituent such as a halogen atom, a nitro group, an amino group, a thiol group, a hydroxy group, or a group in which a hydrogen atom of a hydroxy group is replaced with an acid dissociation group.

The "aryl group of 6 to 40 carbon atoms optionally having a substituent" is not particularly limited, but may be an unsubstituted phenyl group, naphthalene group, biphenyl group, or the like, or may be a phenyl group, a naphthalene group, a biphenyl group, or the like having a substituent such as a halogen atom, a nitro group, an amino group, a thiol group, a hydroxy group, or a group in which a hydrogen atom of a hydroxy group is replaced with an acid dissociation group.

The "alkenyl group of 2 to 30 carbon atoms optionally having a substituent" is not particularly limited, but may be an unsubstituted propenyl group, butenyl group, or the like, or may be a propenyl group, a butenyl group, or the like having a substituent such as a halogen atom, a nitro group, an amino group, a thiol group, a hydroxy group, or a group in which a hydrogen atom of a hydroxy group is replaced with an acid dissociation group.

The "alkoxy group of 1 to 30 carbon atoms optionally having a substituent" is not particularly limited, but may be an unsubstituted methoxy group, ethoxy group, propoxy group, cyclohexyloxy group, phenoxy group, naphthaleneoxy group, or the like, or may be a methoxy group, an ethoxy group, a propoxy group, a cyclohexyloxy group, a phenoxy group, a naphthaleneoxy group, or the like having a substituent such as a halogen atom, a nitro group, an amino group, a thiol group, a hydroxy group, or a group in which a hydrogen atom of a hydroxy group is replaced with an acid dissociation group.

As mentioned later, the "acid dissociation group" refers to a characteristic group that is cleaved in the presence of an acid to form a functional group that changes solubility, such as an alkali soluble group. Examples of the alkali soluble group include a phenolic hydroxy group, a carboxyl group, a sulfonic acid group, and a hexafluoroisopropanol group. A phenolic hydroxy group and a carboxyl group are preferable, and a phenolic hydroxy group is particularly preferable.

The compound represented by the formula (0) preferably has, but not particularly limited to, each of the following (a) to (e), or a combination thereof, from the viewpoint of staining properties or the inhibition of compound decomposition.

(a): In the formula (0), preferably, r moieties in the structural formula within the parentheses [ ] are the same, i.e., sites represented by two aryl structures in the structural formula within the parentheses [ ] have the same structure.

(b): In the formula (0), $R^T$ moieties bonded to the sites represented by two aryl structures in the structural formula within the parentheses [ ] are preferably the same, and bonding sites at the sites represented by the aryl structures are more preferably the same.

(c): In the formula (0), N is preferably 1 or 2 and more preferably 1.

(d): In the formula (0), $R^Y$ is preferably a linear alkyl group of 1 to 30 carbon atoms or a phenyl group and more preferably a methyl group or a phenyl group.

(e): In the formula (0), $R^Z$ is preferably an N-valent group of 1 to 60 carbon atoms.

The compound represented by the above formula (0) is preferably a compound represented by the following formula (0-1) from the viewpoint of easy crosslinking and solubility in an organic solvent.

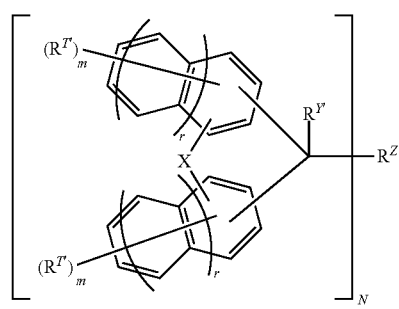

(0-1)

wherein $R^{Y'}$ is a linear, branched, or cyclic alkyl group of 1 to 30 carbon atoms or an aryl group of 6 to 30 carbon atoms;
$R^Z$ is an N-valent group of 1 to 60 carbon atoms or a single bond;
each $R^{T'}$ is independently a linear, branched, or cyclic alkyl group of 1 to 30 carbon atoms, an aryl group of 6 to 30 carbon atoms optionally having a substituent, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein
at least one $R^{T'}$ is a hydroxy group or a group in which a hydrogen atom of a hydroxy group is replaced with an acid dissociation group;
X is an oxygen atom, a sulfur atom, or not a crosslink; each m is independently an integer of 0 to 9, wherein at least one m is an integer of 1 to 9;
N is an integer of 1 to 4, wherein when N is an integer of 2 or larger, N structural formulas within the parentheses [ ] are the same or different; and
each r is independently an integer of 0 to 2.

Hereinafter, the compound represented by the formula (0) and the compound represented by the formula (0-1) will be described with a central focus on a compound represented by the formula (1) and a compound represented by the formula (2). However, the compound represented by the formula (0) and the compound represented by the formula (0-1) are not limited to the description below.

[Compound Represented by Formula (1)]

The compound of the present embodiment is preferably represented by the following formula (1). The compound of the present embodiment has the following structure and therefore has higher heat resistance and also higher solvent solubility.

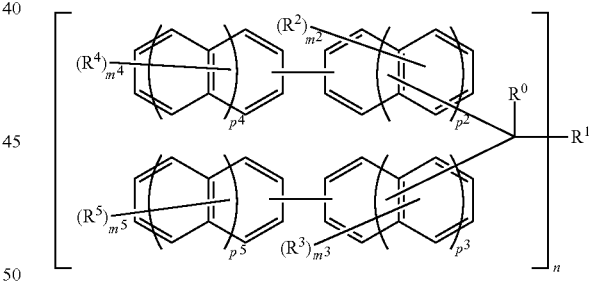

(1)

In the above formula (1), $R^0$ is as defined in the above $R^Y$ and is a linear, branched, or cyclic alkyl group of 1 to 30 carbon atoms or an aryl group of 6 to 30 carbon atoms. Since $R^0$ is a linear, branched, or cyclic alkyl group of 1 to 30 carbon atoms or an aryl group of 6 to 30 carbon atoms, this compound can be prevented from being oxidatively decomposed and stained, have high heat resistance, and improve solvent solubility.

$R^1$ is an n-valent group of 1 to 60 carbon atoms or a single bond, and each aromatic ring is bonded via this $R^1$.

$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group. However, in the formula (1), at least one of $R^2$ to $R^5$ is a hydroxy group or a group in which a hydrogen atom of a hydroxy group is replaced with an acid dissociation group.

$m^2$ and $m^3$ are each independently an integer of 0 to 8, and $m^4$ and $m^5$ are each independently an integer of 0 to 9. However, $m^2$, $m^3$, $m^4$, and $m^5$ are not 0 at the same time.

n is an integer of 1 to 4.

$p^2$ to $p^5$ are each independently an integer of 0 to 2. A site represented by the naphthalene structure in the formula (1) represents a benzene structure when each of $p^2$ to $p^5$ is 0, a naphthalene structure when each of $p^2$ to $p^5$ is 1, and a tricyclic structure such as anthracene or phenanthrene when each of $p^2$ to $p^5$ is 2.

n is as defined in the above N. When n is an integer of 2 or larger, n structural formulas within the parentheses [ ] may be the same or different.

The n-valent group refers to an alkyl group of 1 to 60 carbon atoms when n is 1, an alkylene group of 1 to 60 carbon atoms when n is 2, an alkanepropayl group of 2 to 60 carbon atoms when n is 3, and an alkanetetrayl group of 3 to 60 carbon atoms when n is 4. Examples of the n-valent group include groups having linear hydrocarbon groups, branched hydrocarbon groups, and alicyclic hydrocarbon groups. Herein, the alicyclic hydrocarbon groups also include bridged alicyclic hydrocarbon groups. Also, the n-valent group may have an aromatic group of 6 to 60 carbon atoms.

Also, the n-valent hydrocarbon group may have an alicyclic hydrocarbon group, a double bond, a heteroatom, or an aromatic group of 6 to 60 carbon atoms. Herein, the alicyclic hydrocarbon group also includes bridged alicyclic hydrocarbon groups.

The compound represented by the above formula (1) has high heat resistance attributed to its rigid structure, in spite of its relatively low molecular weight, and can therefore be used even under high temperature baking conditions. Also, the compound represented by the above formula (1) has quaternary carbon in the molecule, which inhibits crystallinity, and is thus suitably used as a film forming composition for lithography that can be used in film production for lithography.

Furthermore, the compound represented by the above formula (1) has high solubility in a safe solvent and has good heat resistance and etching resistance. The resist forming composition for lithography of the present embodiment imparts a good shape to a resist pattern.

Moreover, the compound represented by the formula (1) has a relatively low molecular weight and a low viscosity and therefore facilitates enhancing film smoothness while uniformly and completely filling even the steps of an uneven substrate (particularly having fine space, hole pattern, etc.). As a result, the embedding and smoothing properties of an underlayer film forming composition for lithography containing this compound can be relatively advantageously enhanced. Moreover, the compound has a relatively high carbon concentration and is therefore also provided with high etching resistance.

The compound represented by the formula (1) has high refractive index and is prevented from being stained by heat treatment in a wide range from a low temperature to a high temperature. Therefore, the compound represented by the formula (1) is also useful as various optical component forming compositions. The optical component is used in the form of a film or a sheet and additionally, is also useful as a plastic lens (a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, or a photosensitive optical waveguide.

The compound represented by the above formula (1) is preferably a compound represented by the following formula (1-1) from the viewpoint of easy crosslinking and solubility in an organic solvent.

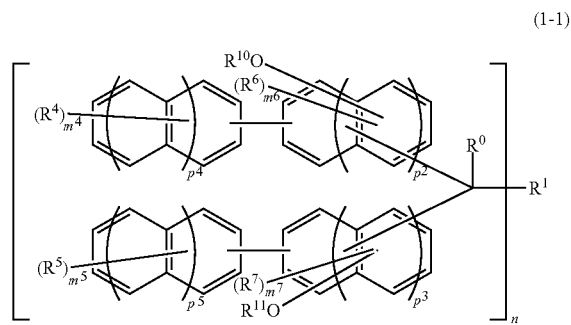

(1-1)

In the formula (1-1), $R^0$, $R^1$, $R^4$, $R^5$, n, $p^2$ to $p^5$, $m^4$, and $m^5$ are as defined above;

$R^6$ and $R^7$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group;

$R^{10}$ and $R^{11}$ are each independently a hydrogen atom or an acid dissociation group; and $m^6$ and $m^7$ are each independently an integer of 0 to 7, provided that $m^4$, $m^5$, $m^6$, and $m^7$ are not 0 at the same time.

When the compound of the formula (1-1) is used as a film forming composition for lithography for alkaline development positive type resists or for organic development negative type resists, at least one of $R^{10}$ and $R^{11}$ is an acid dissociation group. On the other hand, when the compound of the formula (1-1) is used as a film forming composition for lithography for alkaline development negative type resists, a film forming composition for lithography for underlayer films, or an optical component forming composition, at least one of $R^{10}$ and $R^{11}$ is a hydrogen atom.

The compound represented by the above formula (1-1) is also preferably a compound represented by the following formula (1-2) from the viewpoint of easier crosslinking and further solubility in an organic solvent.

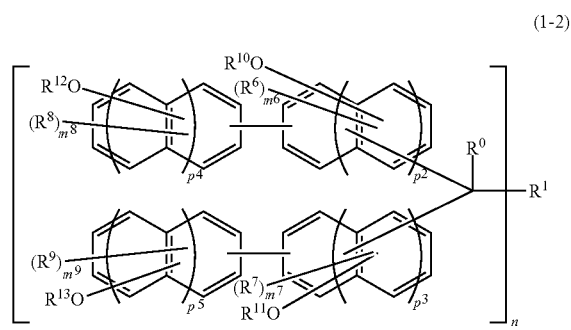

(1-2)

In the formula (1-2),
$R^0$, $R^1$, $R^6$, $R^7$, $R^{10}$, $R^{11}$, n, $p^2$ to $p^5$, $m^6$, and $m^7$ are as defined above;
$R^8$ and $R^9$ are as defined in the above $R^6$ and $R^7$;
$R^{12}$ and $R^{13}$ are as defined in the above $R^1$ and $R^{11}$; and
$m^8$ and $m^9$ are each independently an integer of 0 to 8. However, $m^6$, $m^7$, $m^8$, and $m^9$ are not 0 at the same time.

A compound represented by the following formula (1a) is also preferable from the viewpoint of the supply of raw materials.

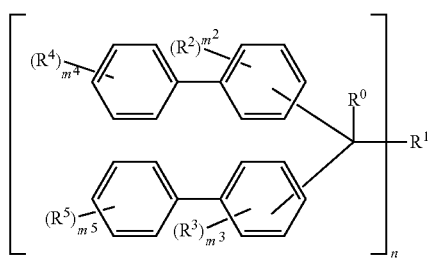

(1a)

In the above formula (1a), $R^0$ to $R^5$, $m^2$ to $m^5$, and n are as defined in the description of the above formula (1).

The compound represented by the above formula (1a) is more preferably a compound represented by the following formula (1b) from the viewpoint of solubility in an organic solvent.

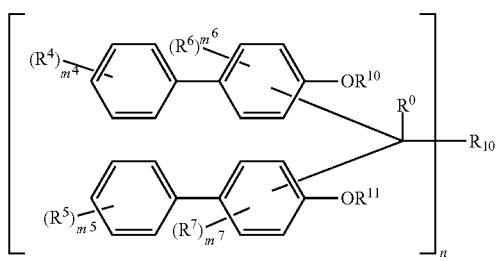

(1b)

In the above formula (1b), $R^0$, $R^1$, $R^4$, $R^5$, $R^{10}$, $R^{11}$, $m^4$, $m^5$, and n are as defined in the description of the above formula (1), and $R^6$, $R^7$, $R^{10}$, $R^{11}$, $m^6$, and $m^7$ are as defined in the description of the above formula (1-1).

The compound represented by the above formula (1a) is still more preferably a compound represented by the following formula (1b') from the viewpoint of reactivity.

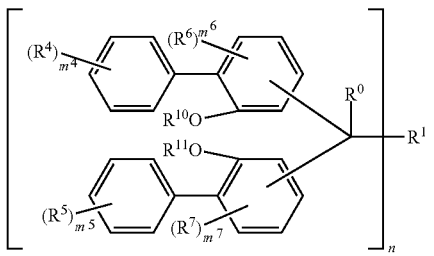

(1b')

In the above formula (1b), $R^0$, $R^1$, $R^4$, $R^5$, $m^4$, $m^5$, and n are as defined in the description of the above formula (1), and $R^6$, $R^7$, $R^{10}$, $R^{11}$, $m^6$, and $m^7$ are as defined in the description of the above formula (1-1).

The compound represented by the above formula (1b) is more preferably a compound represented by the following formula (1c) from the viewpoint of solubility in an organic solvent.

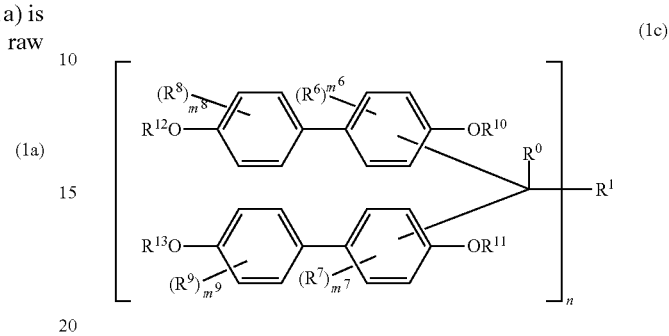

(1c)

In the above formula (1c), $R^0$, $R^1$, $R^6$ to $R^{13}$, $m^6$ to $m^9$, and n are as defined in the description of the above formula (1-2).

The compound represented by the above formula (1b') is more preferably a compound represented by the following formula (1c') from the viewpoint of reactivity.

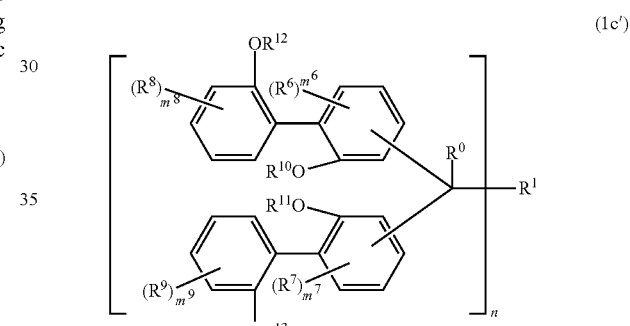

(1c')

In the above formula (1c'), $R^0$, $R^1$, $R^6$ to $R^{13}$, $m^6$ to $m^9$, and n are as defined in the description of the above formula (1-2).

The compound represented by the above formula (1) is particularly preferably a compound represented by any of the following formulas (1d-1) and (1d-2) from the viewpoint of further solubility in an organic solvent.

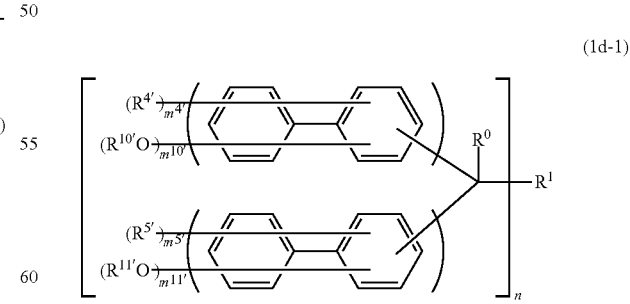

(1d-1)

In the above formula (1d-1), $R^0$, $R^1$, and n are as defined above. $R^{4'}$ and $R^{5'}$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group. Each of $R^{10'}$ and $R^{11'}$ is a hydrogen atom or an acid dissociation group. Each of $m^{4'}$ and $m^{5'}$ is an integer of 0 to 8. Each of $m^{10'}$ and $m^{11'}$ is an integer of 1 to 9. $m^{4'}+m^{10'}$ and $m^{4'}+m^{11'}$ are each independently an integer of 1 to 9.

Examples of $R^0$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a phenyl group, a naphthyl group, an anthracene group, a pyrenyl group, a biphenyl group, and a heptacene group.

Examples of $R^{4'}$ and $R^{5'}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a pyrenyl group, a biphenyl group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^0$, $R^{4'}$, and $R^{5'}$ listed above each includes isomers. For example, a butyl group includes a n-butyl group, an isobutyl group, a sec-butyl group, and a tert-butyl group.

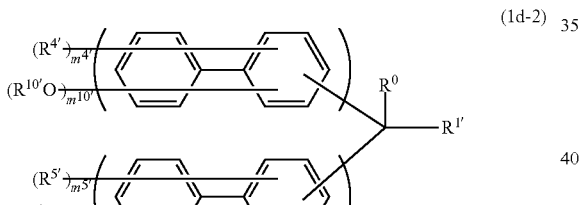

(1d-2)

In the above formula (1d-2), $R^0$, n, $R^{4'}$, $R^{5'}$, $m^{4'}$, $m^{5'}$, $m^{10'}$, and $m^{11'}$ are as defined above, and $R^{1'}$ is a group of 1 to 60 carbon atoms.

A compound represented by any of the following formulas can be used as the compound represented by the formula (1).

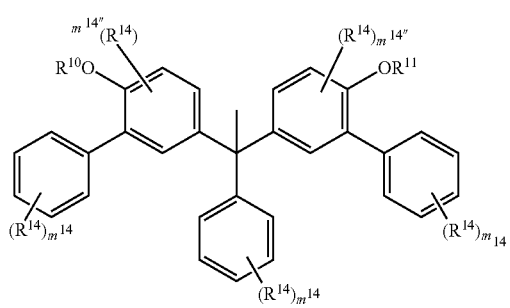

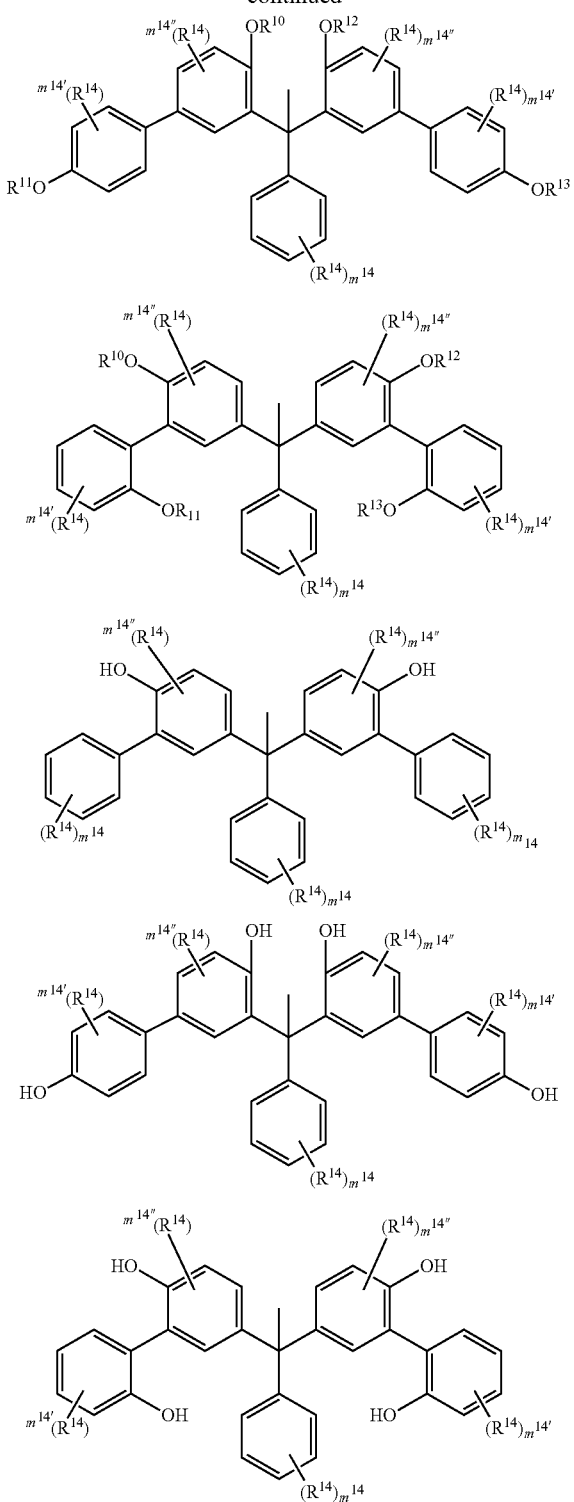

In the above compounds, $R^{10}$ to $R^{13}$ are as defined in the description of the above formula (1-2); each $R^{14}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group; $m^{14}$ is an integer of 0 to 5; $m^{14'}$ is an integer of 0 to 4; and $m^{14''}$ is an integer of 0 to 3.

Examples of $R^{14}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a pyrenyl group, a biphenyl group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{14}$ listed above includes isomers. For example, a butyl group includes a n-butyl group, an isobutyl group, a sec-butyl group, and a tert-butyl group.

A compound represented by any of the following formulas can be further used as the compound represented by the formula (1).

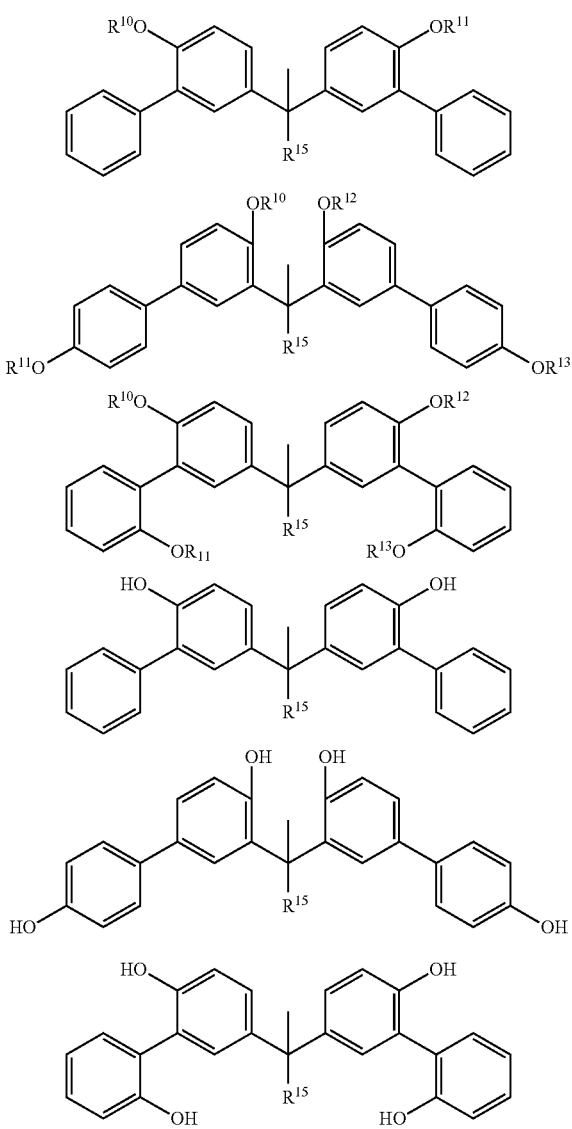
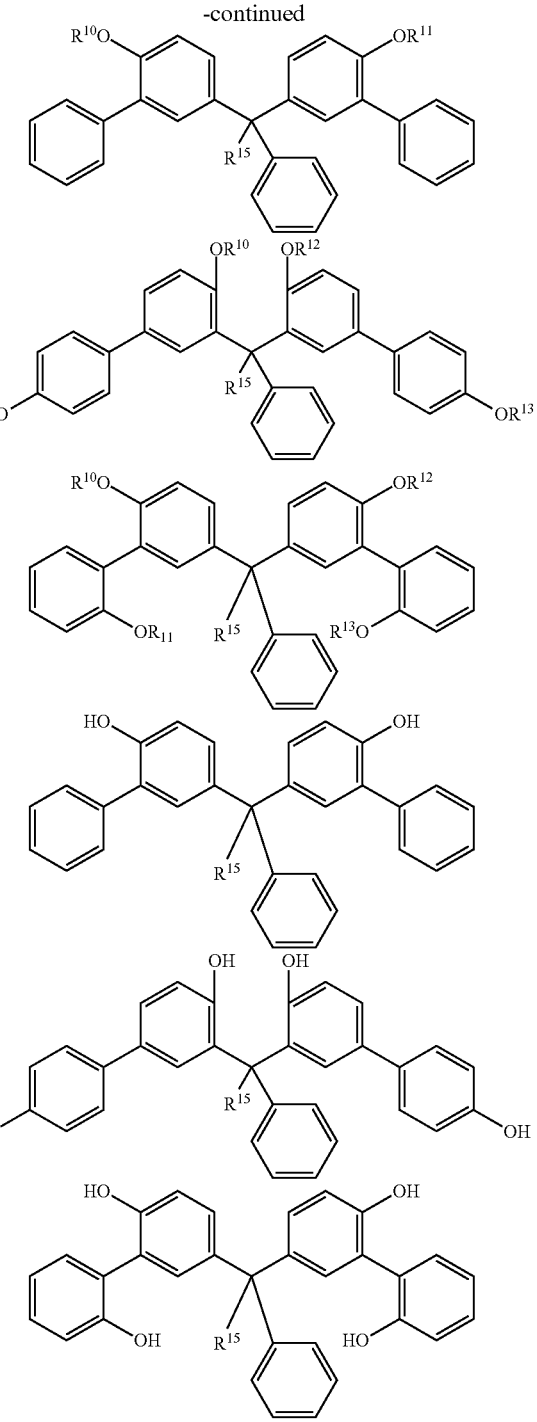

In the above chemical formulas, $R^{10}$ to $R^{13}$ are as defined in the description of the above formula (1-2), and $R^{15}$ is a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group.

Examples of $R^{15}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a pyrenyl group, a biphenyl group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{15}$ listed above includes isomers. For example, a butyl group includes a n-butyl group, an isobutyl group, a sec-butyl group, and a tert-butyl group.

A compound represented by any of the following formulas can be further used as the compound represented by the formula (1).

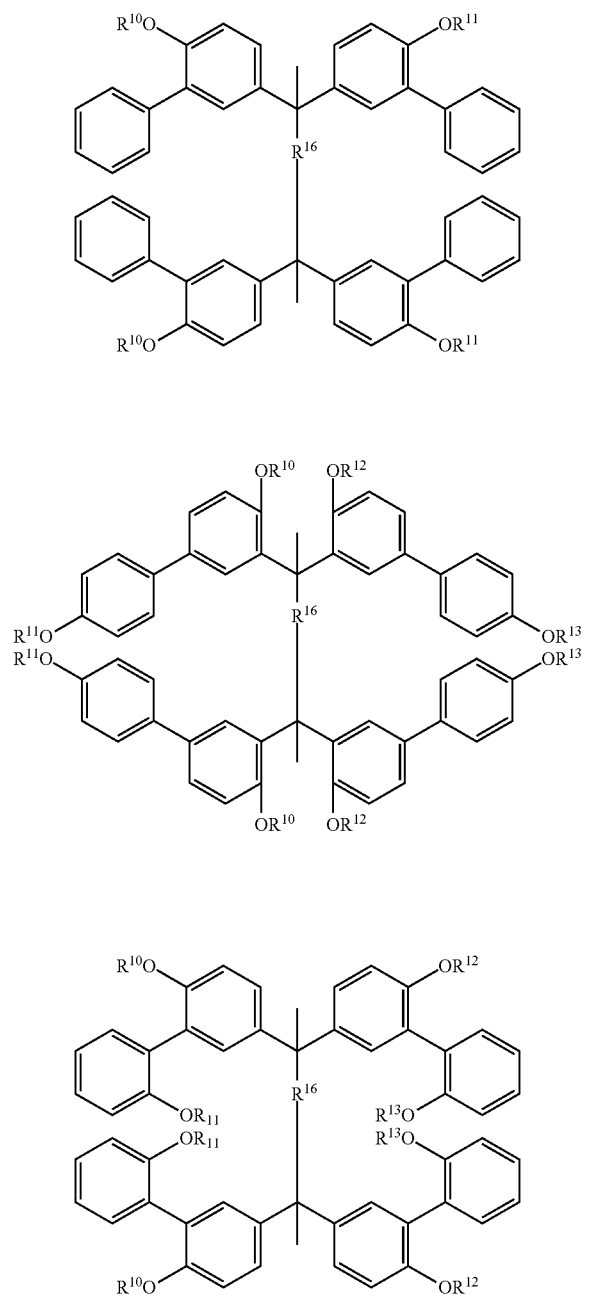

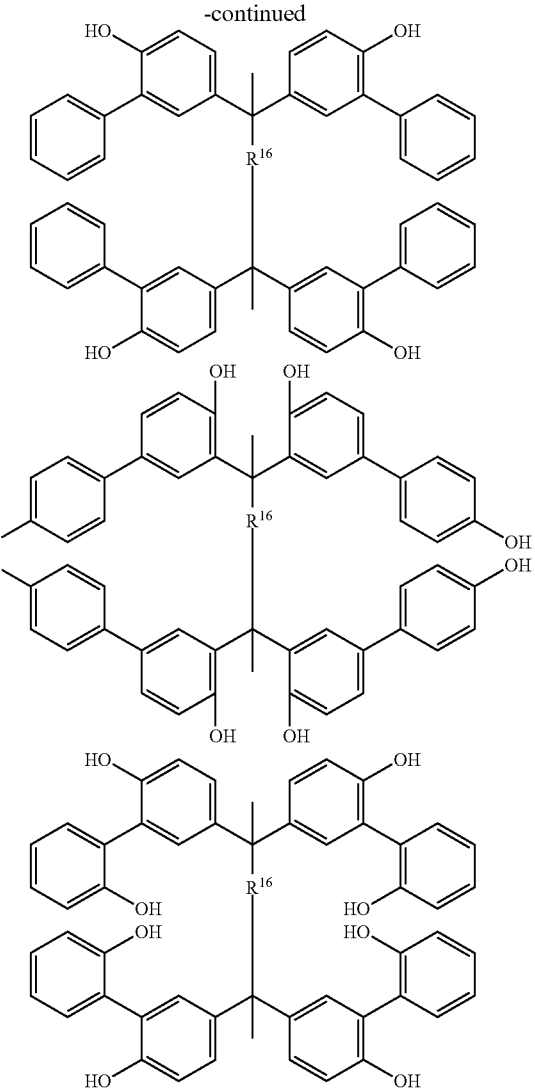

In the above compounds, $R^{10}$ to $R^{13}$ are as defined in the description of the above formula (1-2), and $R^{16}$ is a linear, branched, or cyclic alkylene group of 1 to 30 carbon atoms, a divalent aryl group of 6 to 30 carbon atoms, or a divalent alkenyl group of 2 to 30 carbon atoms.

Examples of $R^{16}$ include a methylene group, an ethylene group, a propene group, a butene group, a pentene group, a hexene group, a heptene group, an octene group, a nonene group, a decene group, an undecene group, a dodecene group, a triacontene group, a cyclopropene group, a cyclobutene group, a cyclopentene group, a cyclohexene group, a cycloheptene group, a cyclooctene group, a cyclononene group, a cyclodecene group, a cycloundecene group, a cyclododecene group, a cyclotriacontene group, a divalent norbornyl group, a divalent adamantyl group, a divalent phenyl group, a divalent naphthyl group, a divalent anthracene group, a divalent pyrene group, a divalent biphenyl group, a divalent heptacene group, a divalent vinyl group, a divalent allyl group, and a divalent triacontenyl group.

$R^{16}$ listed above includes isomers. For example, a butyl group includes a n-butyl group, an isobutyl group, a sec-butyl group, and a tert-butyl group.

A compound represented by any of the following formulas can be further used as the compound represented by the formula (1).

23
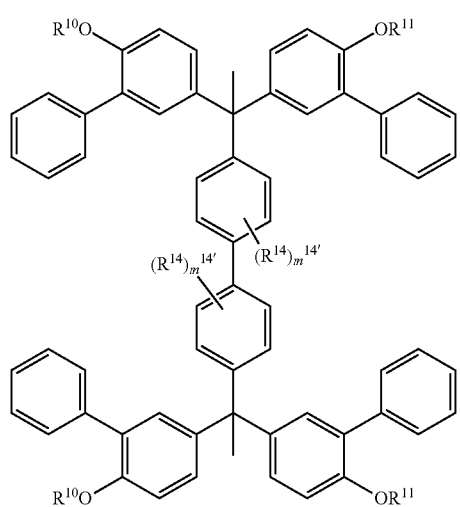
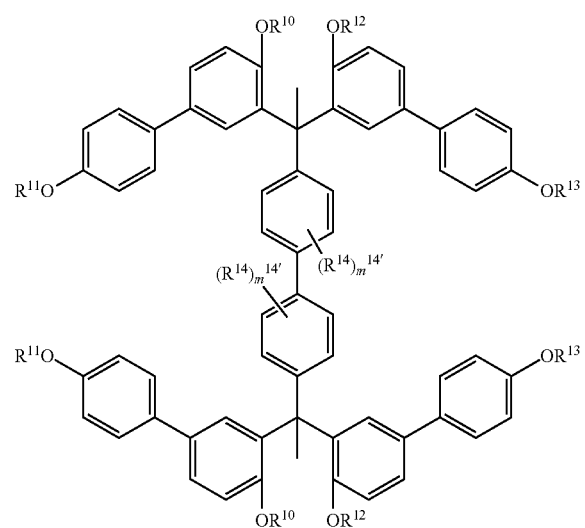
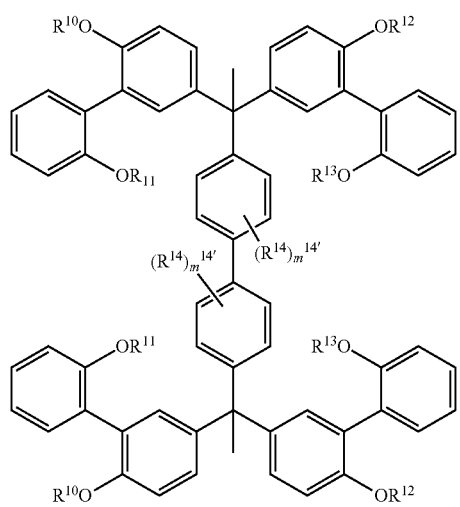
24
-continued
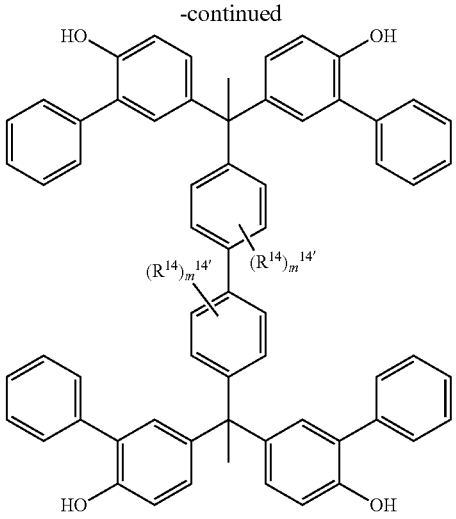
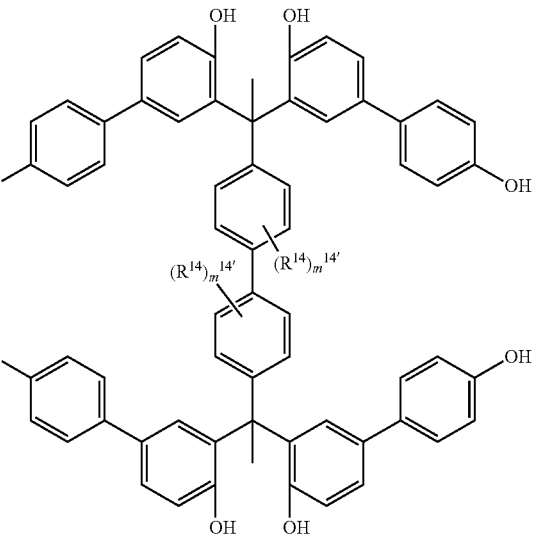
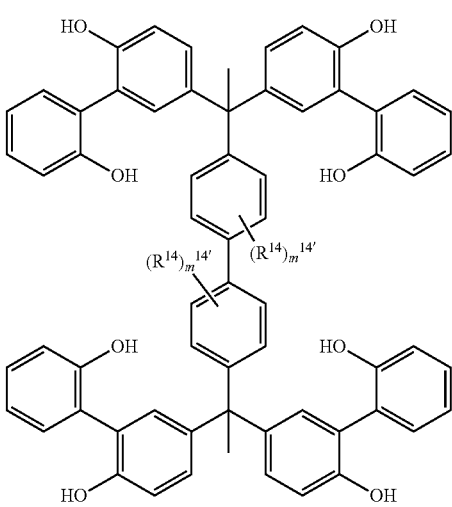

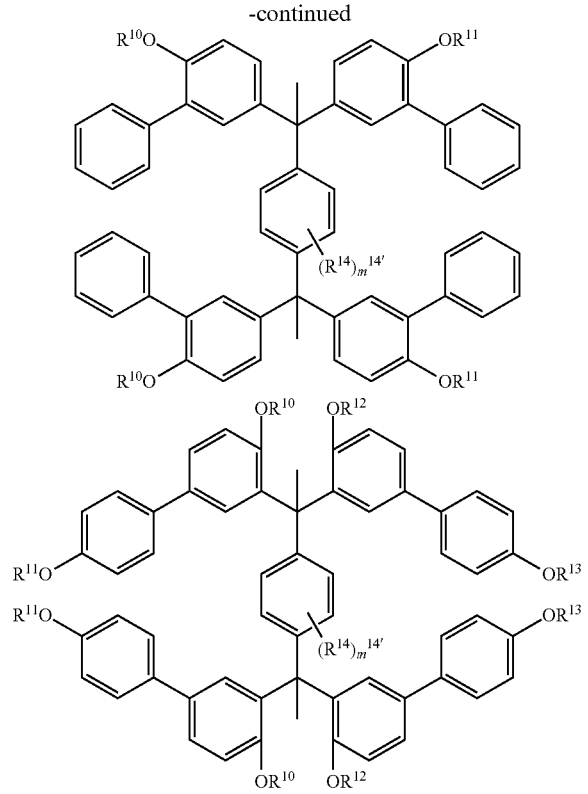
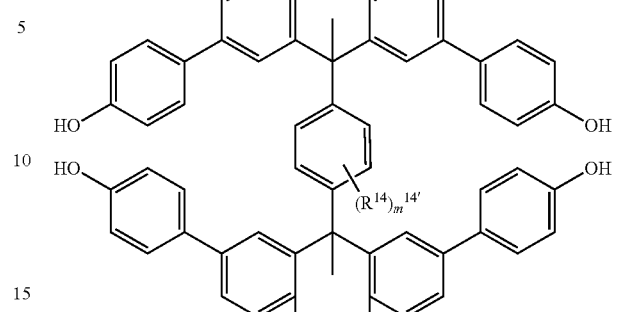
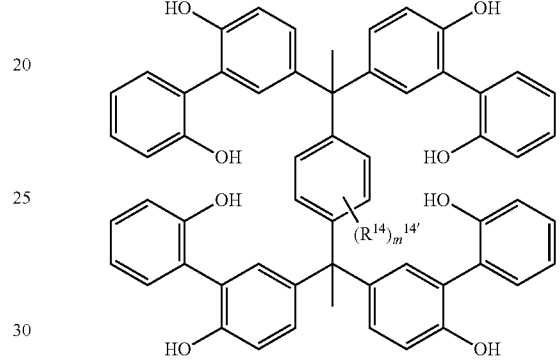
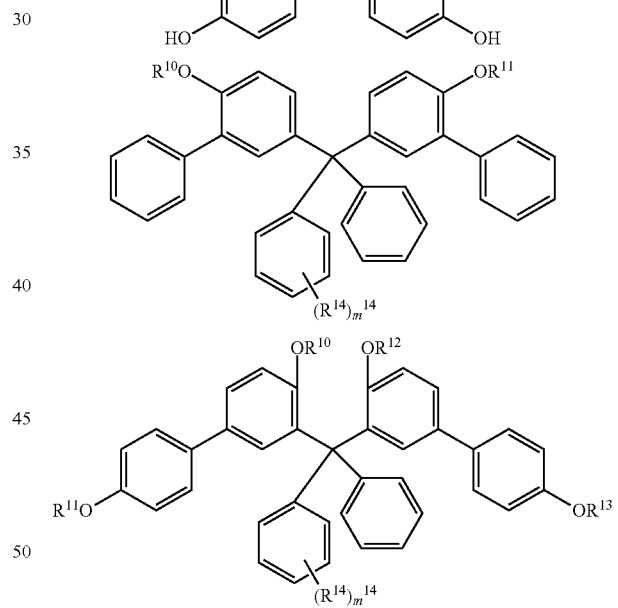
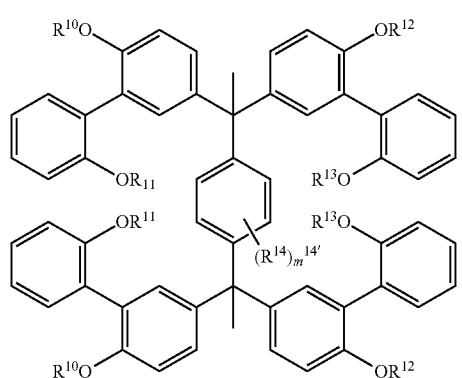
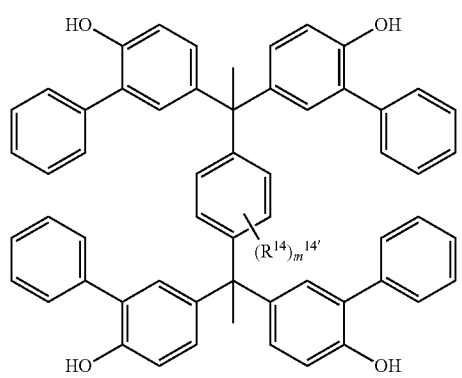
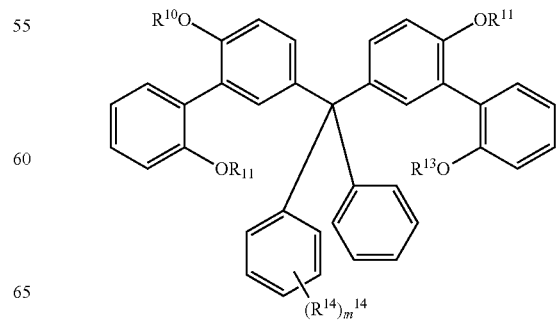

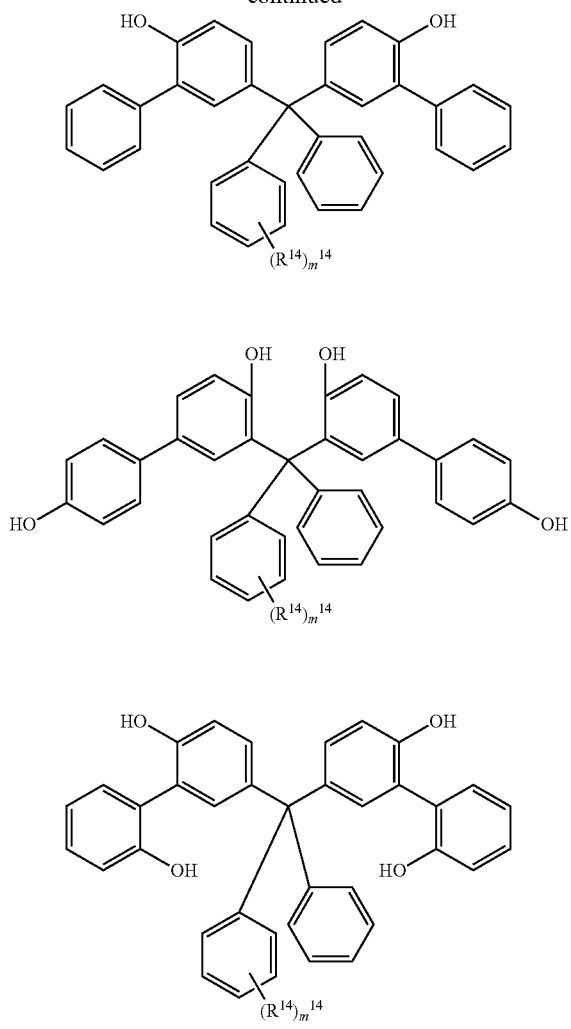

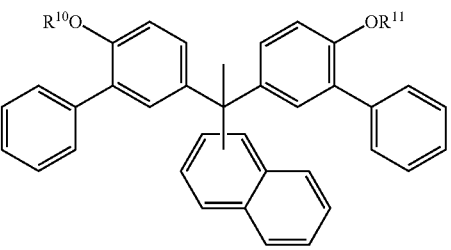

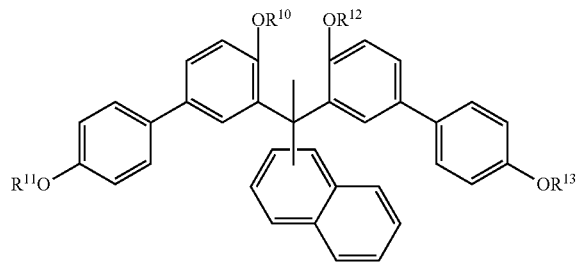

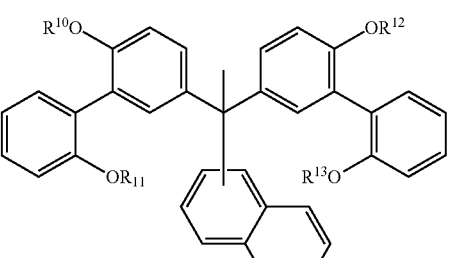

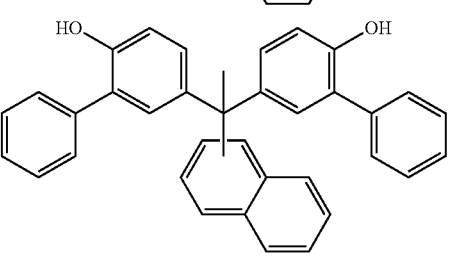

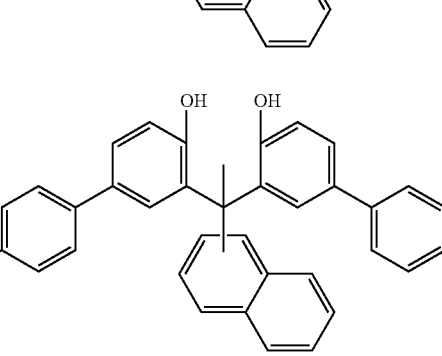

In the compounds of above formulas, $R^{10}$ to $R^{13}$ are as defined in the description of the above formula (1-2); each $R^{14}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group; $m^{14}$ is an integer of 0 to 5.

Examples of $R^{14}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a pyrenyl group, a biphenyl group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{14}$ listed above includes isomers. For example, a butyl group includes a n-butyl group, an isobutyl group, a sec-butyl group, and a tert-butyl group.

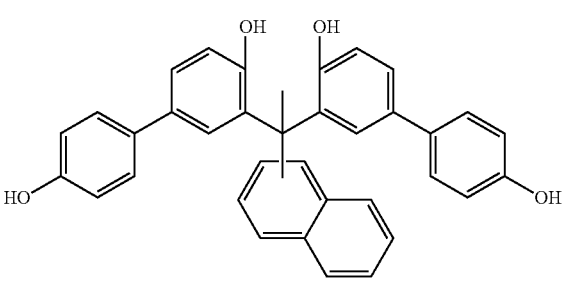

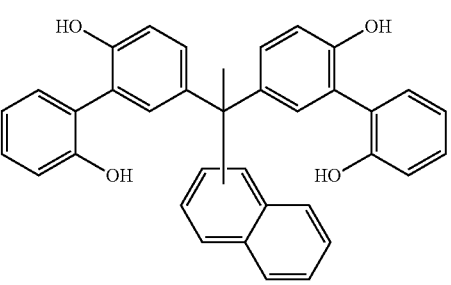

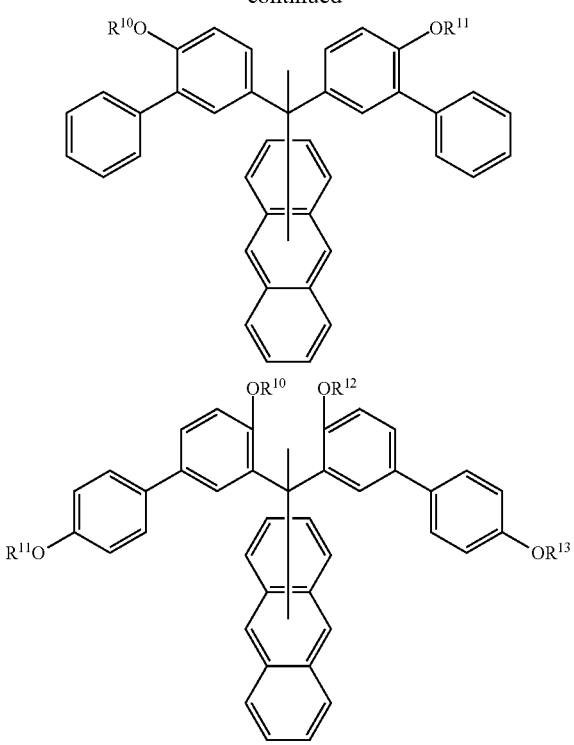
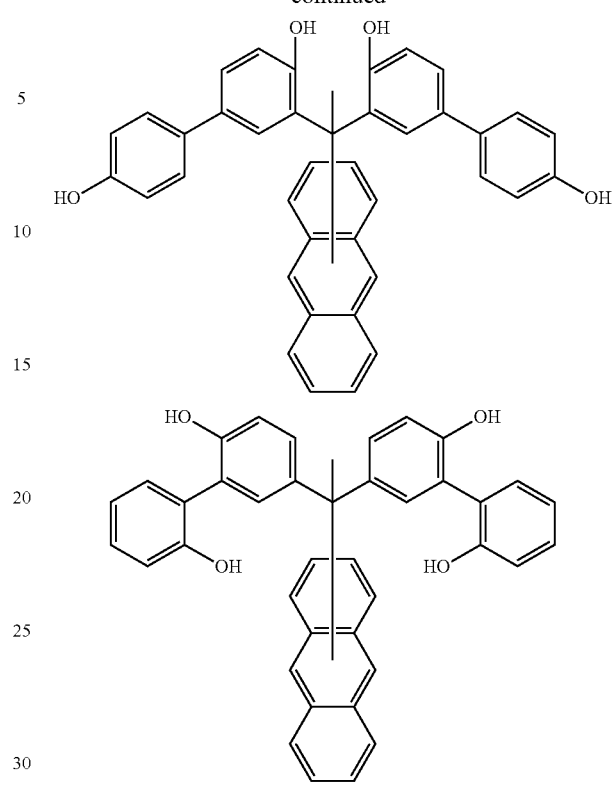
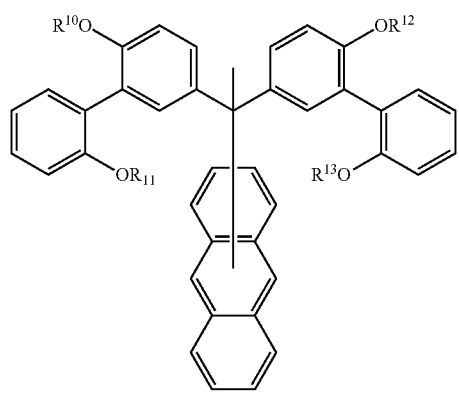
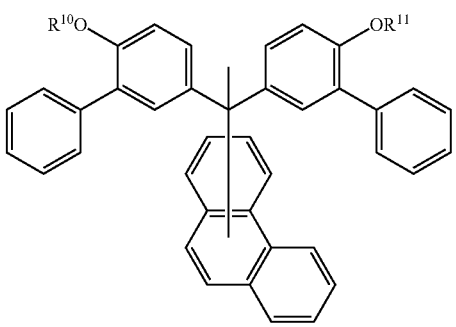
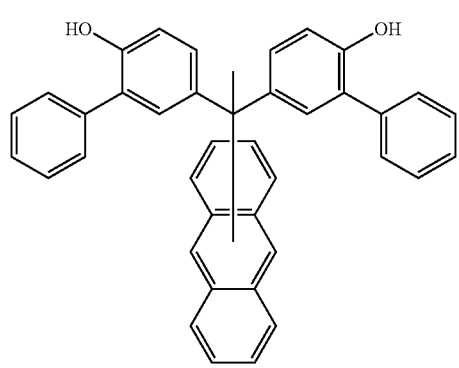
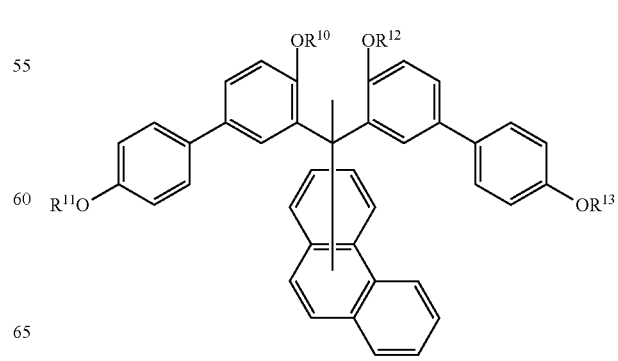

31
-continued
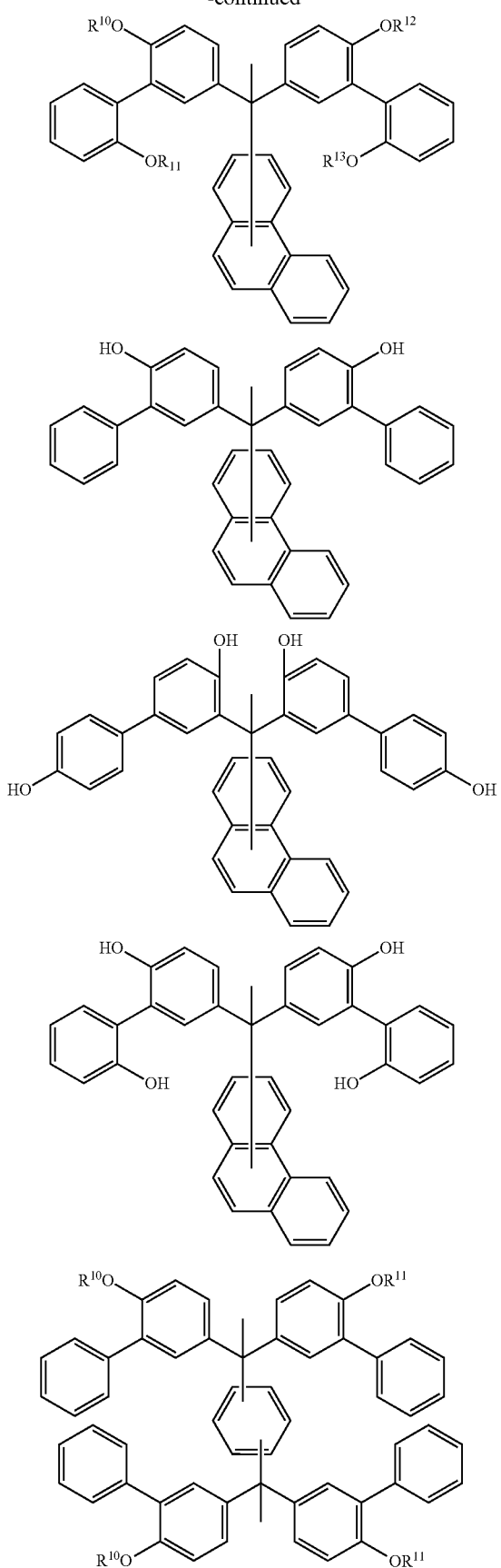
32
-continued
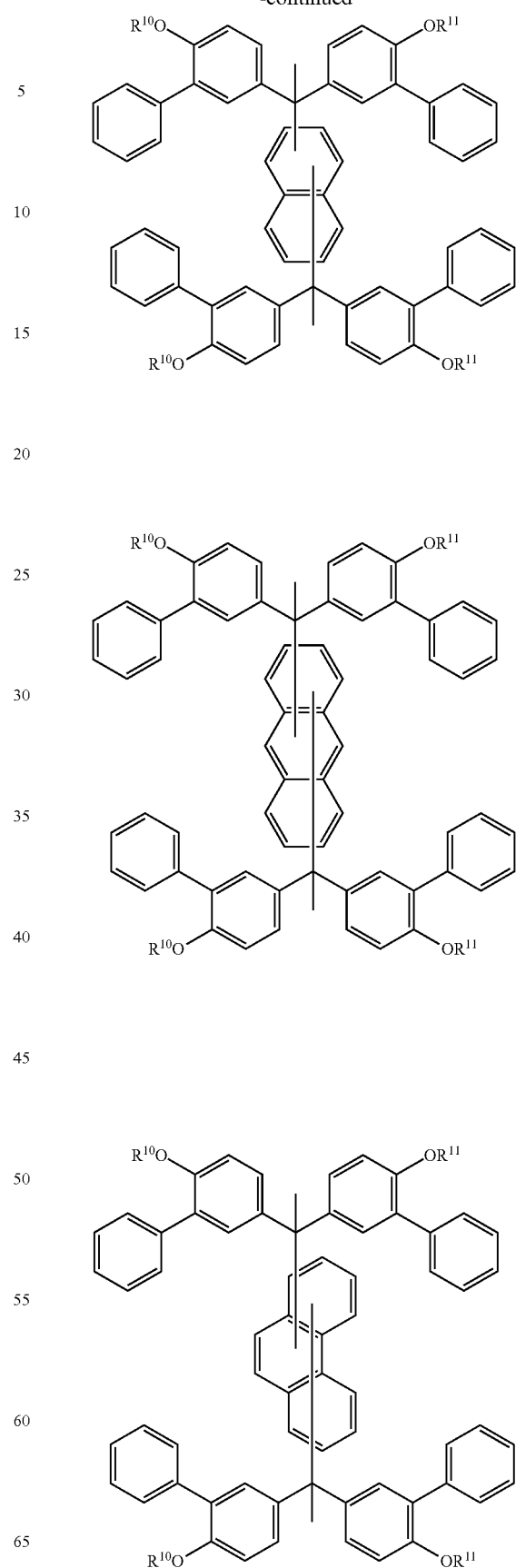

33
-continued
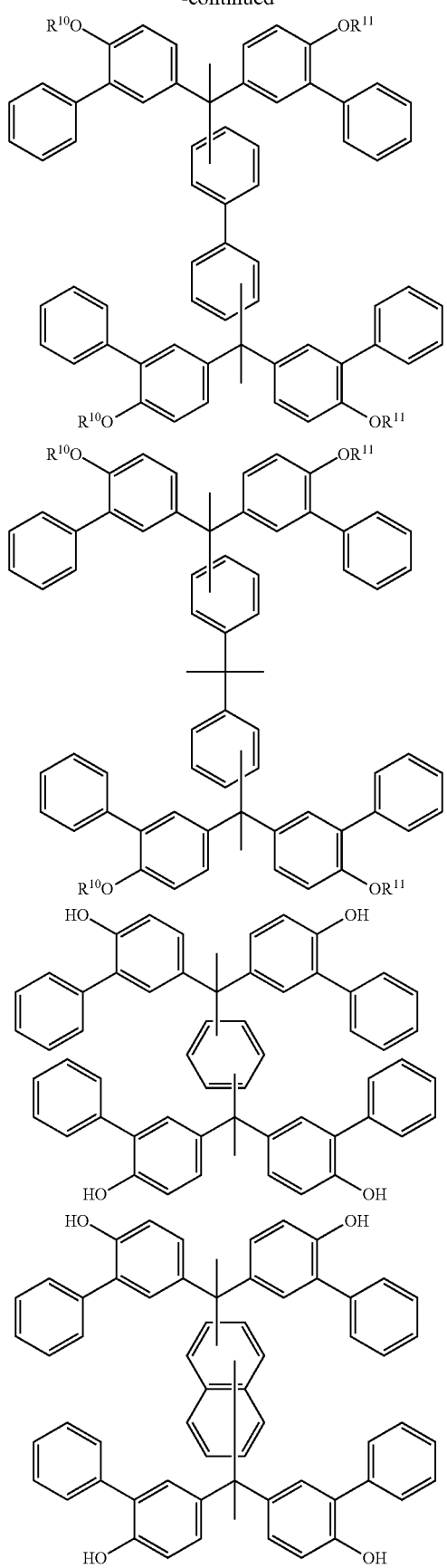
34
-continued
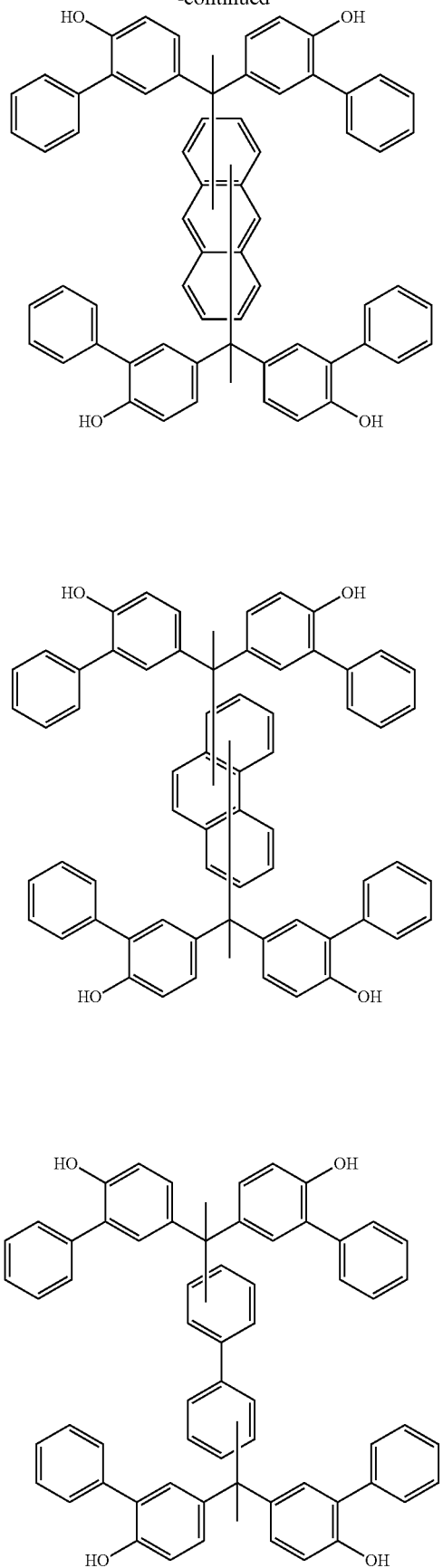

35
-continued
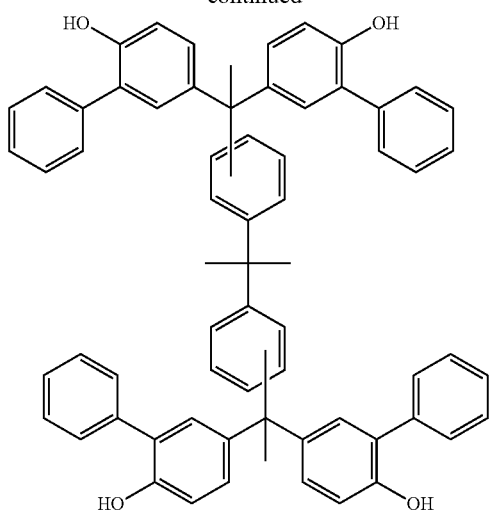
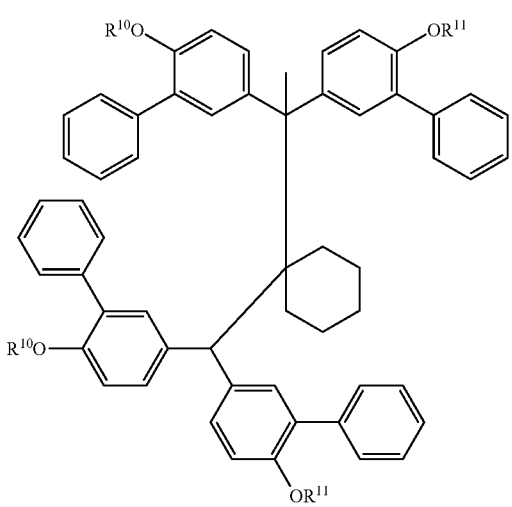
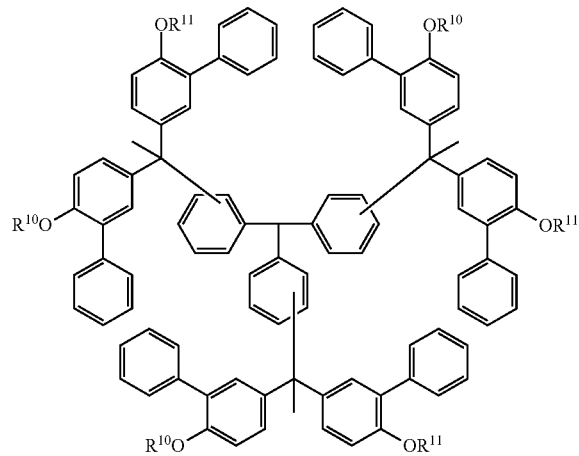
36
-continued
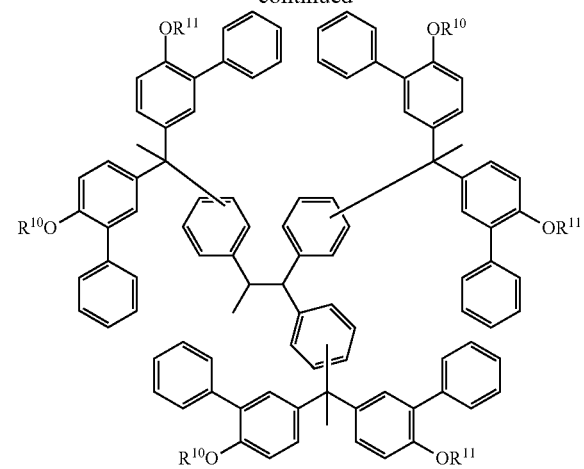
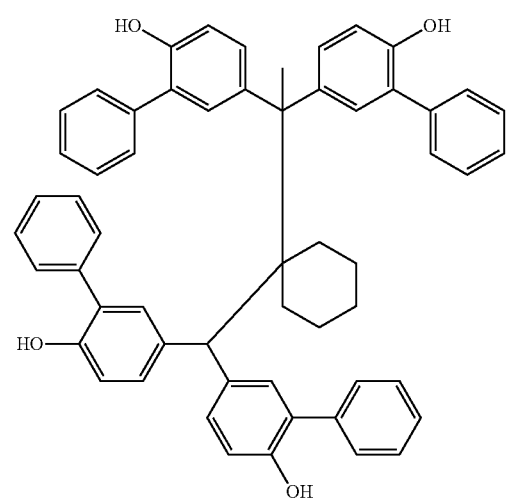
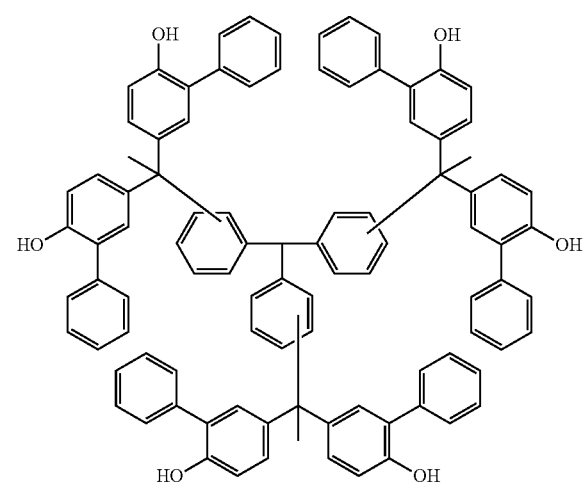

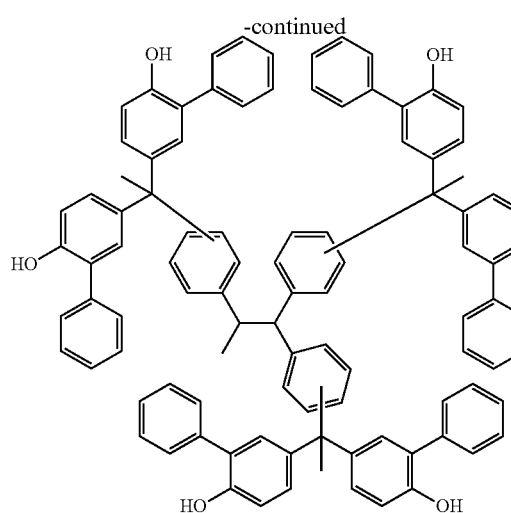

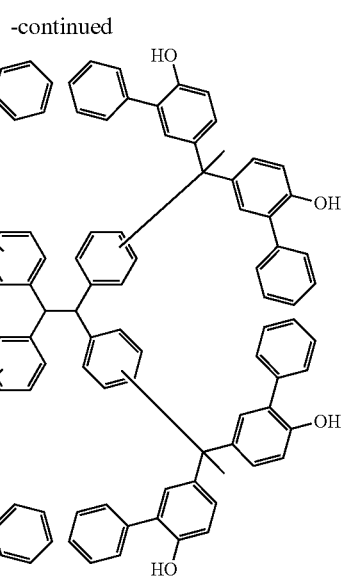

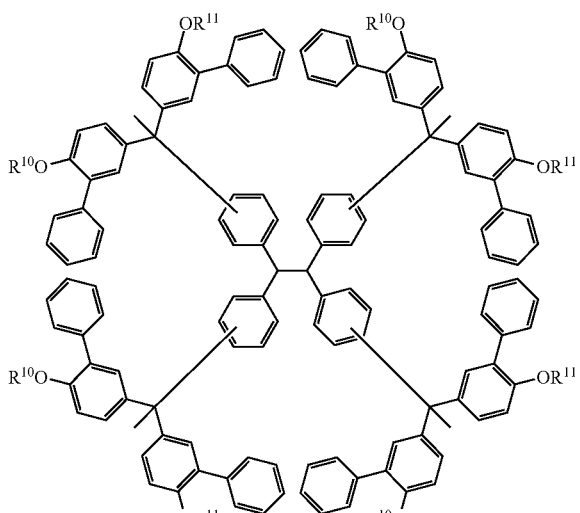

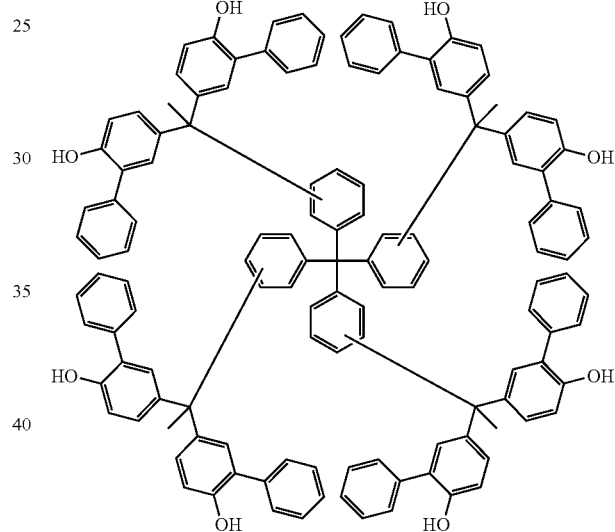

In the compounds of the above formulas, $R^{10}$ to $R^{13}$ are as defined in the description of the above formula (1-2).

A compound represented by any of the following formulas can be further used as the compound represented by the formula (1).

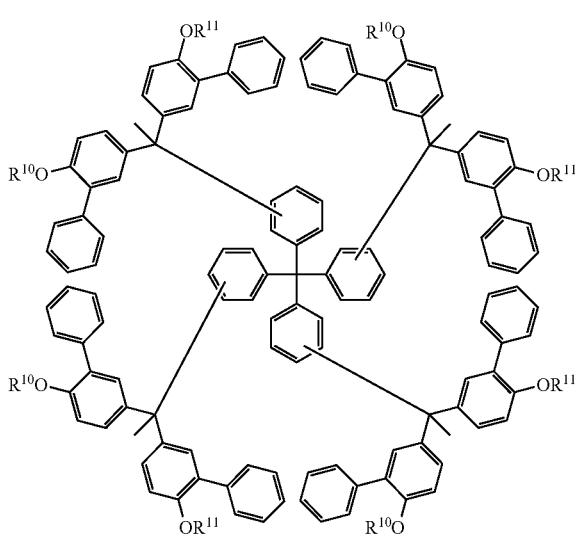

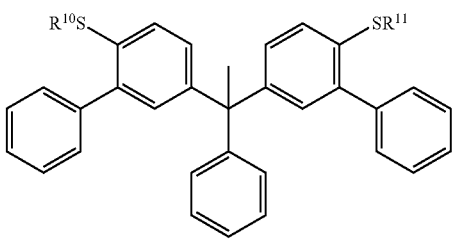

A compound represented by any of the following formulas is still more preferable from the viewpoint of the availability of raw materials.

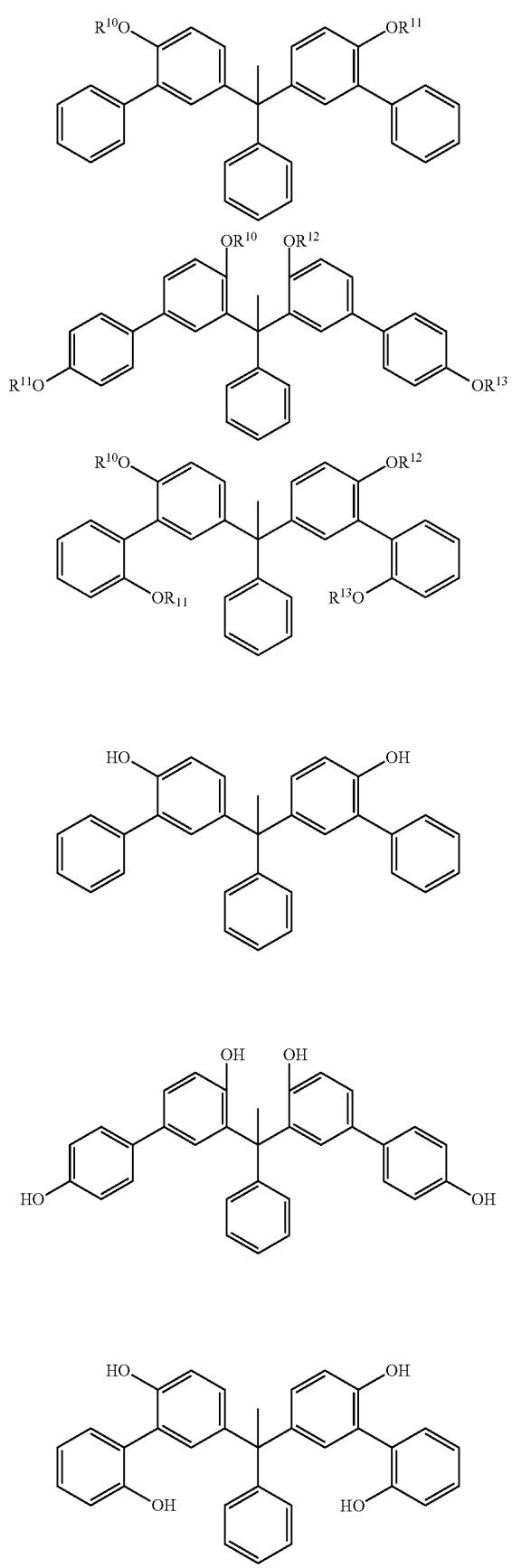
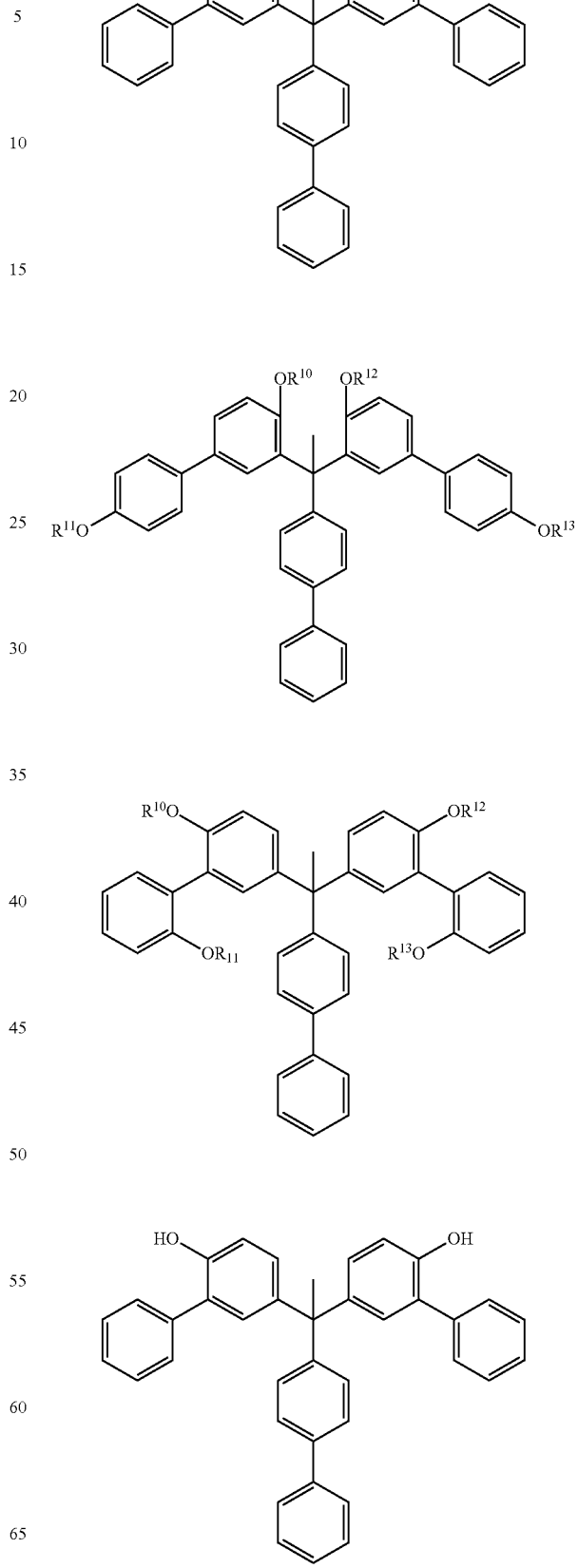

41
-continued
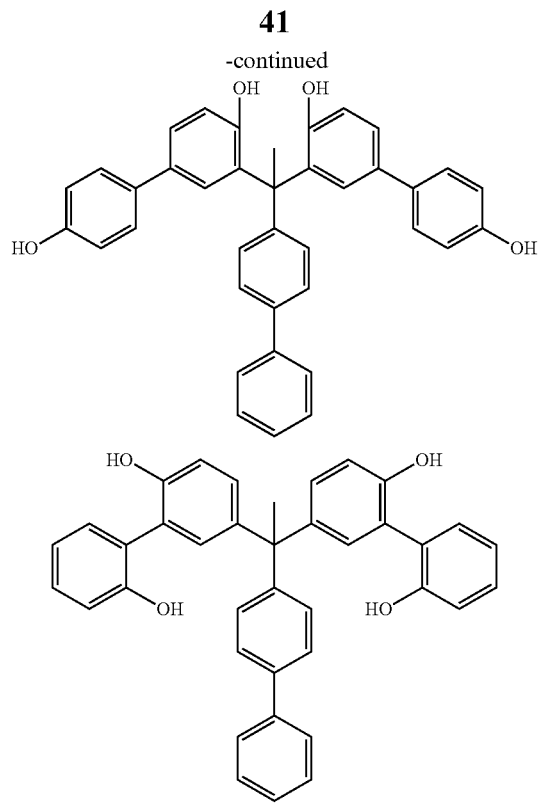
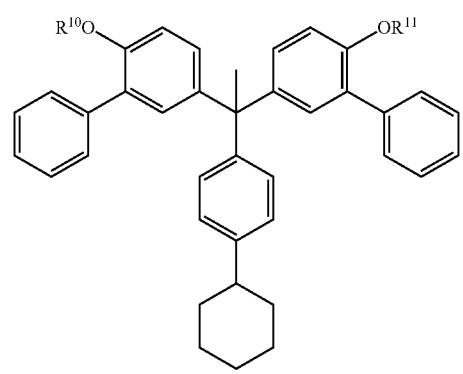
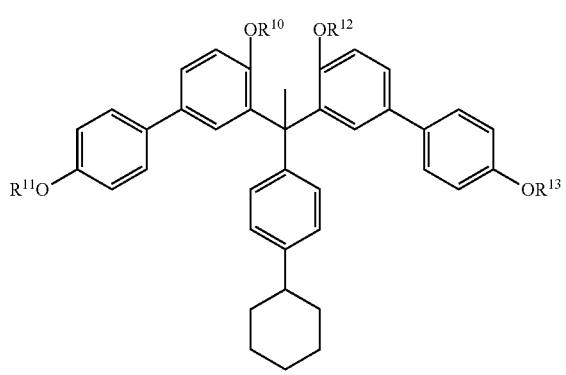
42
-continued
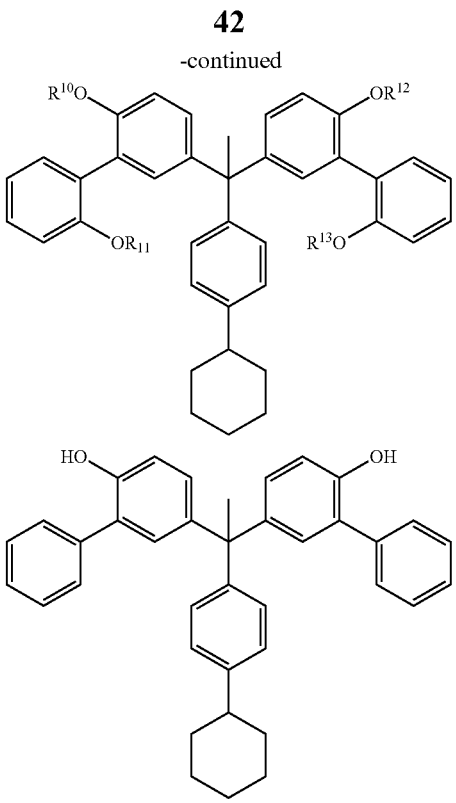
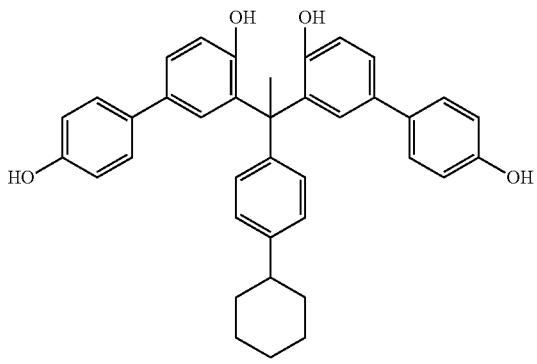
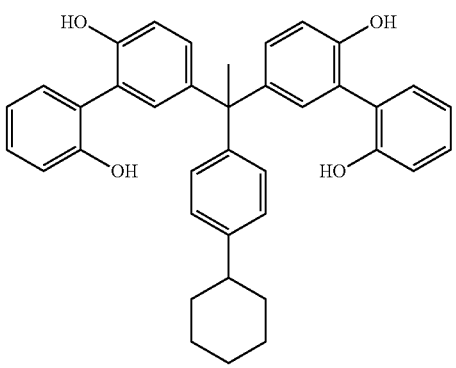

-continued
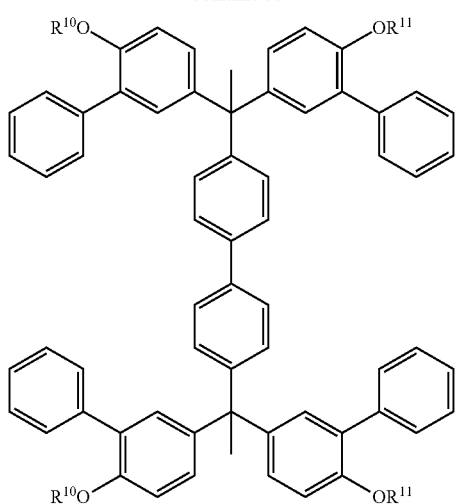
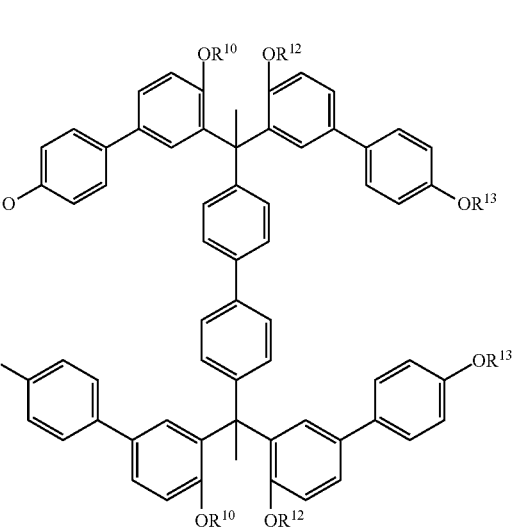
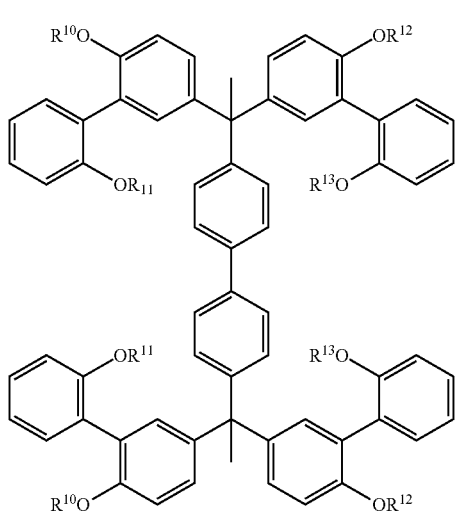
-continued
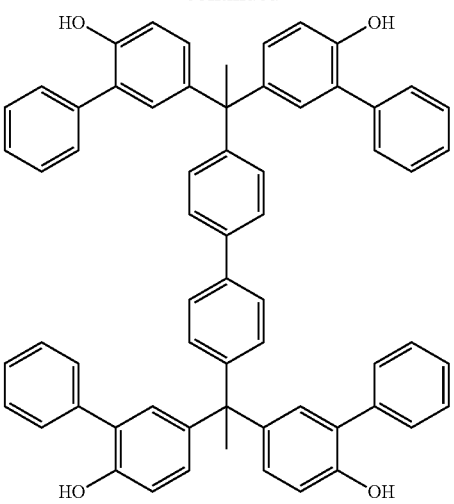
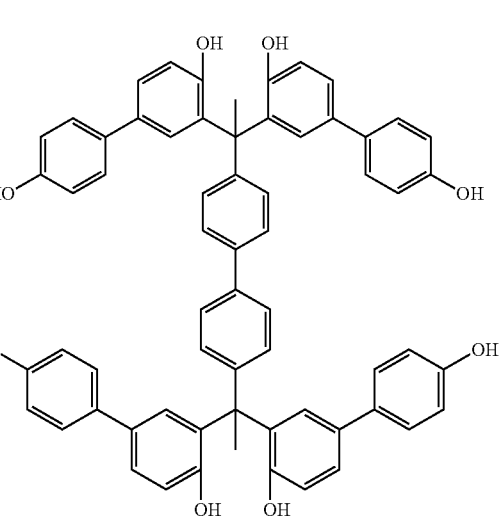
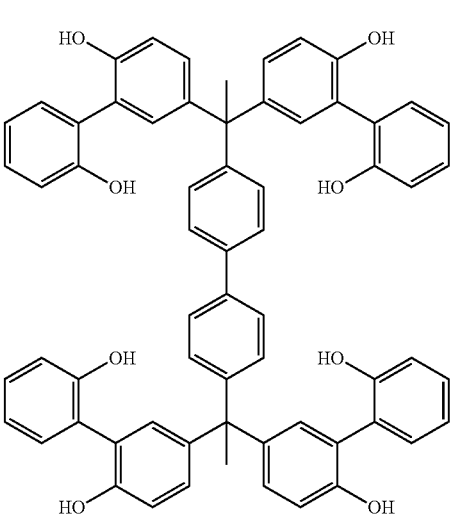

-continued
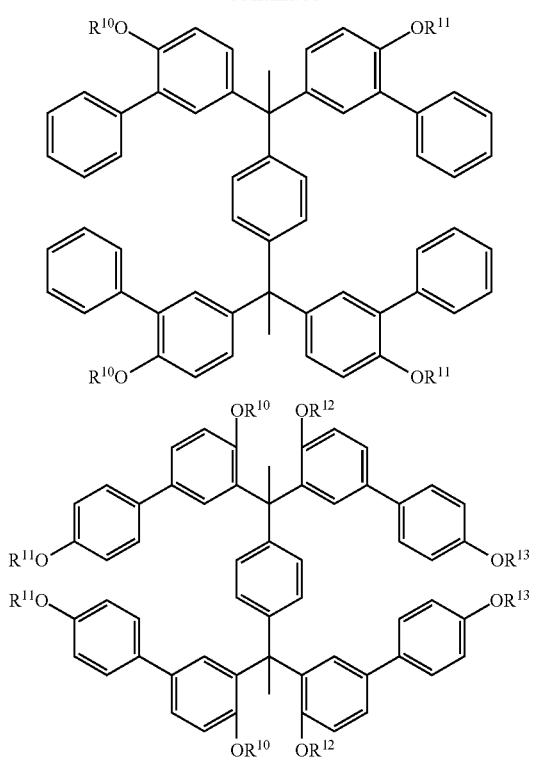
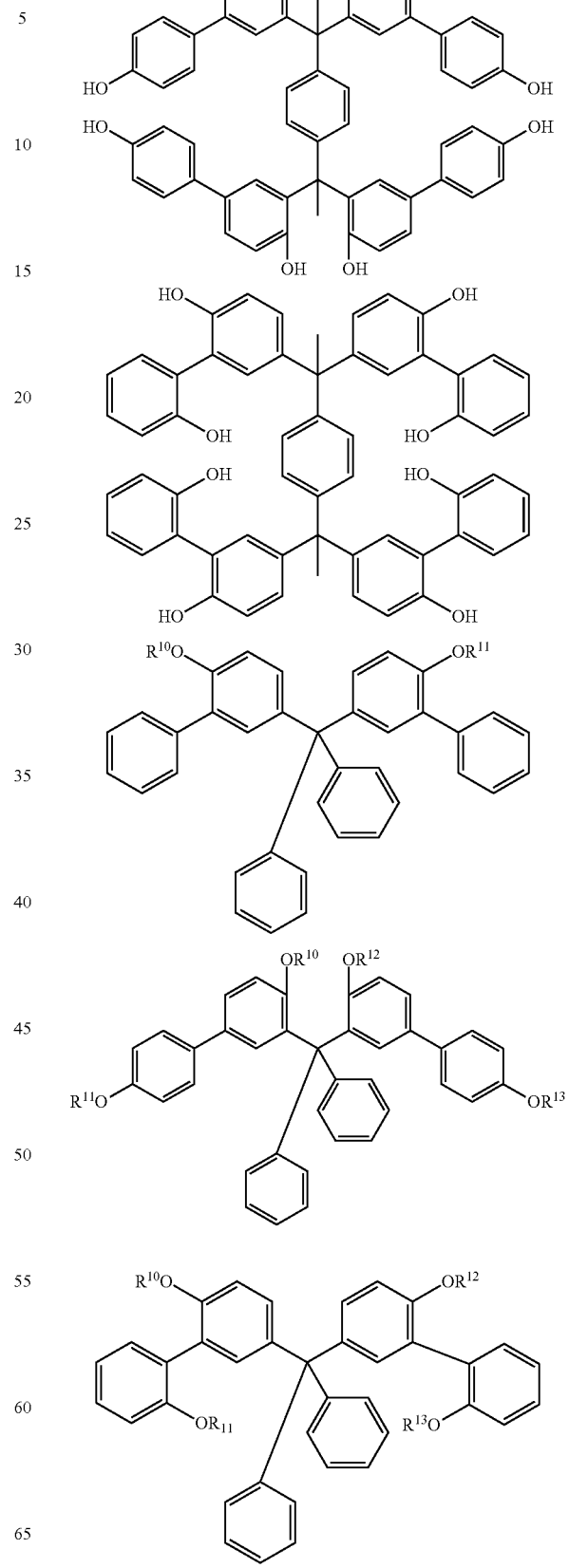

-continued
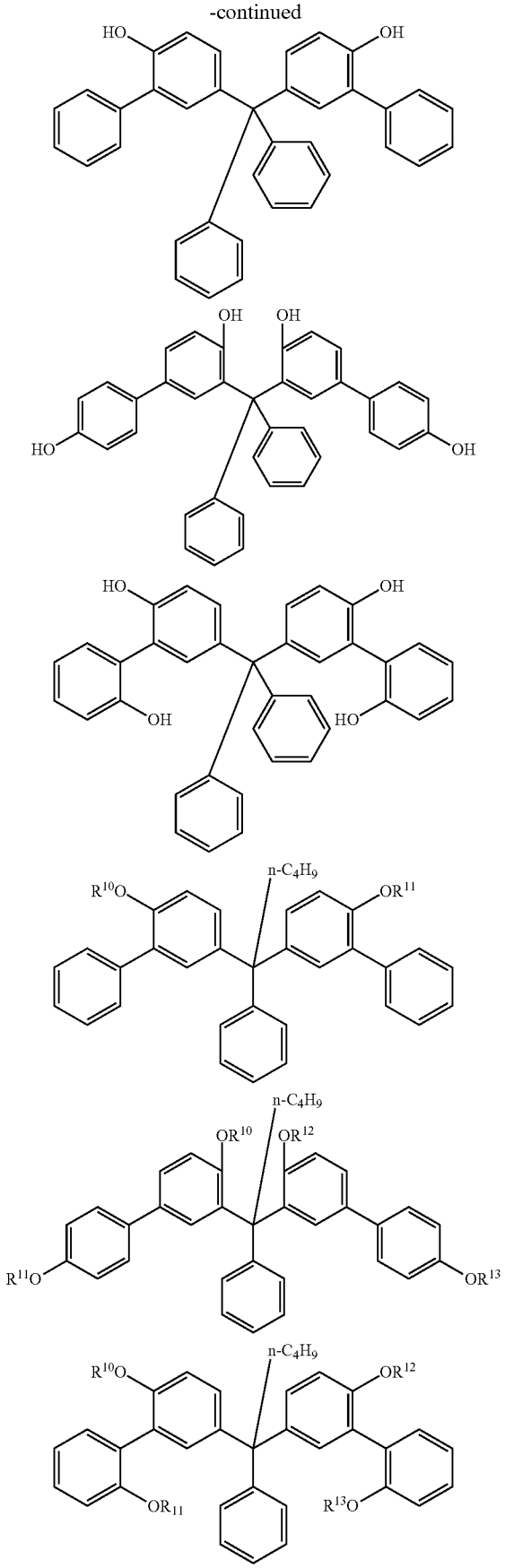
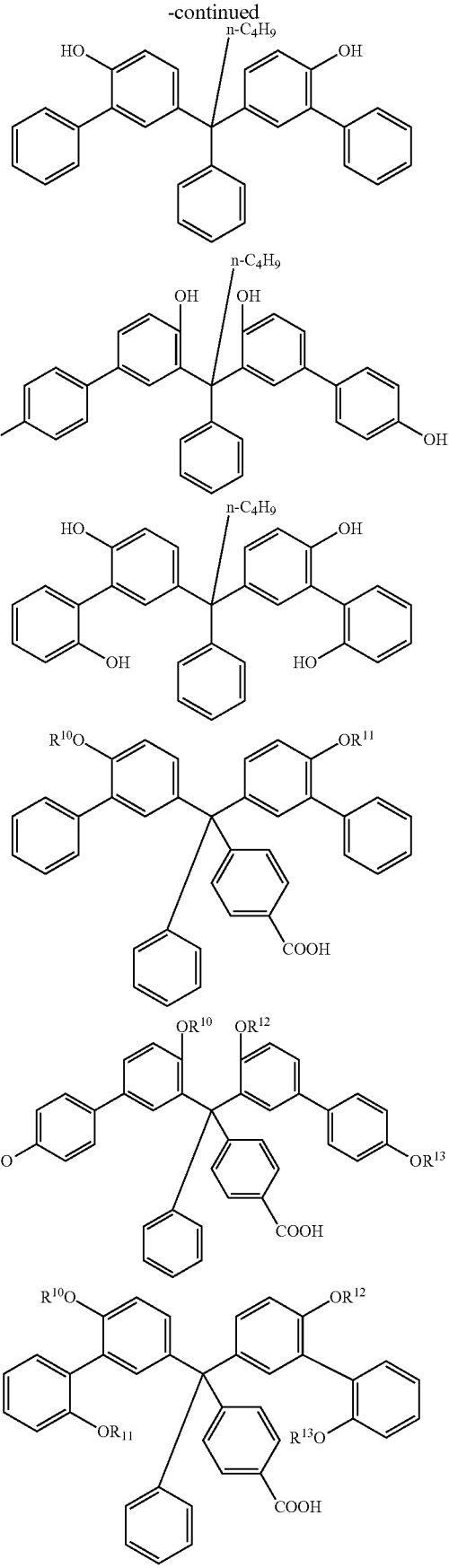

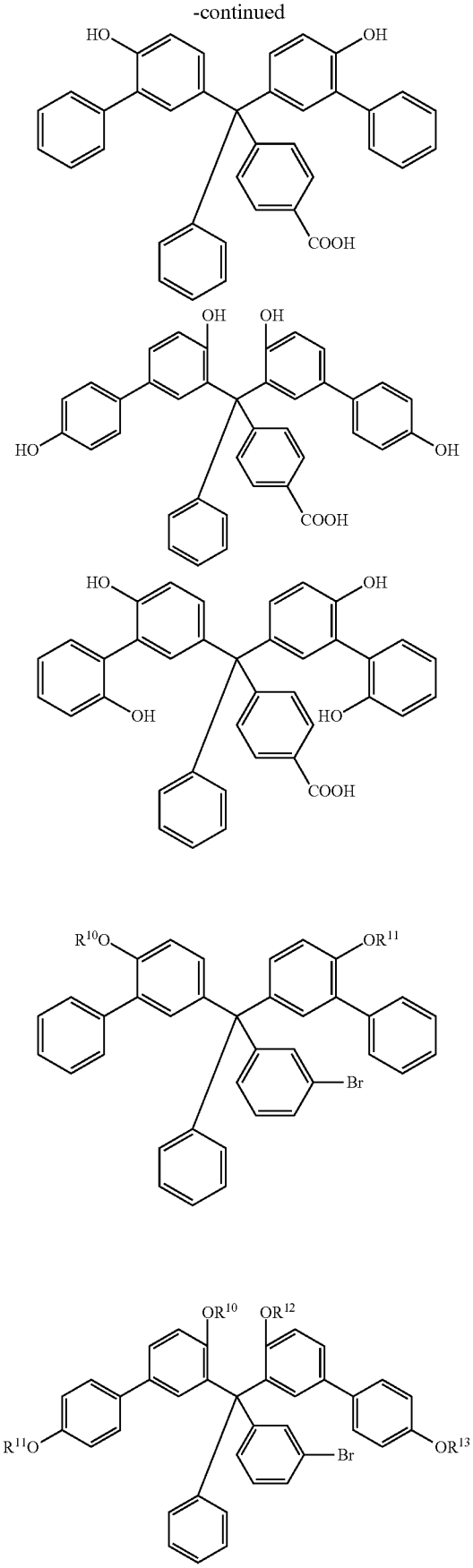
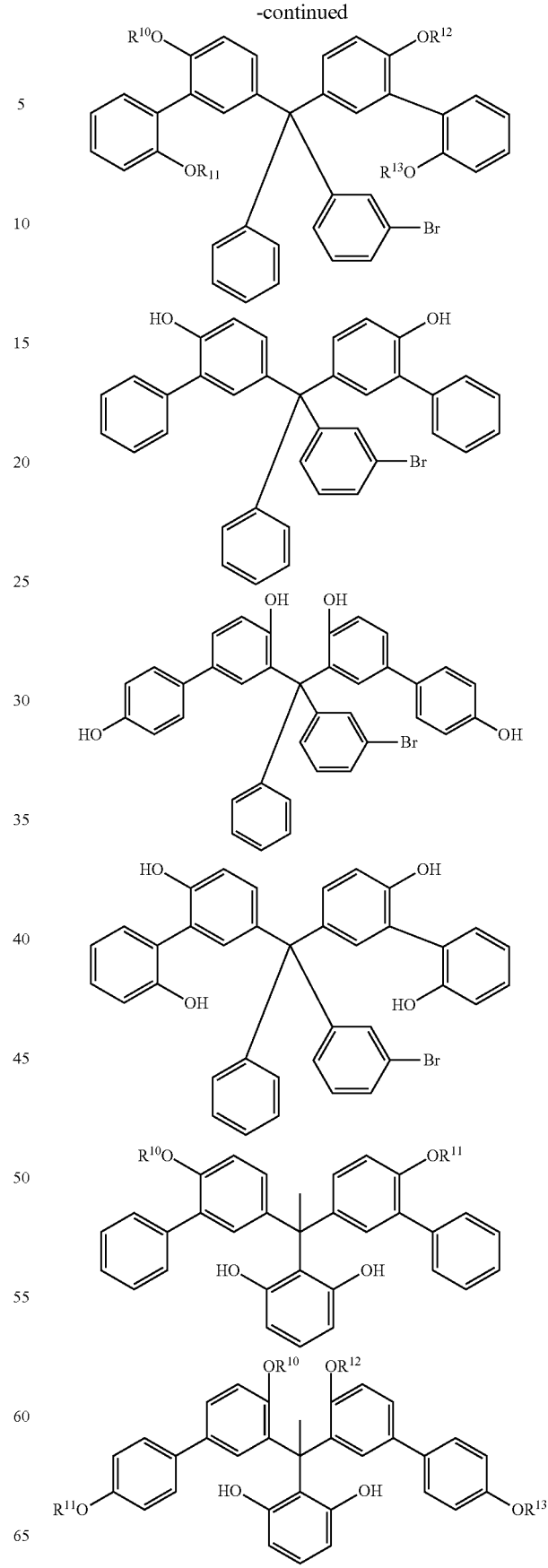

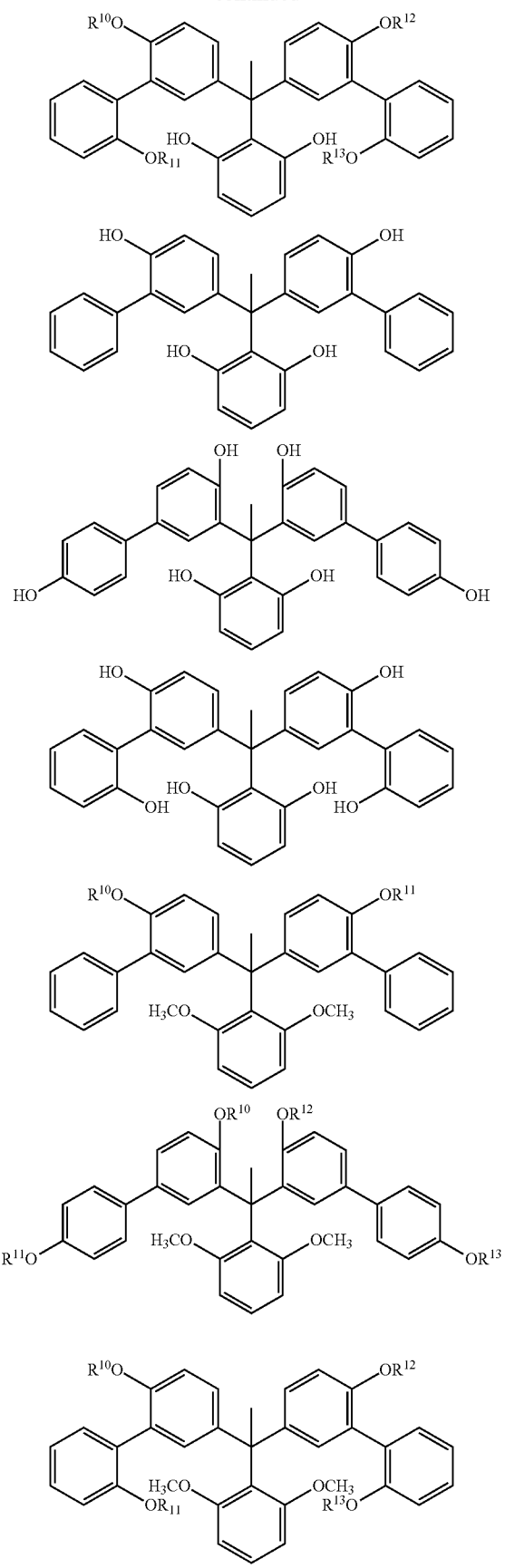
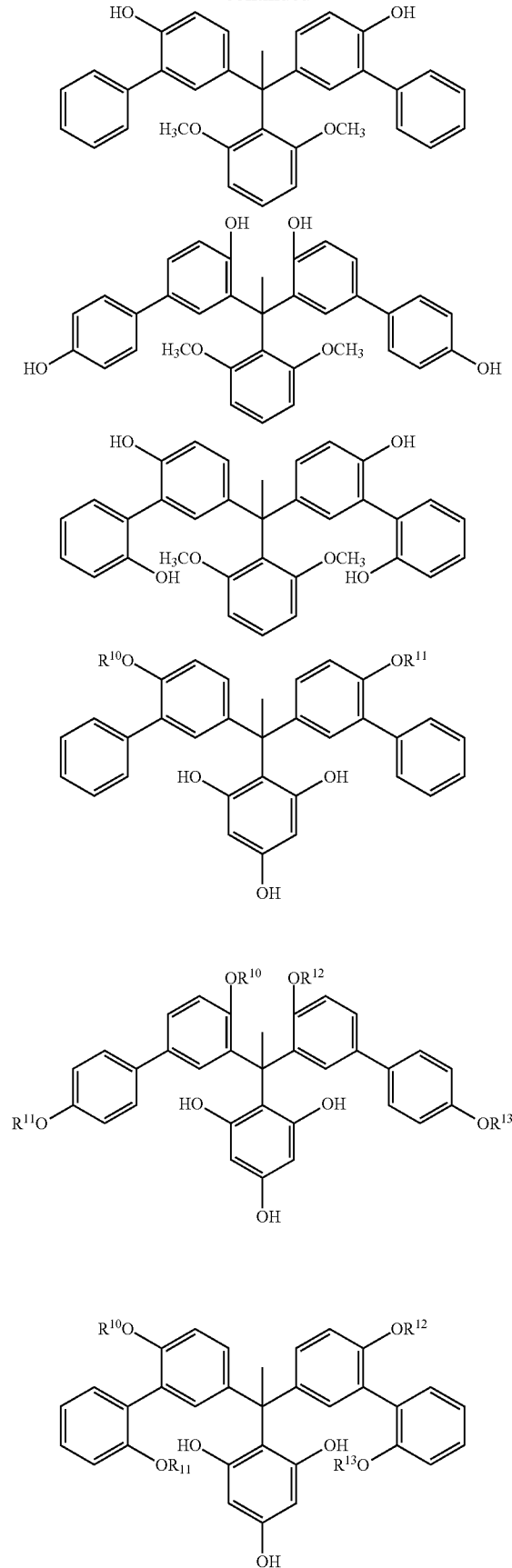

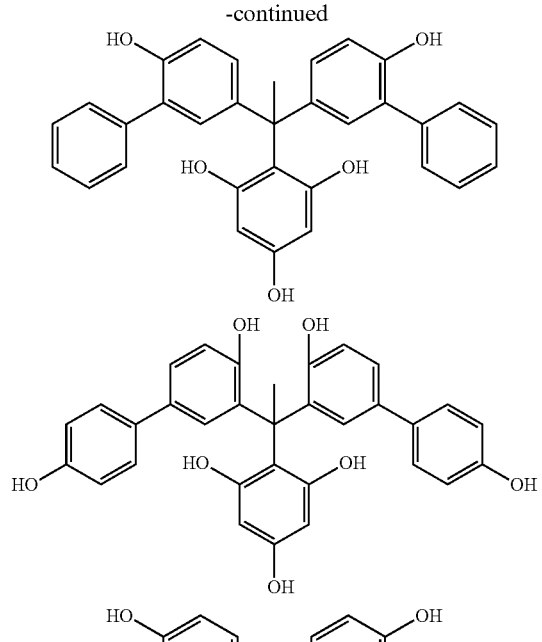
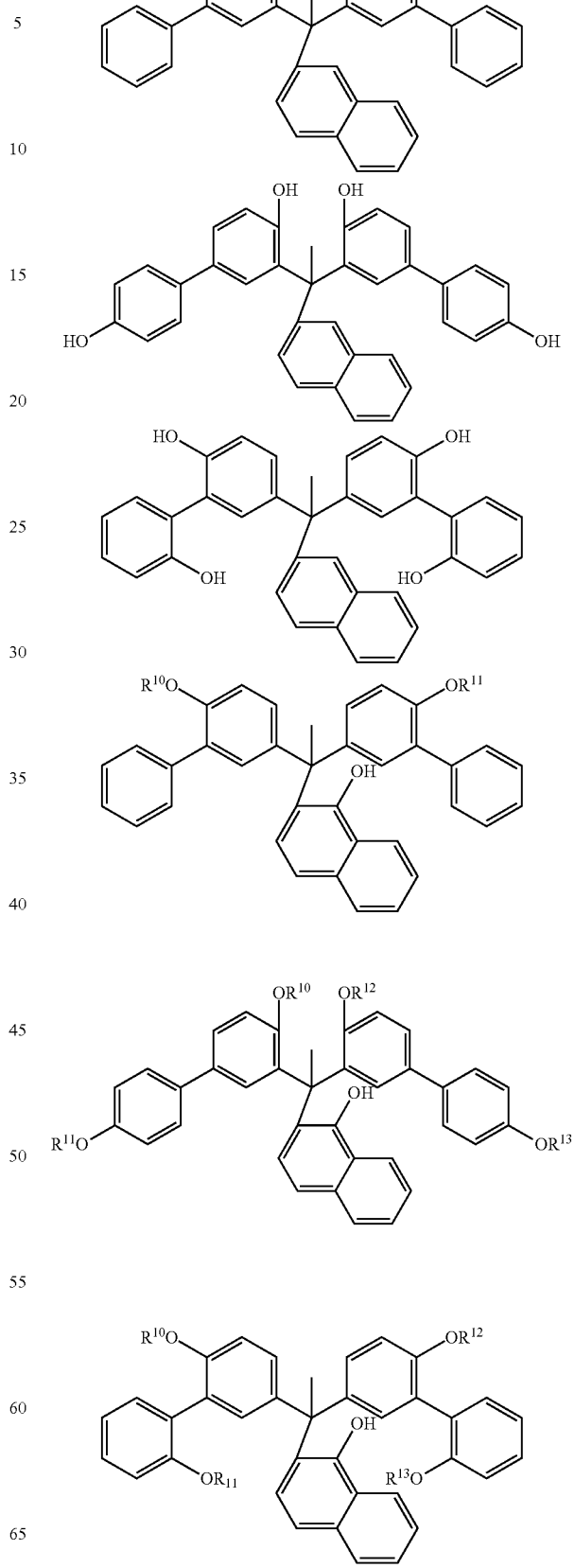

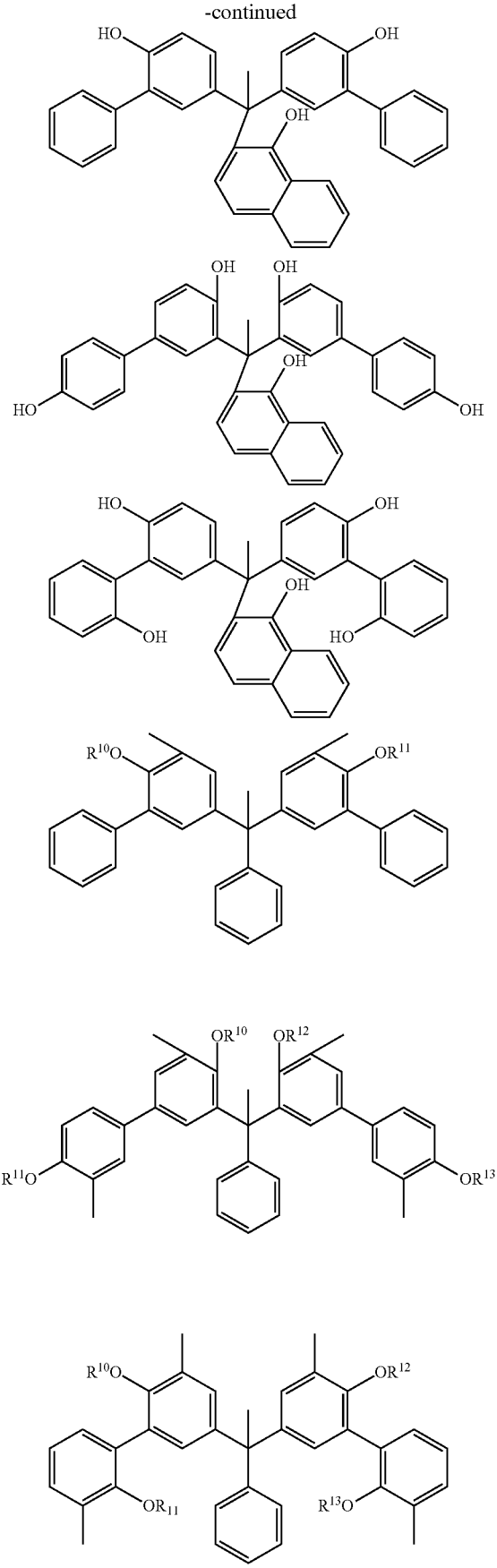
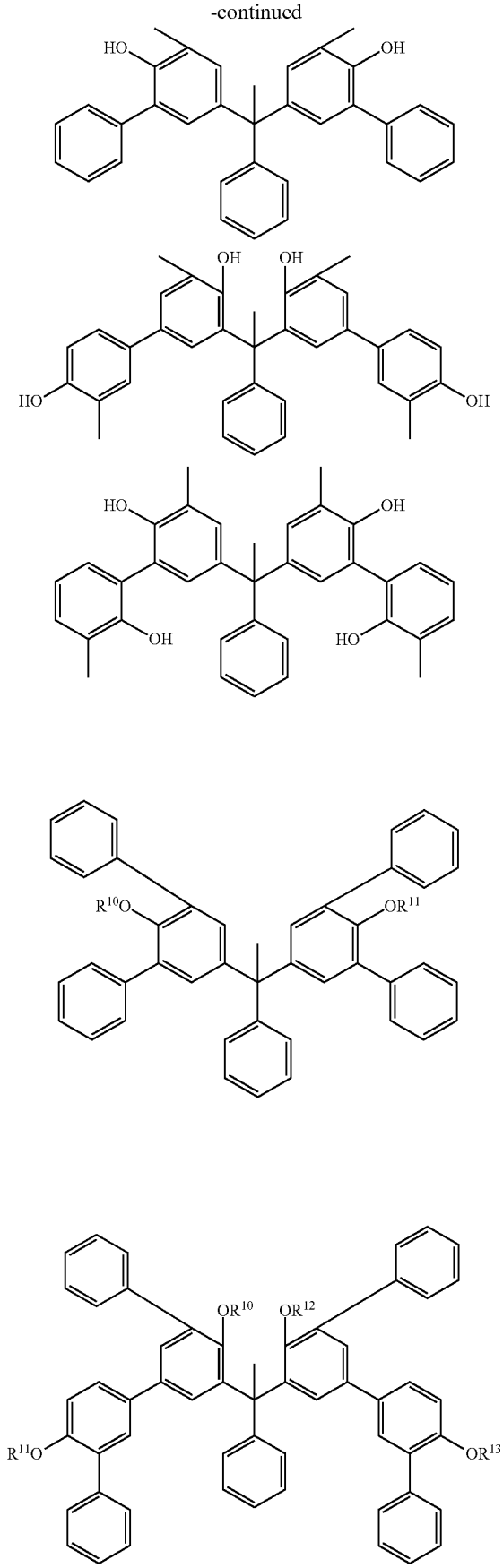

-continued

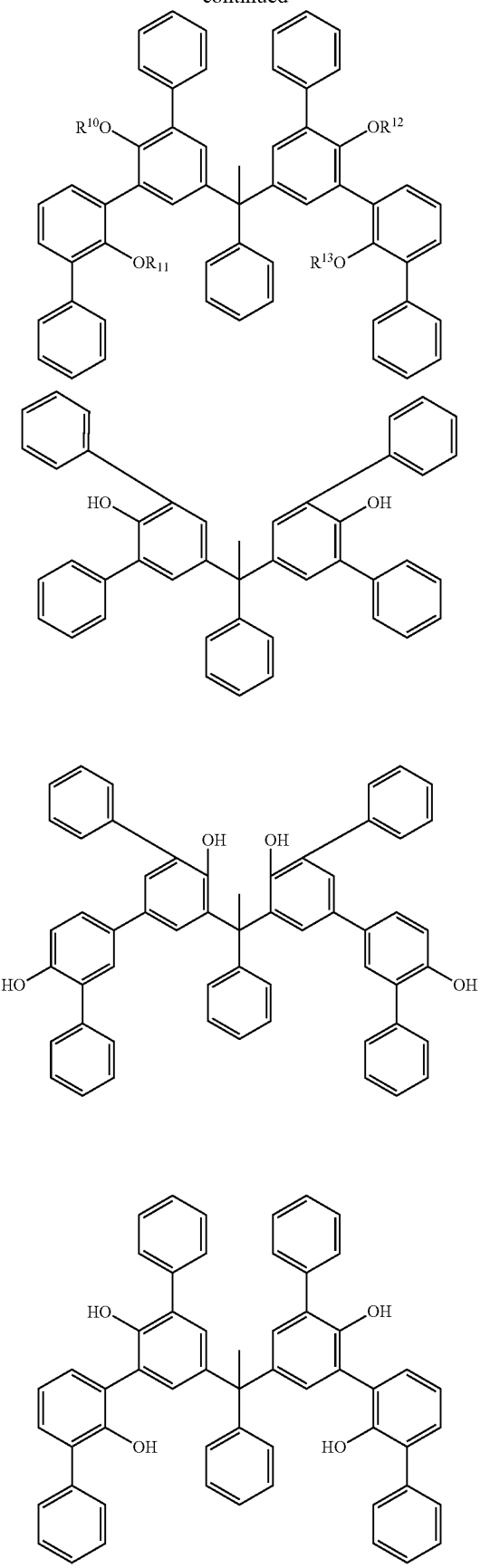

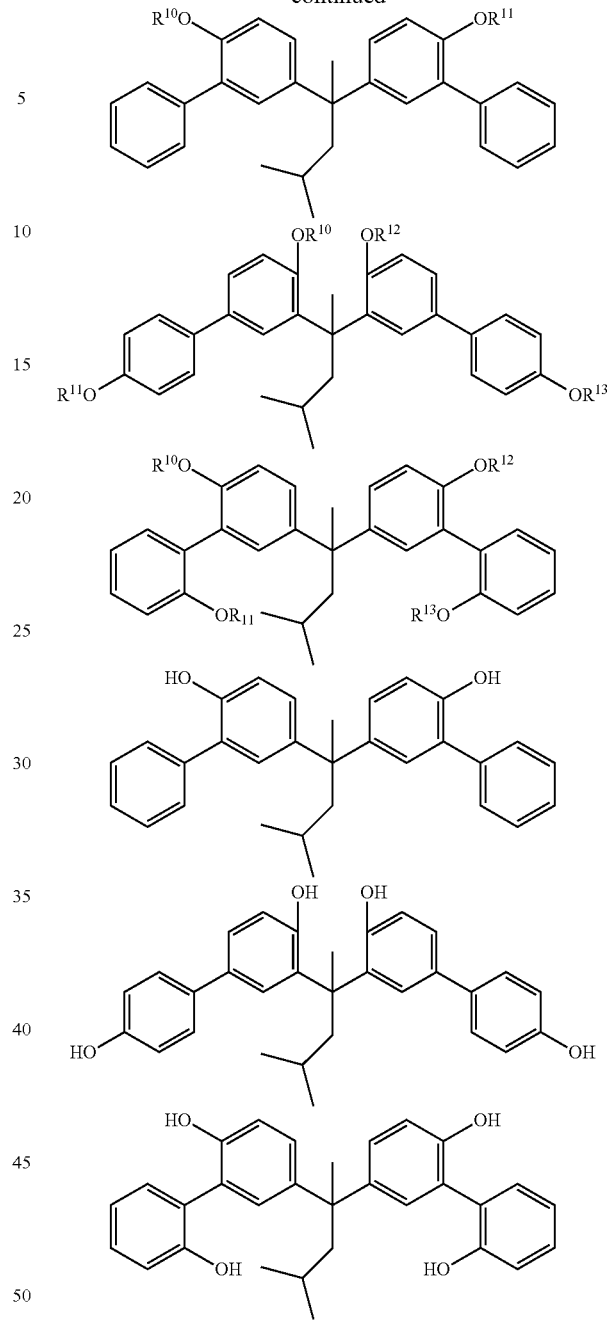

In the above compounds, $R^{10}$ to $R^{13}$ are as defined in the description of the above formula (1-2)

[Method for Producing Compound Represented by Formula (1)]

The compound represented by the formula (1) used in the present embodiment can be arbitrarily synthesized by the application of a publicly known approach, and the synthesis approach is not particularly limited. Examples thereof include (i) a method of subjecting a biphenol, a binaphthol, or a bianthracenol and a corresponding ketone to polycondensation reaction in the presence of an acid catalyst, and (ii) a method of polycondensing a biphenol, a binaphthol, or a bianthracenol with a corresponding aldehyde in the presence of an acid catalyst, followed by the substitution of a methine site of the obtained triarylmethane or xanthene.

Examples of the method (i) of subjecting a biphenol, a binaphthol, or a bianthracenol and a corresponding ketone to polycondensation reaction in the presence of an acid catalyst include (a) a method of performing the reaction in an organic solvent, (b) a method of performing the reaction in a water solvent, and (c) a method of performing the reaction in the absence of a solvent.

In the method (i) (a) of subjecting a biphenol, a binaphthol, or a bianthracenol and a corresponding ketone to polycondensation reaction in the presence of an acid catalyst in an organic solvent, the compound represented by the above formula (1) can be obtained by subjecting a biphenol, a binaphthol, or a bianthracenol and a corresponding ketone to polycondensation reaction in the presence of an acid catalyst at normal pressure. Also, an acid dissociation group can be introduced to at least one phenolic hydroxy group of the compound by a publicly known method. If necessary, this reaction can also be carried out under increased pressure.

In the method (i) of subjecting a biphenol, a binaphthol, or a bianthracenol and a corresponding ketone to polycondensation reaction in the presence of an acid catalyst in a water solvent (method (i)(b)) or in the absence of a solvent (method (i)(c)), the compound represented by the above formula (1) can be obtained by subjecting a biphenol, a binaphthol, or a bianthracenol and a corresponding ketone to polycondensation reaction in the presence of acid and mercapto catalysts. Also, an acid dissociation group can be introduced to at least one phenolic hydroxy group of the compound by a publicly known method. This reaction can be carried out under reduced pressure, at normal pressure, or under increased pressure.

Examples of the biphenol include, but not particularly limited to, biphenol, methylbiphenol, and methoxybiphenol. These biphenols can be used alone as one kind or can be used in combination of two or more kinds. Among them, biphenol is more preferably used from the viewpoint of the stable supply of raw materials.

Examples of the binaphthol include, but not particularly limited to, binaphthol, methylbinaphthol, and methoxybinaphthol. These binaphthols can be used alone as one kind or can be used in combination of two or more kinds. Among them, binaphthol is more preferably used from the viewpoint of increasing a carbon atom concentration and improving heat resistance.

Examples of the above bianthracenol include, but not particularly limited to, bianthracenol, methylbianthracenol, and methoxybianthracenol. These bianthracenols can be used alone as one kind or can be used in combination of two or more kinds. Among them, bianthracenol is more preferably used from the viewpoint of increasing a carbon atom concentration and improving heat resistance.

Examples of the ketone include, but not particularly limited to, acetone, methyl ethyl ketone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones can be used alone as one kind or can be used in combination of two or more kinds. Among them, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, or diphenylcarbonylbiphenyl is preferably used from the viewpoint of providing high heat resistance, and acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, or diphenylcarbonylbiphenyl is more preferably used because of high etching resistance.

As the ketone, a ketone having an aromatic ring is preferably used because both high heat resistance and high etching resistance are achieved.

The acid catalyst used in the reaction can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferably used from the viewpoint of production such as easy availability and handleability. The acid catalysts can be used alone as one kind or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

The mercapto catalyst used in the reaction can be arbitrarily selected and used from publicly known catalysts and is not particularly limited. Alkylthiols and mercaptocarboxylic acids are widely known as such mercapto catalysts. Examples of the alkylthiol include, but not particularly limited to, alkylmercaptans of 1 to 12 carbon atoms, preferably n-octylmercaptan, n-decylmercaptan, and n-dodecylmercaptan, and examples of the mercaptocarboxylic acid include, but not particularly limited to, 2-mercaptopropionic acid and 3-mercaptopropionic acid. Among them, n-octylmercaptan, n-decylmercaptan, or n-dodecylmercaptan is preferable from the viewpoint of production. The mercapto catalysts can be used alone as one kind or can be used in combination of two or more kinds. Also, the amount of the mercapto catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Upon the reaction, a reaction solvent may be used. The reaction solvent is not particularly limited as long as the reaction of the ketone used with the biphenol, the binaphthol, or the bianthracenediol proceeds, and can be arbitrarily selected and used from publicly known solvents. Examples include water, methanol, ethanol, propanol, butanol, tetrahydrofuran, dioxane, ethylene glycol dimethyl ether, ethylene glycol diethyl ether, and a mixed solvent thereof. The solvents can be used alone as one kind or can be used in combination of two or more kinds.

Also, the amount of these reaction solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature in the reaction can be arbitrarily selected according to the reactivity of the reaction raw materials and is not particularly limited, but is usually within the range of 10 to 200° C.

In order to obtain the compound represented by the formula (1) of the present embodiment, a higher reaction temperature is more preferable. Specifically, the range of 60 to 200° C. is preferable. The reaction method can be arbitrarily selected and used from publicly known approaches and is not particularly limited, and there are a method of charging the biphenol, the binaphthol, or the bianthracenediol, the ketone, and the catalyst in one portion, and a method of dropping the biphenol, the binaphthol, or the bianthracenediol, and the ketone, in the presence of the catalyst. After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, the compound that is the target compound can be obtained.

As preferable reaction conditions, the reaction proceeds by using 1.0 mol to an excess of the biphenol, the binaphthol, or the bianthracenediol and 0.001 to 1 mol of the acid catalyst based on 1 mol of the ketone, and reacting them at 50 to 150° C. at normal pressure for about 20 minutes to 100 hours.

The target compound can be isolated by a publicly known method after the reaction terminates. The compound represented by the above formula (1) which is the target compound can be obtained, for example, by concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying.

In the method (ii) of polycondensing a biphenol, a binaphthol, or a bianthracenol with a corresponding aldehyde in the presence of an acid catalyst, followed by the substitution of a methine site of the obtained triarylmethane or xanthene, compound (A) which is a compound represented by the above formula (1) wherein $R^Y$ is replaced with a hydrogen atom is obtained by subjecting a biphenol, a binaphthol, or a bianthracenol and a corresponding aldehyde to polycondensation reaction in the presence of an acid catalyst. A hydroxy group of the compound (A) is replaced with a protective group using a protective group introducing agent to prepare compound (B). Then, an alkyl group corresponding to the $R^Y$ moiety of the compound represented by the above formula (1) is introduced to the compound (B) by reacting a hydrogen atom corresponding to the $R^Y$ moiety of the compound represented by the above formula (1) with an alkylating agent in the presence of a basic catalyst. Then, the compound of the above formula (1) is further obtained by deprotecting the protective group added on the hydroxy group in the compound (B). Also, an acid dissociation group can be introduced to at least one phenolic hydroxy group of the compound by a publicly known method. If necessary, this reaction can also be carried out under increased pressure. The alkylating agent can be arbitrarily selected and used from publicly known alkylating agents and is not particularly limited. Examples thereof include alkyl chlorides, alkyl bromides, and alkyl iodides.

In the above production method, the method for introducing an alkyl group corresponding to the $R^Y$ moiety of the compound represented by the above formula (1) to a hydrogen atom corresponding to the $R^Y$ moiety of the compound represented by the above formula (1) in the compound (B) may be performed, instead of the method of reacting the hydrogen atom with an alkylating agent in the presence of a basic catalyst in the production method, by replacing the hydrogen atom corresponding to the $R^Y$ moiety of the compound represented by the above formula (1) with a halogen atom through a reaction of the compound (B) with a halogenating agent, and then reacting the resultant with an alkylating agent to obtain the compound of the above formula (1). The alkylating agent can be arbitrarily selected and used from publicly known alkylating agents and is not particularly limited. Examples thereof include Grignard reagents and alkyllithiums.

Examples of the biphenol include, but not particularly limited to, biphenol, methylbiphenol, and methoxybiphenol. These biphenols can be used alone as one kind or can be used in combination of two or more kinds. Among them, biphenol is more preferably used from the viewpoint of the stable supply of raw materials.

Examples of the binaphthol include, but not particularly limited to, binaphthol, methylbinaphthol, and methoxybinaphthol. These binaphthols can be used alone as one kind or can be used in combination of two or more kinds. Among them, binaphthol is more preferably used from the viewpoint of increasing a carbon atom concentration and improving heat resistance.

Examples of the above bianthracenol include, but not particularly limited to, bianthracenol, methylbianthracenol, and methoxybianthracenol. These bianthracenols can be used alone as one kind or can be used in combination of two or more kinds. Among them, bianthracenol is more preferably used from the viewpoint of increasing a carbon atom concentration and improving heat resistance.

Examples of the aldehyde include, but not particularly limited to, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural.

The method for introducing an acid dissociation group to at least one phenolic hydroxy group of a polyphenol compound is publicly known. For example, an acid dissociation group can be introduced to at least one phenolic hydroxy group of the above compound as follows. The compound for introducing the acid dissociation group can be synthesized or easily obtained by a publicly known method. Examples thereof include, but not particularly limited to, acid chlorides, acid anhydrides, active carboxylic acid derivative compounds such as dicarbonate, alkyl halides, vinyl alkyl ethers, dihydropyran, and halocarboxylic acid alkyl esters.

For example, the compound is dissolved or suspended in an aprotic solvent such as acetone, tetrahydrofuran (THF), or propylene glycol monomethyl ether acetate. Subsequently, a vinyl alkyl ether such as ethyl vinyl ether, or dihydropyran is added to the solution or the suspension, and the mixture is reacted at 20 to 60° C. at normal pressure for 6 to 72 hours in the presence of an acid catalyst such as pyridinium p-toluenesulfonate. The reaction solution is neutralized with an alkali compound and added to distilled water to precipitate a white solid. Then, the separated white solid can be washed with distilled water and dried to obtain a compound in which a hydrogen atom of a hydroxy group is replaced with an acid dissociation group.

Alternatively, for example, the above compound having a hydroxy group is dissolved or suspended in an aprotic solvent such as acetone, THF, or propylene glycol monomethyl ether acetate. Subsequently, an alkyl halide such as ethyl chloromethyl ether or a halocarboxylic acid alkyl ester such as methyladamantyl bromoacetate is added to the solution or the suspension, and the mixture is reacted at 20 to 110° C. at normal pressure for 6 to 72 hours in the presence of an alkali catalyst such as potassium carbonate. The reaction solution is neutralized with an acid such as hydrochloric acid and added to distilled water to precipitate a white solid. Then, the separated white solid can be washed with distilled water and dried to obtain a compound in which a hydrogen atom of a hydroxy group is replaced with an acid dissociation group.

As for the timing of introducing an acid dissociation group, the introduction may be carried out after condensation reaction of the binaphthol with the ketone or may be carried out at a stage previous to the condensation reaction. Alternatively, the introduction may be carried out after production of a resin mentioned later.

In the present embodiment, the acid dissociation group refers to a characteristic group that is cleaved in the presence of an acid to form a functional group that changes solubility, such as an alkali soluble group. Examples of the alkali soluble group include a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The acid dissociation group preferably has properties of causing chain cleavage reaction in the presence of an acid in order to enable pattern formation with higher sensitivity and higher resolution.

[Resin Obtained with Compound Represented by Formula (1) as Monomer]

The compound represented by the above formula (1) can be used directly as a film forming composition for lithography. Also, a resin obtained with the compound represented by the above formula (1) as a monomer can be used. For example, a resin obtained by reacting the compound represented by the above formula (1) with a crosslinking compound can also be used.

Examples of the resin obtained with the compound represented by the above formula (1) as a monomer include resins having a structure represented by the following formula (3). That is, the film forming composition for lithography of the present embodiment may contain a resin having a structure represented by the following formula (3).

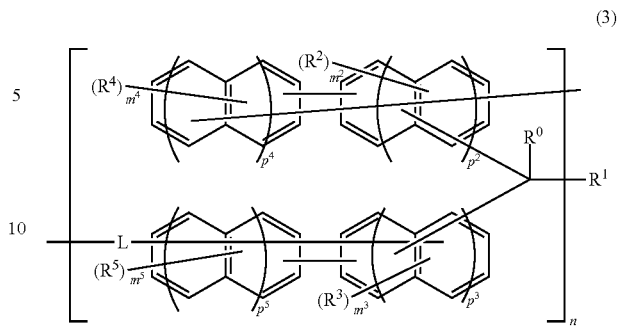

In the formula (3), L is a linear or branched alkylene group of 1 to 30 carbon atoms or a single bond. $R^0$, $R^1$, $R^2$ to $R^5$, $m^2$ and $m^3$, $m^4$ and $m^5$, $p^2$ to $p^5$, and n are as defined in the above formula (1), provided that $m^2$, $m^3$, $m^4$, and $m^5$ are not 0 at the same time, and at least one of $R^2$ to $R^5$ is a hydroxy group or a group in which a hydrogen atom of a hydroxy group is replaced with an acid dissociation group.

[Method for Producing Resin Obtained with Compound Represented by Formula (1) as Monomer]

The resin of the present embodiment is obtained by reacting the compound represented by the above formula (1) with a crosslinking compound. As the crosslinking compound, a publicly known monomer can be used without particular limitations as long as it can oligomerize or polymerize the compound represented by the above formula (1). Specific examples thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

Specific examples of the resin having the structure represented by the above formula (1) include resins that are made novolac by, for example, a condensation reaction between the compound represented by the above formula (1) with an aldehyde and/or a ketone that is a crosslinking compound.

Herein, examples of the aldehyde used when making the compound represented by the above formula (1) novolac include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural. Examples of the ketone include, but not particularly limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones can be used alone as one kind or may be used in combination of two or more kinds. Among them, formaldehyde is more preferable. These aldehydes and/or ketones can be used alone as one kind or may be used in combination of two or more kinds. The amount of the above aldehydes and/or ketones used is not particularly limited, but is preferably 0.2 to 5 mol and more preferably 0.5 to 2 mol based on 1 mol of the compound represented by the above formula (1).

A catalyst can also be used in the condensation reaction between the compound represented by the above formula (1) and the aldehyde and/or ketones. The acid catalyst used herein can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferable from the viewpoint of production such as easy availability and handleability. The acid catalysts can be used alone as one kind, or can be used in combination of two or more kinds.

Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials. The aldehyde is not necessarily needed in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, and limonene.

A reaction solvent can also be used in the condensation reaction between the compound represented by the above formula (1) and the aldehyde and/or ketones. The reaction solvent in the polycondensation can be arbitrarily selected and used from publicly known solvents and is not particularly limited, and examples include water, methanol, ethanol, propanol, butanol, tetrahydrofuran, dioxane, or a mixed solvent thereof. The solvents can be used alone as one kind, or can be used in combination of two or more kinds.

Also, the amount of these solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. The reaction method can be arbitrarily selected and used from publicly known approaches and is not particularly limited, and there are a method of charging the compound represented by the above formula (1), the aldehyde and/or ketones, and the catalyst in one portion, and a method of dropping the compound represented by the above formula (1) and the aldehyde and/or ketones in the presence of the catalyst.

After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, a novolac resin that is the target compound can be obtained.

Herein, the resin having the structure represented by the above formula (3) may be a homopolymer of a compound represented by the above formula (1), or may be a copolymer with a further phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

The resin having the structure represented by the above formula (3) may be a copolymer with a polymerizable monomer other than the above-described further phenols. Examples of such a copolymerization monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin having the structure represented by the above formula (2) may be a copolymer of two or more components (for example, a binary to quaternary system) composed of the compound represented by the above formula (1) and the above-described phenol, may be a copolymer of two or more components (for example, a binary to quaternary system) composed of the compound represented by the above formula (1) and the above-described copolymerization monomer, or may be a copolymer of three or more components (for example, a tertiary to quaternary system) composed of the compound represented by the above formula (1), the above-described phenol, and the above-described copolymerization monomer.

The molecular weight of the resin having the structure represented by the above formula (3) is not particularly limited, and the weight average molecular weight (Mw) in terms of polystyrene is preferably 500 to 30,000 and more preferably 750 to 20,000. The resin having the structure represented by the above formula (3) preferably has dispersibility (weight average molecular weight Mw/number average molecular weight Mn) within the range of 1.2 to 7 from the viewpoint of enhancing crosslinking efficiency while suppressing volatile components during baking. The above Mn can be determined by a method described in Examples mentioned later.

The resin having the structure represented by the above formula (3) preferably has high solubility in a solvent from the viewpoint of easier application to a wet process, etc. More specifically, in the case of using 1-methoxy-2-propanol (PGME) and/or propylene glycol monomethyl ether acetate (PGMEA) as a solvent, these compounds and/or resins preferably have a solubility of 10% by mass or more in the solvent. Herein, the solubility in PGME and/or PGMEA is defined as "mass of the resin/(mass of the resin+mass of the solvent)×100 (% by mass)". For example, when 10 g of the resin is dissolved in 90 g of PGMEA, the solubility of the resin in PGMEA is "10% by mass or more";

and when 10 g of the resin is not dissolved in 90 g of PGMEA, the solubility is "less than 10% by mass".

[Compound Represented by Formula (2)]

The compound of the present embodiment is preferably represented by the following formula (2). The compound of the present embodiment has the following structure and therefore has higher heat resistance and also higher solvent solubility.

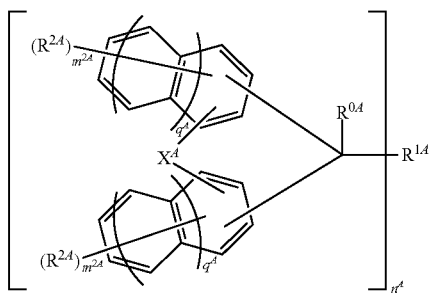

In the formula (2), $R^{0A}$ is as defined in the above $R^Y$ and is a linear, branched, or cyclic alkyl group of 1 to 30 carbon atoms or an aryl group of 6 to 30 carbon atoms.

$R^{1A}$ is an $n^A$-valent group of 1 to 60 carbon atoms or a single bond.

Each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, and may be the same or different between the same naphthalene rings or benzene rings. However, in the formula (2), at least one $R^{2A}$ is a hydroxy group or a group in which a hydrogen atom of a hydroxy group is replaced with an acid dissociation group.

$n^A$ is an integer of 1 to 4. Herein, in the formula (2), when $n^A$ is an integer of 2 or larger, $n^A$ structural formulas within the parentheses [ ] may be the same or different.

Each $X^A$ is independently an oxygen atom, a sulfur atom, or not a crosslink. Herein, $X^A$ is preferably an oxygen atom or a sulfur atom and more preferably an oxygen atom, because there is a tendency to exhibit high heat resistance. Preferably, $X^A$ is not a crosslink from the viewpoint of solubility.

Each $m^{2A}$ is independently an integer of 0 to 6. However, at least one $m^{2A}$ is an integer of 1 to 6.

Each $q^A$ is independently 0 or 1. A site represented by the naphthalene structure in the formula (2) represents a benzene structure when $q^A$ is 0, and a naphthalene structure when $q^A$ is 1.

The $n^A$-valent group refers to an alkyl group of 1 to 60 carbon atoms when $n^A$ is 1, an alkylene group of 1 to 30 carbon atoms when $n^A$ is 2, an alkanepropayl group of 2 to 60 carbon atoms when $n^A$ is 3, and an alkanetetrayl group of 3 to 60 carbon atoms when $n^A$ is 4. Examples of the $n^A$-valent group include groups having linear hydrocarbon groups, branched hydrocarbon groups, and alicyclic hydrocarbon groups. Herein, the alicyclic hydrocarbon groups also include bridged alicyclic hydrocarbon groups. Also, the $n^A$-valent group may have an aromatic group of 6 to 60 carbon atoms.

Also, the $n^A$-valent hydrocarbon group may have an alicyclic hydrocarbon group, a double bond, a heteroatom, or an aromatic group of 6 to 60 carbon atoms. Herein, the alicyclic hydrocarbon group also includes bridged alicyclic hydrocarbon groups.

Also, the $n^A$-valent hydrocarbon group may have an alicyclic hydrocarbon group, a double bond, a heteroatom, or an aromatic group of 6 to 30 carbon atoms. Herein, the alicyclic hydrocarbon group also includes bridged alicyclic hydrocarbon groups.

The compound represented by the above formula (2) has high heat resistance attributed to its rigid structure, in spite of its relatively low molecular weight, and can therefore be used even under high temperature baking conditions. Also, the compound represented by the above formula (2) has quaternary carbon in the molecule, which inhibits crystallinity, and is thus suitably used as a film forming composition for lithography that can be used in film production for lithography.

Furthermore, the compound represented by the above formula (2) has high solubility in a safe solvent and has good heat resistance and etching resistance. The resist forming composition for lithography of the present embodiment imparts a good shape to a resist pattern.

Moreover, the compound represented by the formula (2) has a relatively low molecular weight and a low viscosity and therefore facilitates enhancing film smoothness while uniformly and completely filling even the steps of an uneven substrate (particularly having fine space, hole pattern, etc.). As a result, the embedding and smoothing properties of an underlayer film forming composition for lithography containing this compound can be relatively advantageously enhanced. Moreover, the compound has a relatively high carbon concentration and is therefore also provided with high etching resistance.

The compound represented by the formula (2) has high refractive index and is prevented from being stained by heat treatment in a wide range from a low temperature to a high temperature. Therefore, the compound represented by the formula (2) is also useful as various optical component forming compositions. The optical component is used in the form of a film or a sheet and additionally, is also useful as a plastic lens (a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, or a photosensitive optical waveguide.

The compound represented by the above formula (2) is preferably a compound represented by the following formula (2-1) from the viewpoint of easy crosslinking and solubility in an organic solvent.

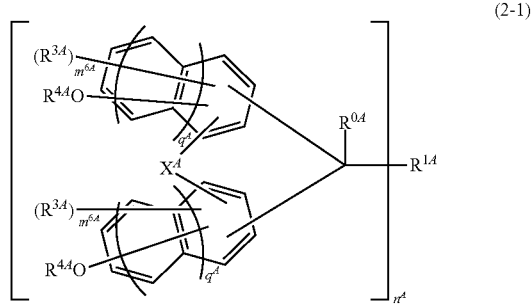

In the formula (2-1), $R^{0A}$, $R^{1A}$, $n^A$, $q^A$, and $X^A$ are as defined in the description of the above formula (2).

Each $R^{3A}$ is independently a halogen atom, a linear, branched, or cyclic alkyl group of 1 to 30 carbon atoms, an aryl group of 6 to 30 carbon atoms, or an alkenyl group of 2 to 30 carbon atoms, and may be the same or different between the same naphthalene rings or benzene rings.

Each $R^{4A}$ is independently a hydrogen atom or an acid dissociation group.

Each $m^{6A}$ is independently an integer of 0 to 5.

When the compound represented by the above formula (2-1) is used as a film forming composition for lithography for alkaline development positive type resists or for organic development negative type resists, at least one $R^{4A}$ is an acid dissociation group. On the other hand, when the compound represented by the formula (2-1) is used as a film forming composition for lithography for alkaline development negative type resists, a film forming composition for lithography for underlayer films, or an optical component forming composition, at least one $R^{4A}$ is a hydrogen atom.

A compound represented by the following formula (2a) is also preferable from the viewpoint of the supply of raw materials.

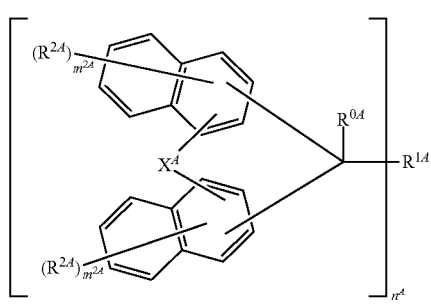

(2a)

In the above formula (2a), $X^A$, $R^{0A}$ to $R^{2A}$, $m^{2A}$, and $n^A$ are as defined in the description of the above formula (2).

A compound represented by the following formula (2b) is more preferable from the viewpoint of solubility in an organic solvent.

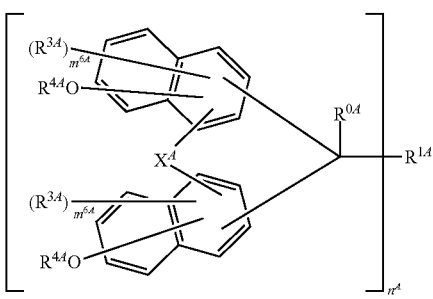

(2b)

In the above formula (2b), $X^A$, $R^{0A}$, $R^{1A}$, $R^{3A}$, $R^{4A}$, $m^{6A}$, and $n^A$ are as defined in the description of the above formula (2-1).

A compound represented by the following formula (2c) is still more preferable from the viewpoint of solubility in an organic solvent.

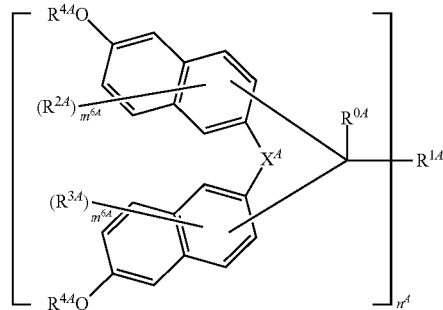

(2c)

In the above formula (2c), $X^A$, $R^{0A}$, $R^{1A}$, $R^{3A}$, $R^{4A}$, $m^{6A}$, and $n^A$ are as defined in the description of the above formula (2-1).

The compound represented by the above formula (2) is particularly preferably a compound represented by any of the following formulas (2d-1) and (2d-2) from the viewpoint of further solubility in an organic solvent.

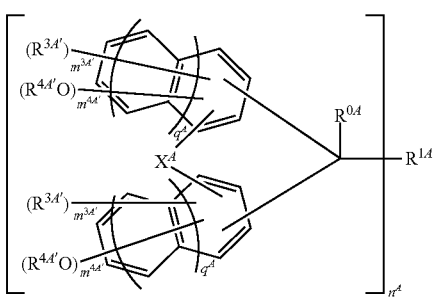

(2d-1)

In the above formula (2d-1), $R^{0A}$, $R^{1A}$, $n^A$, $q^A$, and $X^A$ are as defined above. Each $R^{3A'}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, or a halogen atom, and $R^{4A'}$ is a hydrogen atom or an acid dissociation group. $m^{3A'}$ is an integer of 0 to 6. $m^{4A'}$ is an integer of 1 to 7. $m^{3A'}+m^{4A'}$ is each independently an integer of 1 to 7.

Examples of $R^{0A}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a phenyl group, a naphthyl group, an anthracene group, a pyrenyl group, a biphenyl group, and a heptacene group.

Examples of $R^{3A'}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a pyrenyl group, a biphenyl group, a heptacene group, a vinyl group, an allyl group, a triacontenyl group, a methoxy group, an ethoxy group, a triacontyloxy group, a fluorine atom, a chlorine atom, a bromine atom, and an iodine atom.

$R^{0A}$ and $R^{3A'}$ listed above each include isomers. For example, a butyl group includes a n-butyl group, an isobutyl group, a sec-butyl group, and a tert-butyl group.

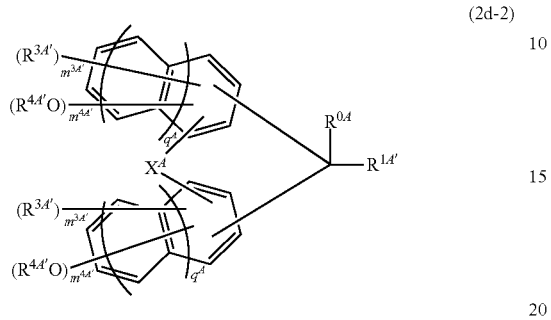

(2d-2)

In the above formula (2d-2), $R^{0A}$, $R^{3A'}$, $R^{4A'}$, $m^{3A'}$, $m^{4A'}$, $q^A$, and $X^A$ are as defined above, and $R^{1A'}$ is a group of 1 to 60 carbon atoms.

The compound represented by the above formula (2) preferably has any of the following structures from the viewpoint of the availability of raw materials.

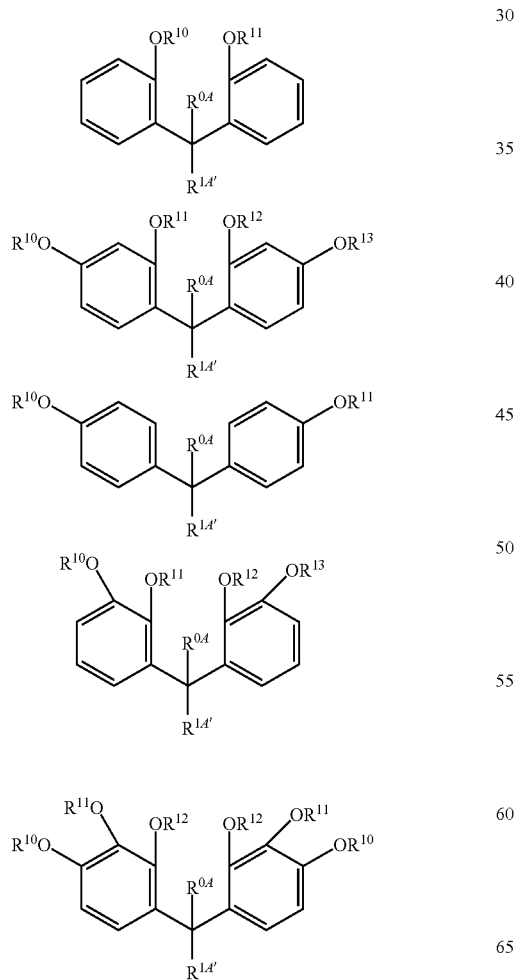

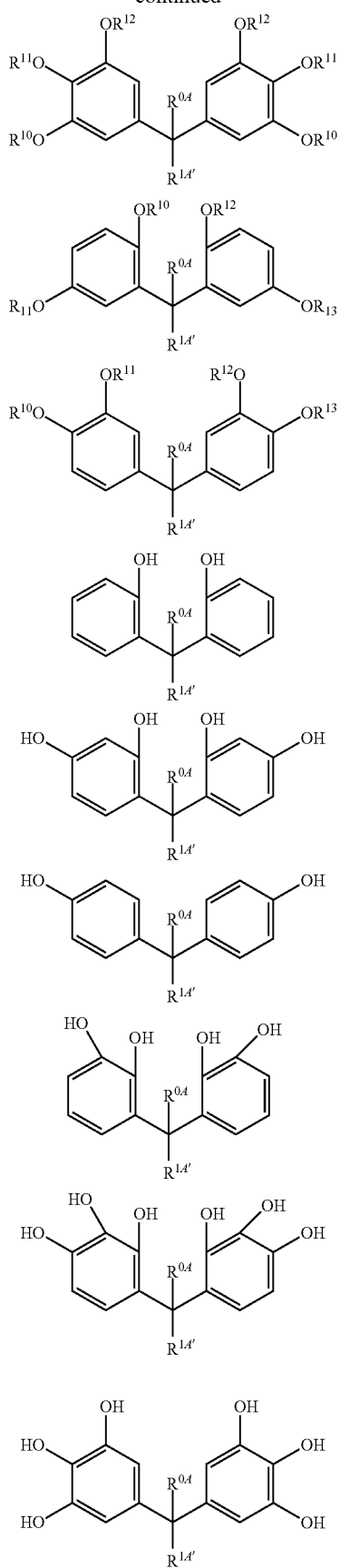

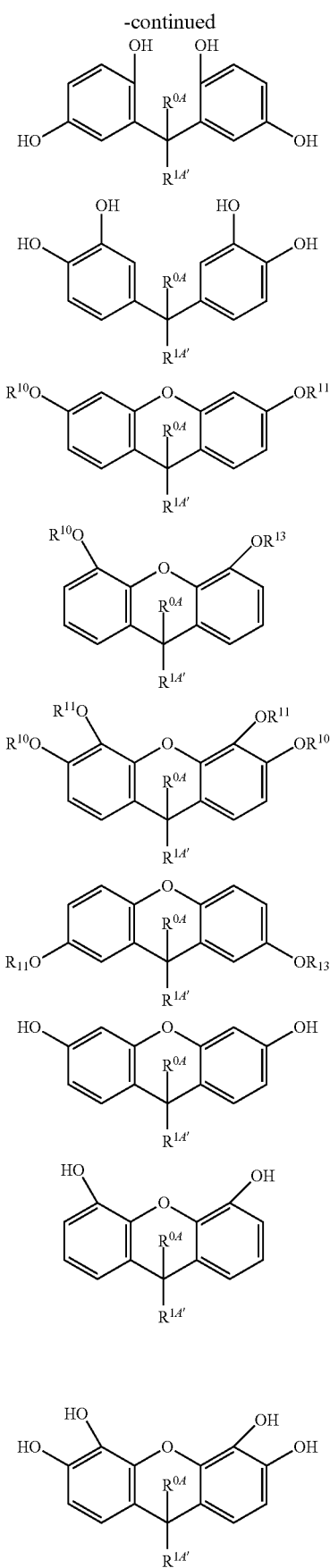
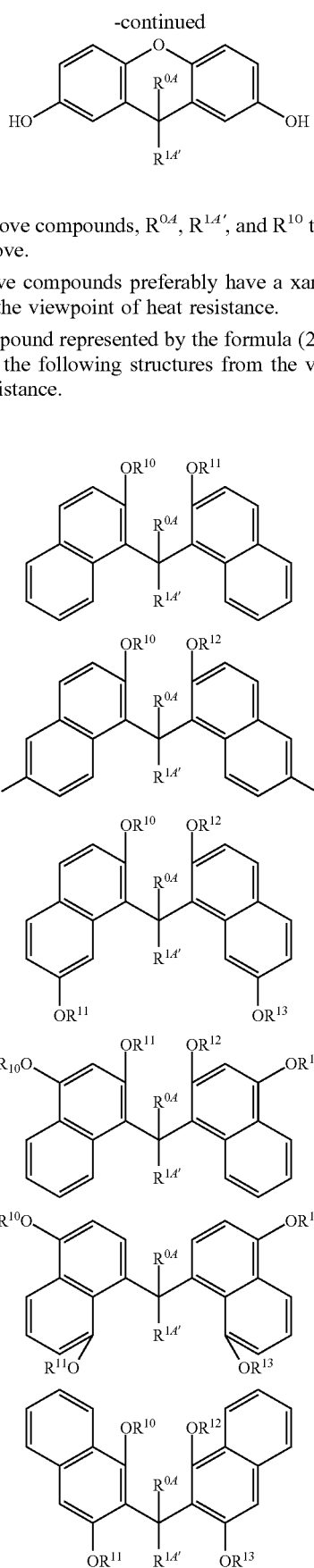
In the above compounds, $R^{0A}$, $R^{1A'}$, and $R^{10}$ to $R^{13}$ are as defined above.
The above compounds preferably have a xanthene skeleton from the viewpoint of heat resistance.
The compound represented by the formula (2) preferably has any of the following structures from the viewpoint of etching resistance.

75
-continued
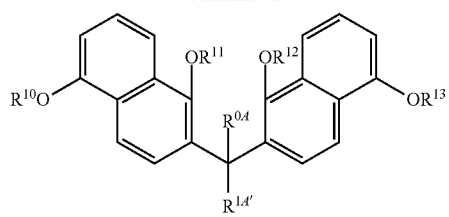
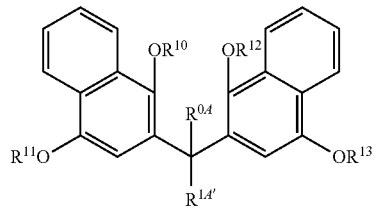
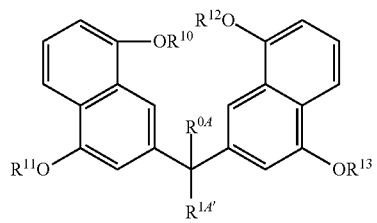
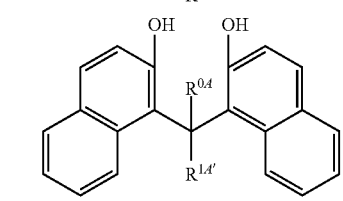
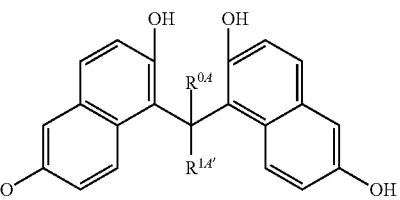
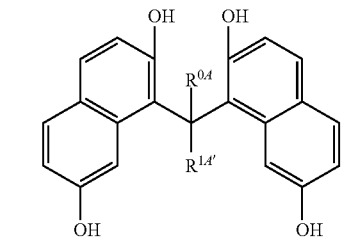
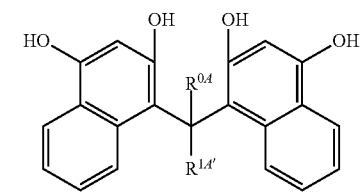
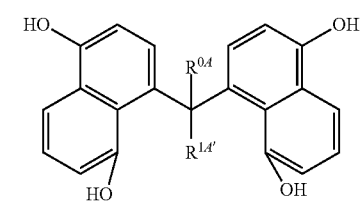
76
-continued
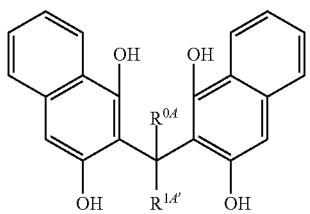
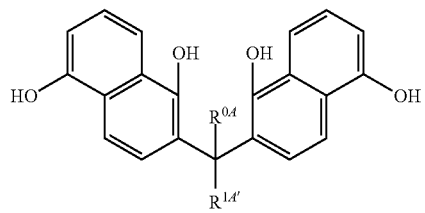
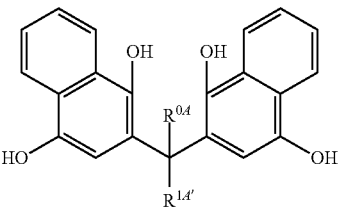
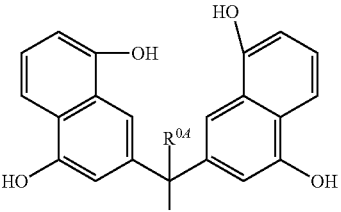
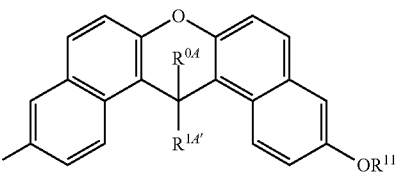
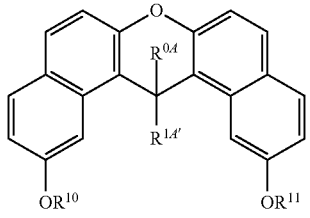
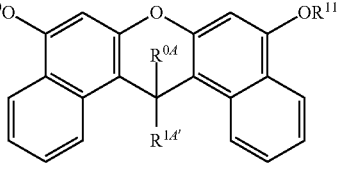
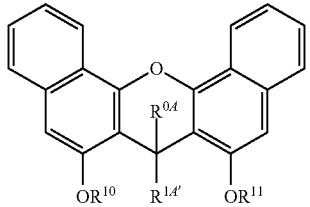

-continued
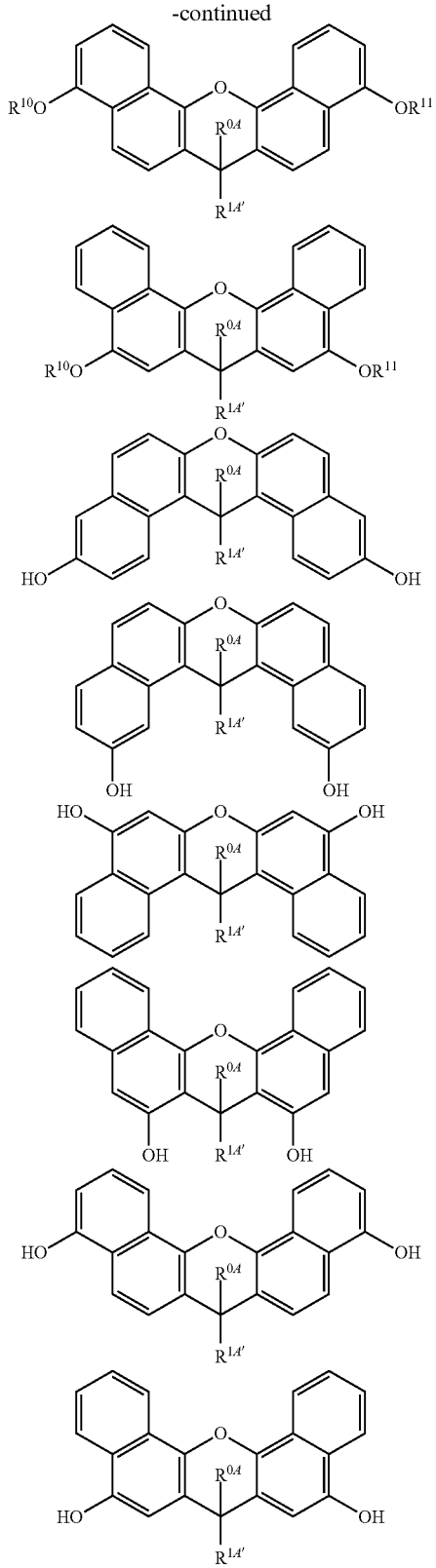
In the above compounds, $R^{OA}$, $R^{1A'}$, and $R^{10}$ to $R^{13}$ are as defined above.
The above compounds preferably have a dibenzoxanthene skeleton from the viewpoint of heat resistance.
Examples of the compound represented by the formula (2) include compounds having the following structures.
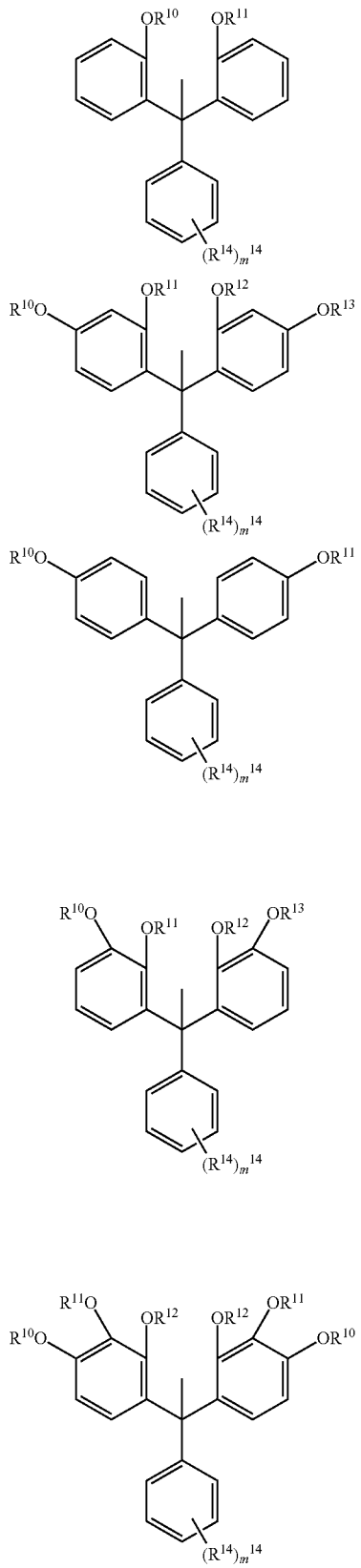

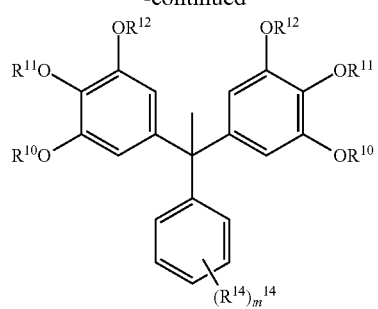
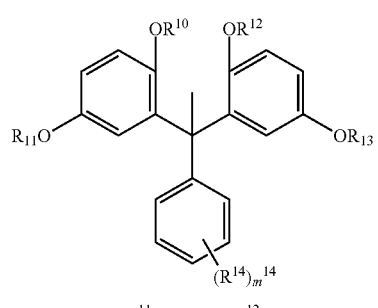
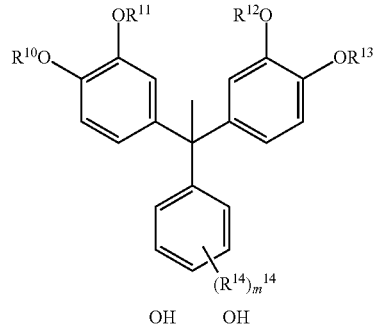
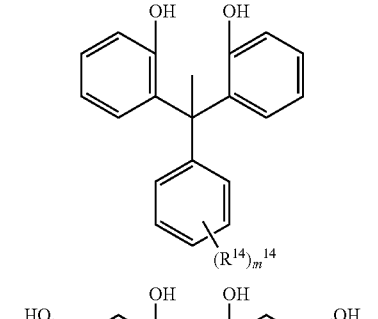
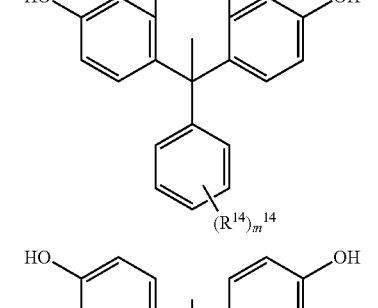
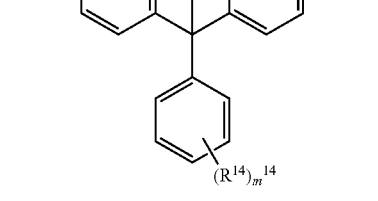
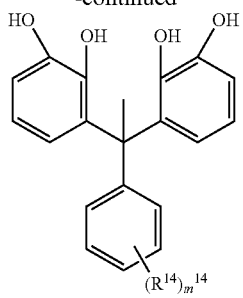
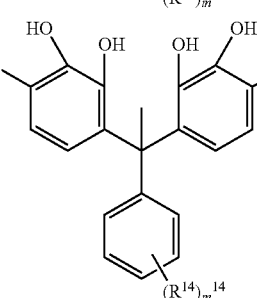
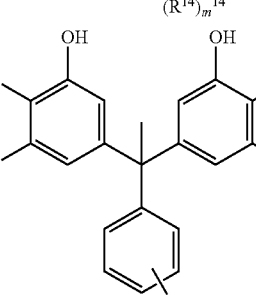
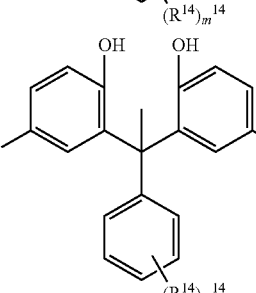
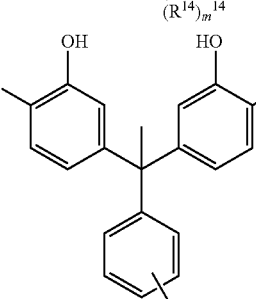
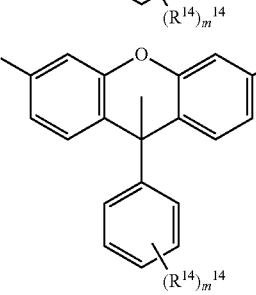

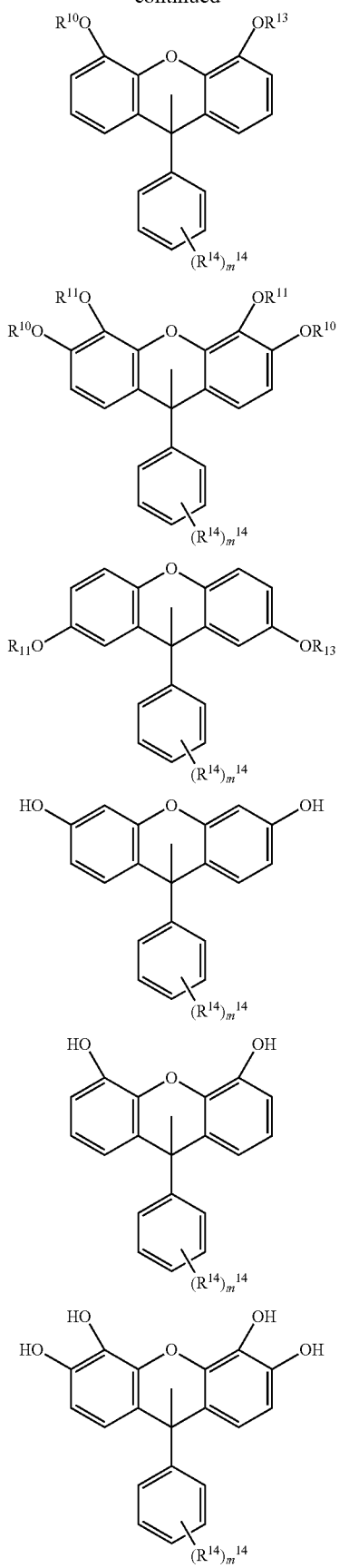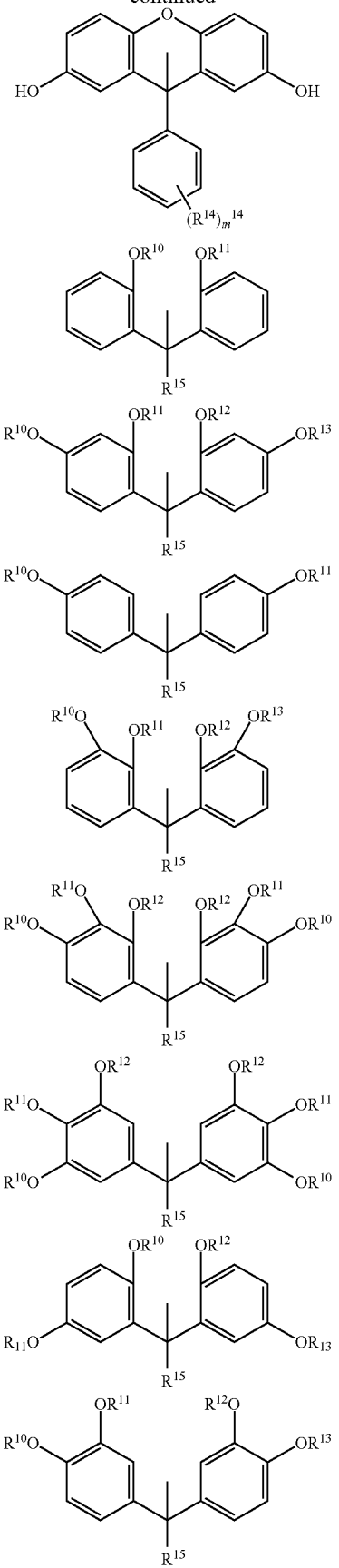

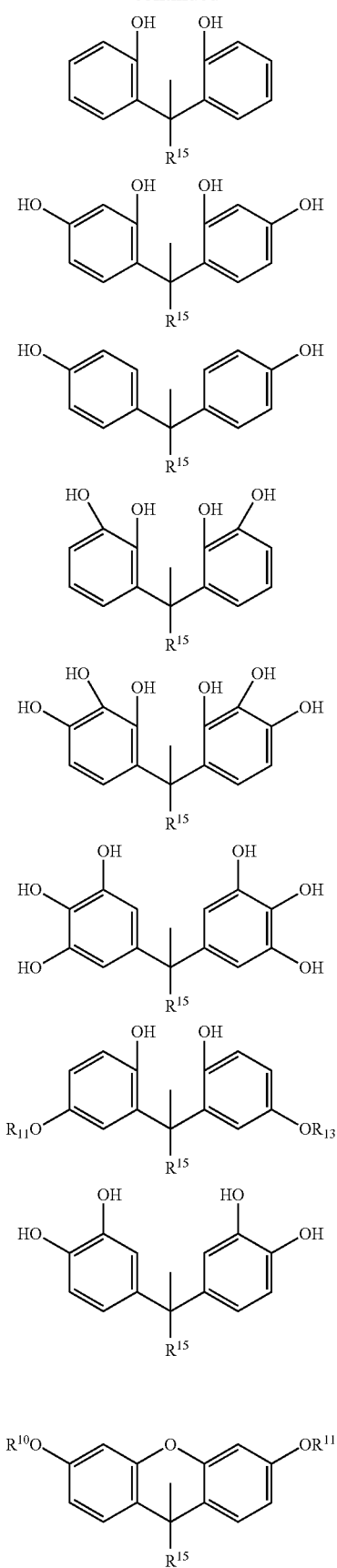
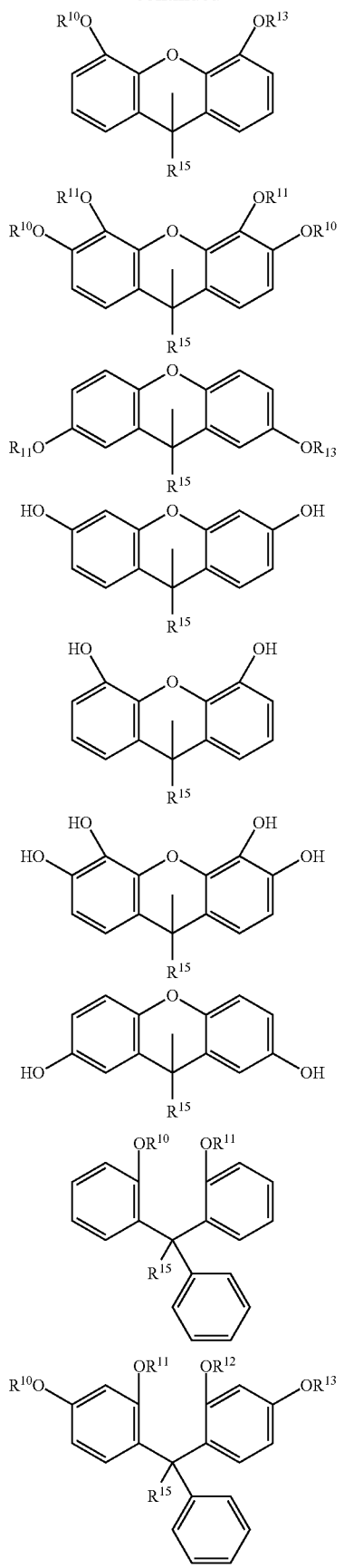

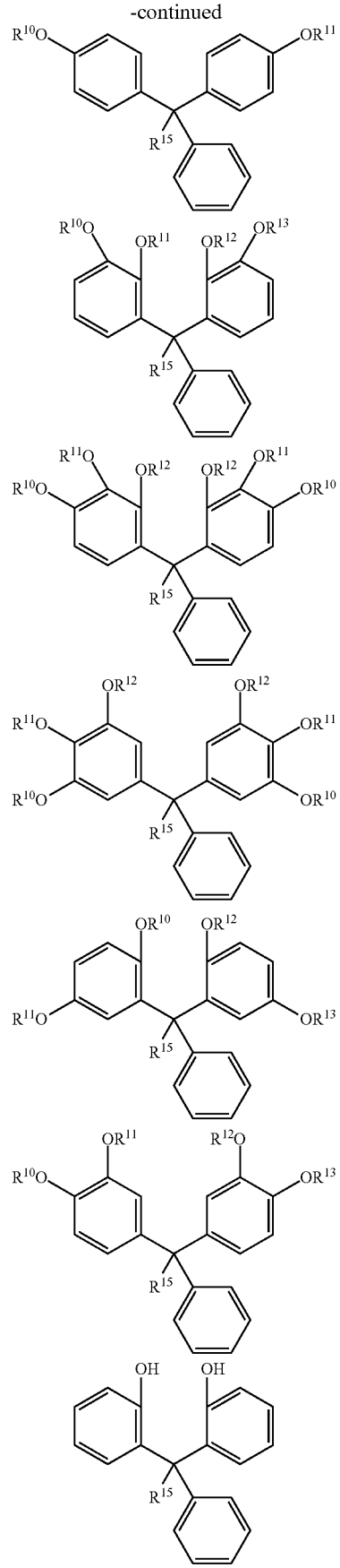

87
-continued
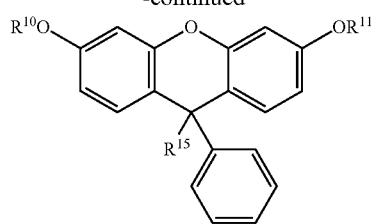
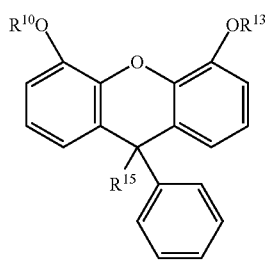
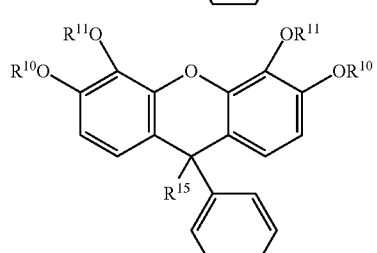
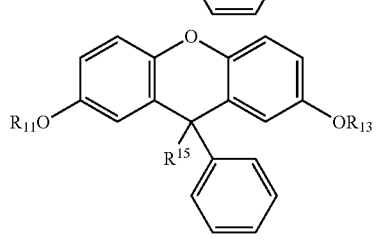
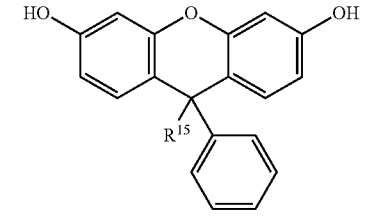
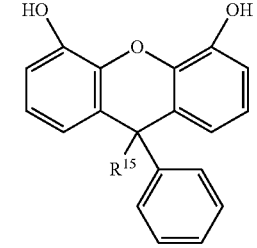
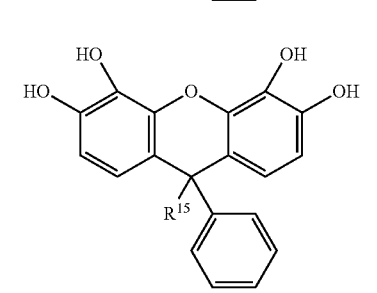
88
-continued
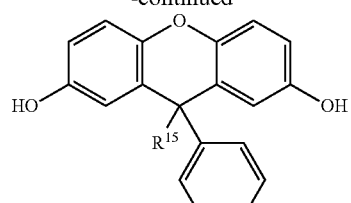
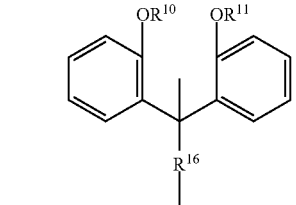
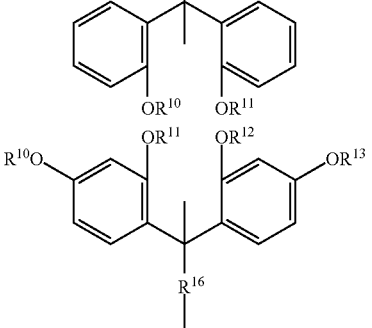
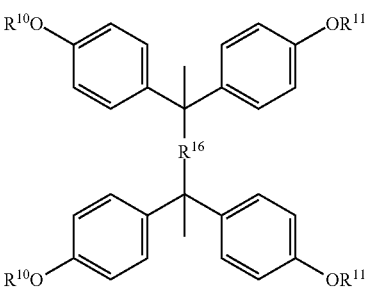
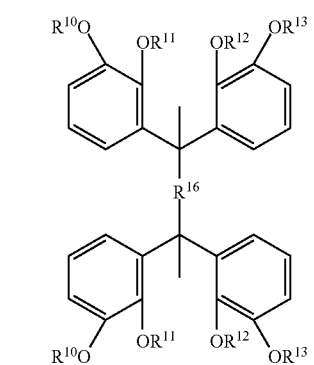

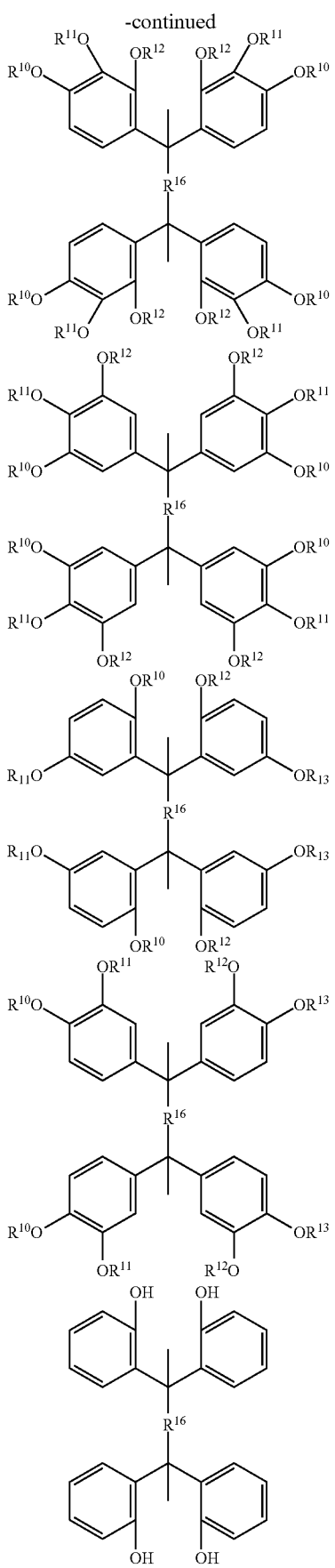
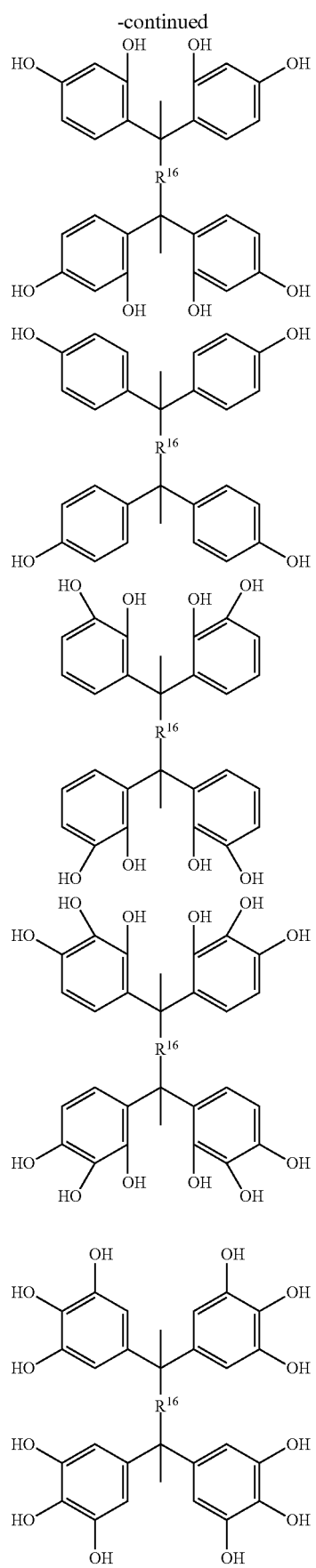

-continued
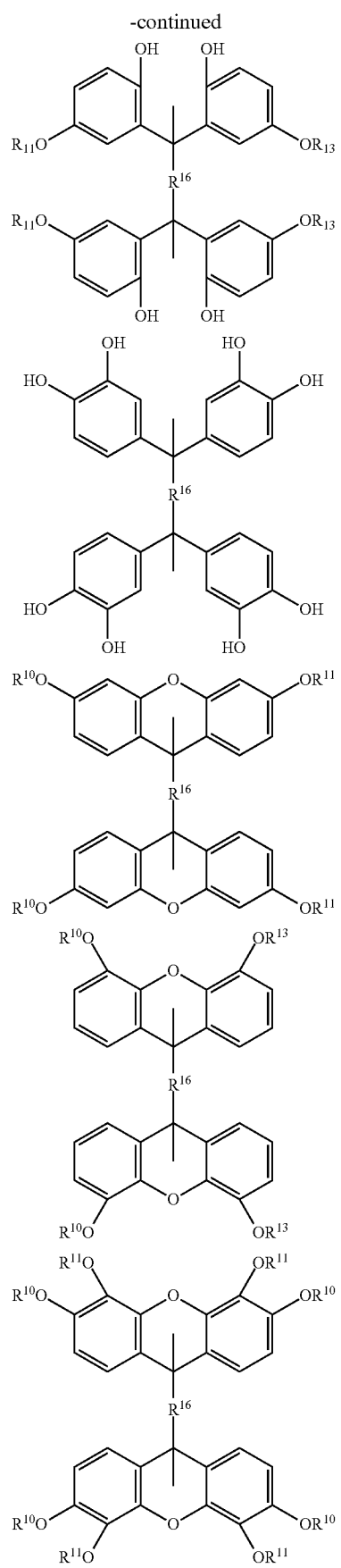
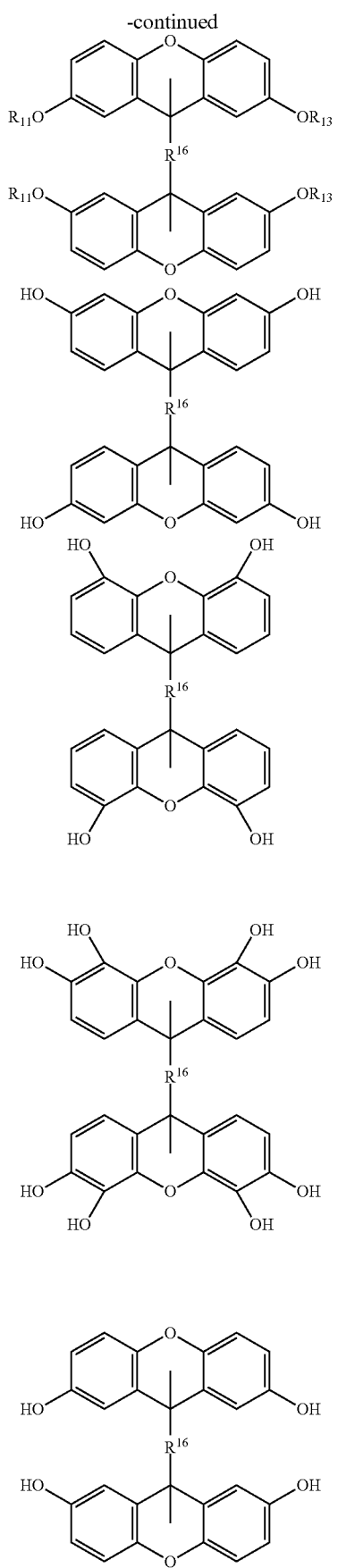

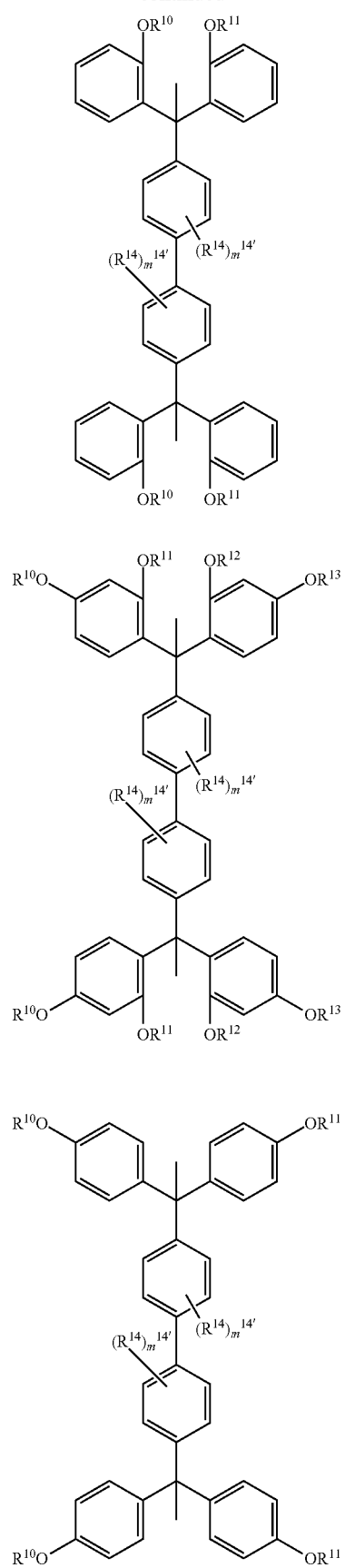
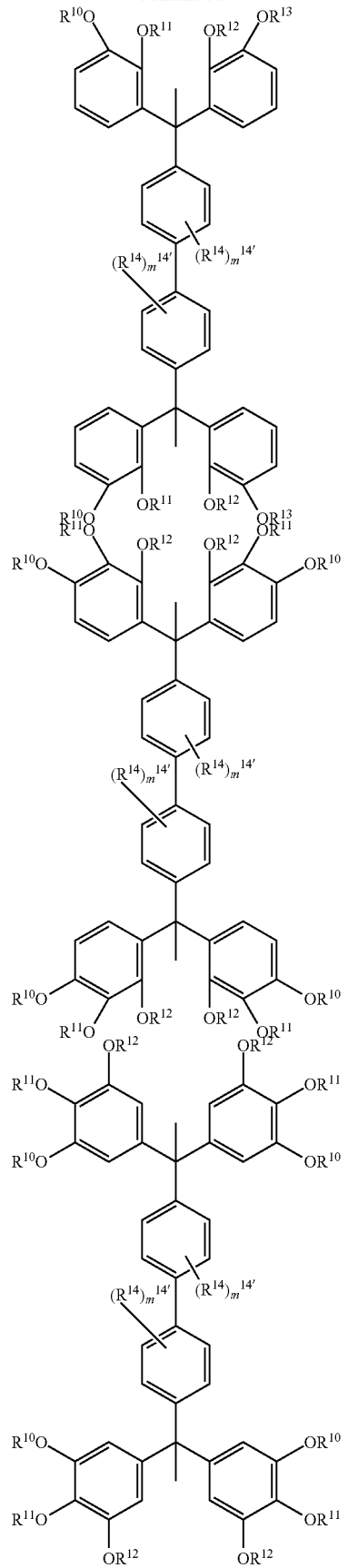

95
-continued
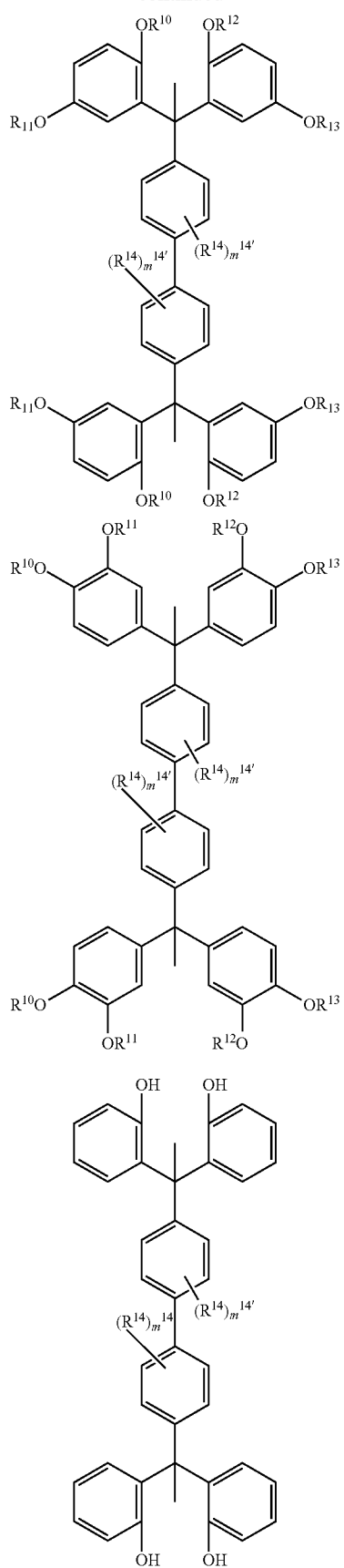
96
-continued
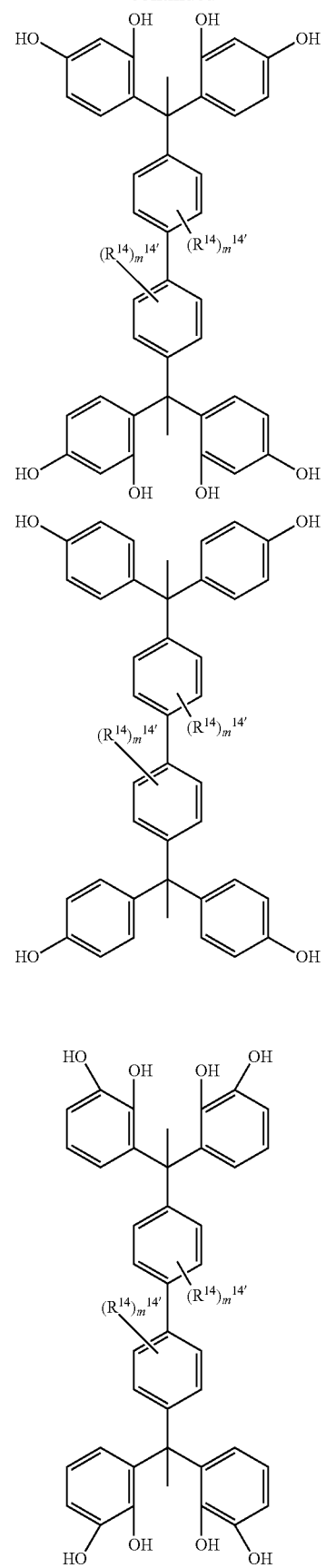

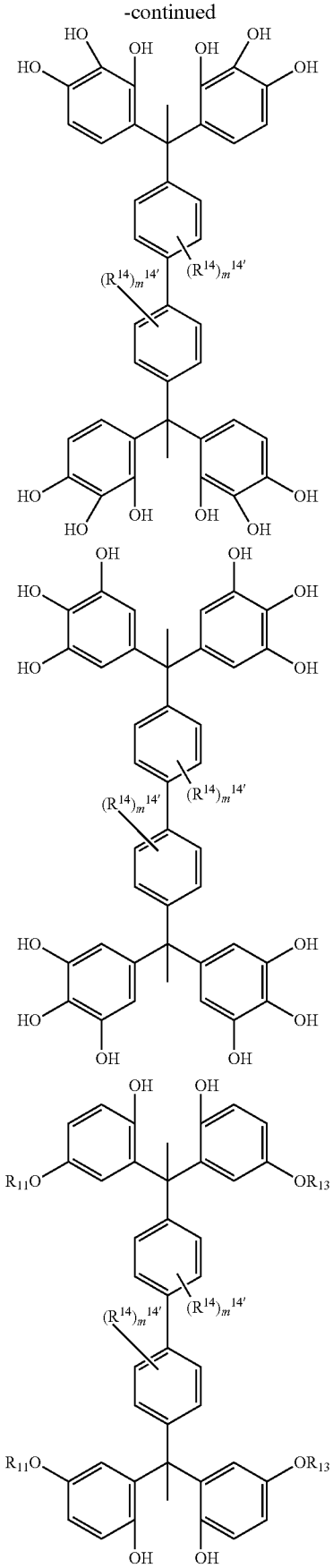
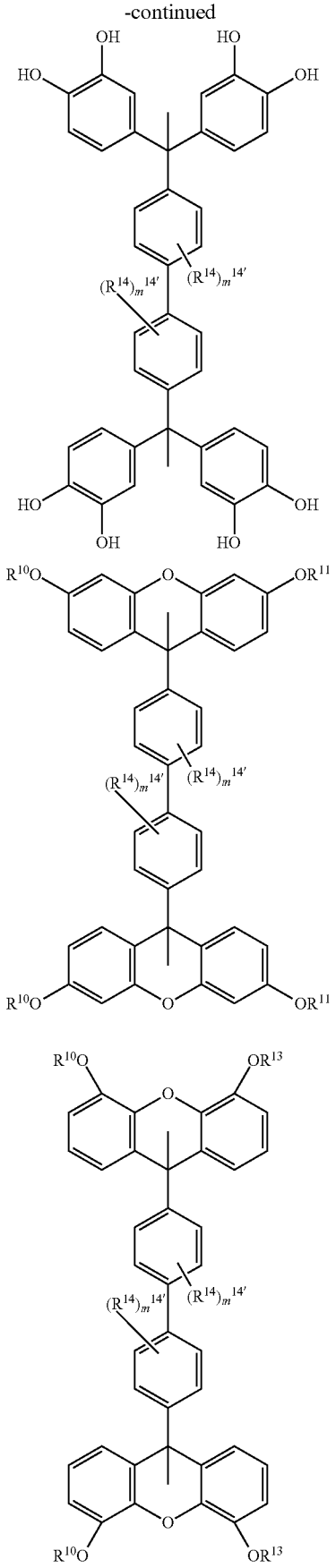

99
-continued
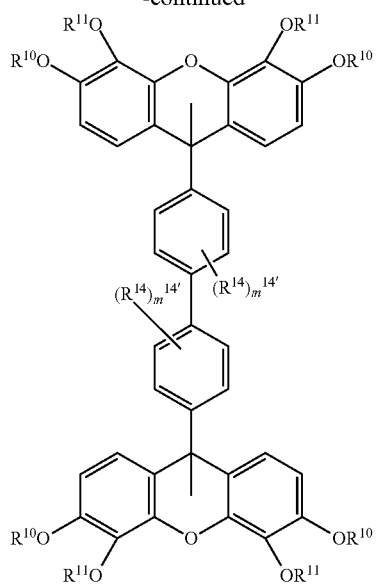
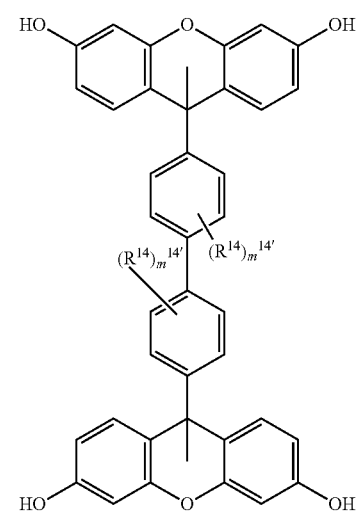
100
-continued
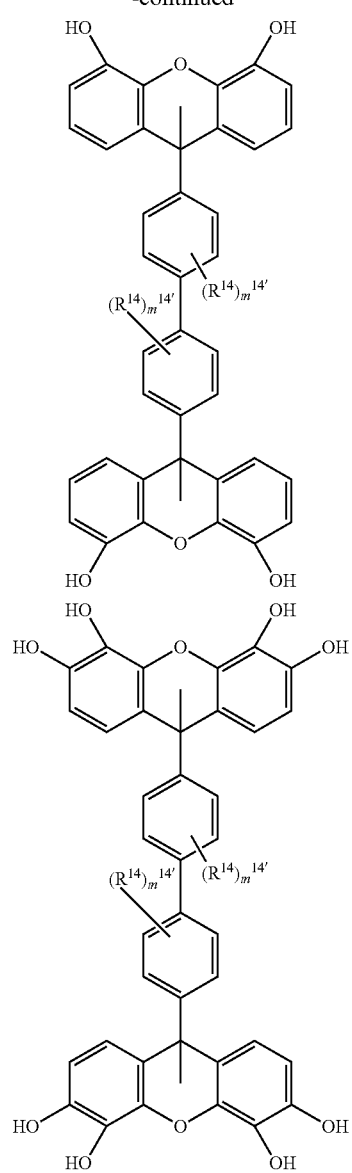
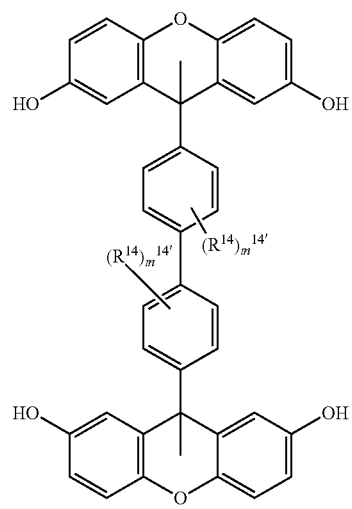

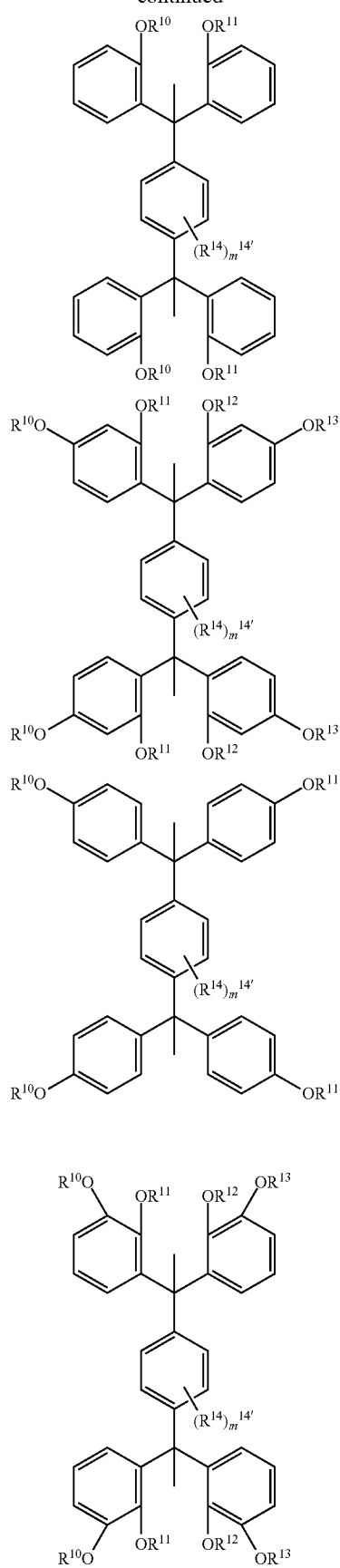
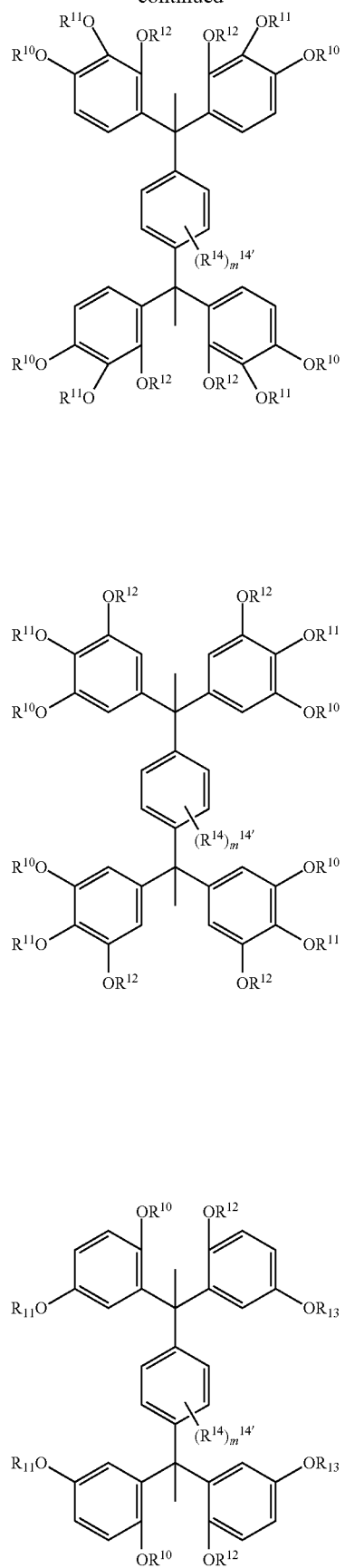

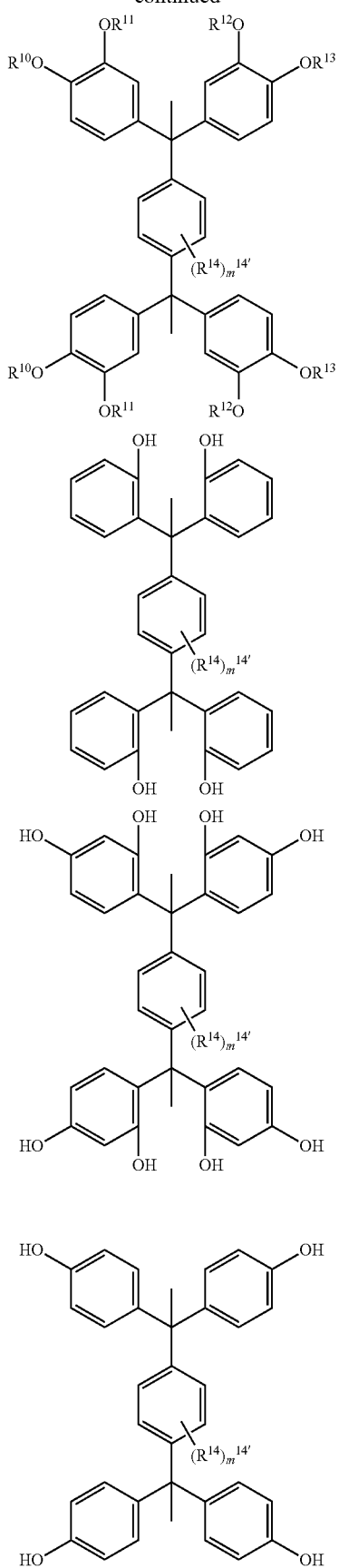
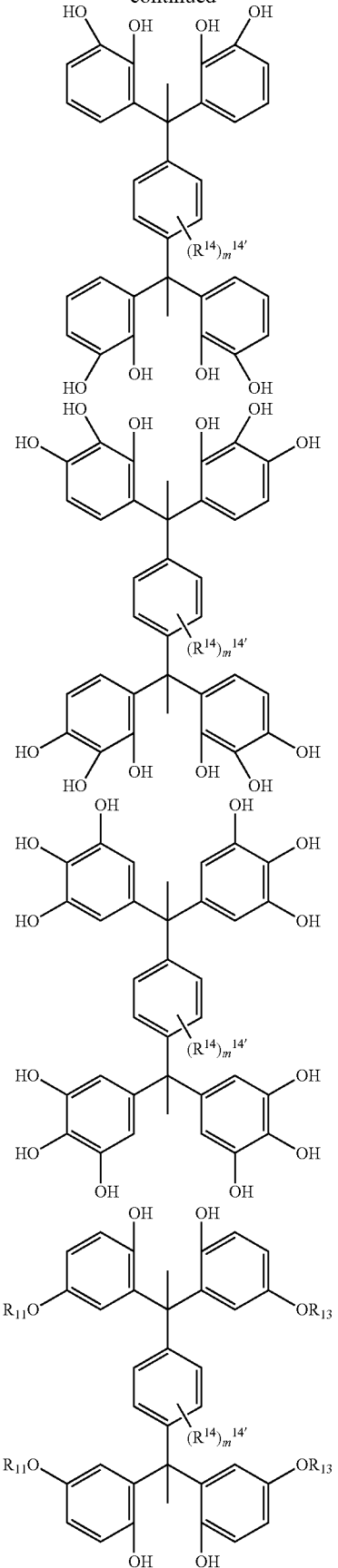

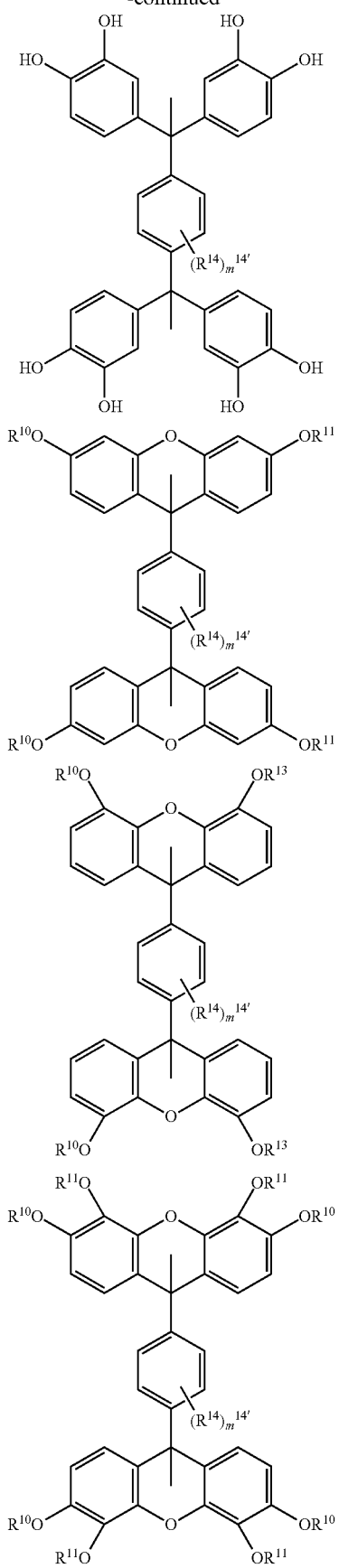
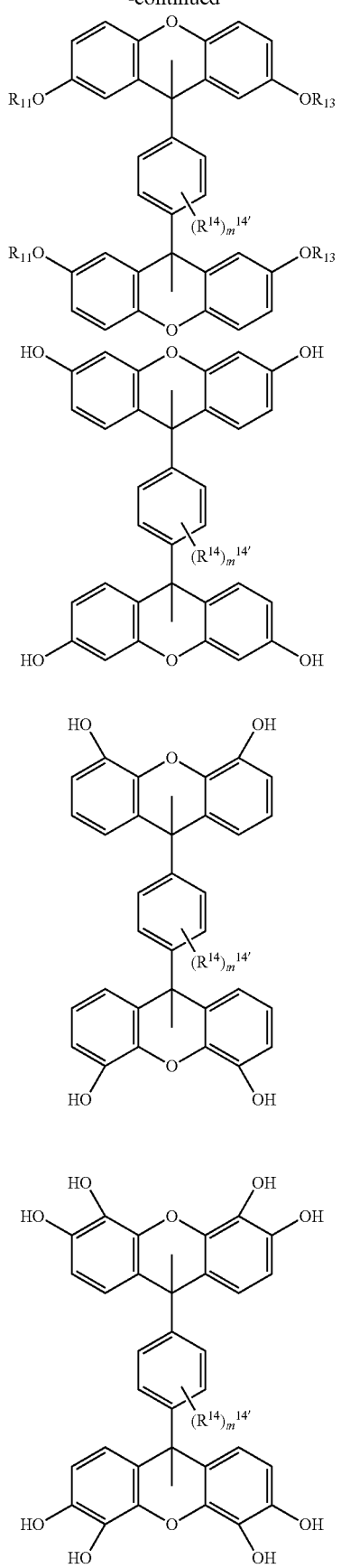

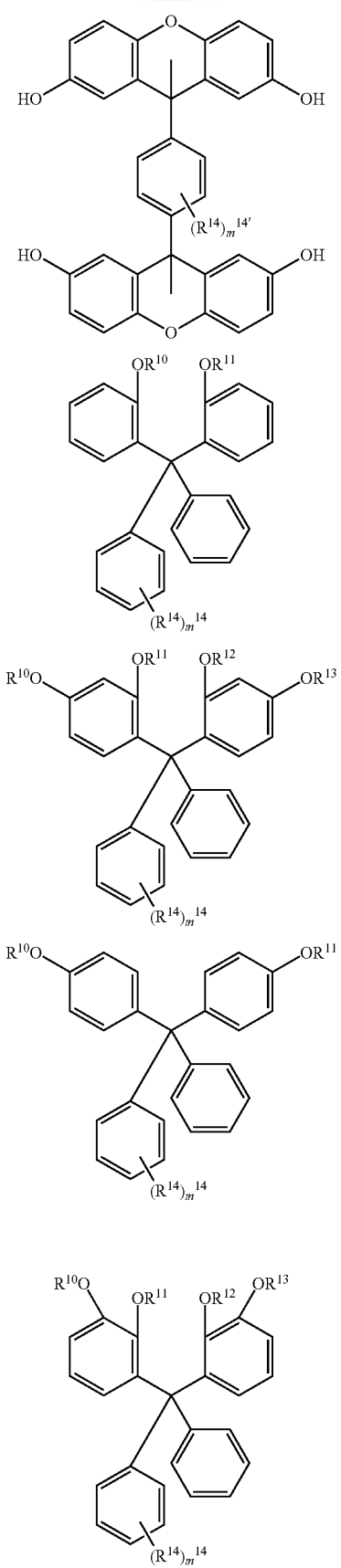
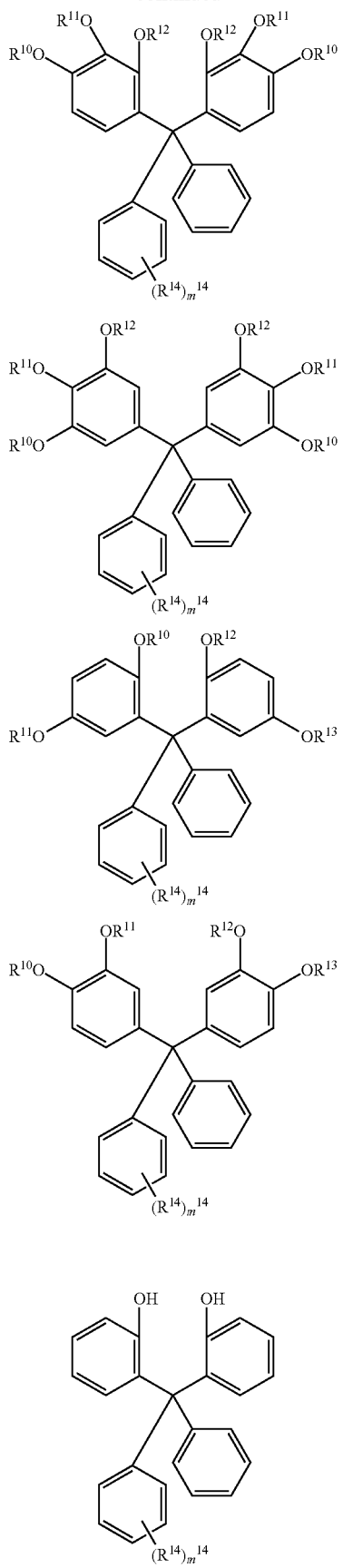

-continued
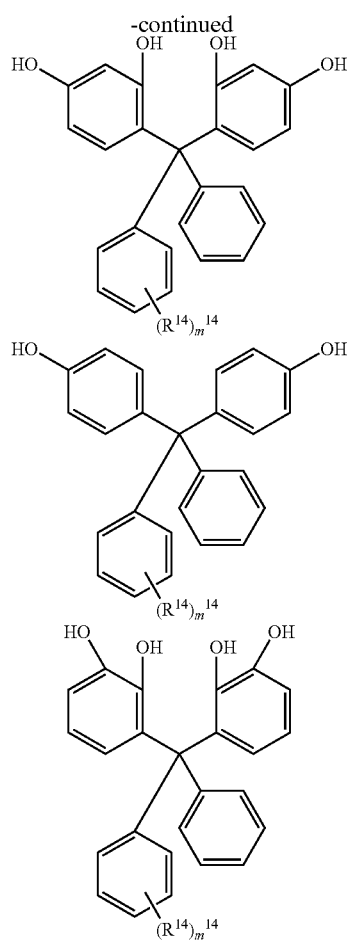
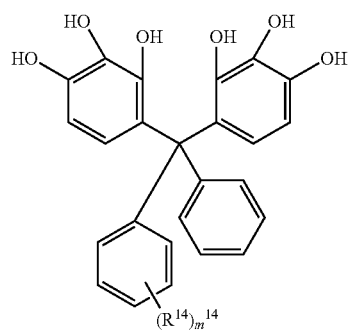
-continued
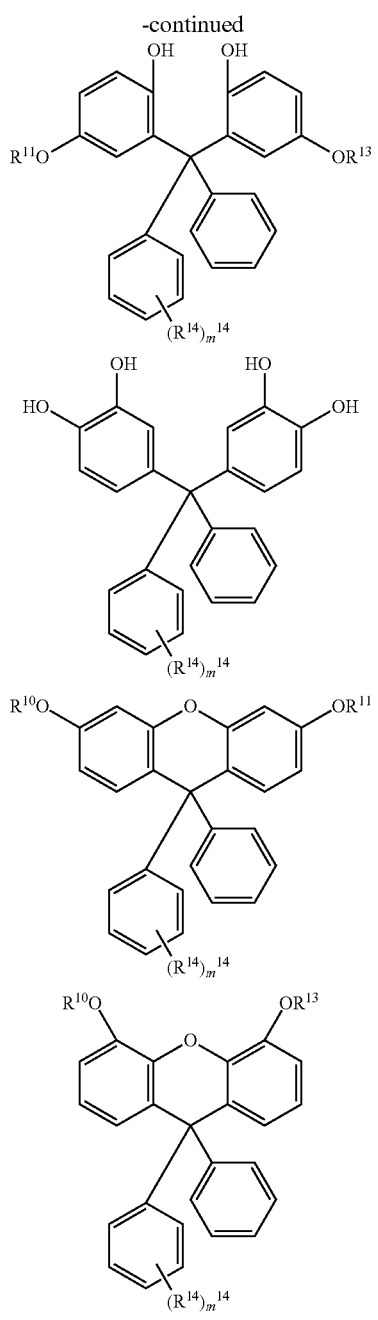
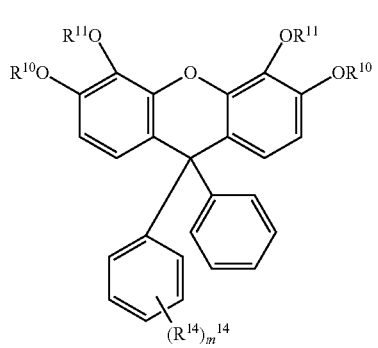

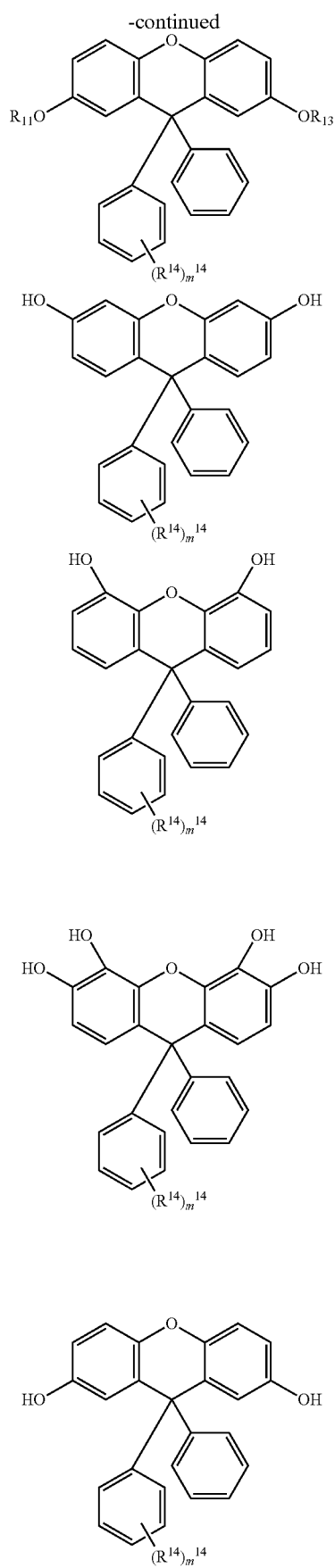
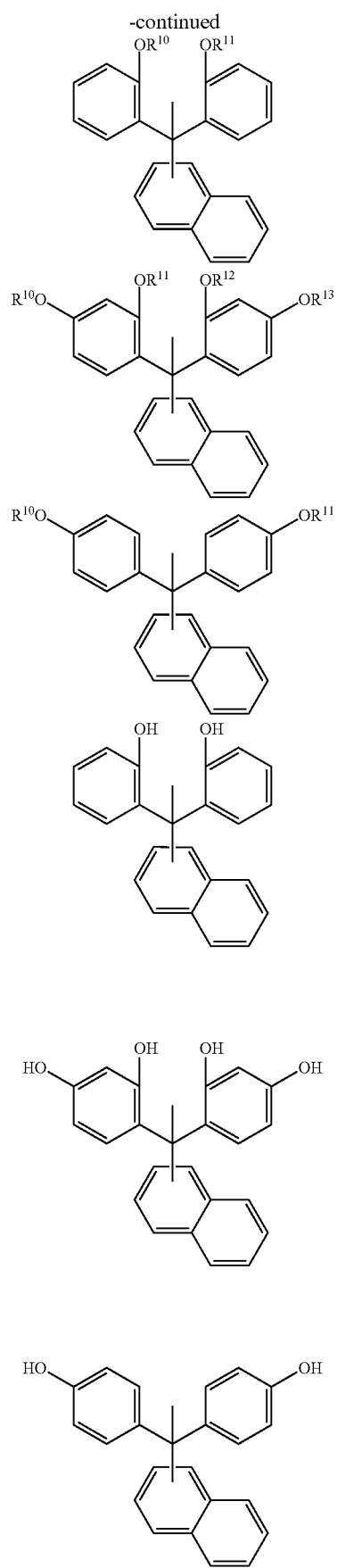

113
-continued
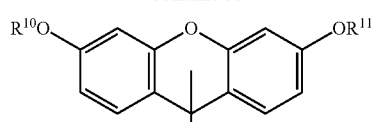
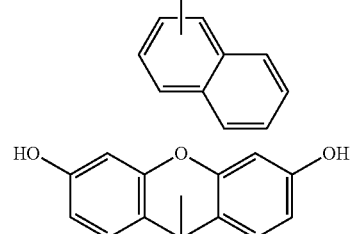
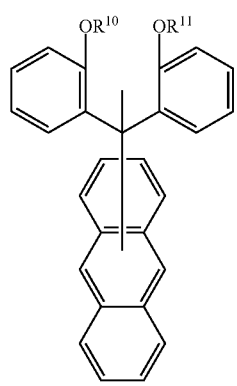
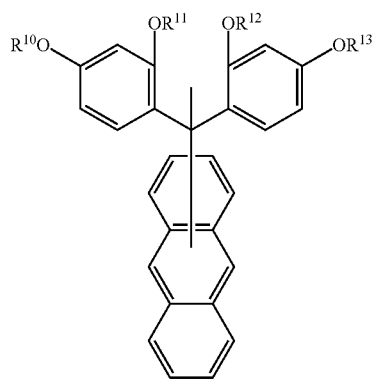
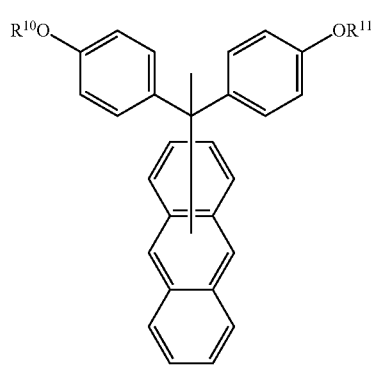
114
-continued
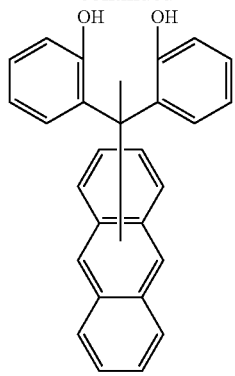
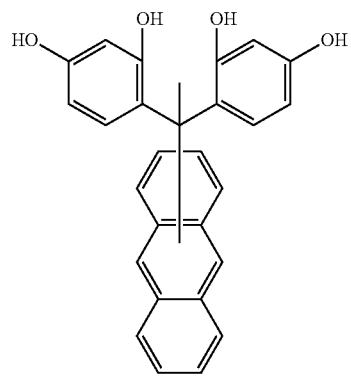
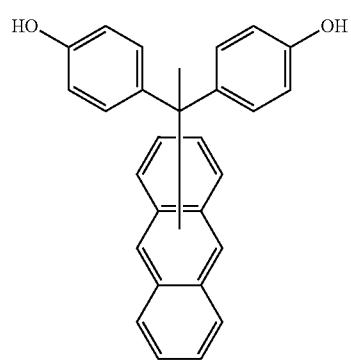
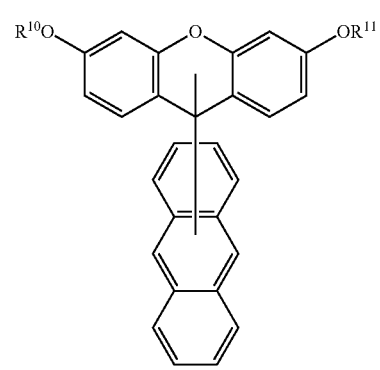

115
-continued
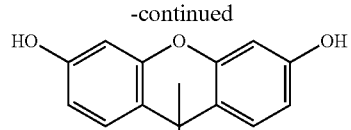
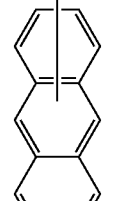
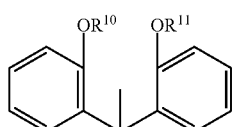
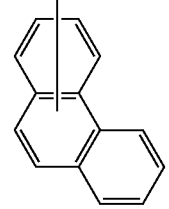
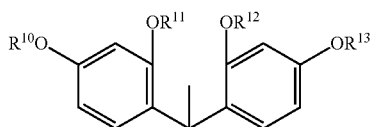
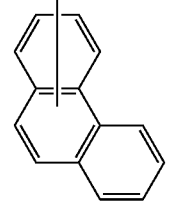
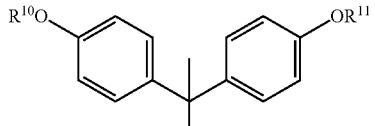
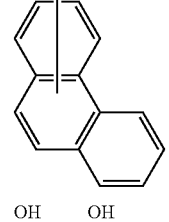
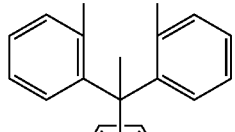
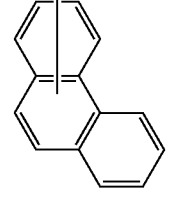
116
-continued
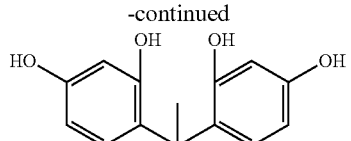
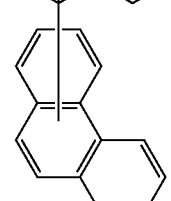
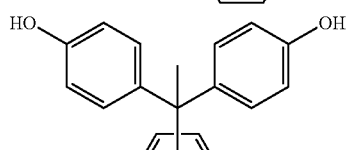
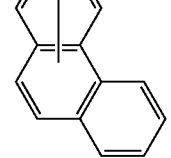
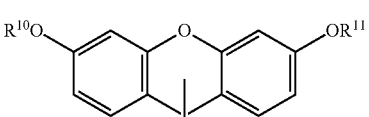
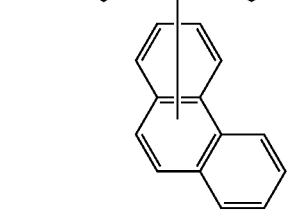
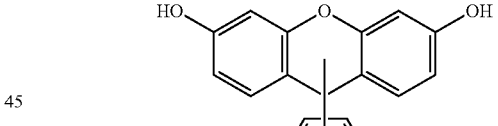
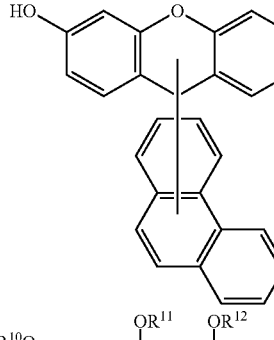
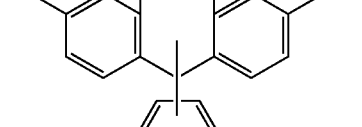
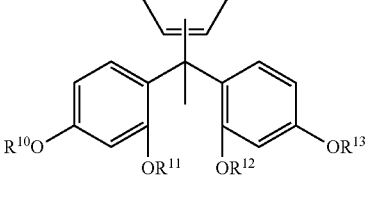

-continued
117
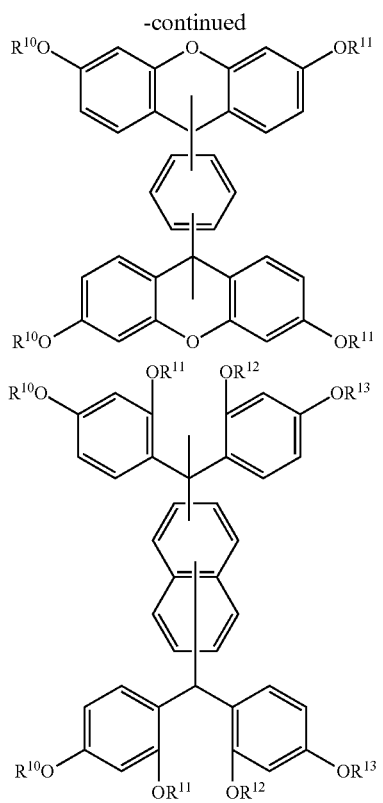
118
-continued
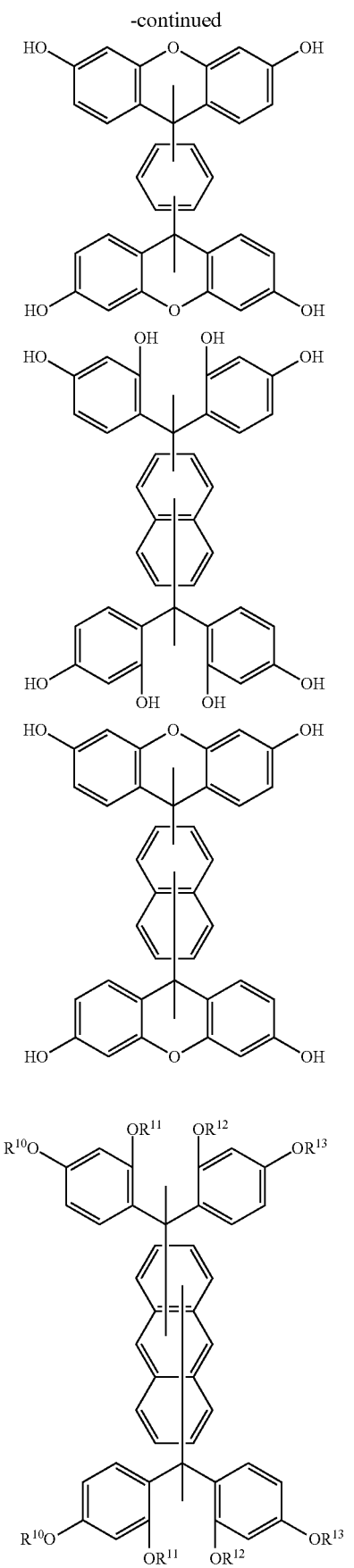

-continued
119
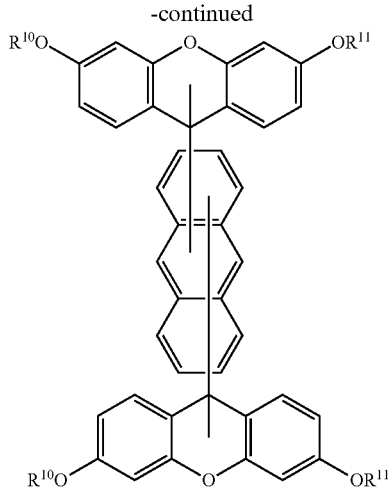
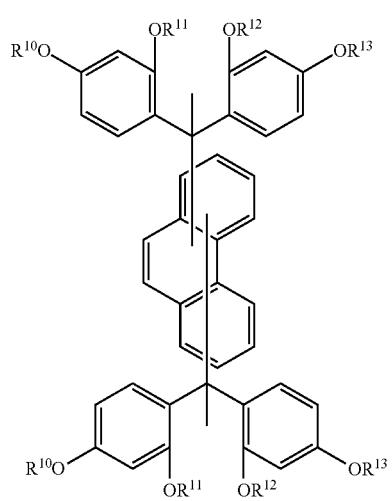
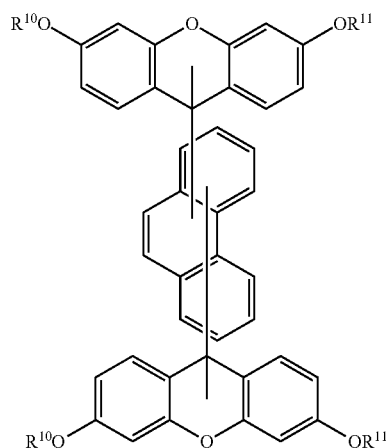
-continued
120
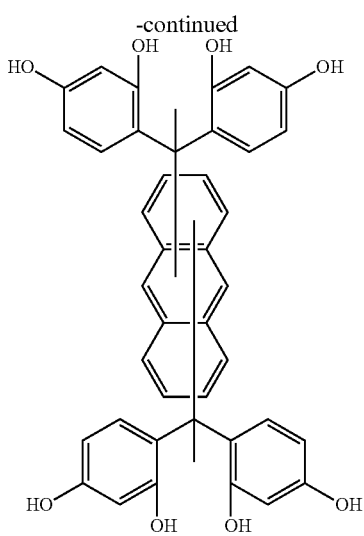
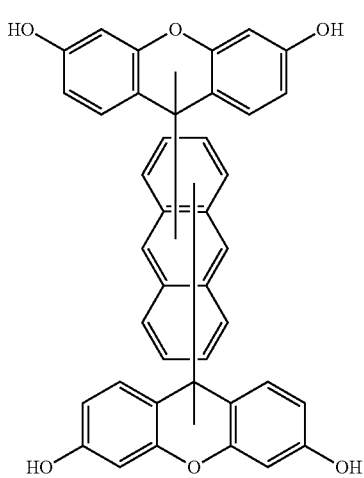
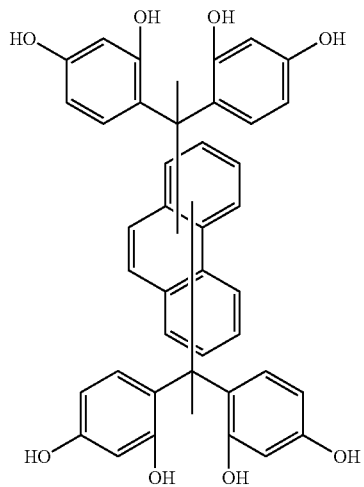

121
-continued
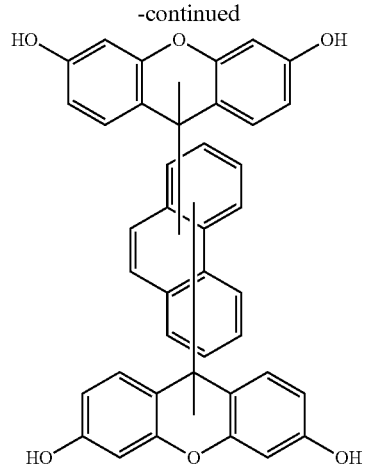
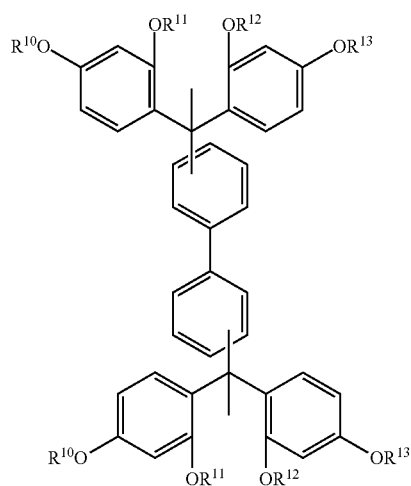
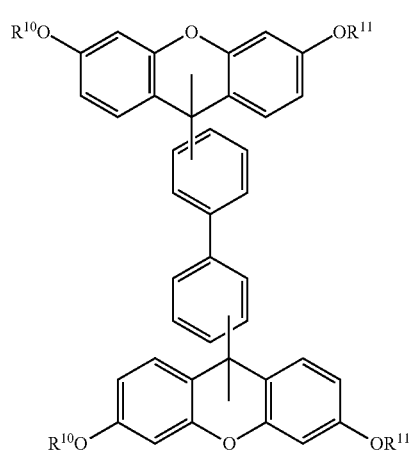
122
-continued
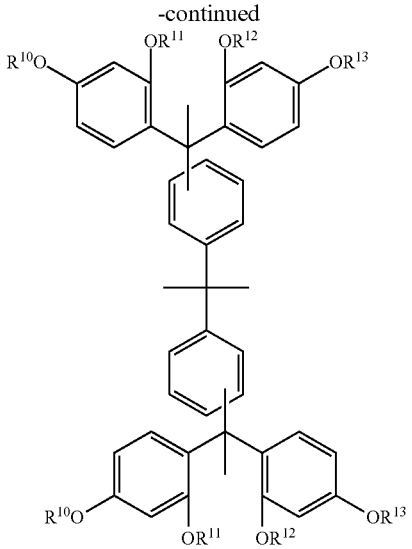
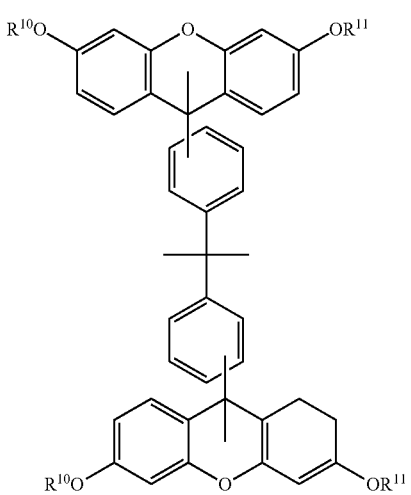
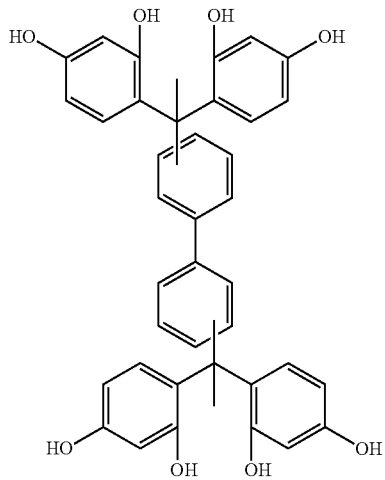

-continued
123
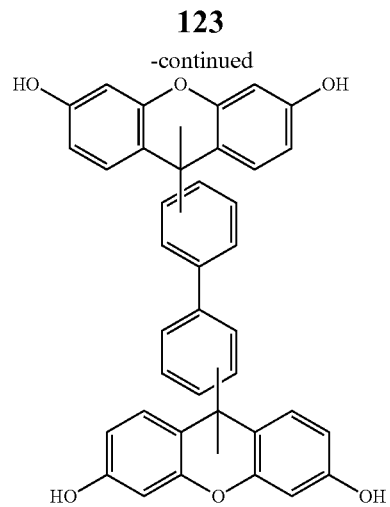
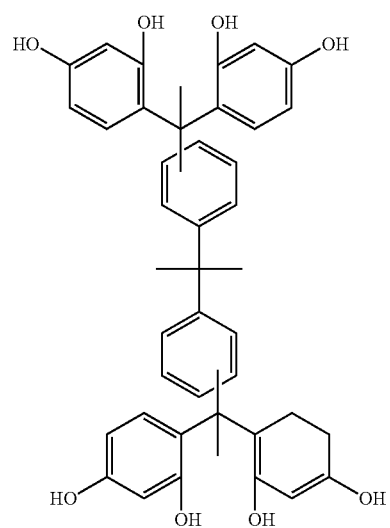
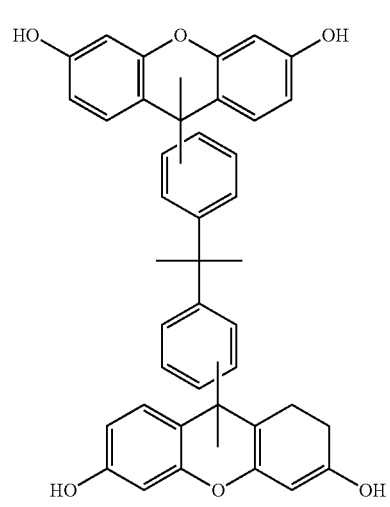
124
-continued
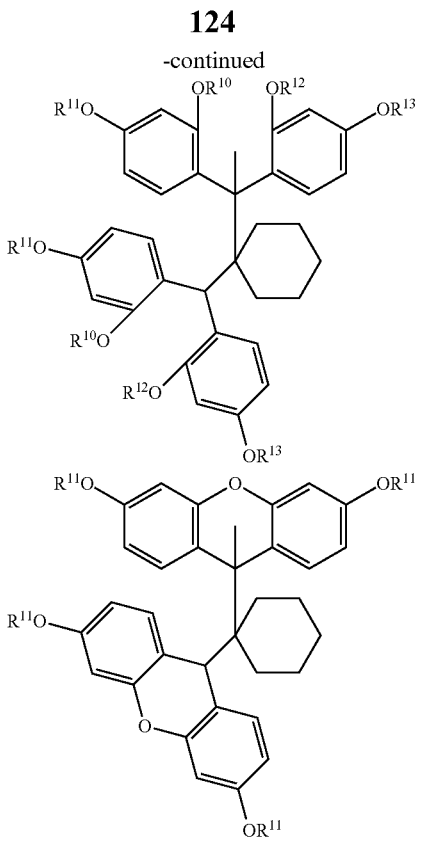
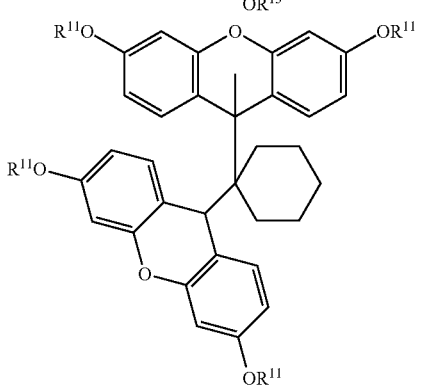
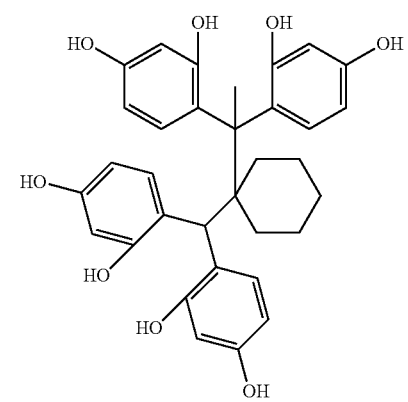
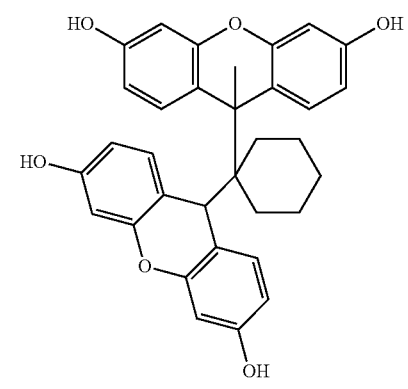

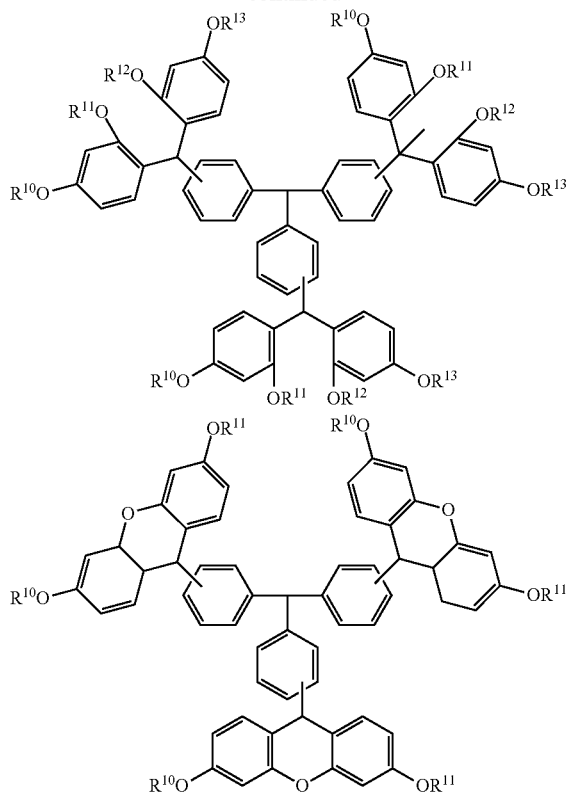
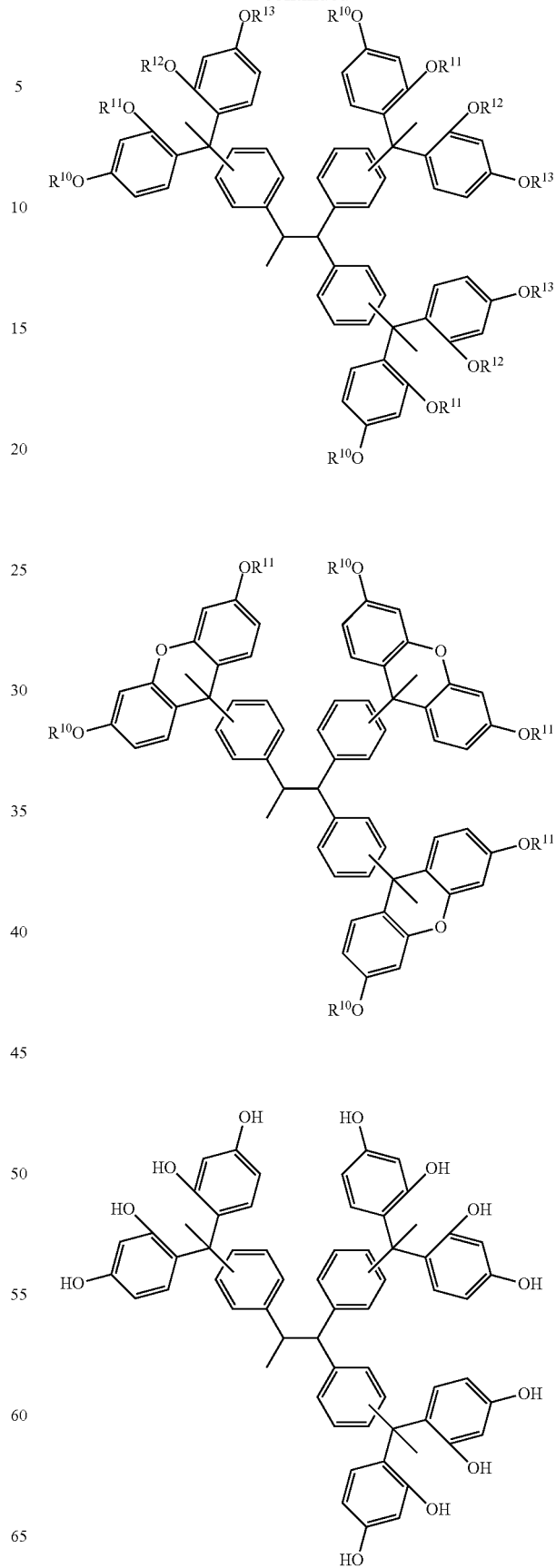

127
-continued
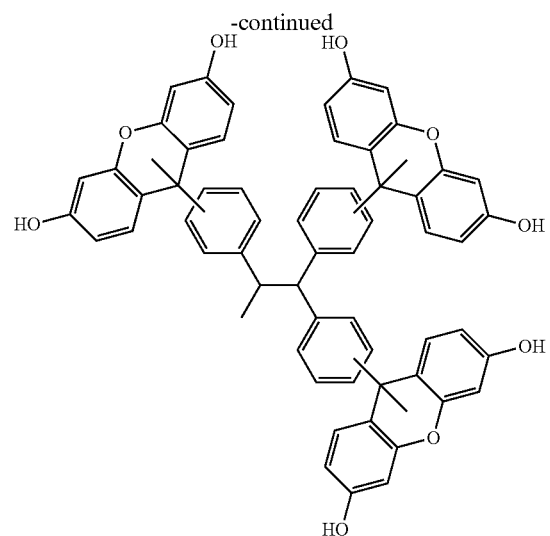
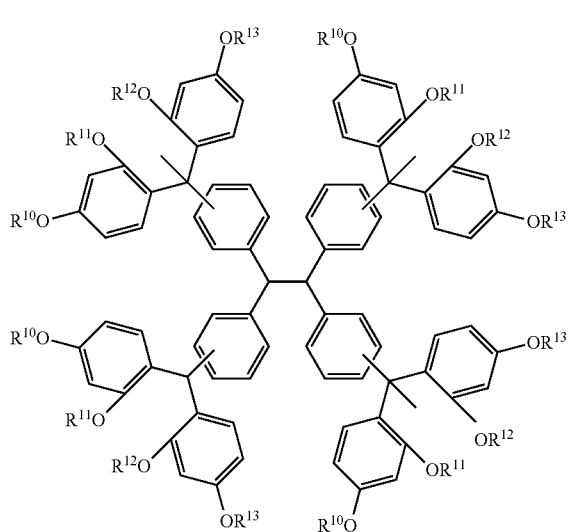
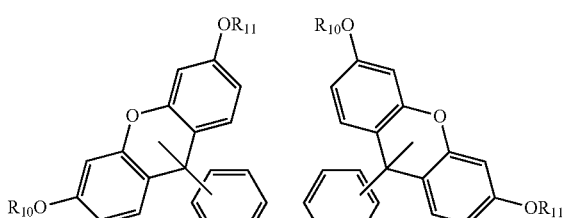
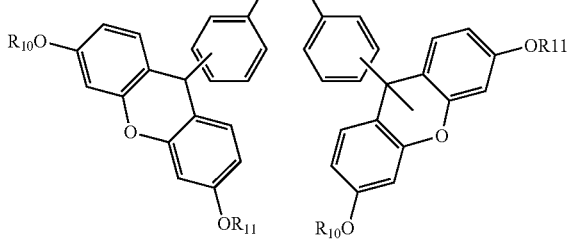
128
-continued
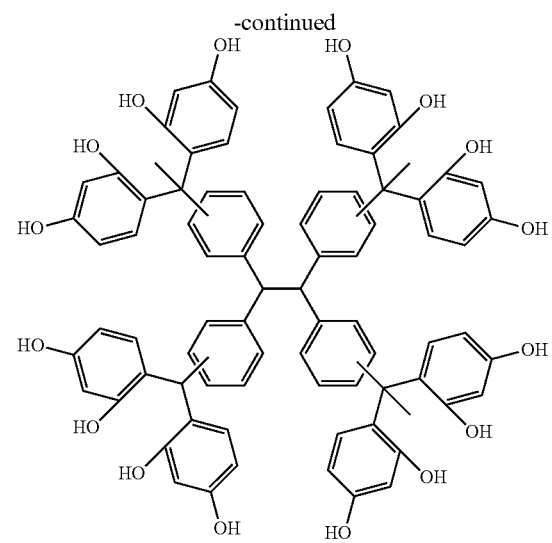
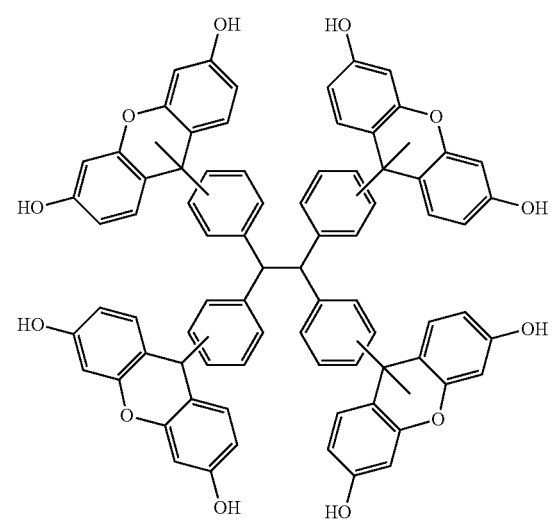
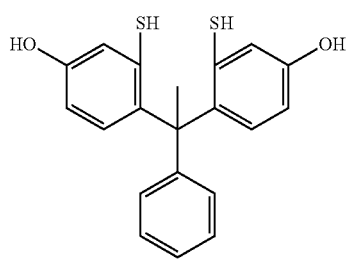
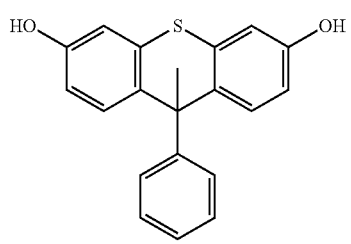

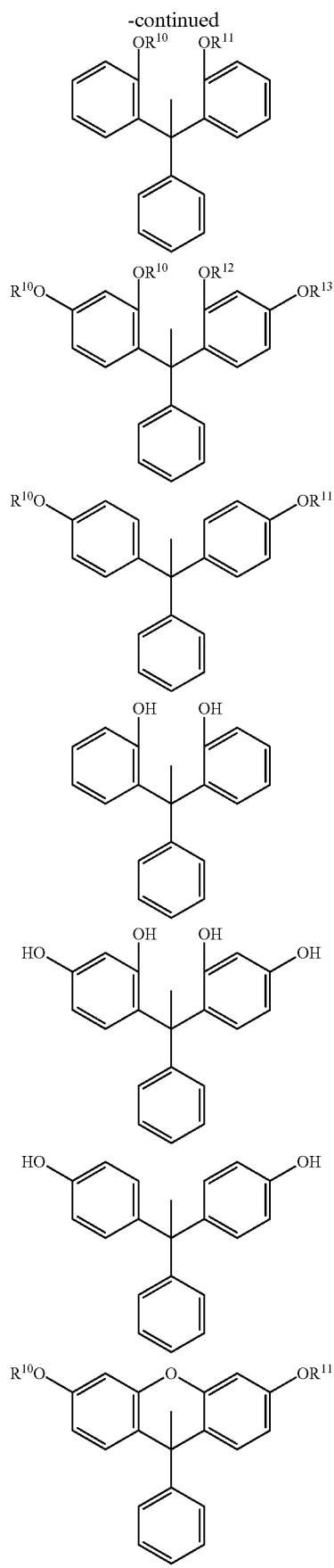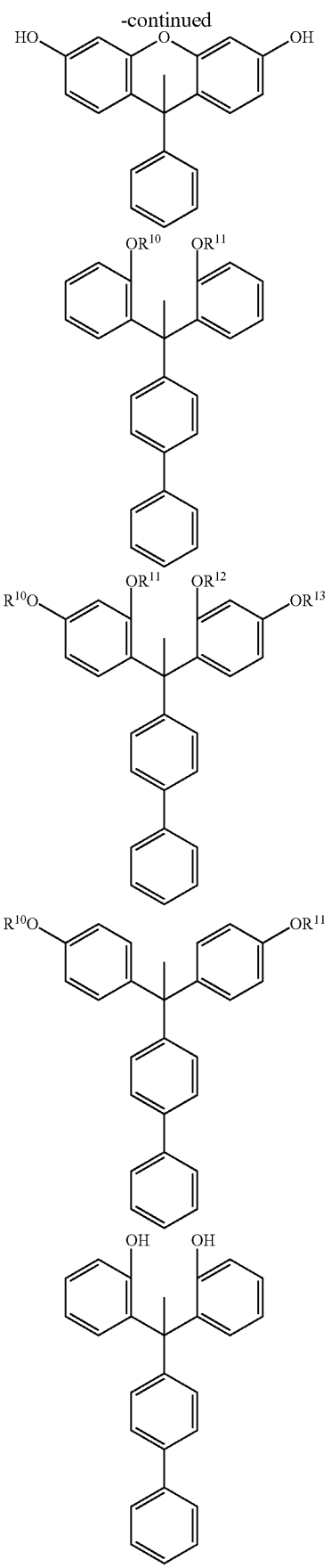

131
-continued
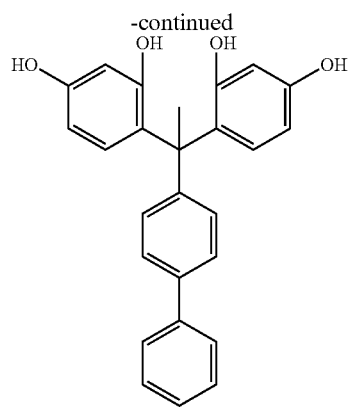
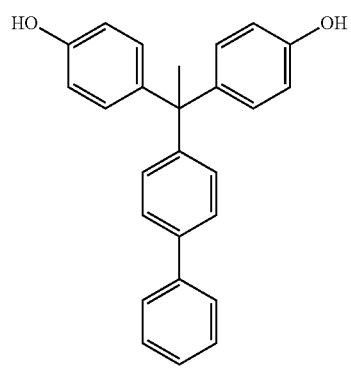
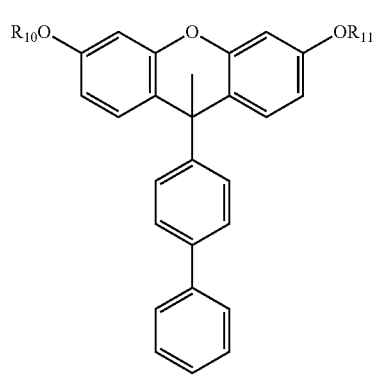
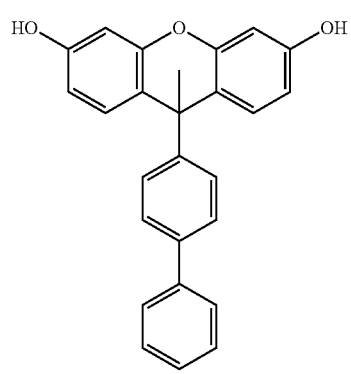
132
-continued
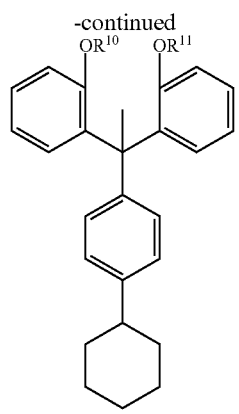
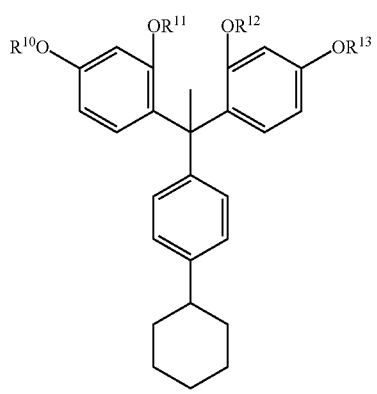
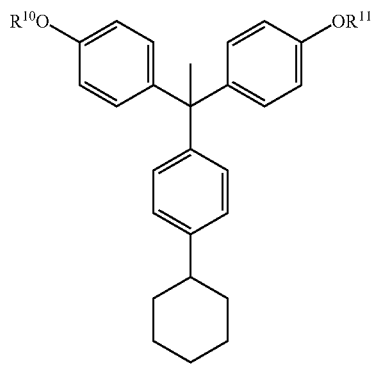
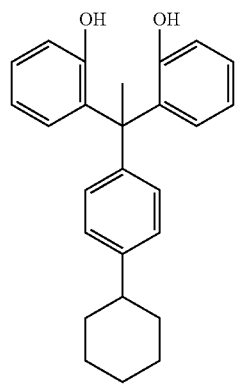

133
-continued
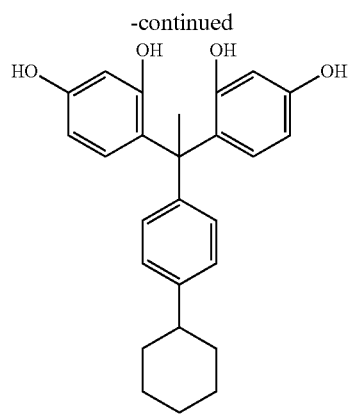
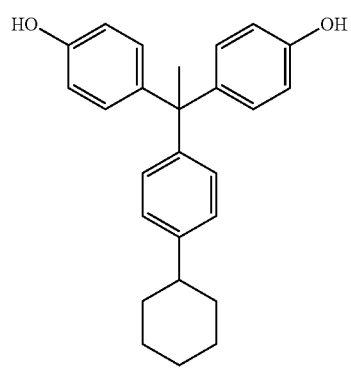
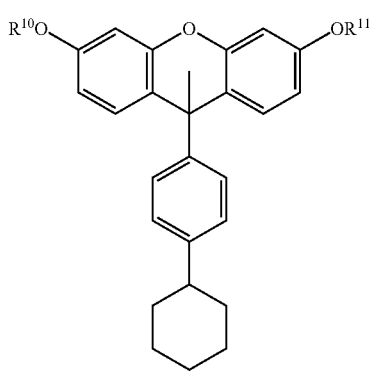
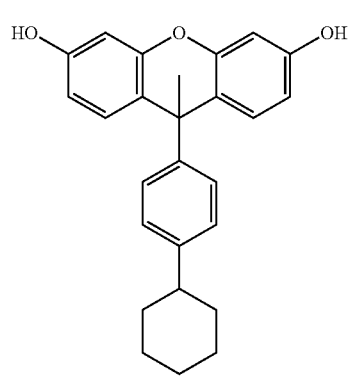
134
-continued
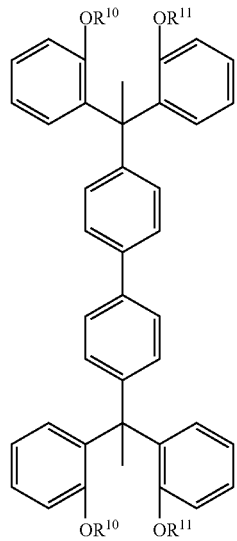
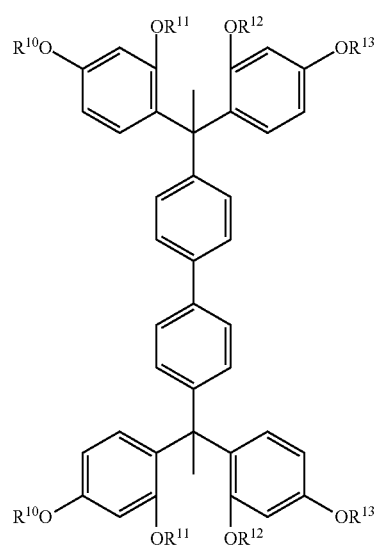
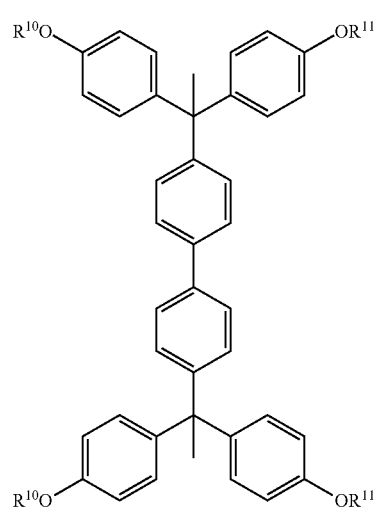

135
-continued
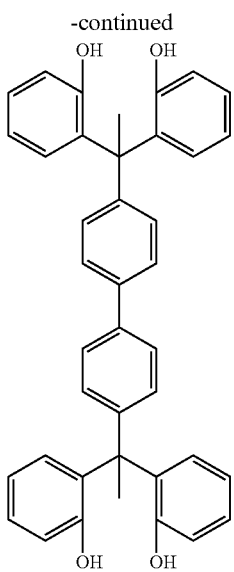
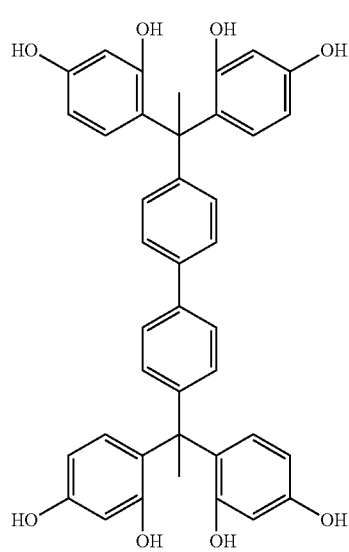
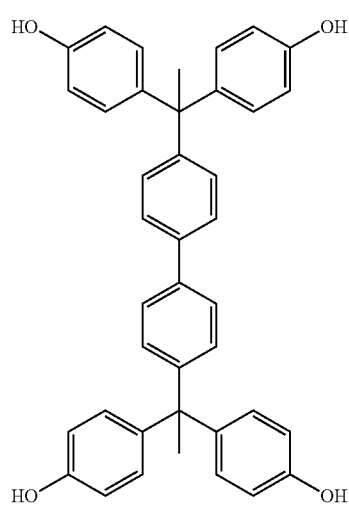
136
-continued
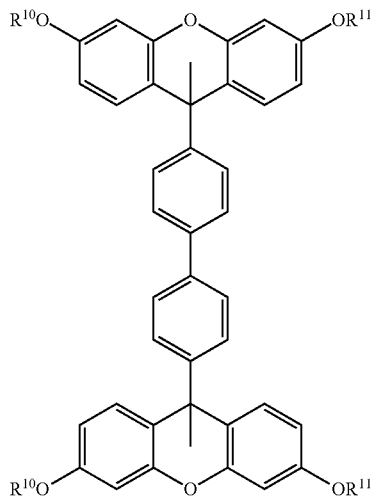
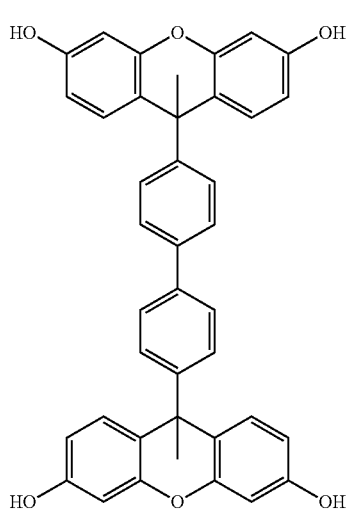
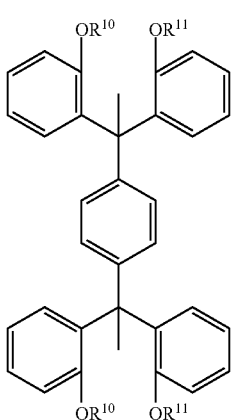

137
-continued
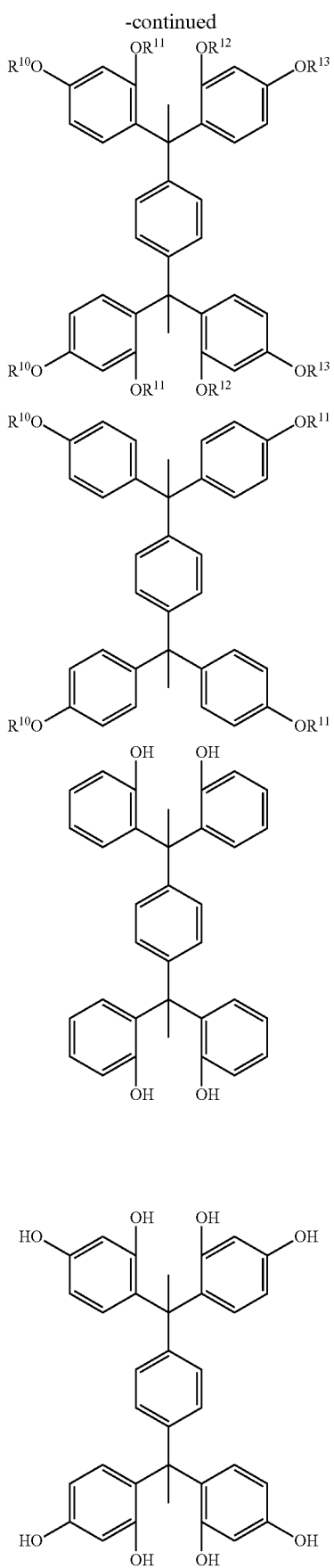
138
-continued
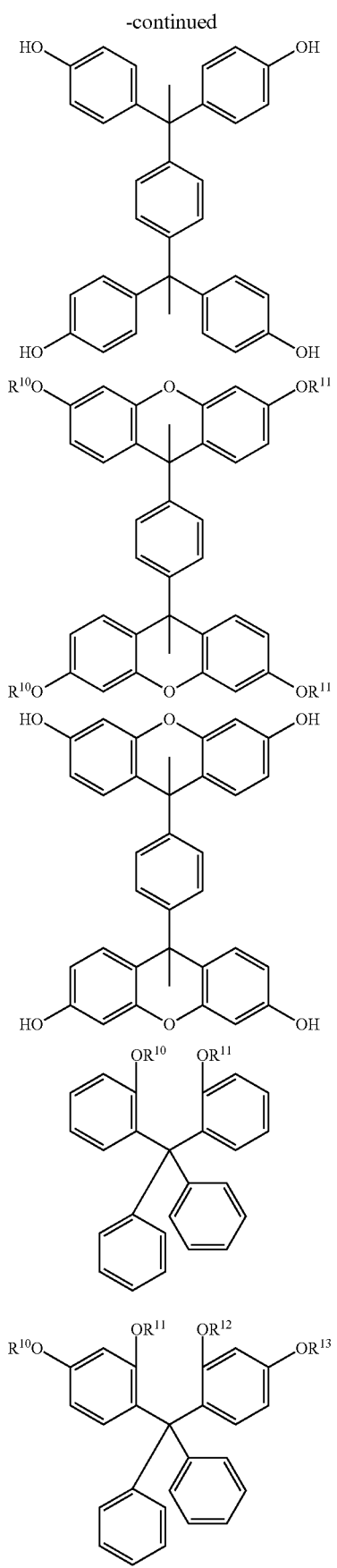

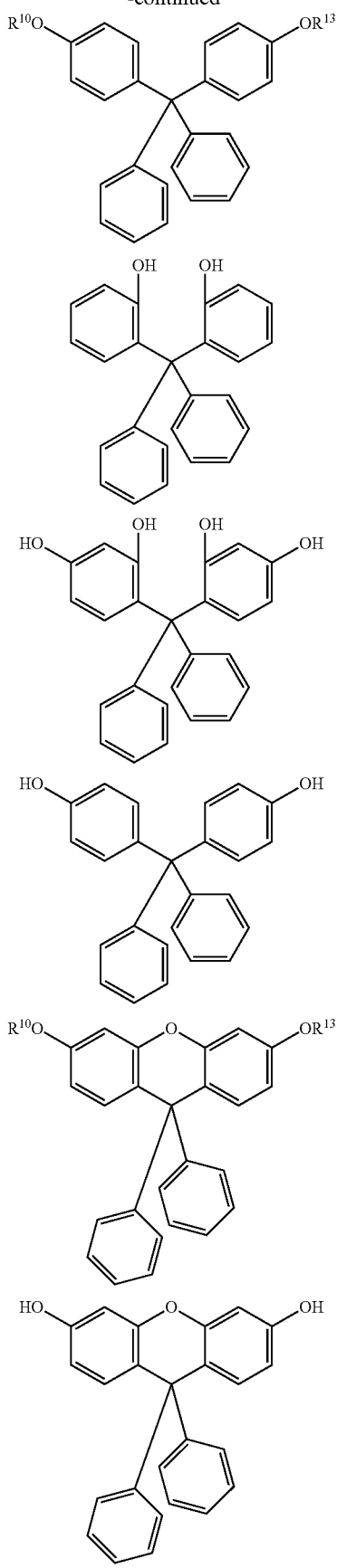
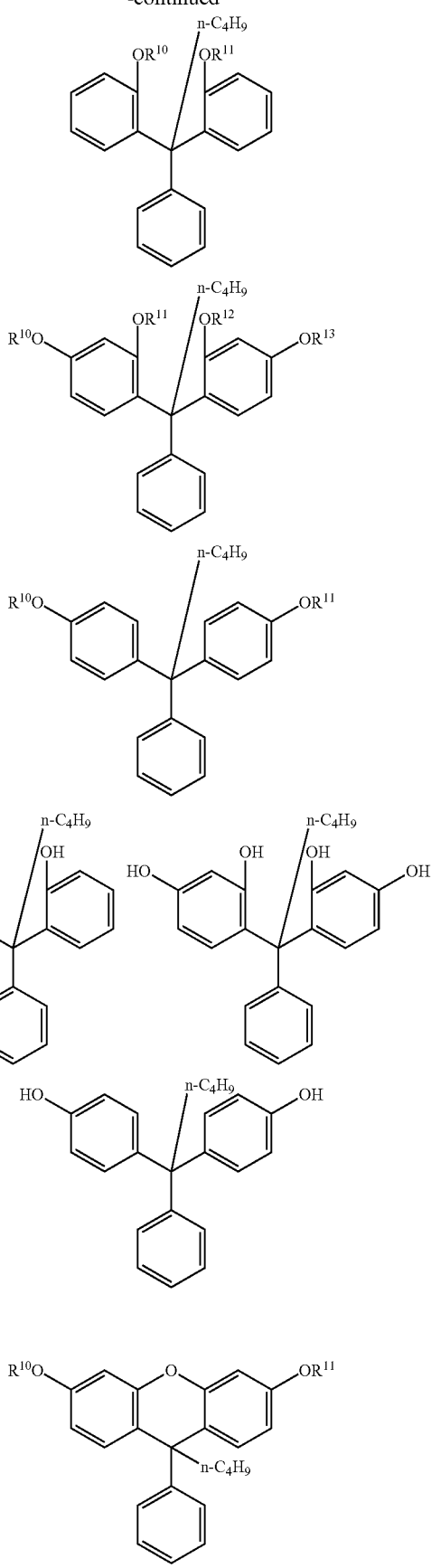

141
-continued
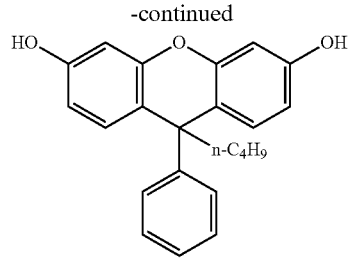
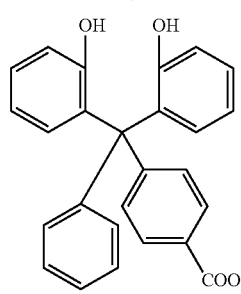
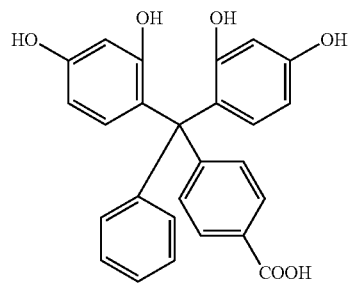
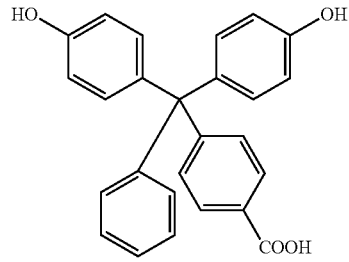
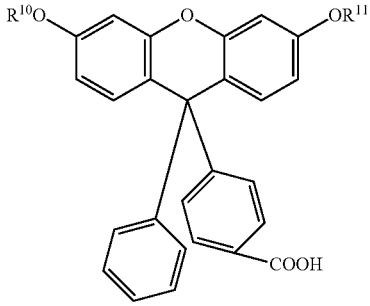
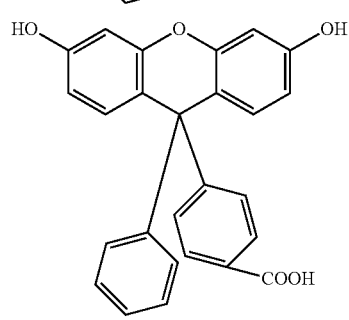
142
-continued
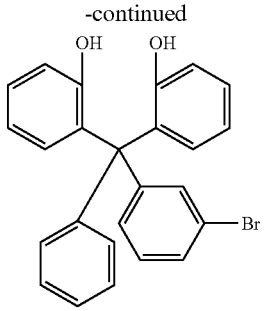
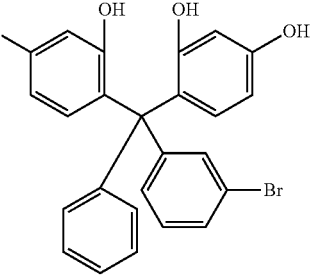
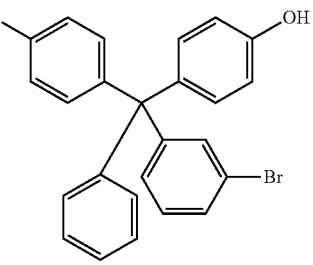
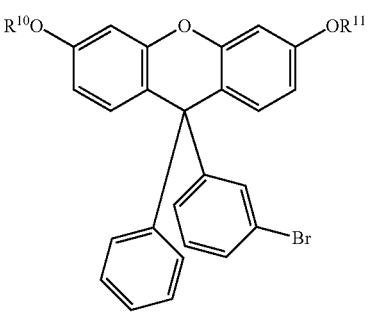
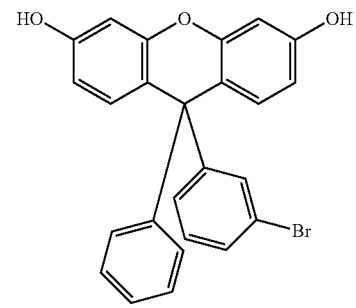
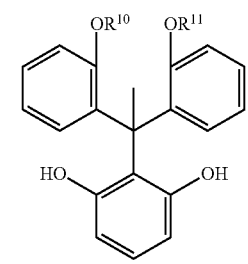

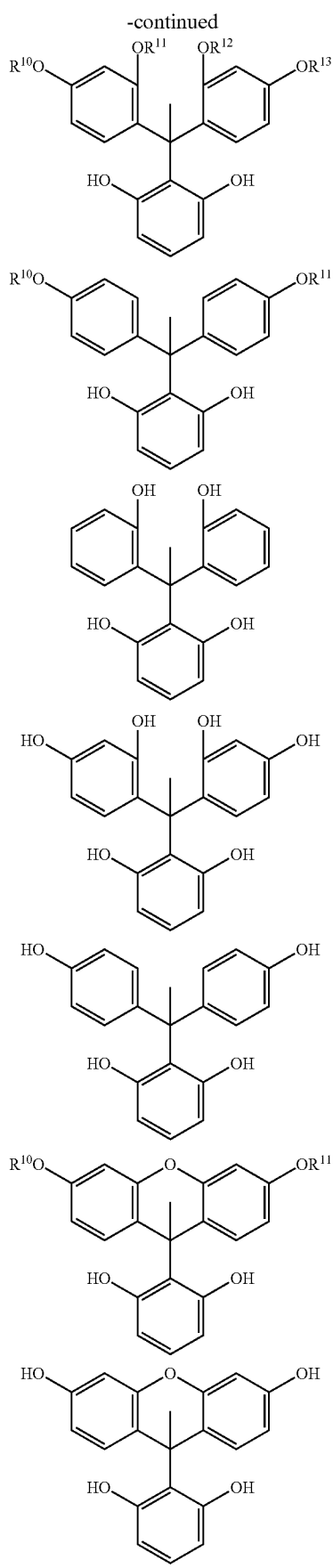
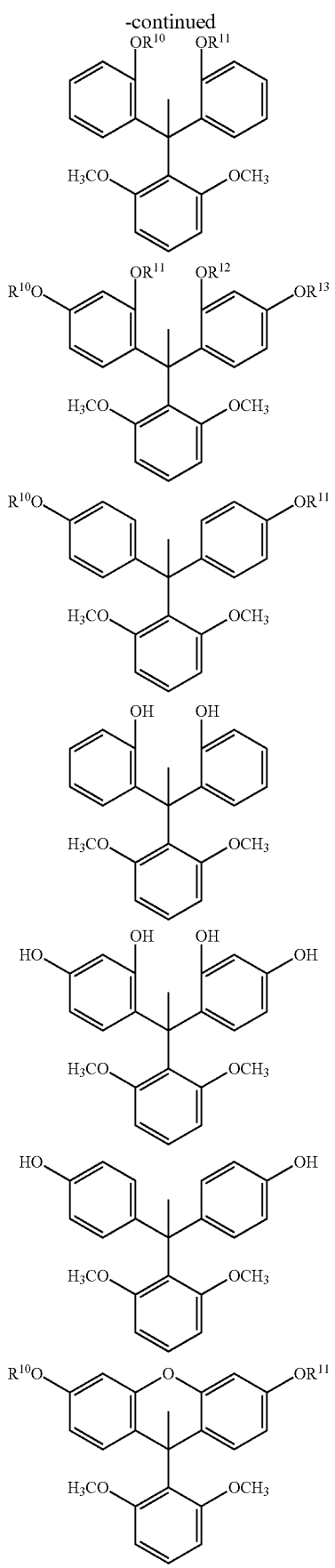

-continued
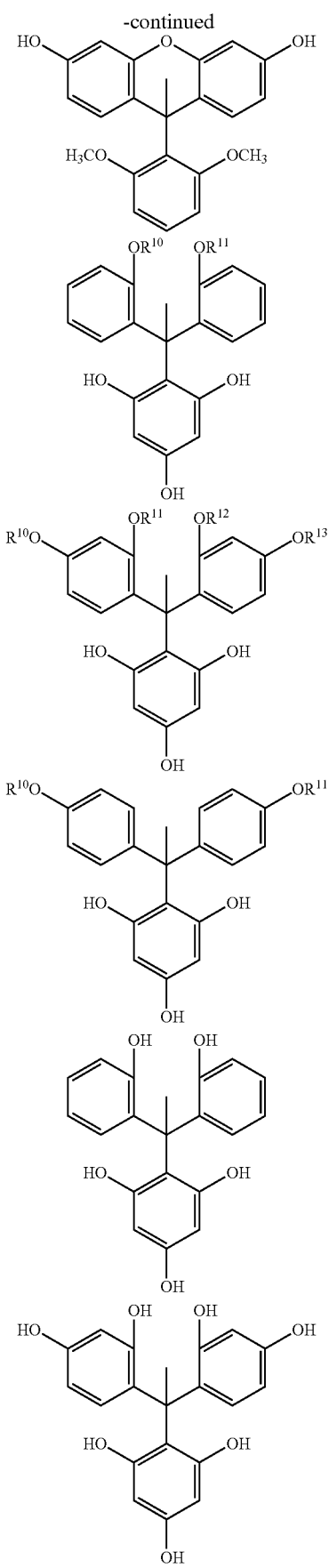
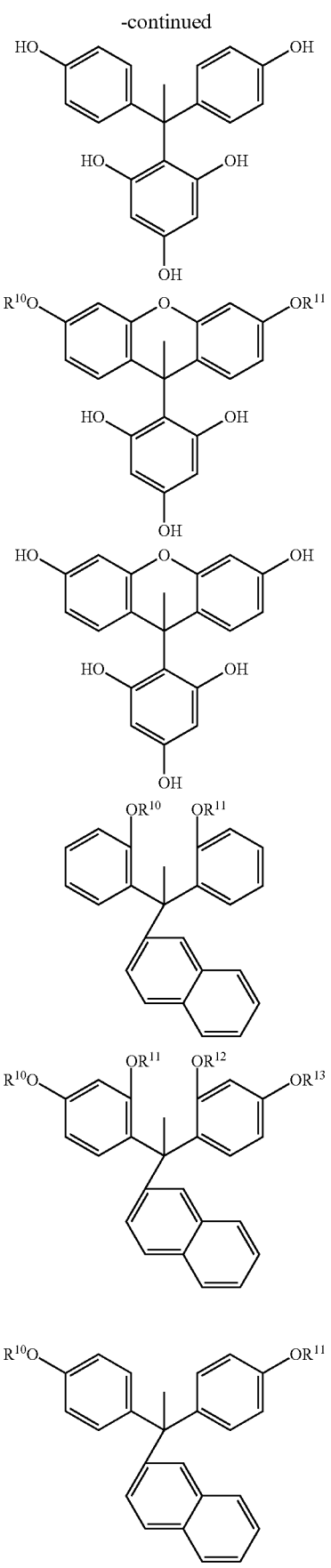

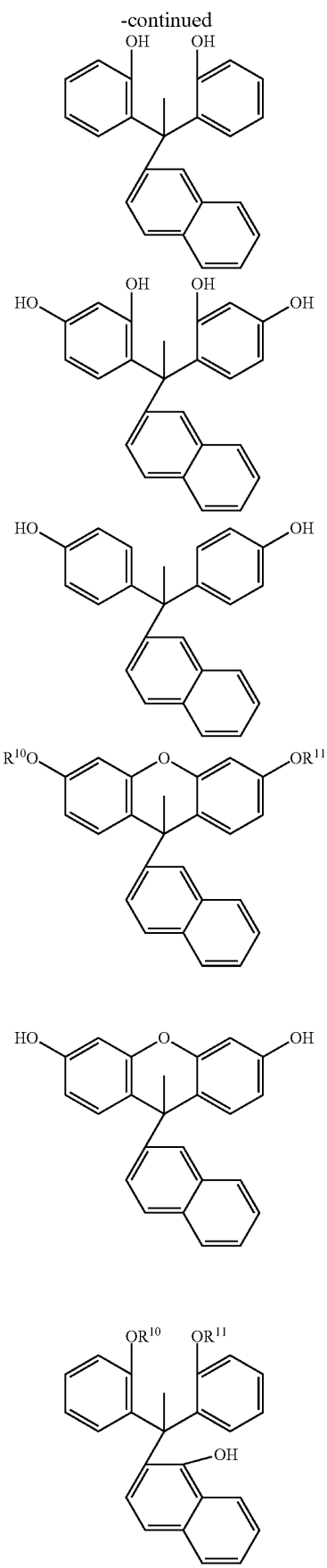

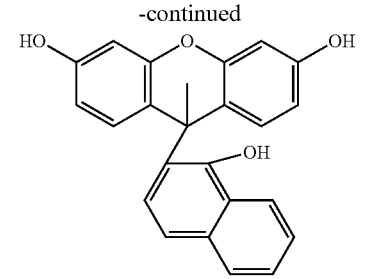
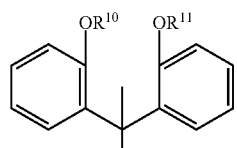
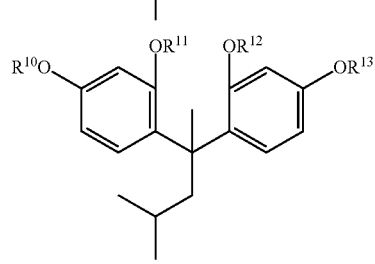
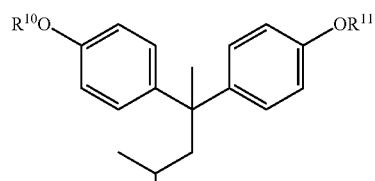
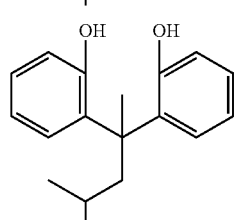
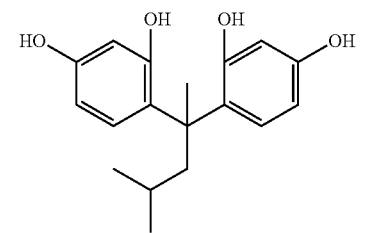
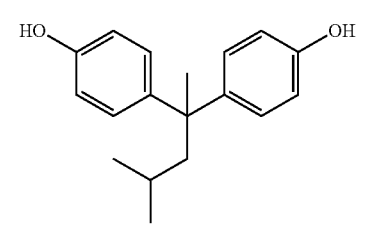
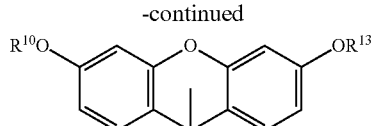
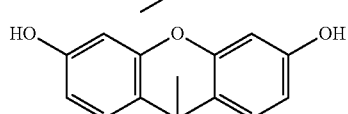
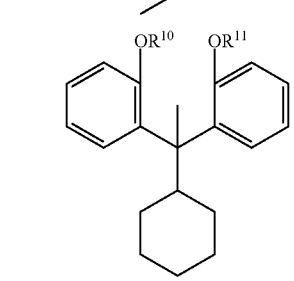
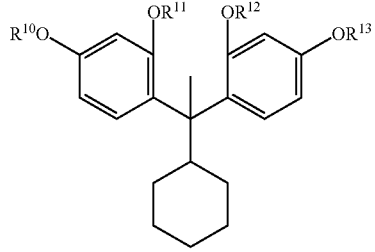
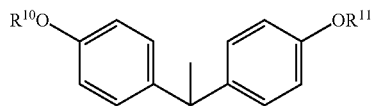
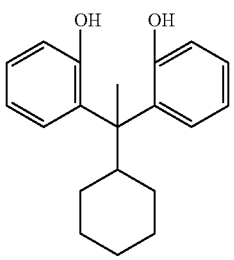
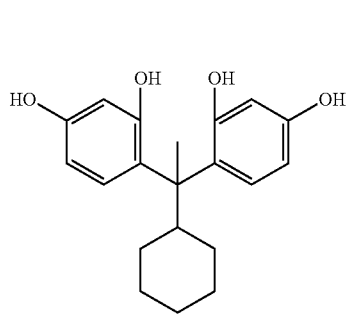

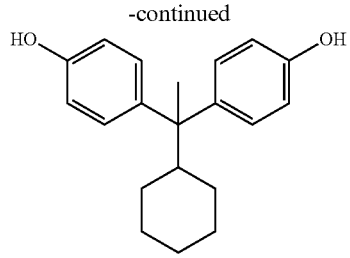
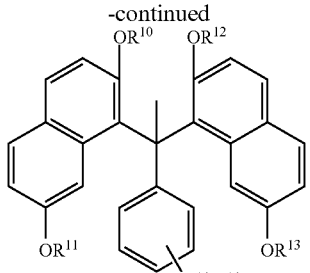
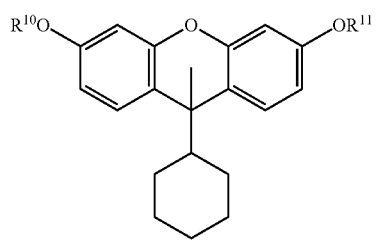
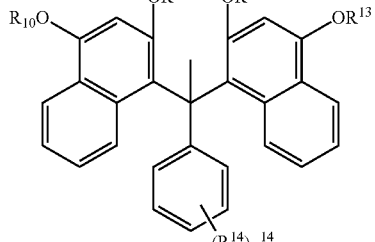
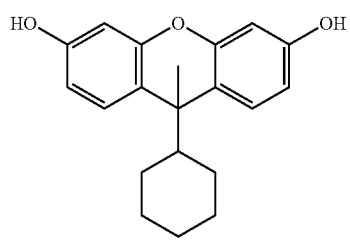
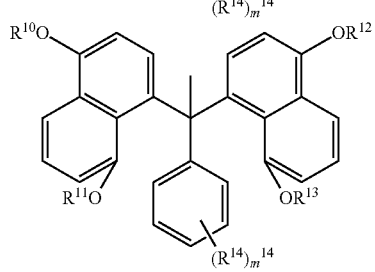
The above compounds preferably have a xanthene skeleton from the viewpoint of heat resistance.
The compound represented by the formula (2) more preferably has any of the following structures from the viewpoint of etching resistance.
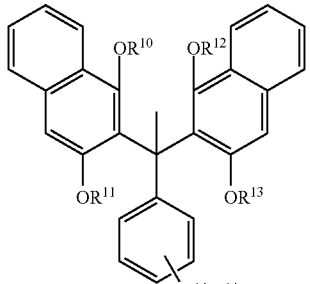
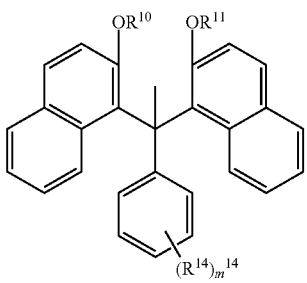
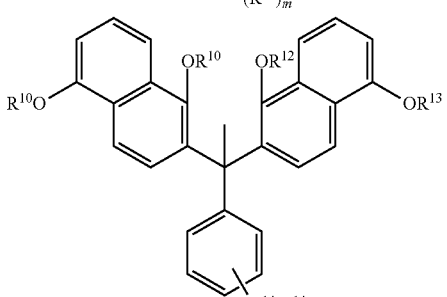
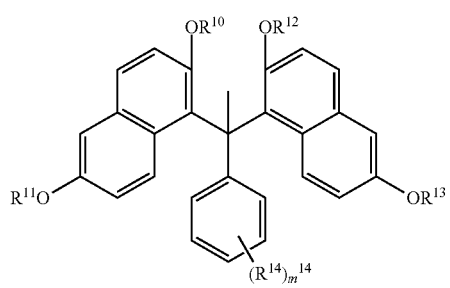
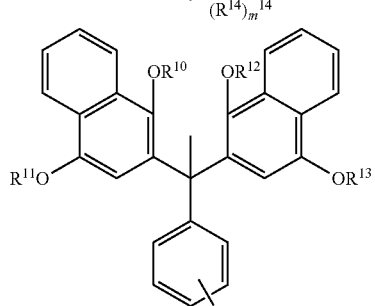

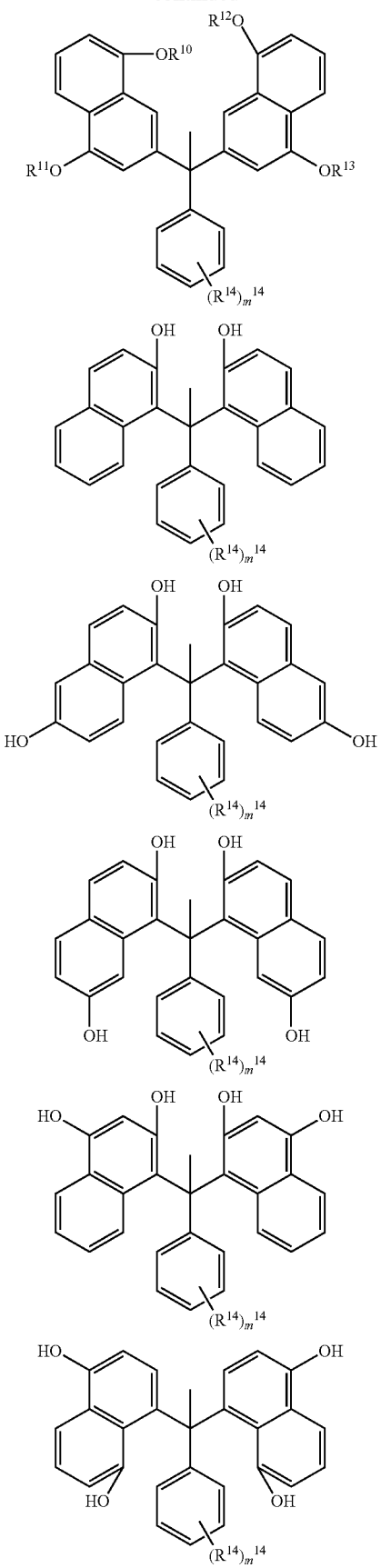
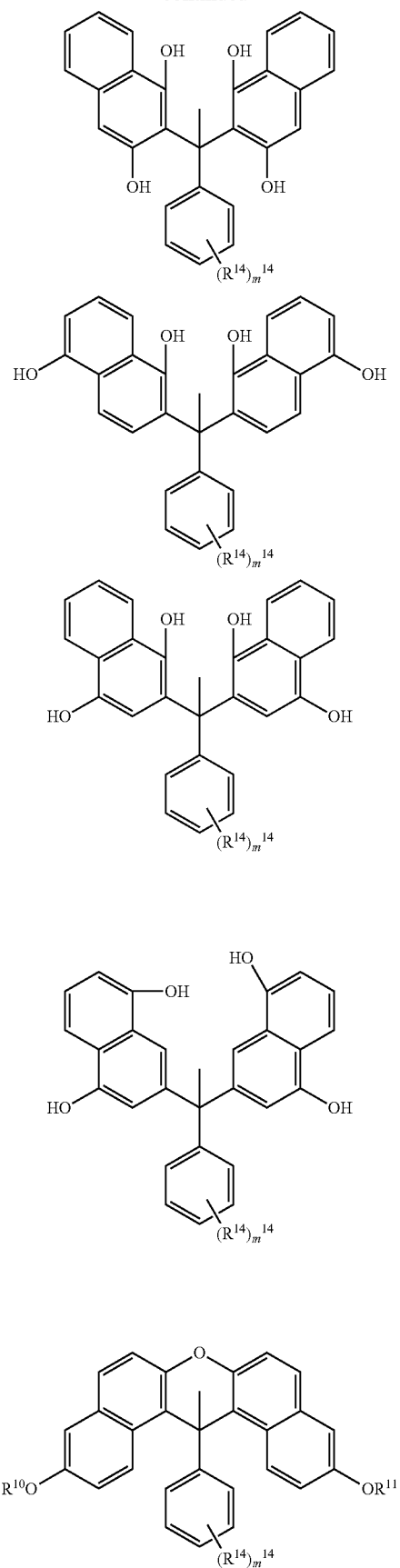

-continued

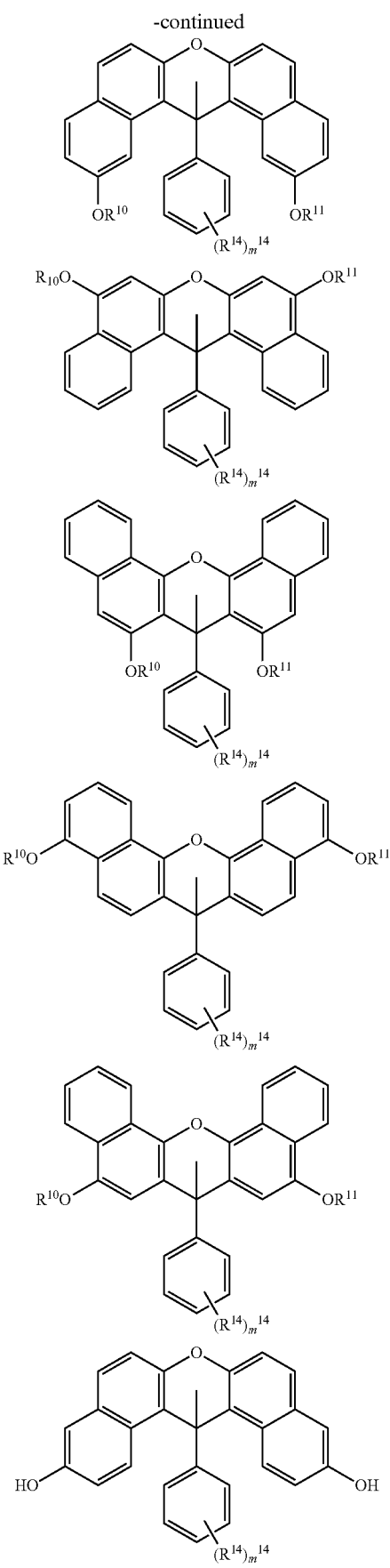

-continued

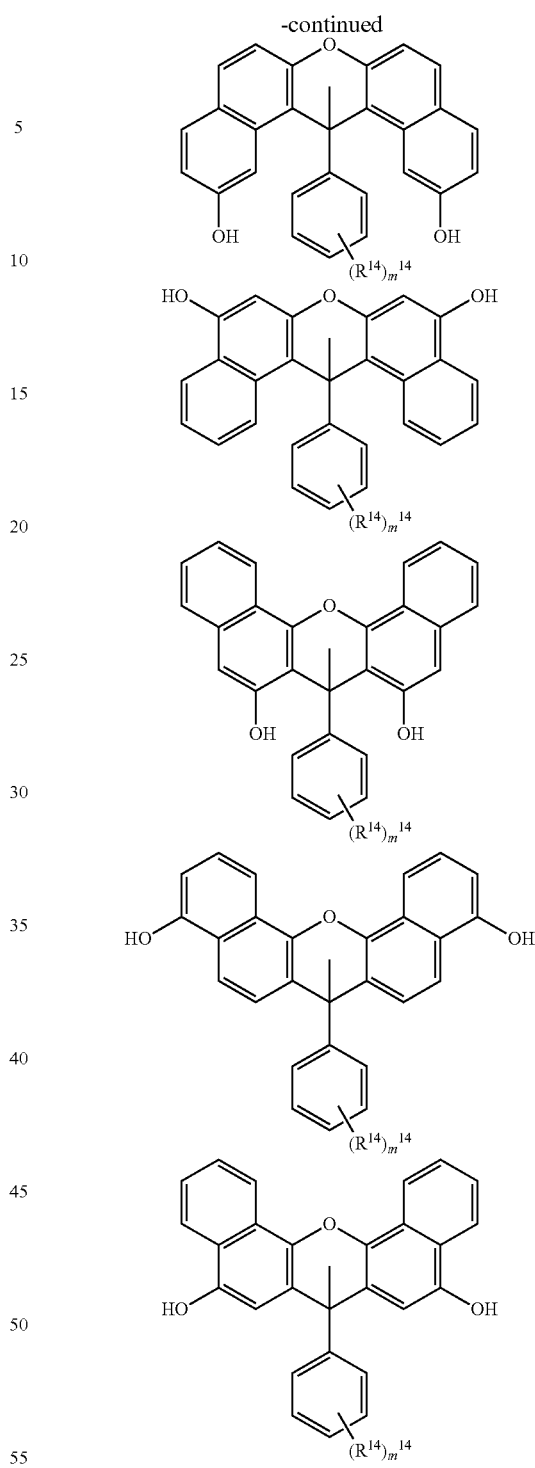

In the above compounds, $R^{10}$ to $R^{13}$ are as defined in the description of the above formula (1-2); each $R^{14}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group; and $m^{14'}$ is an integer of 0 to 4.

Examples of $R^{14}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{14}$ listed above includes isomers. For example, a butyl group includes a n-butyl group, an isobutyl group, a sec-butyl group, and a tert-butyl group.

Further examples of the compound represented by the formula (2) include compounds having the following structures.

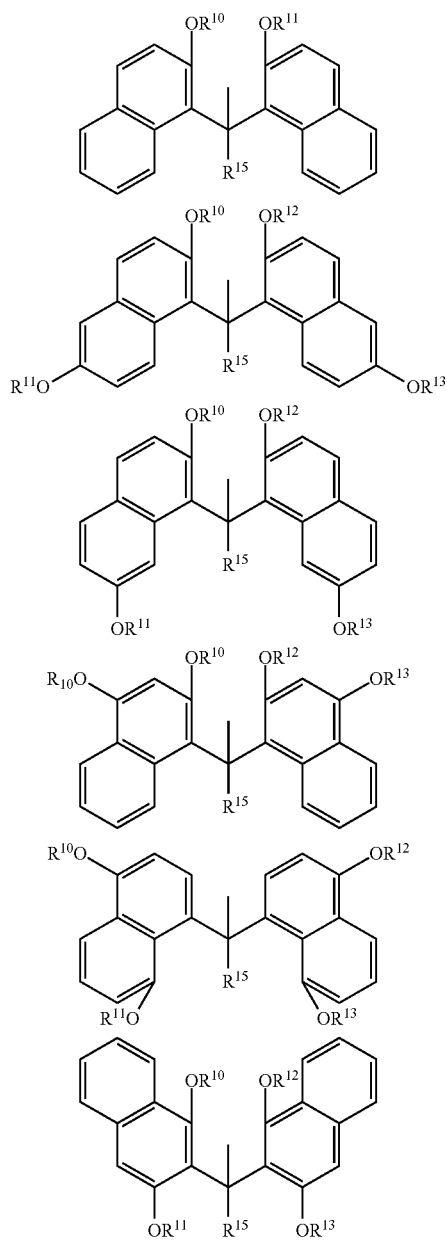

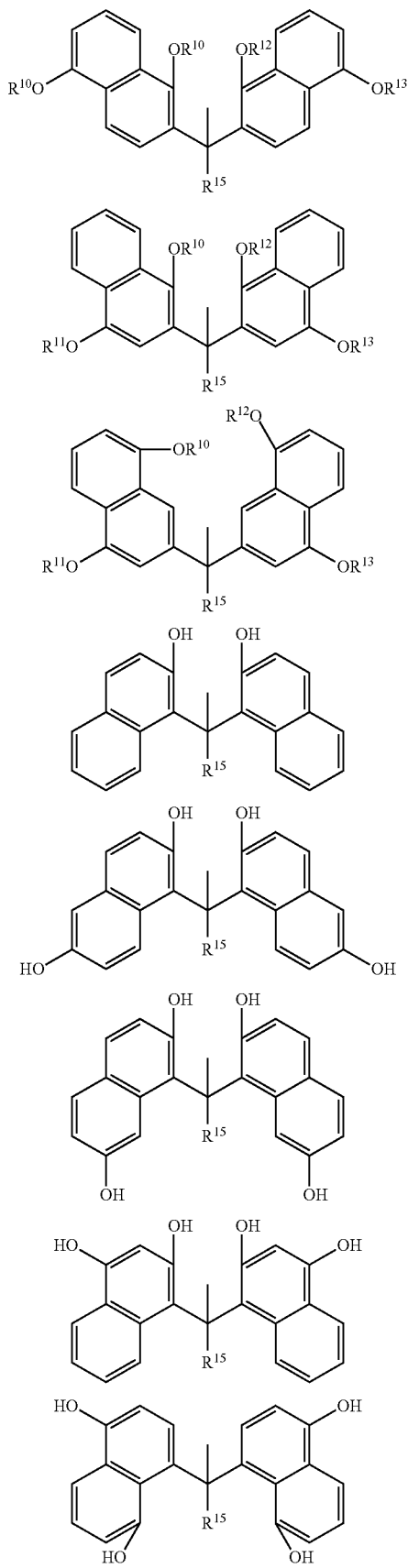

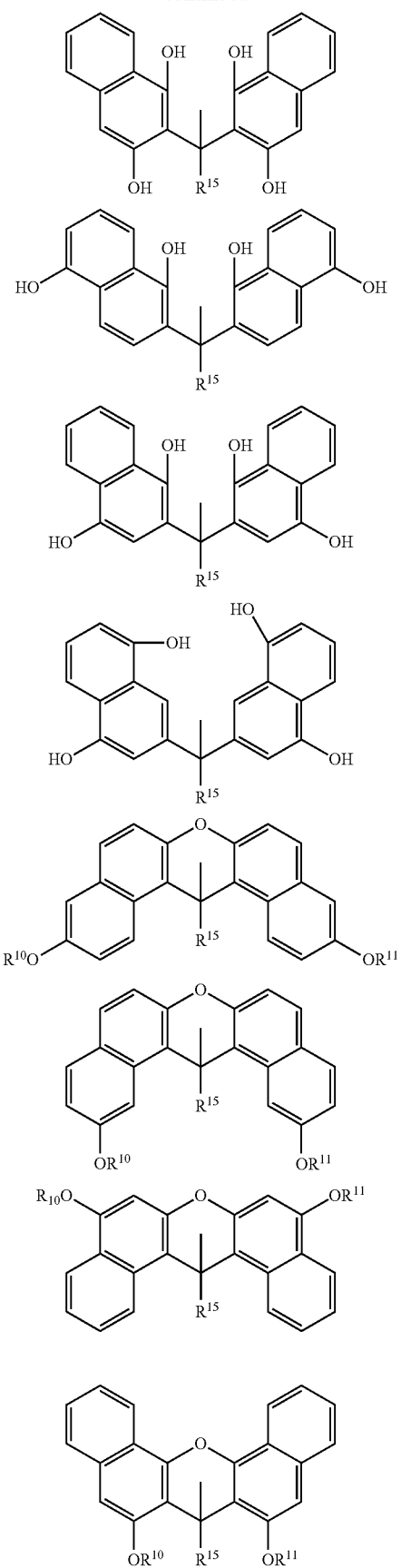
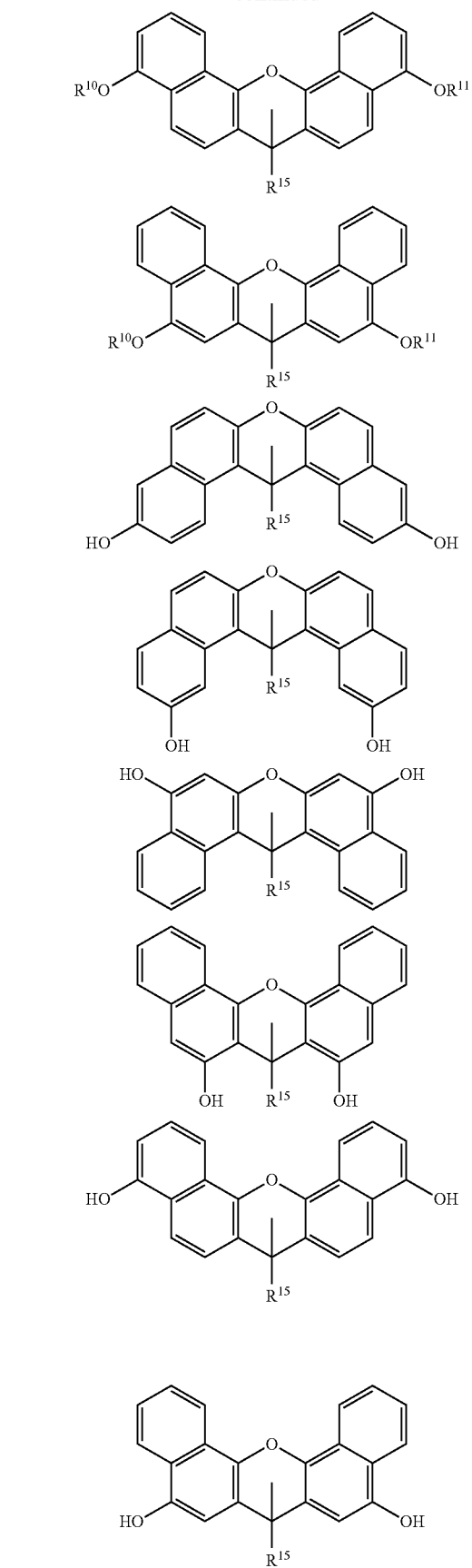

-continued
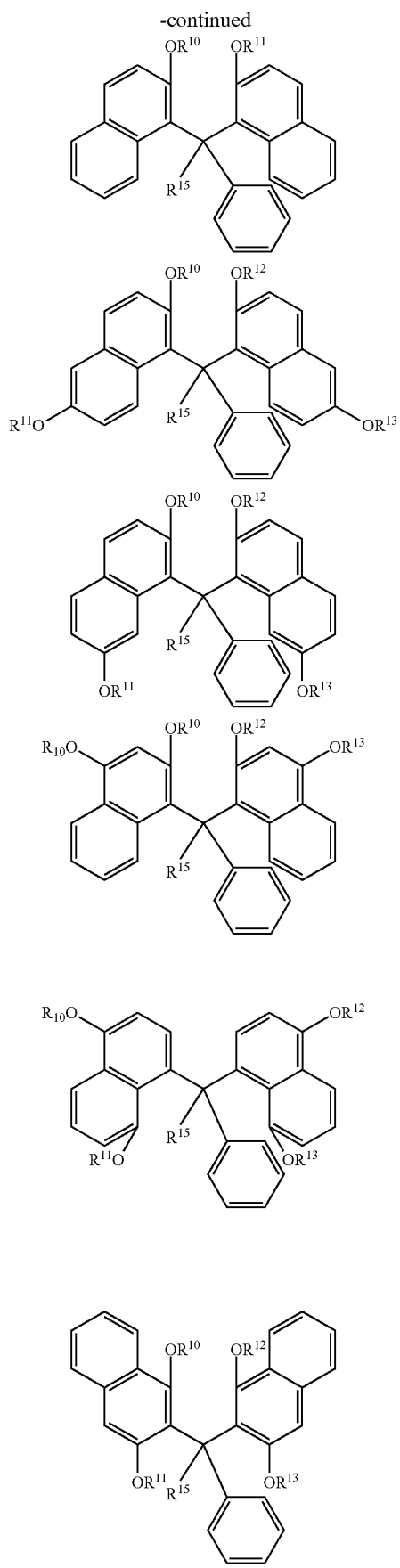
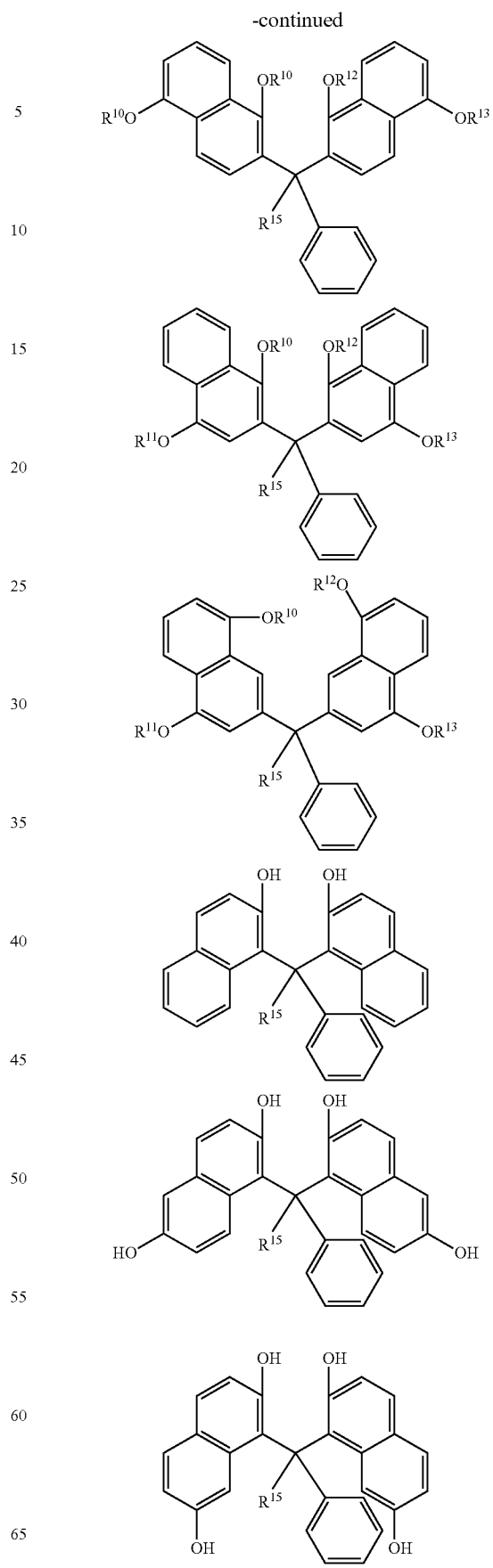

-continued
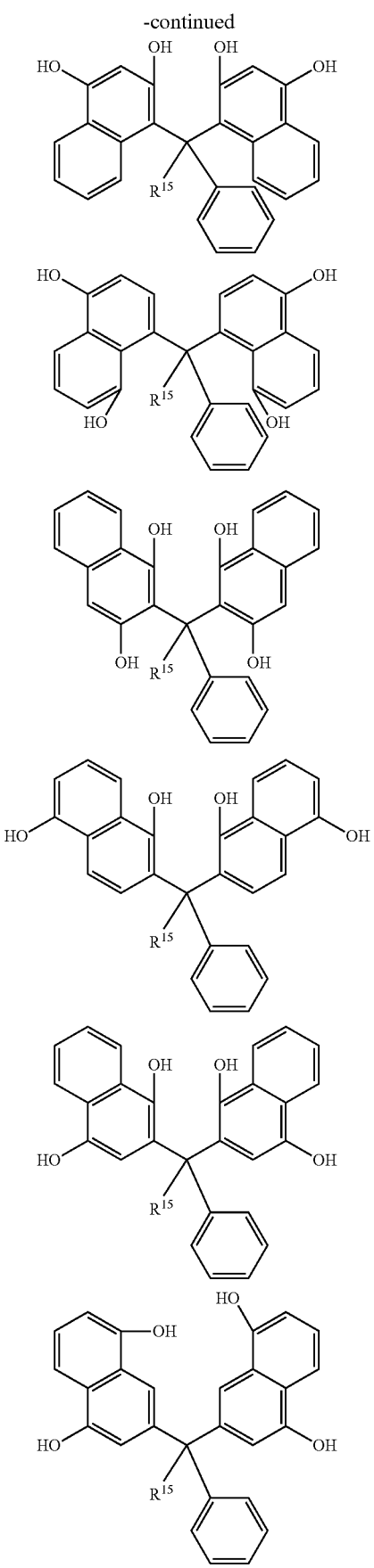
-continued
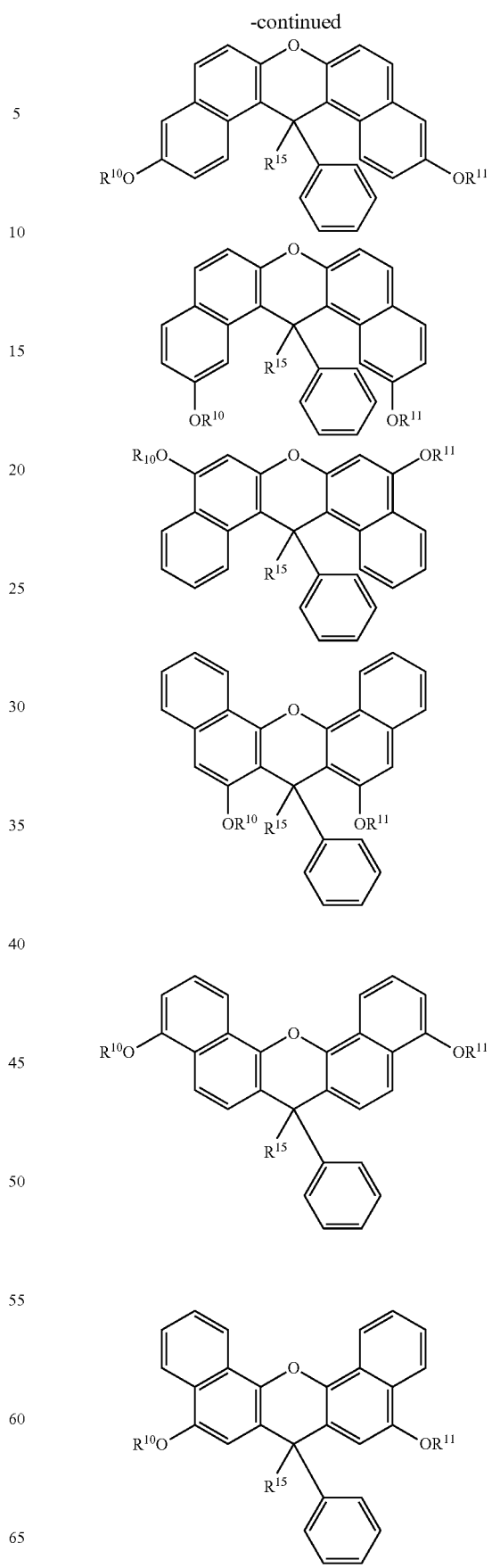

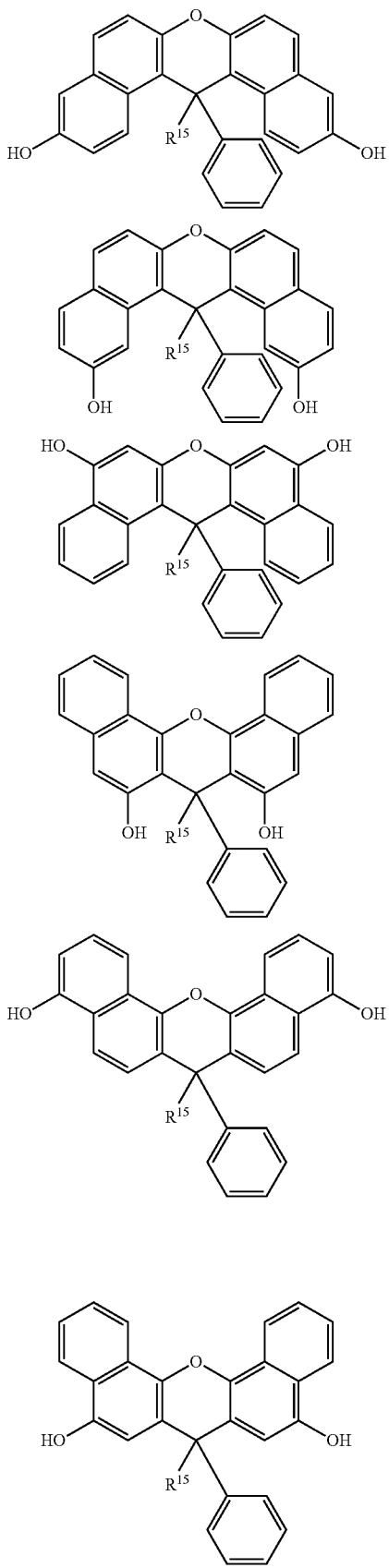

In the above compounds, $R^{10}$ to $R^{13}$ are as defined in the description of the above formula (1-2), and $R^{15}$ is a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group.

Examples of $R^{15}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a heptacene group, a vinyl group, an allyl group, a triacontenyl group, a methoxy group, an group, group, a triacontyloxy group, a fluorine atom, a chlorine atom, a bromine atom, an iodine atom, and a thiol group.

$R^{15}$ listed above includes isomers. For example, a butyl group includes a n-butyl group, an isobutyl group, a sec-butyl group, and a tert-butyl group.

Further examples of the compound represented by the formula (2) include compounds having the following structures.

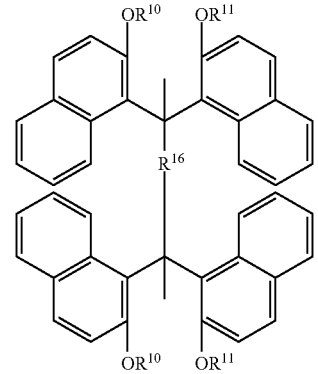

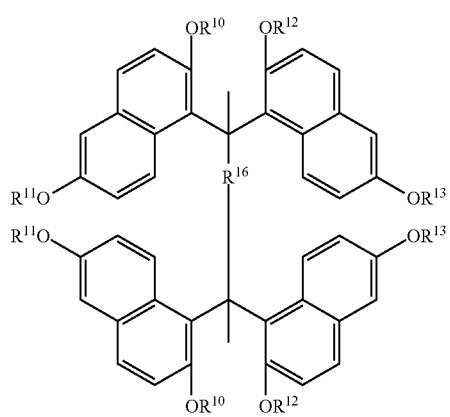

-continued
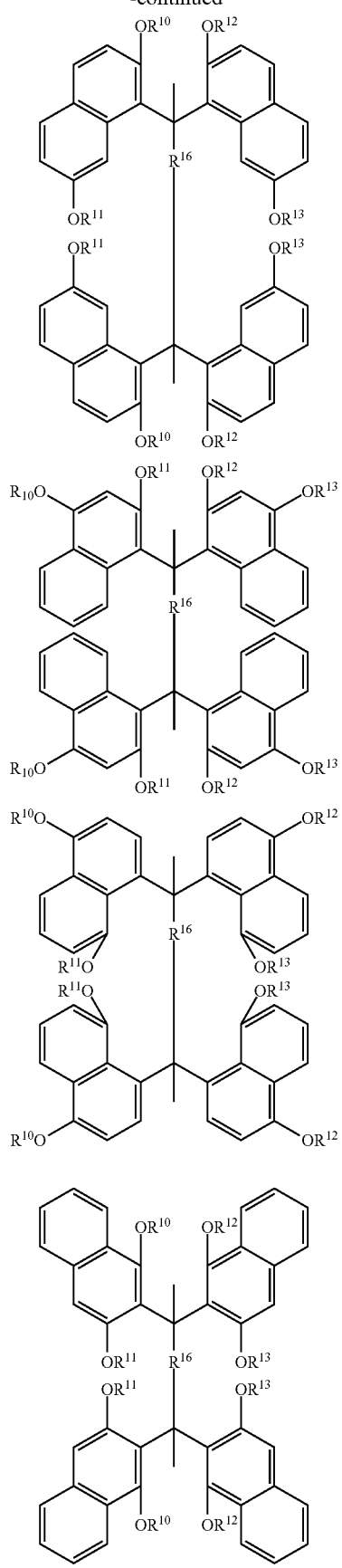
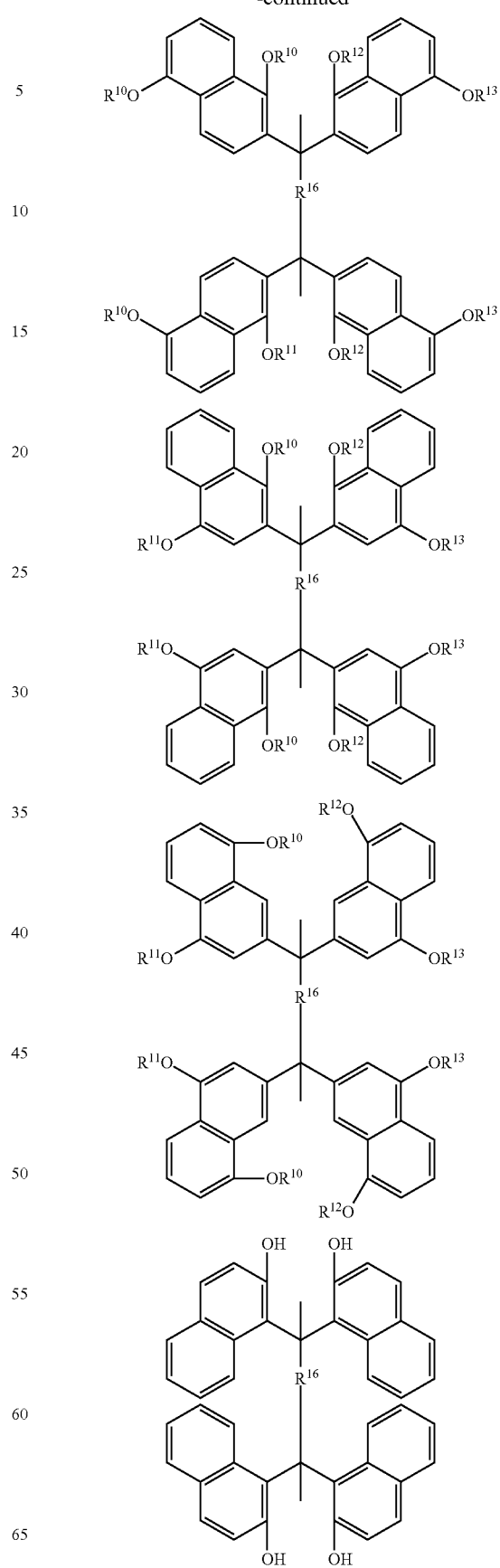

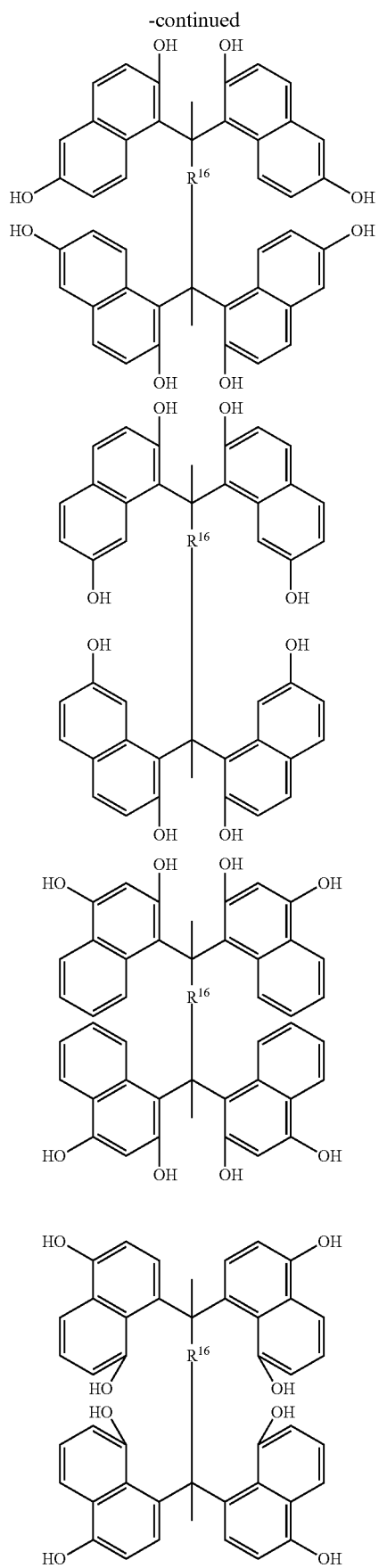
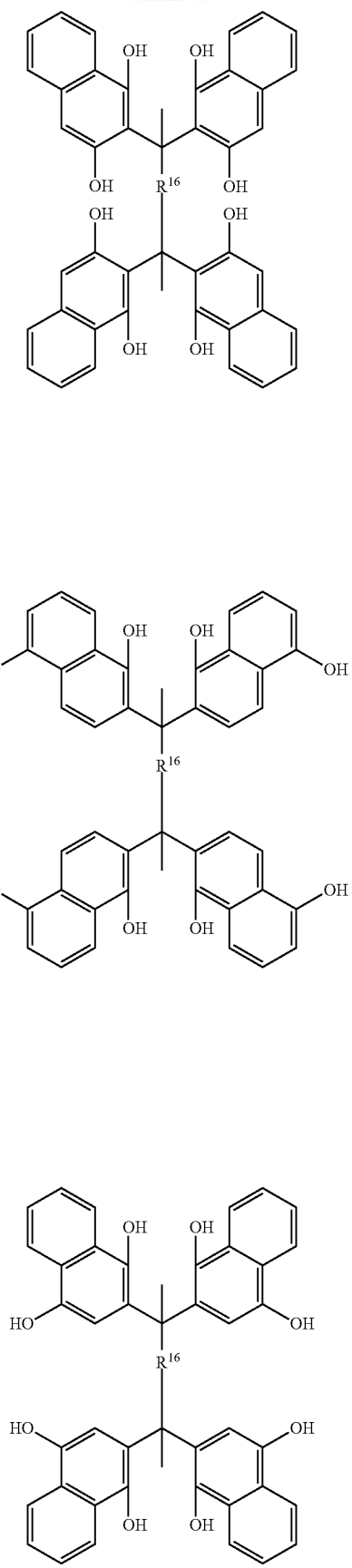

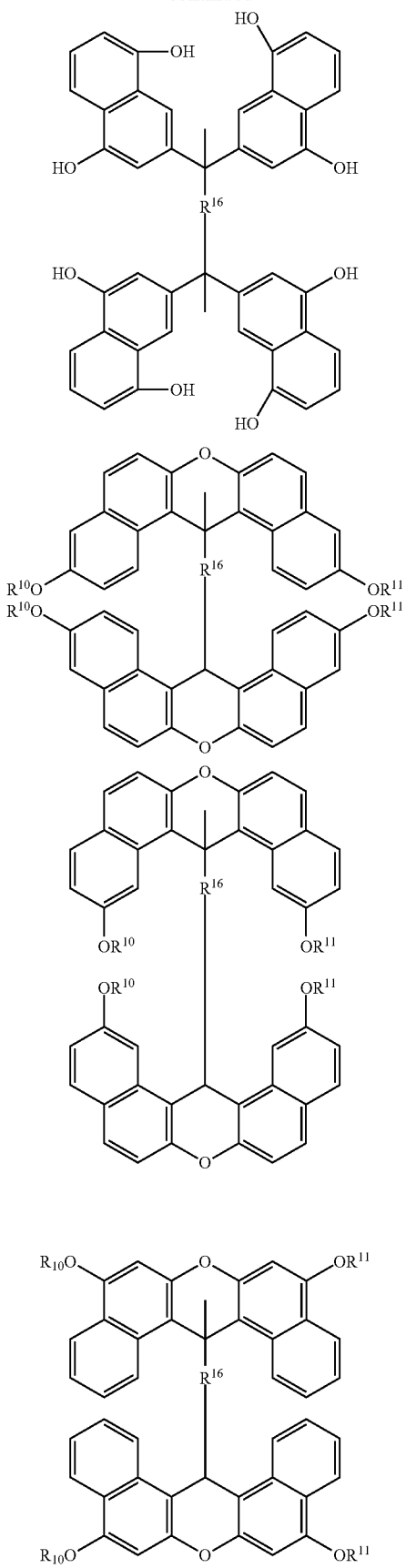
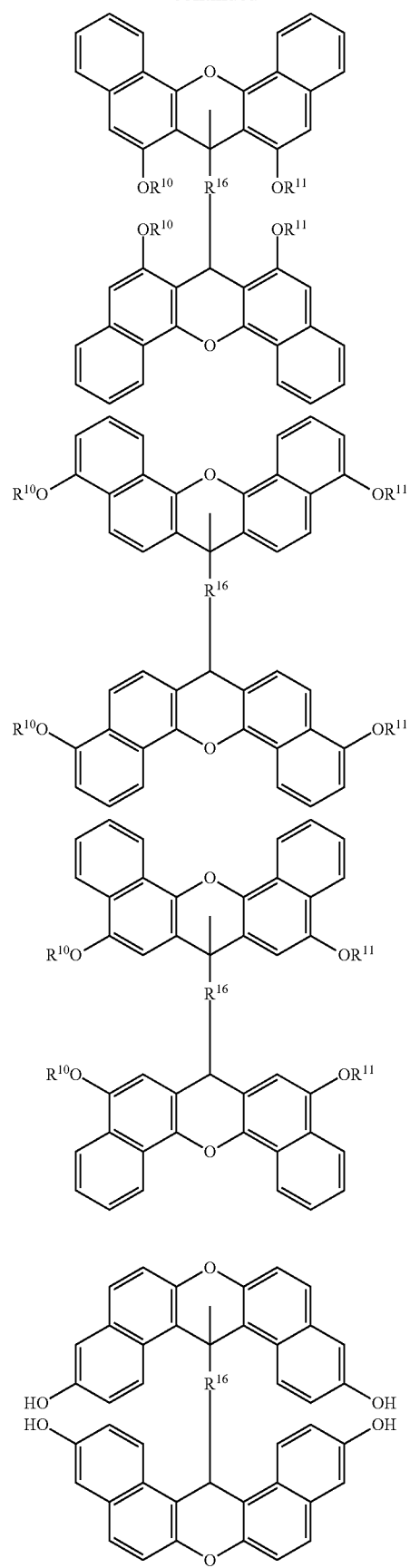

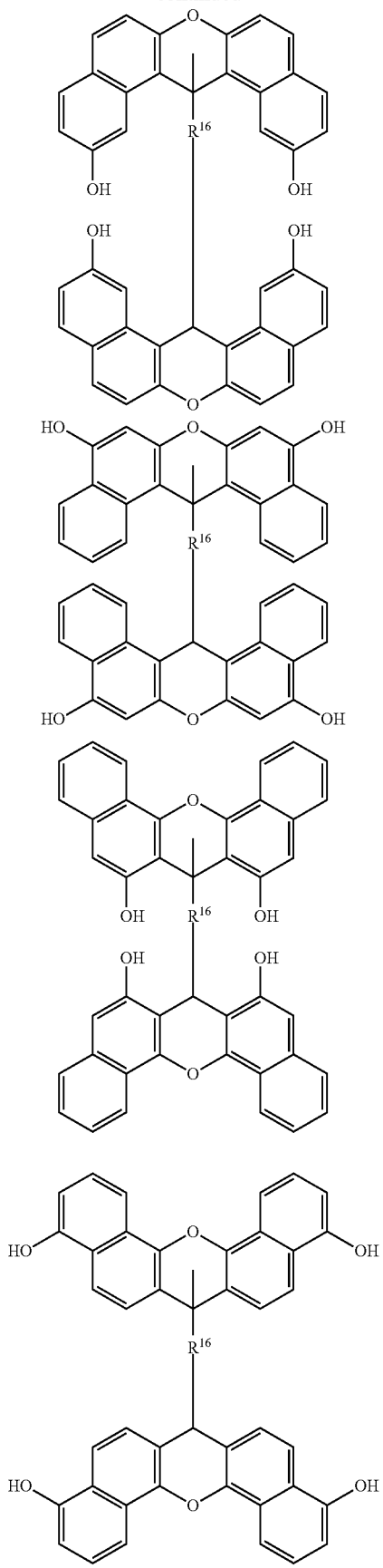

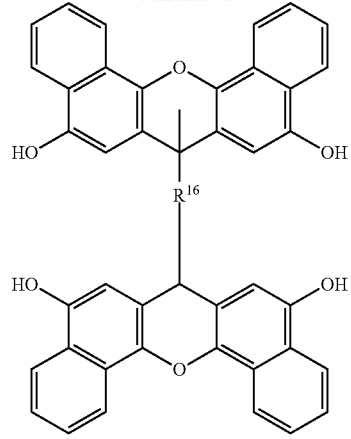

In the above compounds, $R^{10}$ to $R^{13}$ are as defined in the description of the above formula (1-2), and $R^{16}$ is a linear, branched, or cyclic alkylene group of 1 to 30 carbon atoms, a divalent aryl group of 6 to 30 carbon atoms, or a divalent alkenyl group of 2 to 30 carbon atoms.

Examples of $R^{16}$ include a methylene group, an ethylene group, a propene group, a butene group, a pentene group, a hexene group, a heptene group, an octene group, a nonene group, a decene group, an undecene group, a dodecene group, a triacontene group, a cyclopropene group, a cyclobutene group, a cyclopentene group, a cyclohexene group, a cycloheptene group, a cyclooctene group, a cyclononene group, a cyclodecene group, a cycloundecene group, a cyclododecene group, a cyclotriacontene group, a divalent norbornyl group, a divalent adamantyl group, a divalent phenyl group, a divalent naphthyl group, a divalent anthracene group, a divalent heptacene group, a divalent vinyl group, a divalent allyl group, and a divalent triacontenyl group.

$R^{16}$ listed above includes isomers. For example, a butyl group includes a n-butyl group, an isobutyl group, a sec-butyl group, and a tert-butyl group.

Further examples of the compound represented by the formula (2) include compounds having the following structures.

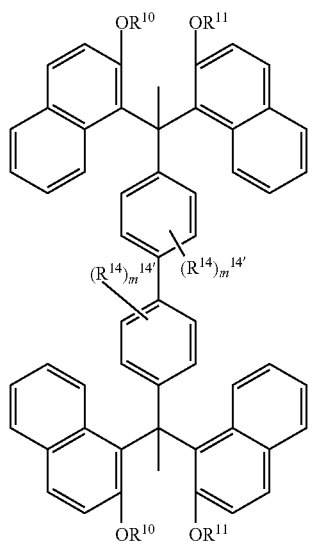

-continued
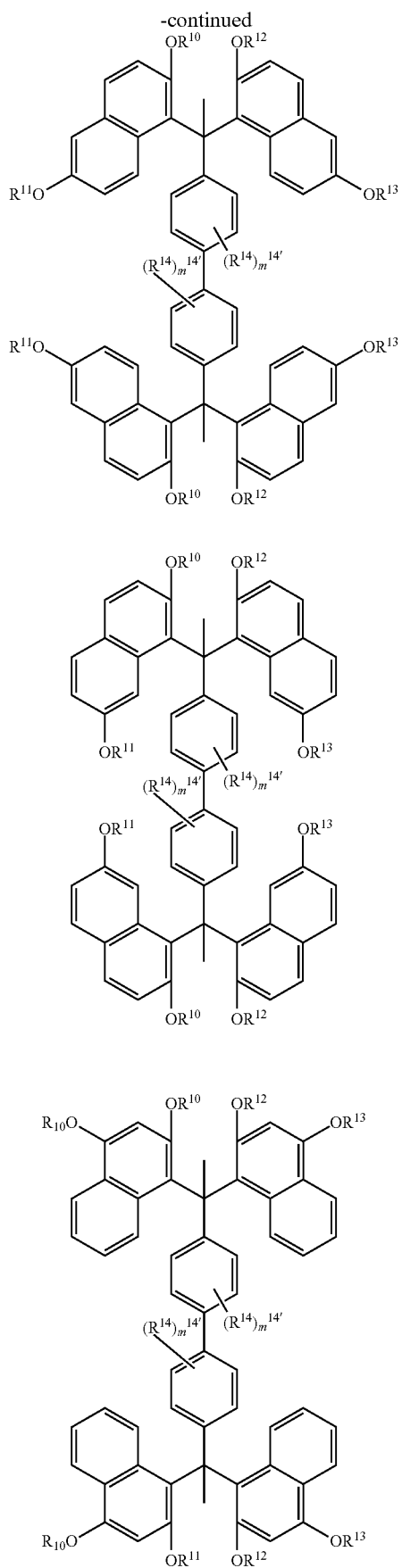
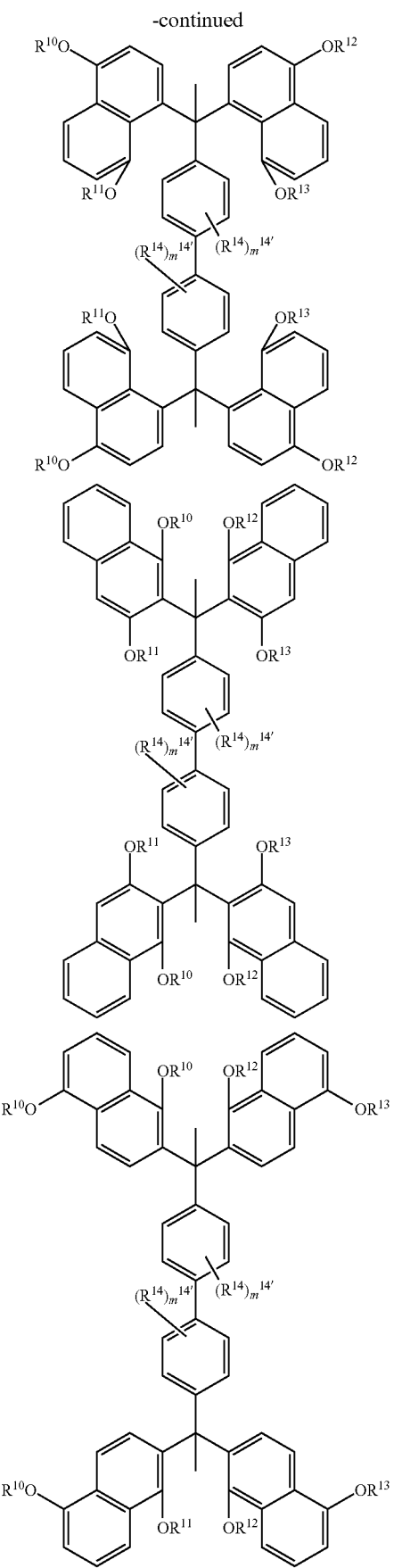

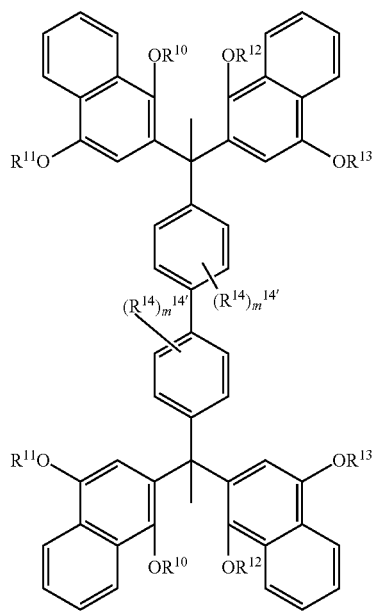
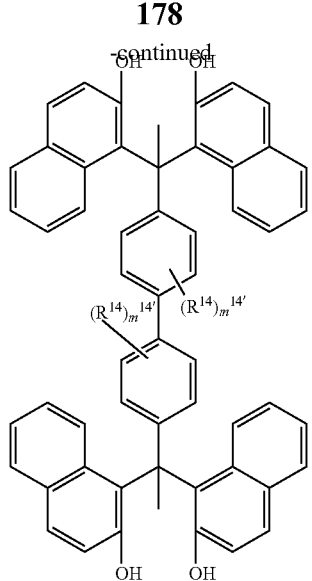

179
-continued
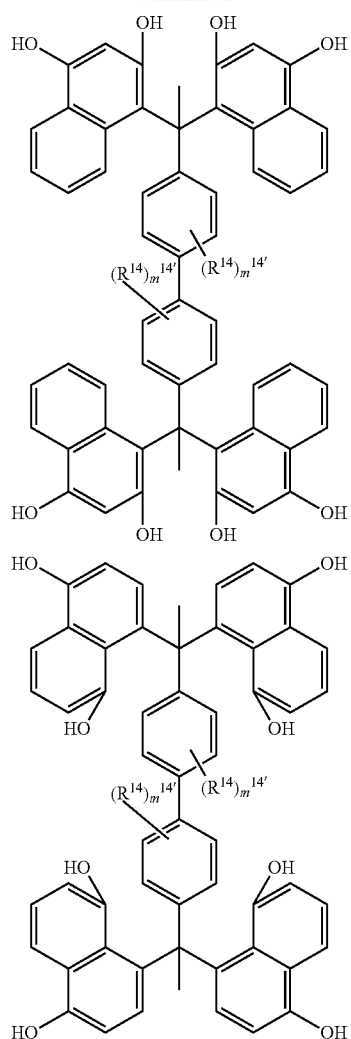
180
-continued
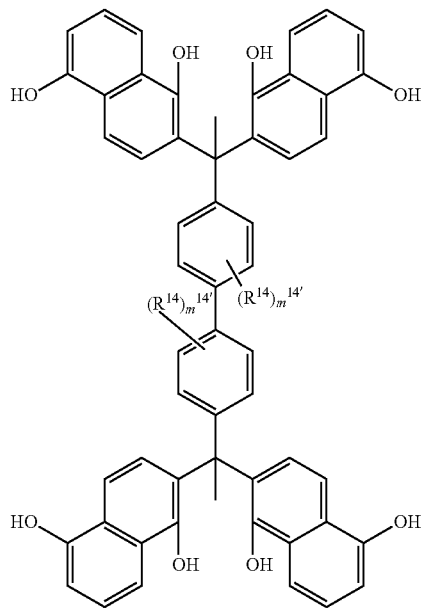
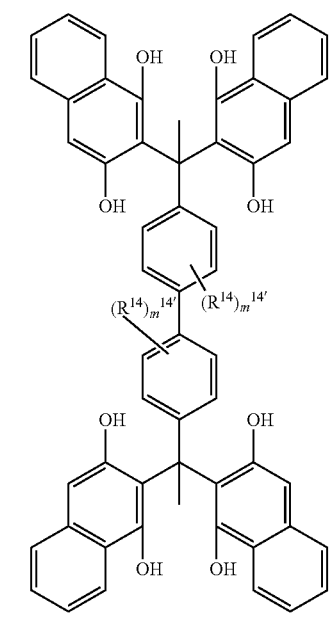

-continued
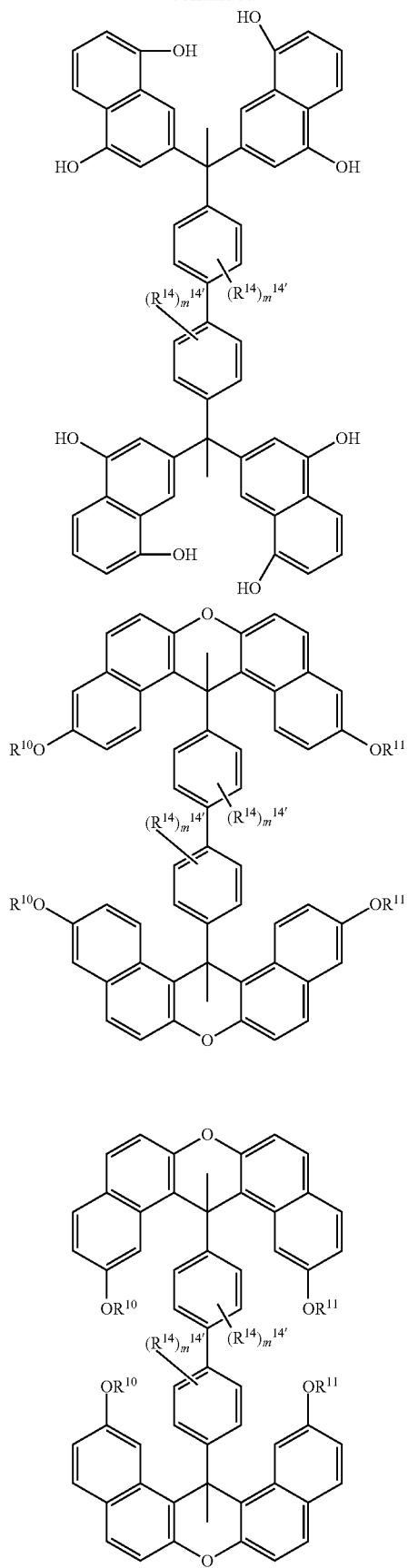
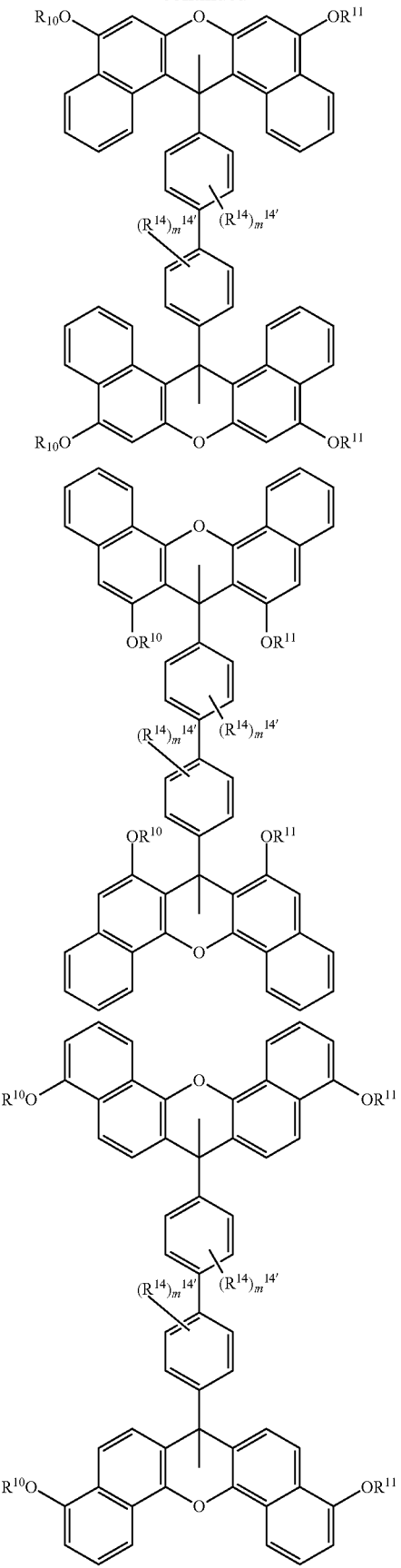

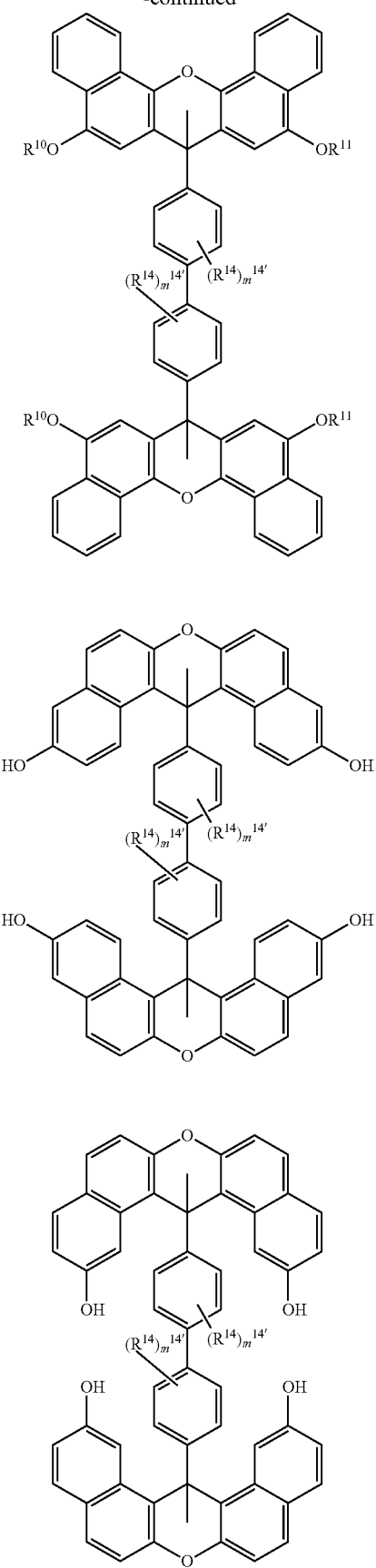
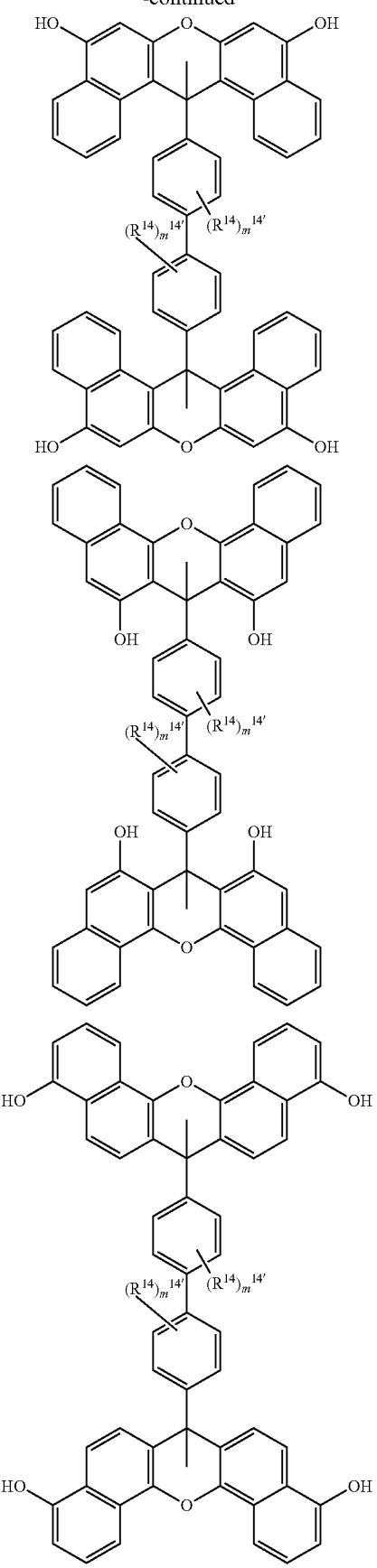

-continued
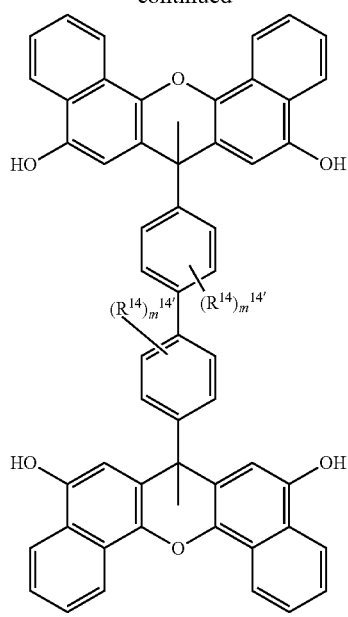
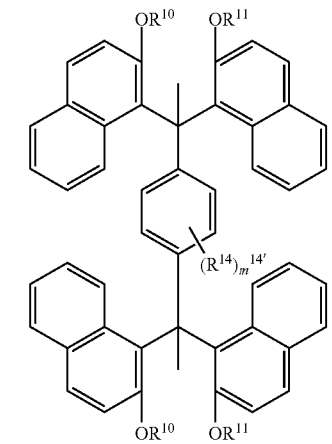
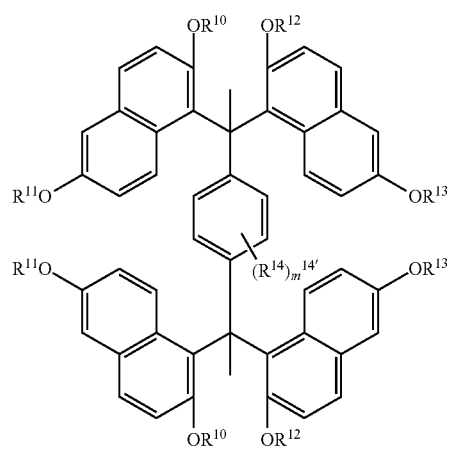
-continued
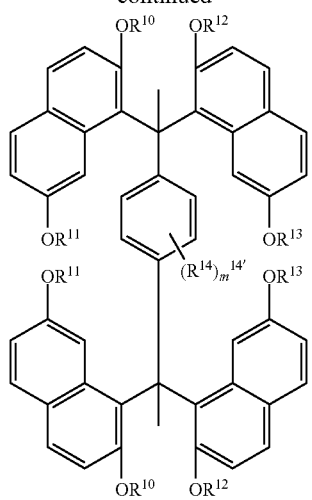
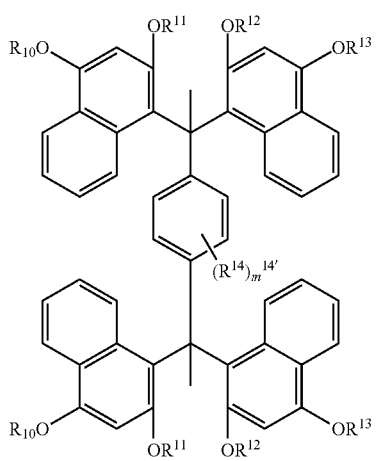
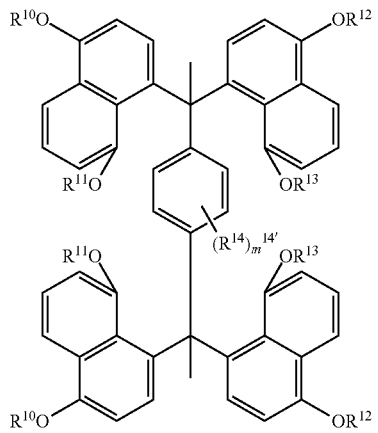

-continued
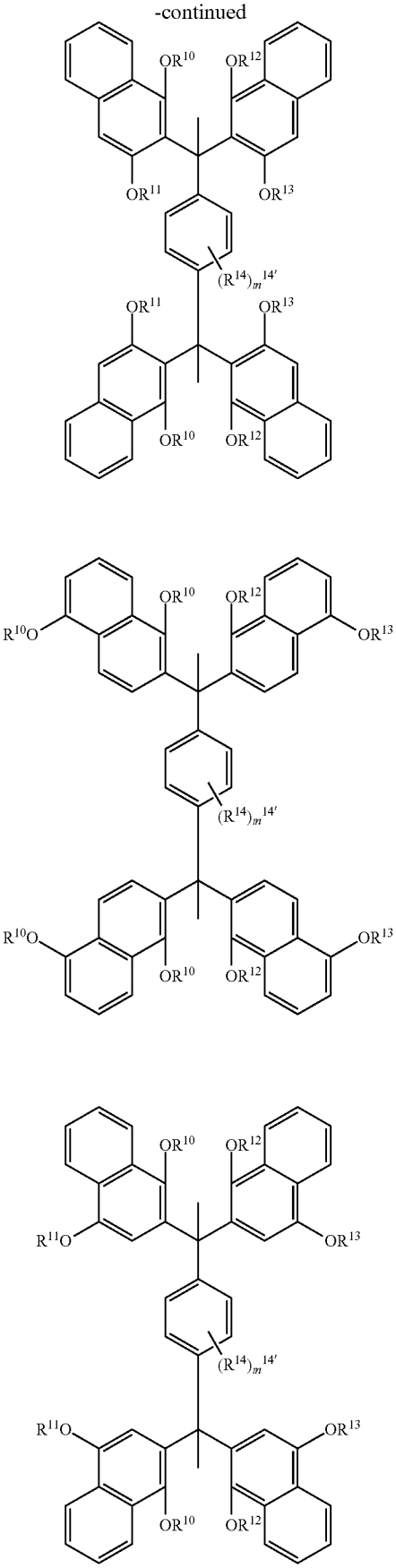
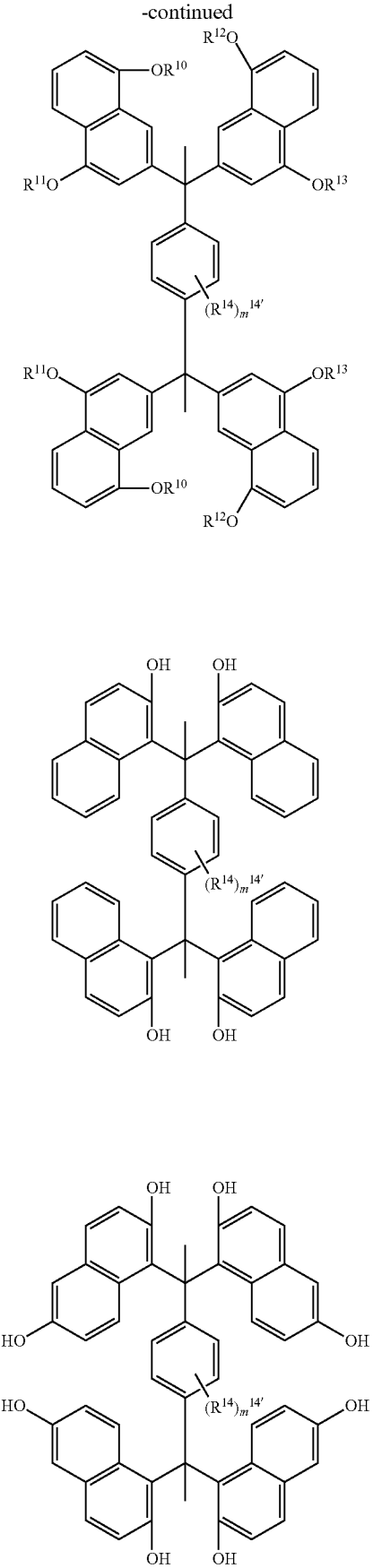

189
-continued
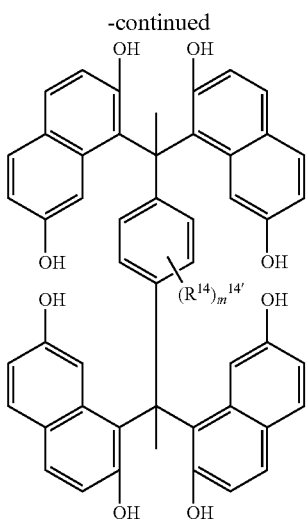
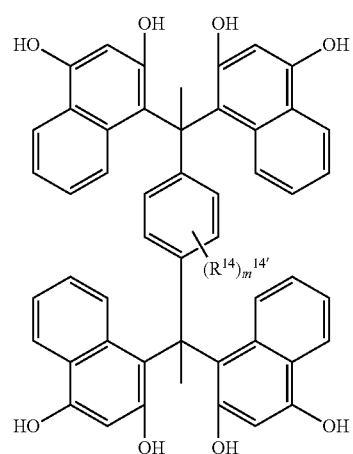
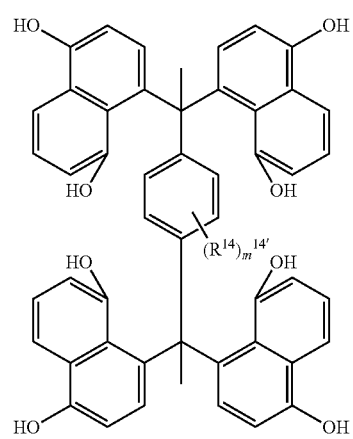
190
-continued
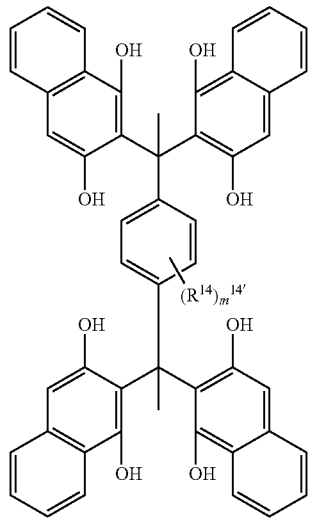
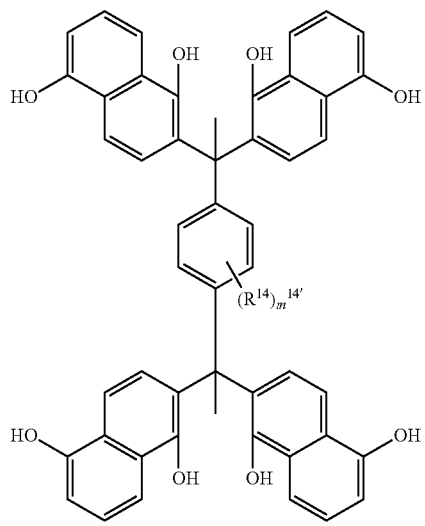
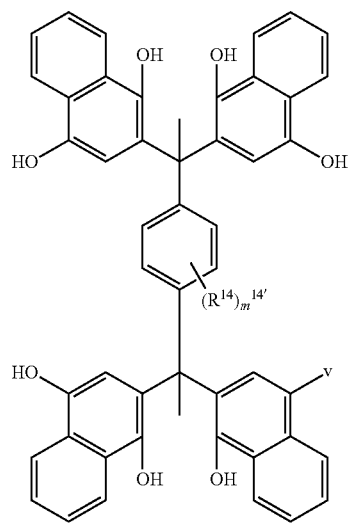

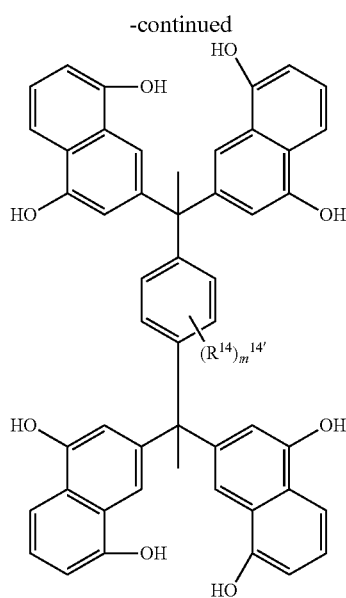
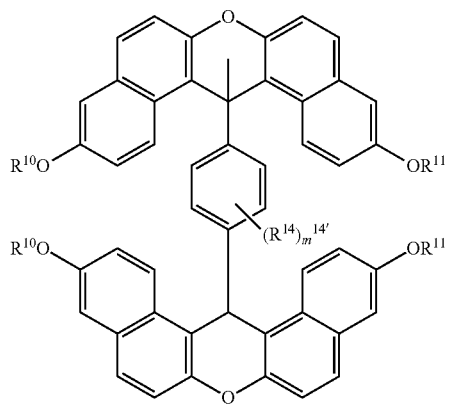
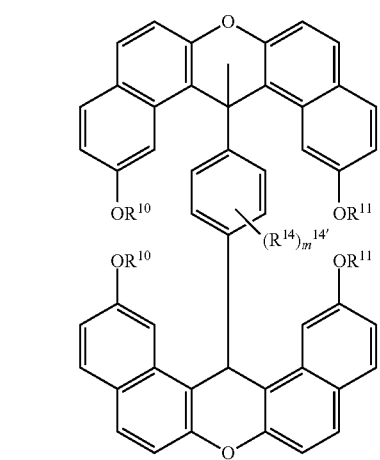
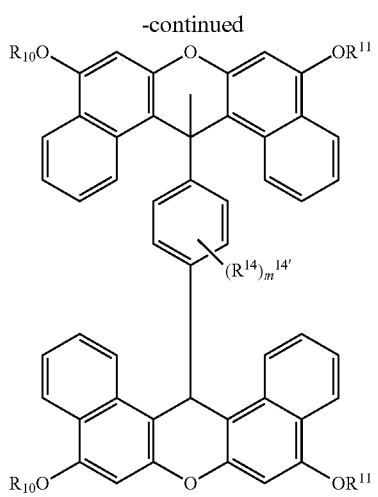
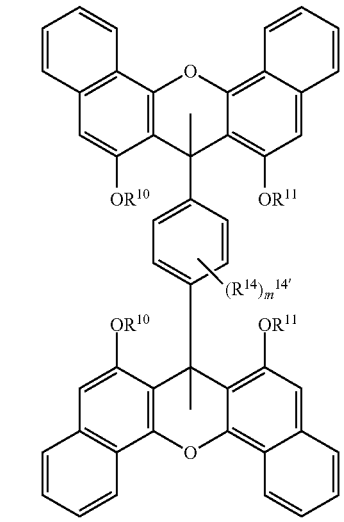
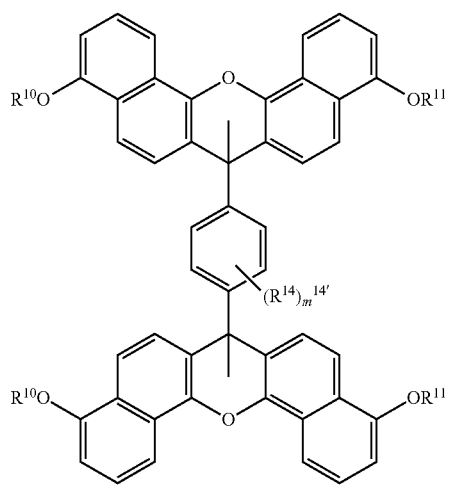

-continued
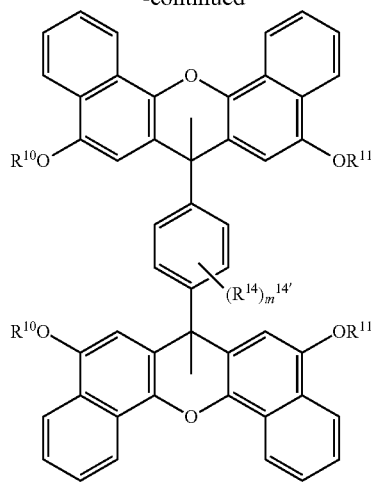
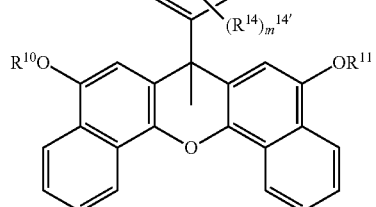
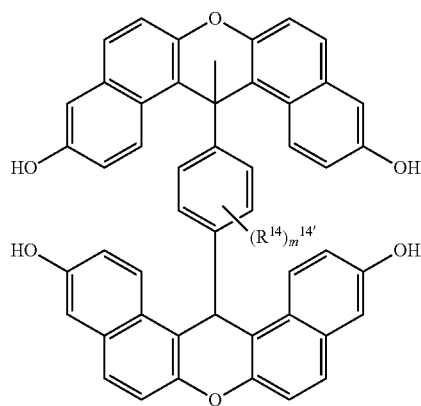
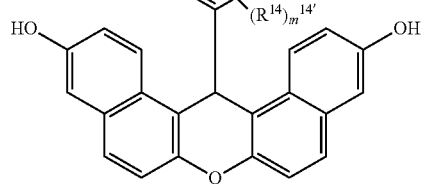
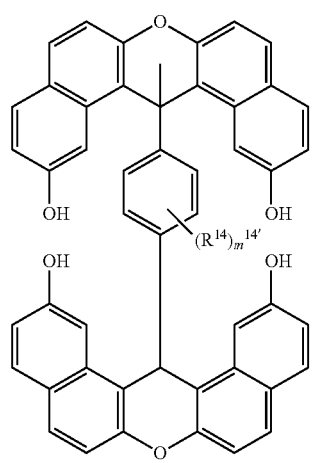
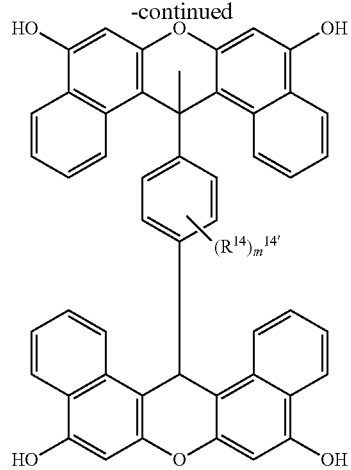
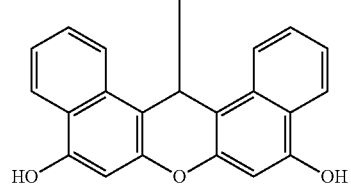
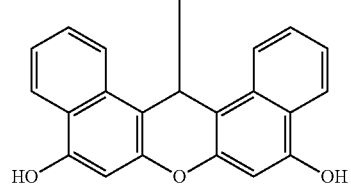
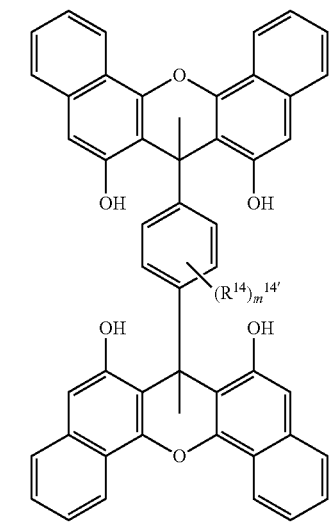
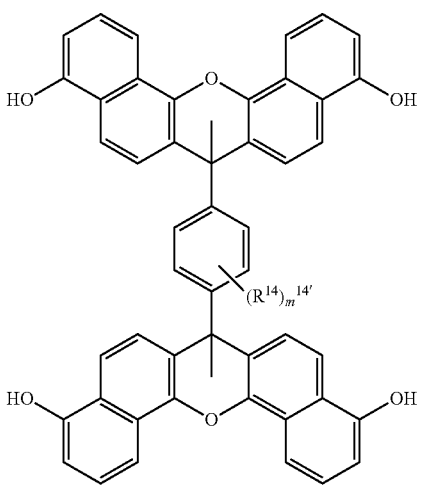

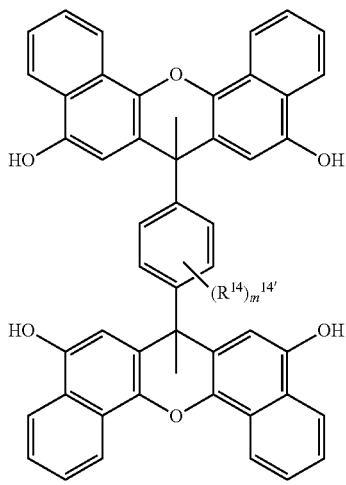

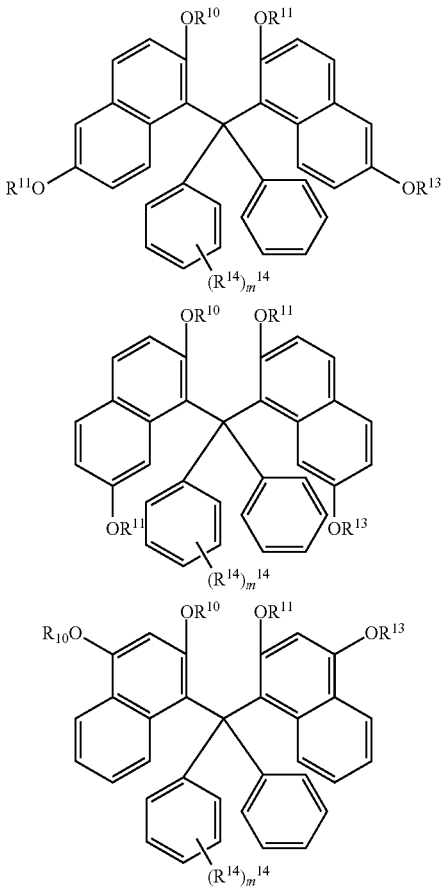

In the above compounds, $R^{10}$ to $R^{13}$ are as defined in the description of the above formula (1-2); each $R^{14}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group; $m^{14'}$ is an integer of 0 to 4.

Examples of $R^{14}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{14}$ listed above includes isomers. For example, a butyl group includes a n-butyl group, an isobutyl group, a sec-butyl group, and a tert-butyl group.

Further examples of the compound represented by the formula (2) include compounds having the following structures.

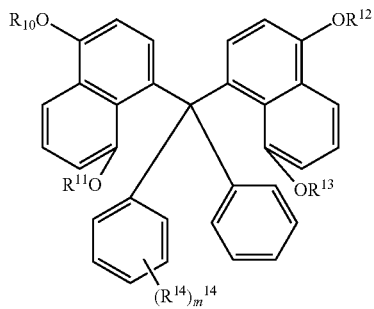

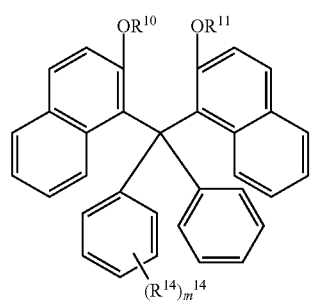

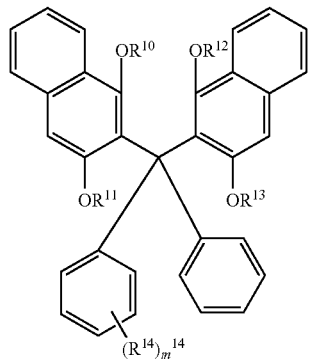

-continued
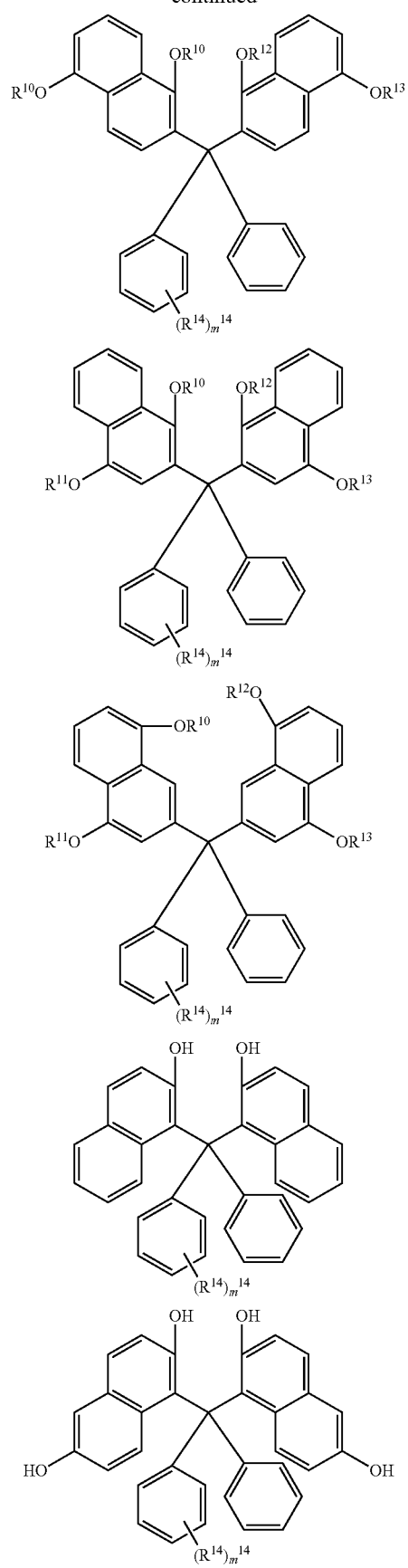
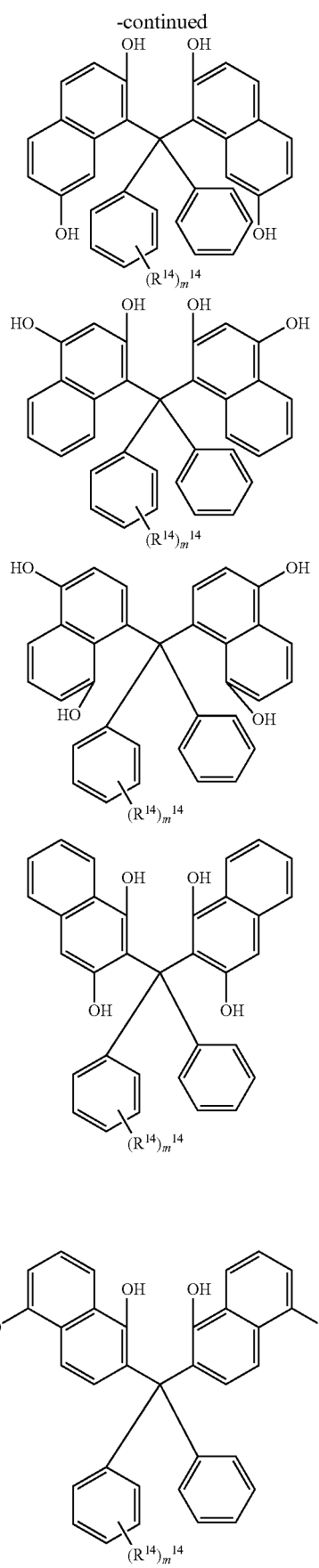

199
-continued
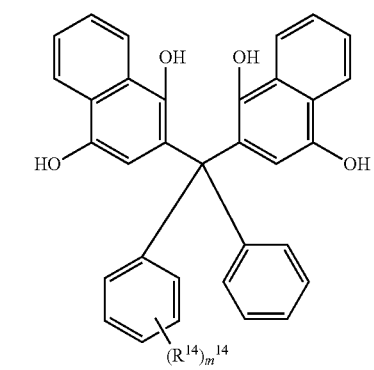
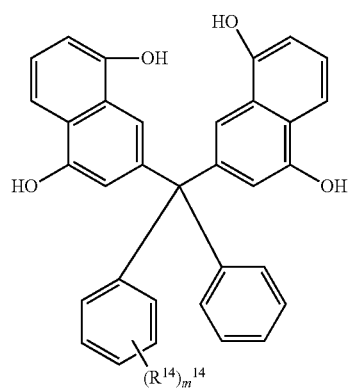
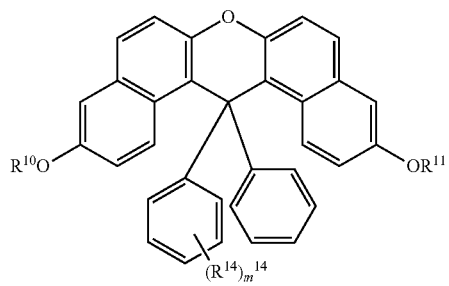
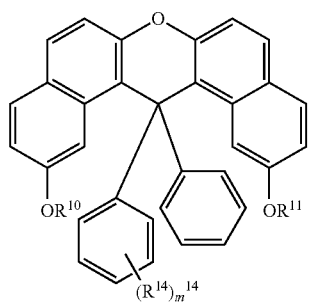
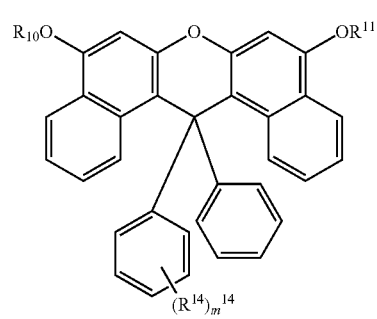
200
-continued
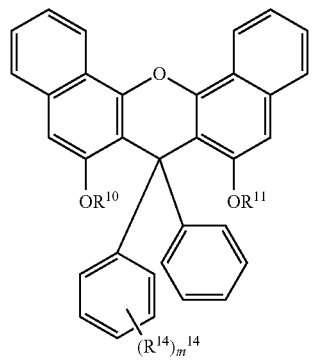
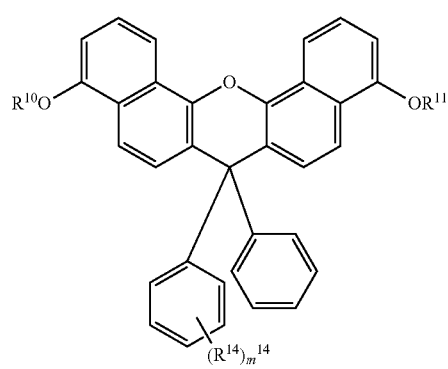
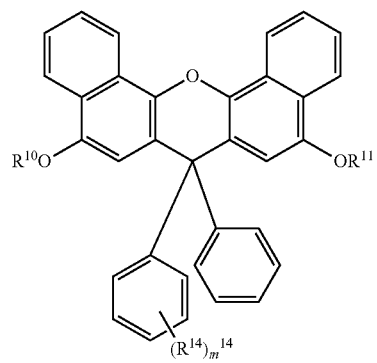
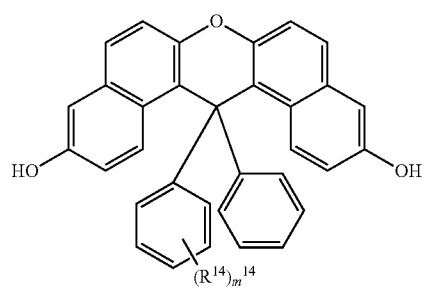
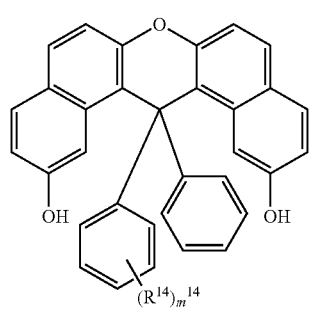

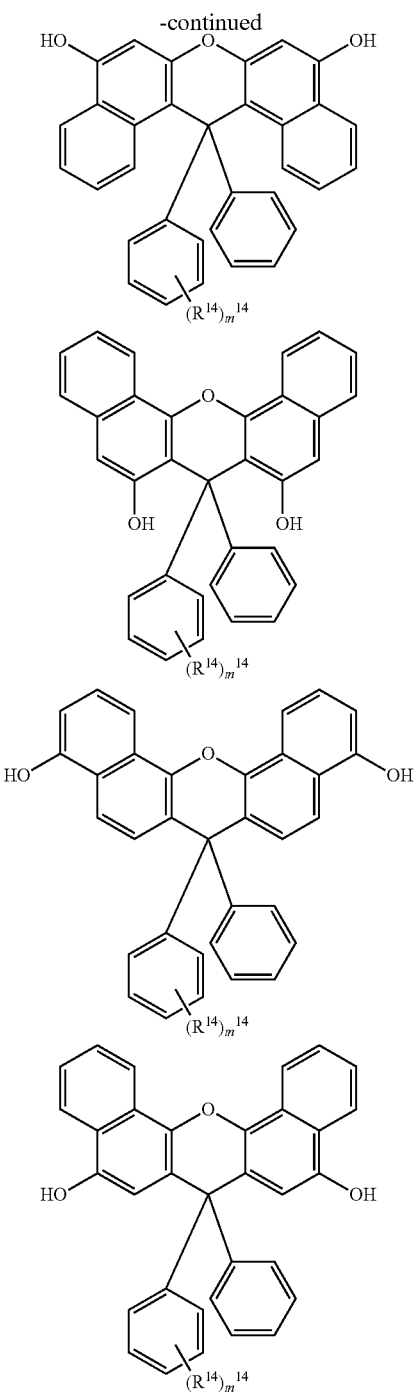

a cyclononyl group, a cyclodecyl group, a cycloundecyl group, a cyclododecyl group, a cyclotriacontyl group, a norbornyl group, an adamantyl group, a phenyl group, a naphthyl group, an anthracene group, a heptacene group, a vinyl group, an allyl group, a triacontenyl group, a methoxy group, an ethoxy group, a triacontyloxy group, a fluorine atom, a chlorine atom, a bromine atom, an iodine atom, and a thiol group.

$R^{14}$ listed above includes isomers. For example, a butyl group includes a n-butyl group, an isobutyl group, a sec-butyl group, and a tert-butyl group.

Further examples of the compound represented by the formula (2) include compounds having the following structures.

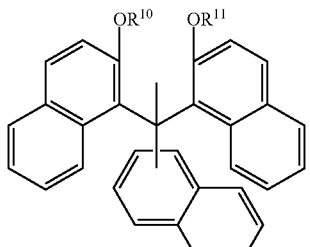

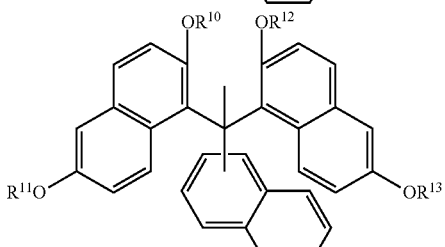

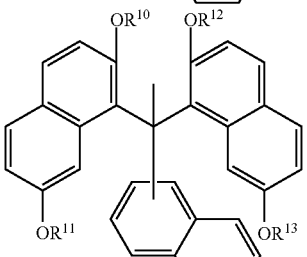

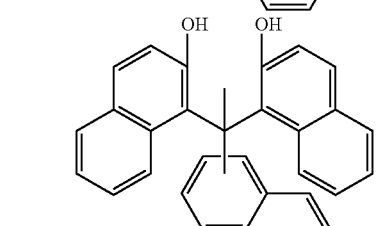

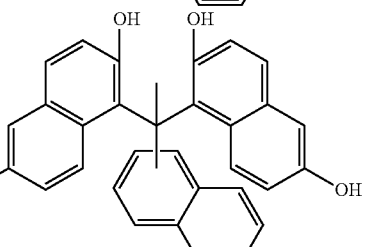

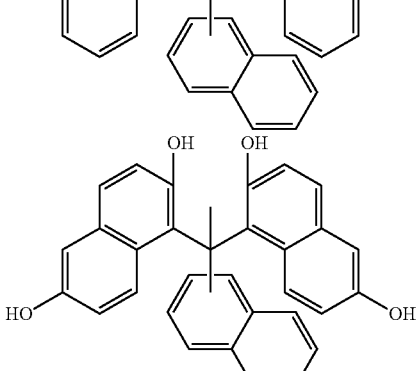

In the above compounds, $R^{10}$ to $R^{13}$ are as defined in the description of the above formula (1-2); each $R^{14}$ is independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group; and $m^{14}$ is an integer of 0 to 5.

Examples of $R^{14}$ include a methyl group, an ethyl group, a propyl group, a butyl group, a pentyl group, a hexyl group, a heptyl group, an octyl group, a nonyl group, a decyl group, an undecyl group, a dodecyl group, a triacontyl group, a cyclopropyl group, a cyclobutyl group, a cyclopentyl group, a cyclohexyl group, a cycloheptyl group, a cyclooctyl group,

203
-continued
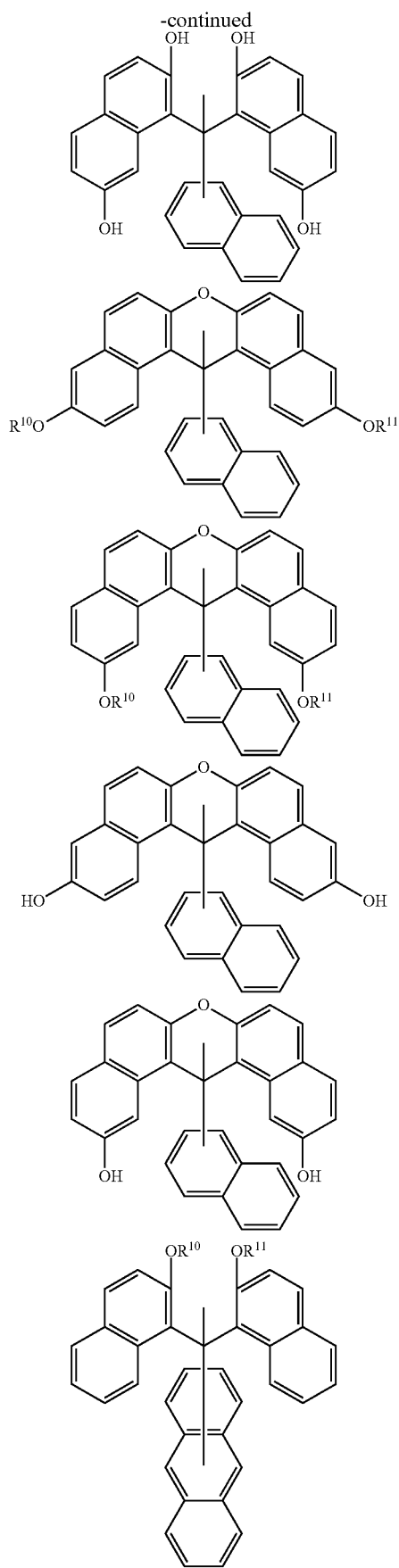
204
-continued
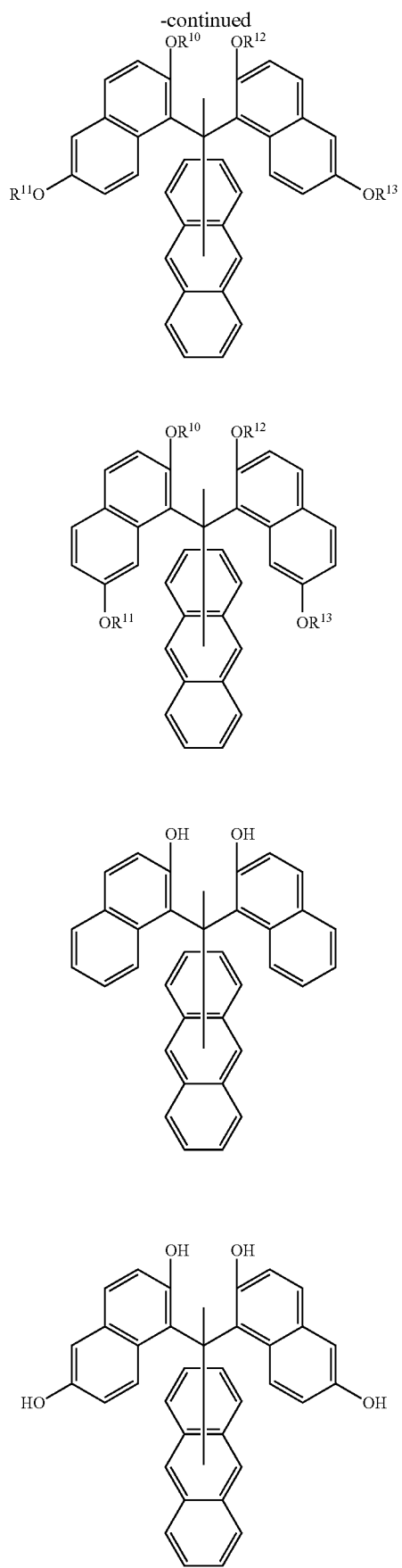

205
-continued
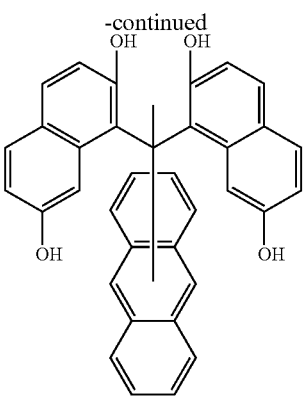
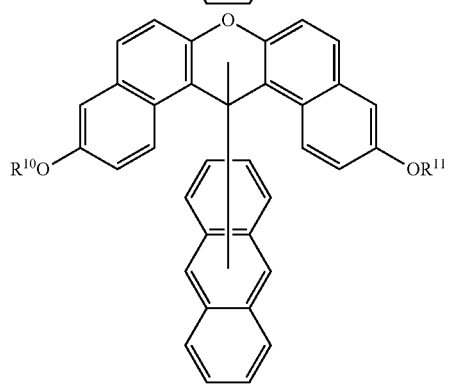
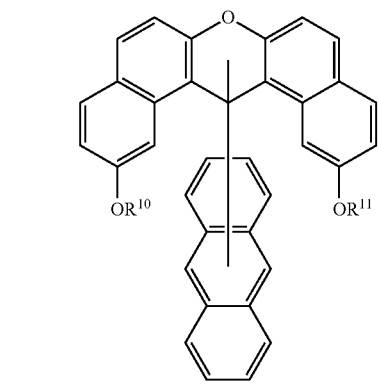
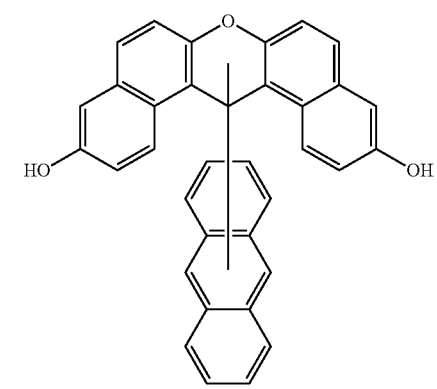
206
-continued
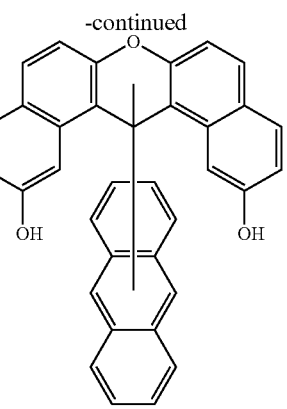
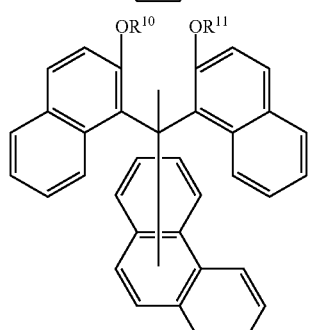
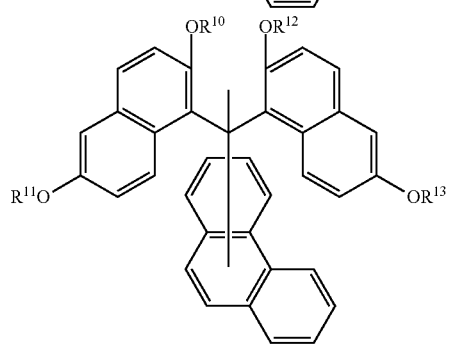
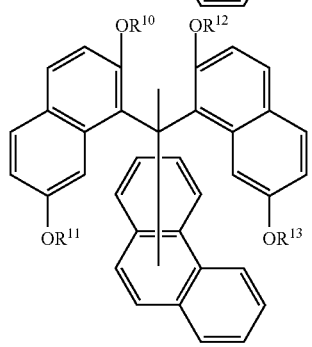
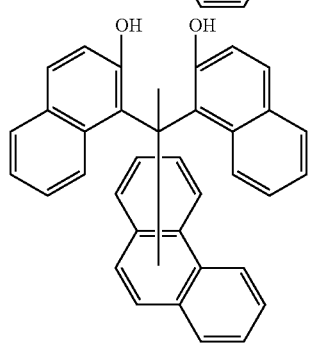

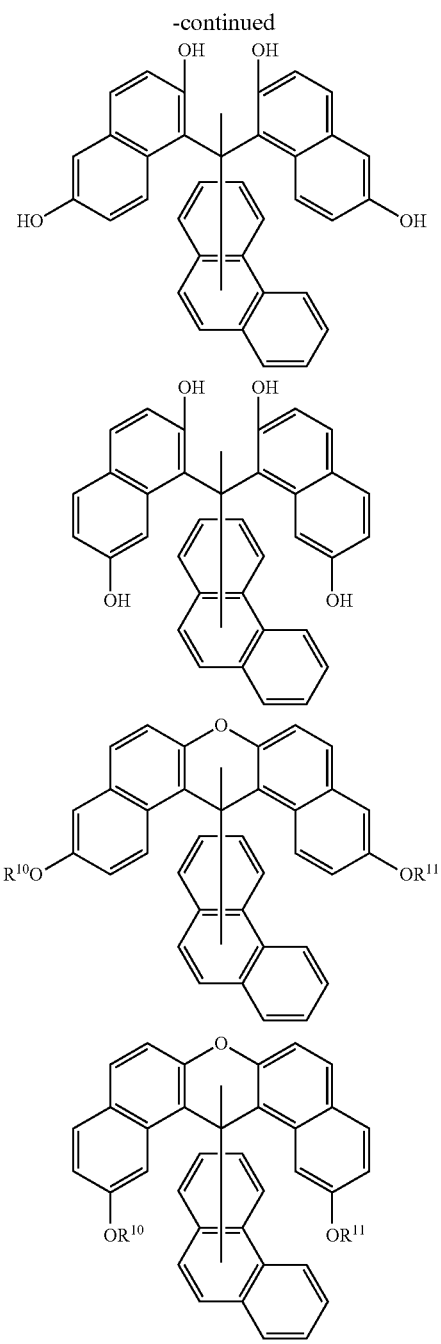
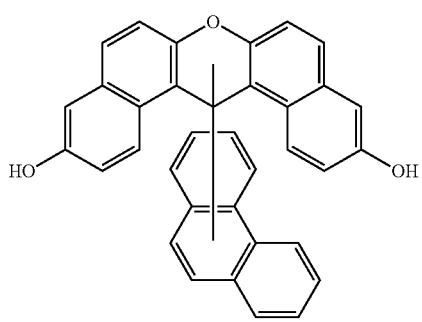
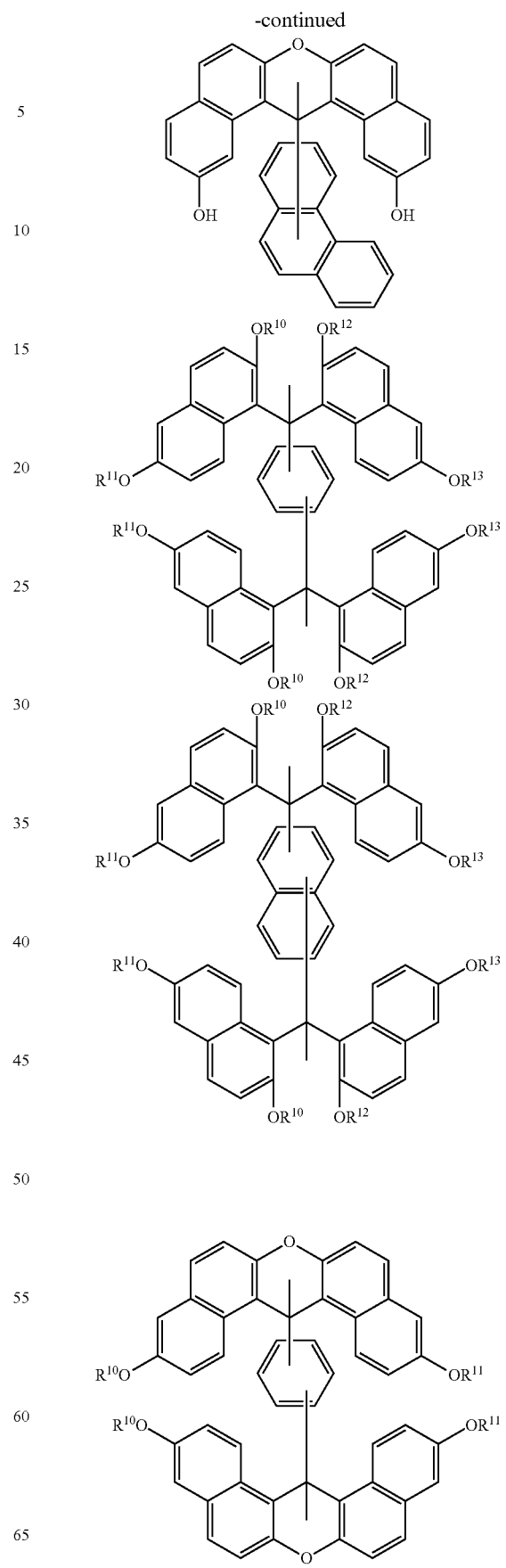

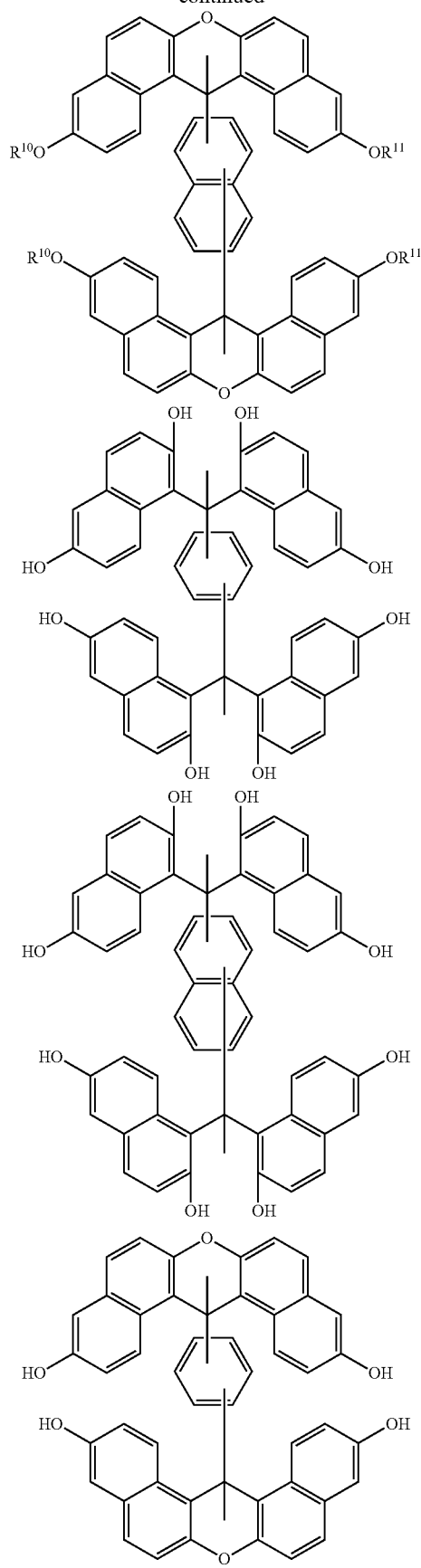
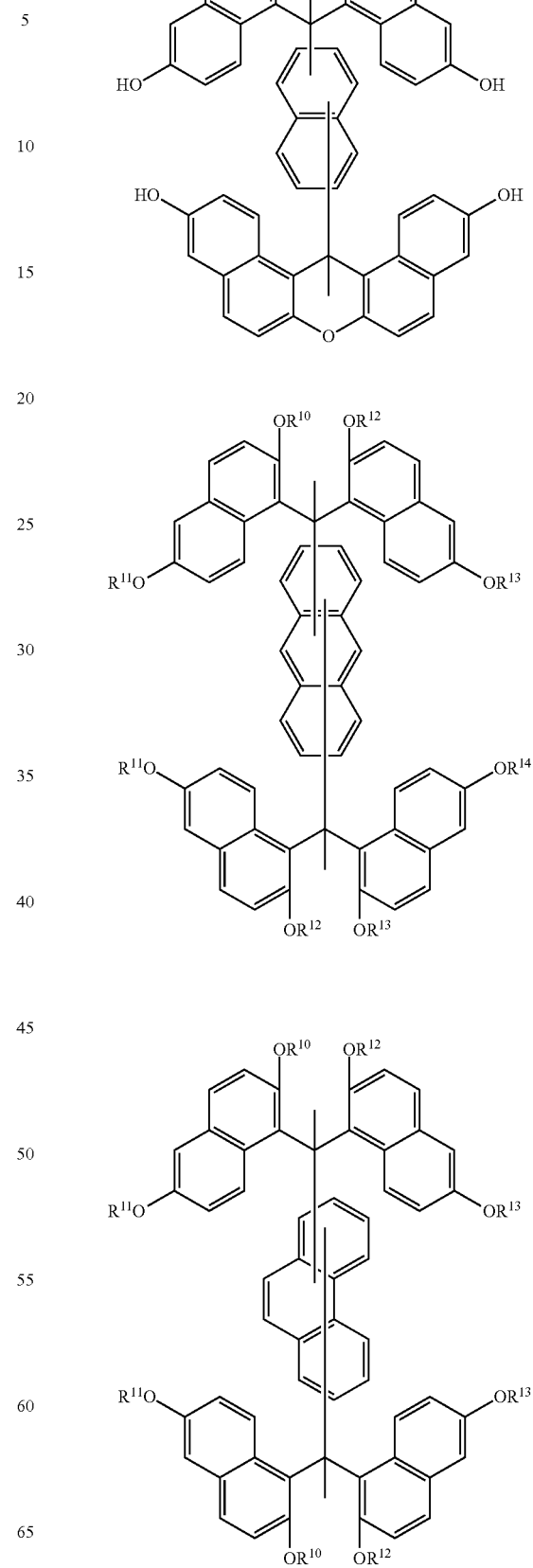

211
-continued
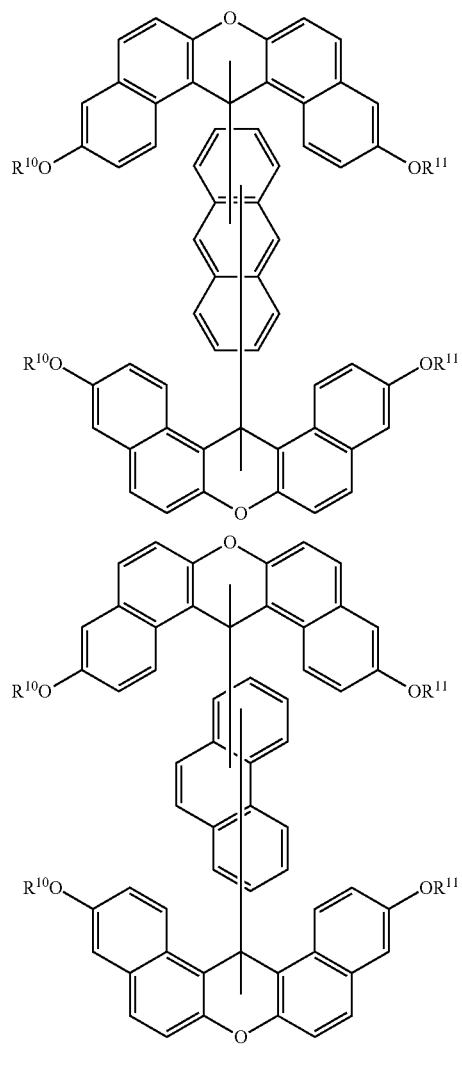
212
-continued
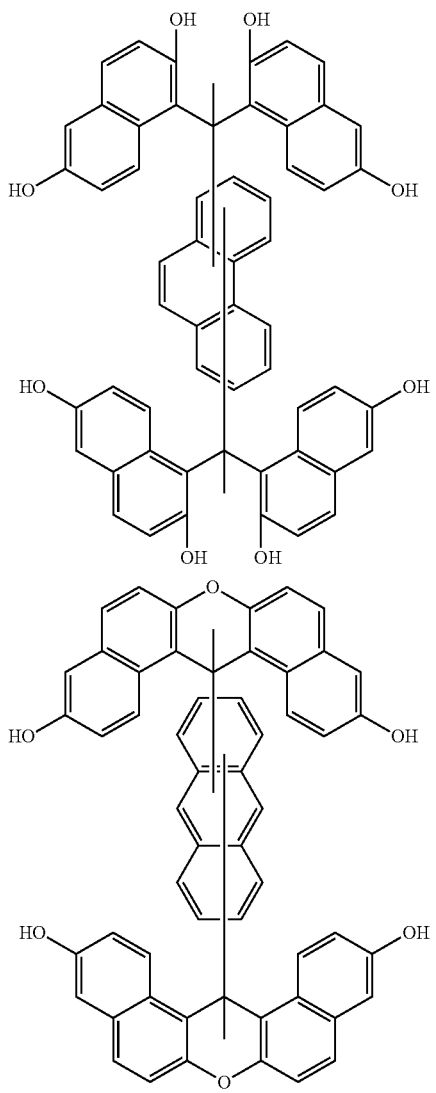
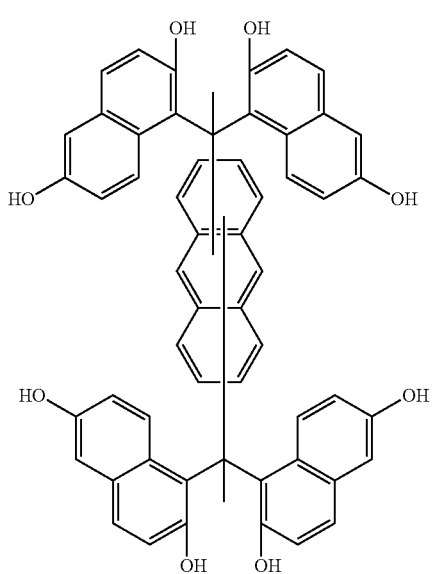
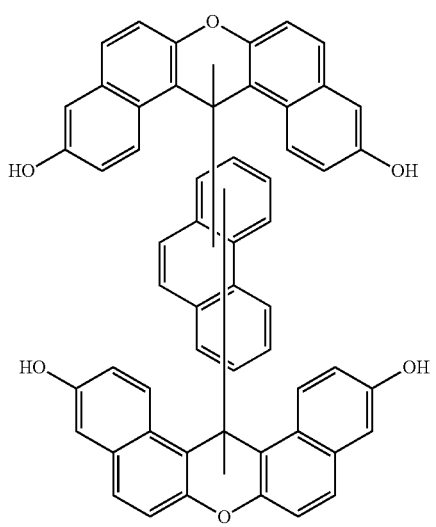

213
-continued
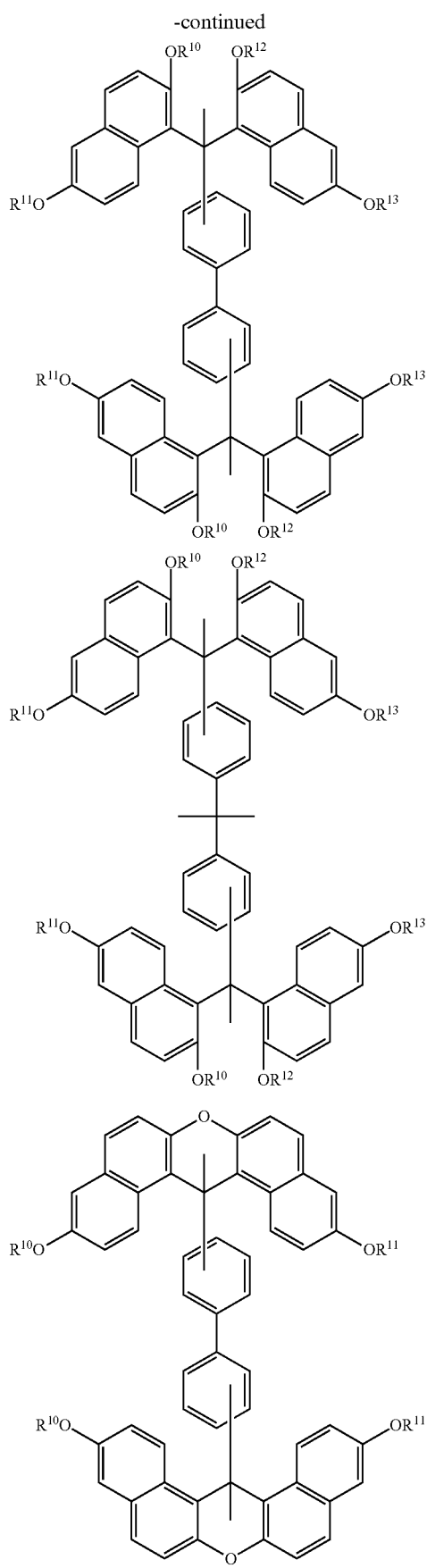
214
-continued
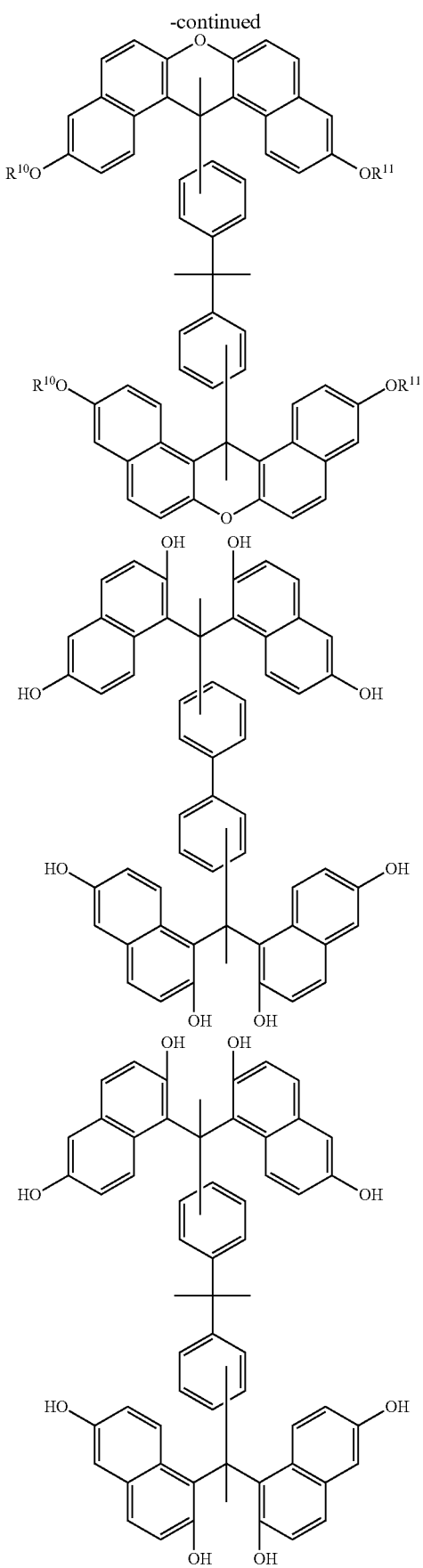

215
-continued
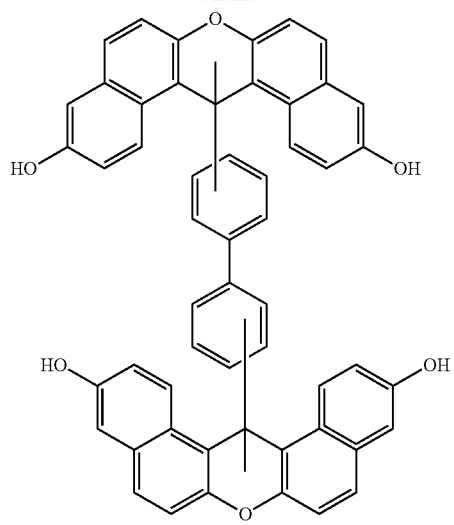
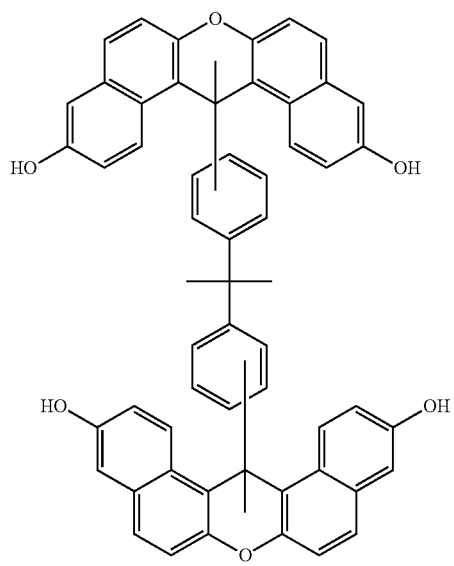
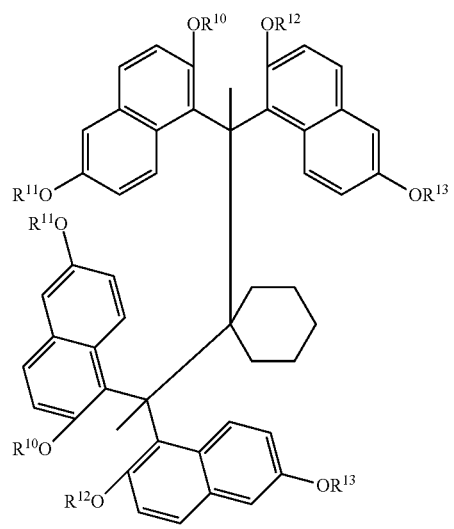
216
-continued
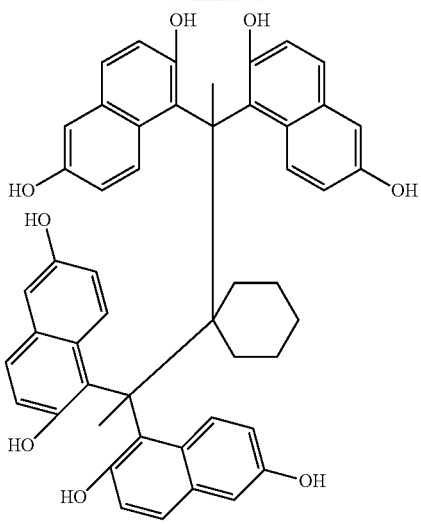
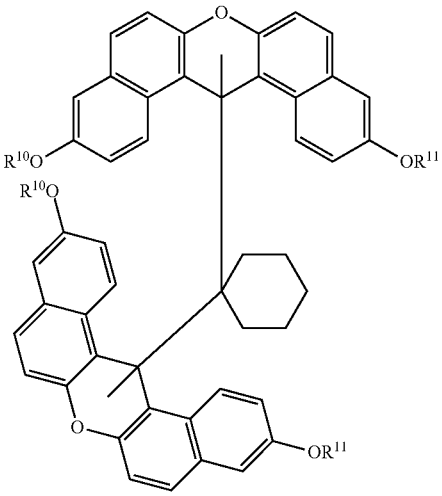
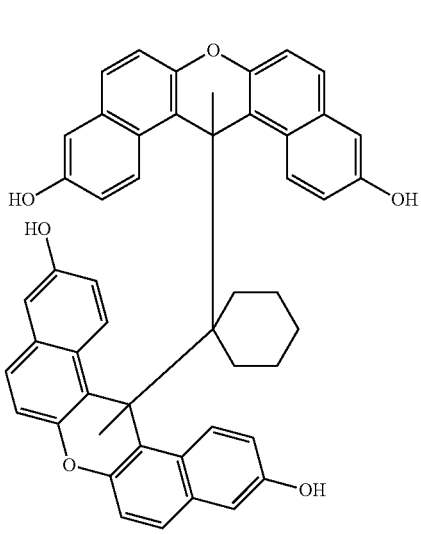

217
-continued
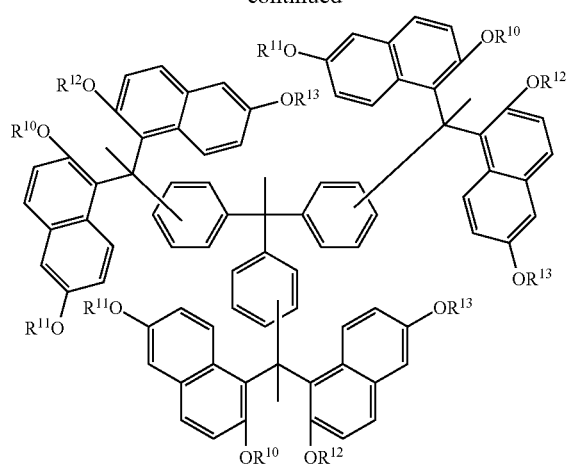
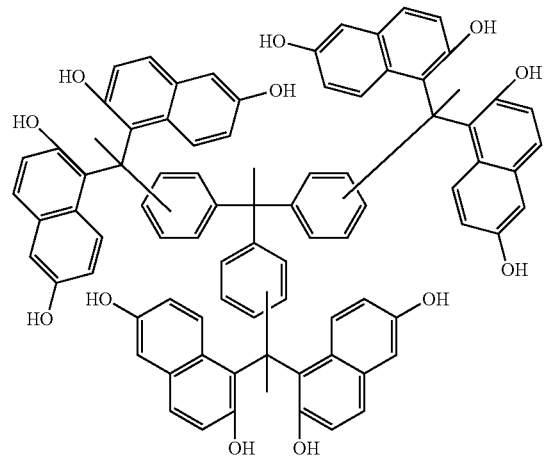
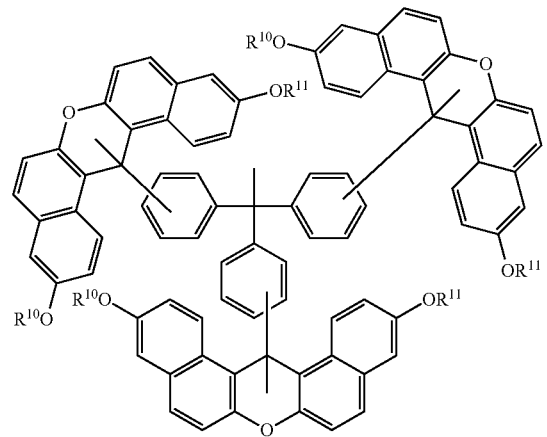
218
-continued
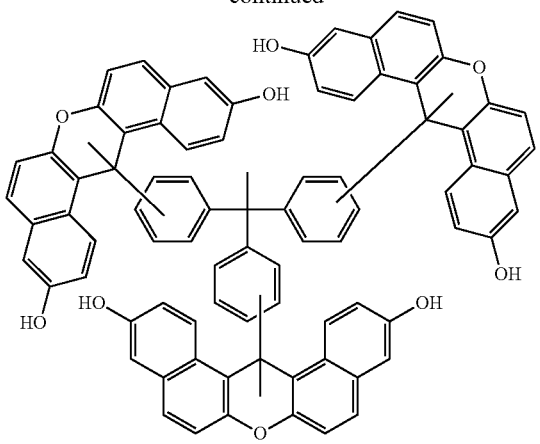
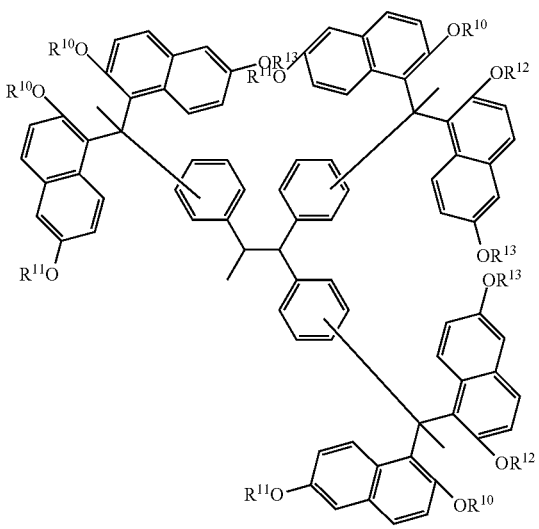
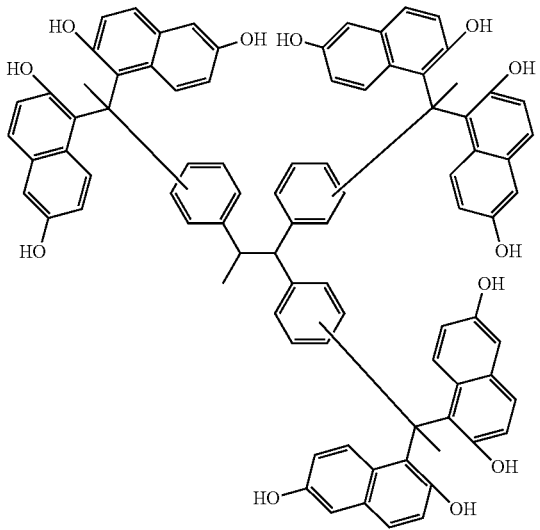

-continued
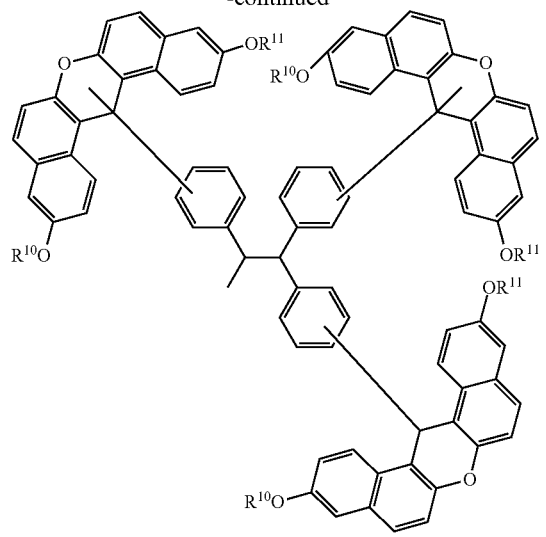
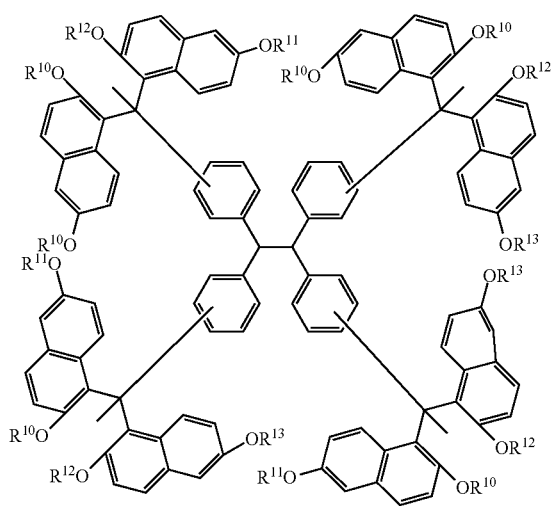
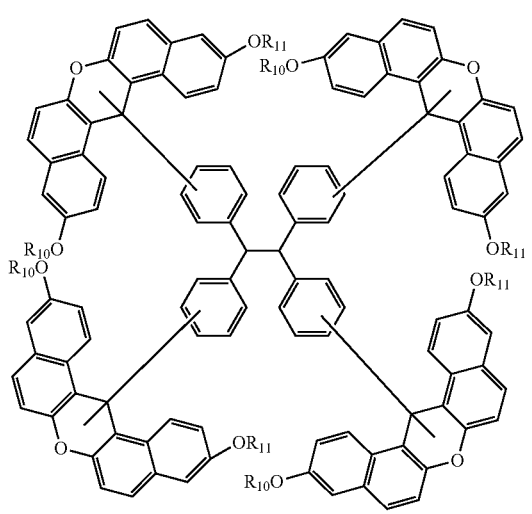
-continued
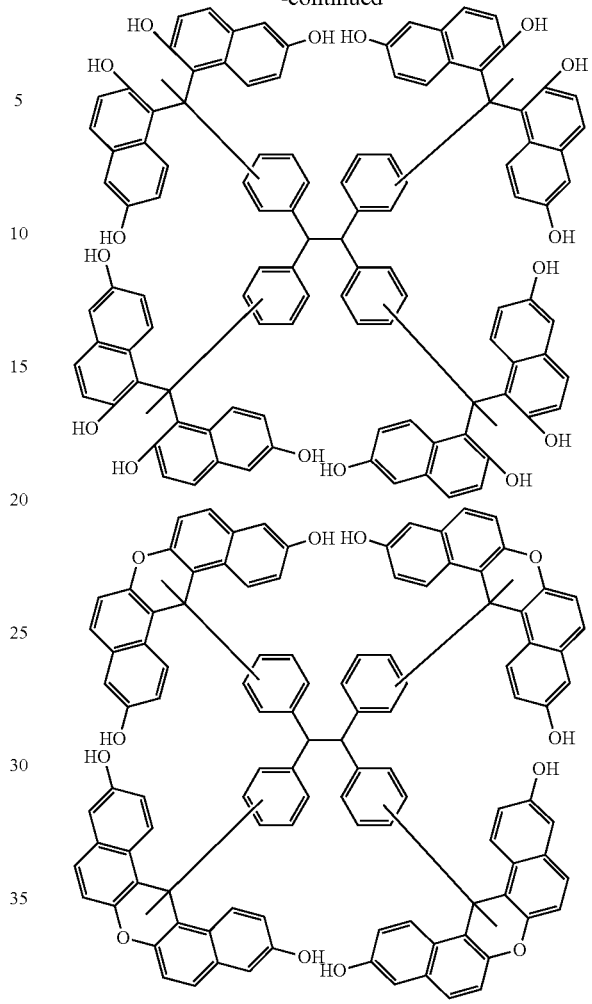
In the above compounds, $R^{10}$ to $R^{13}$ are as defined in the description of the above formula (1-2).
Examples of the compound represented by the formula (2) also include compounds having the following structures.
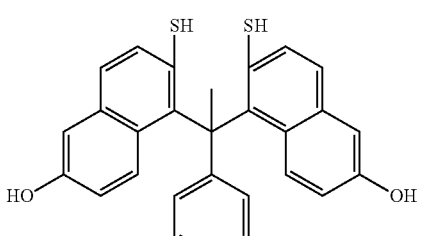
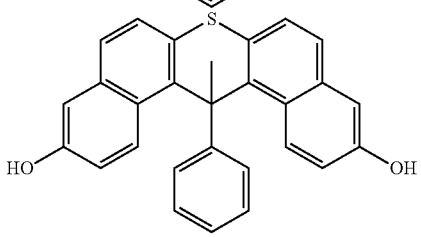
The above compounds preferably have a dibenzoxanthene skeleton from the viewpoint of heat resistance.

The compound represented by the formula (2) is still more preferably a compound represented by any of the following formulas from the viewpoint of the availability of raw materials.
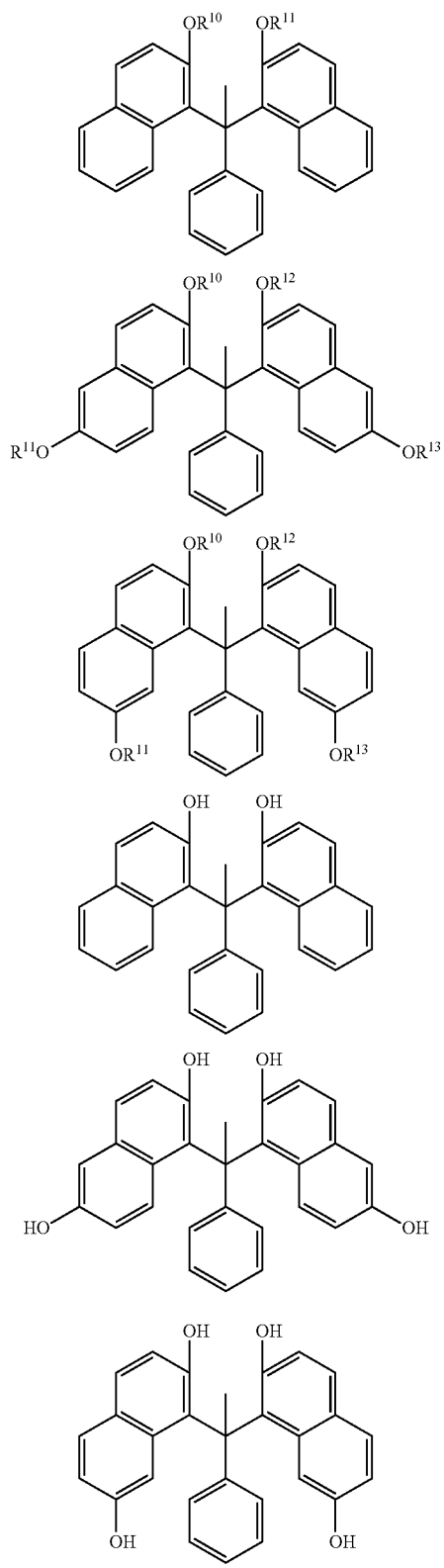
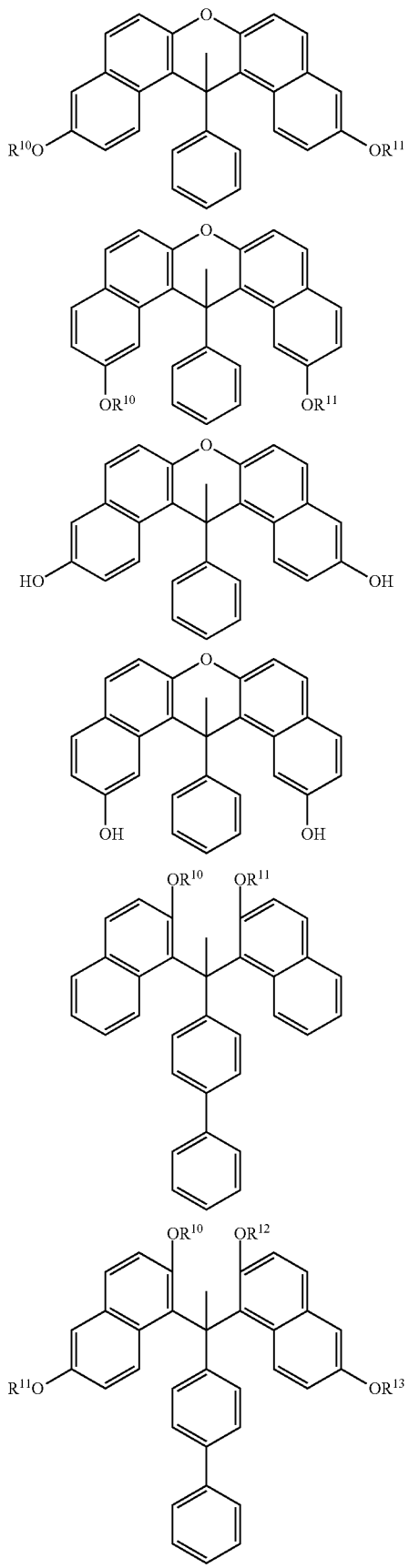

223
-continued
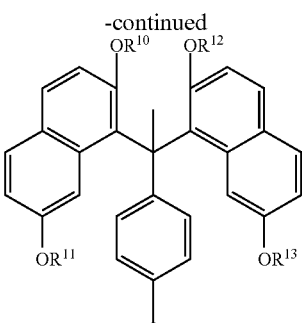
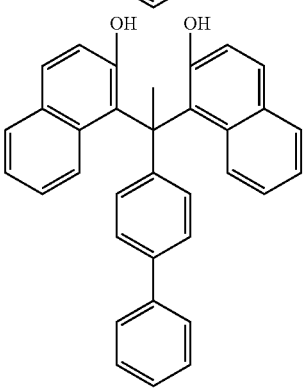
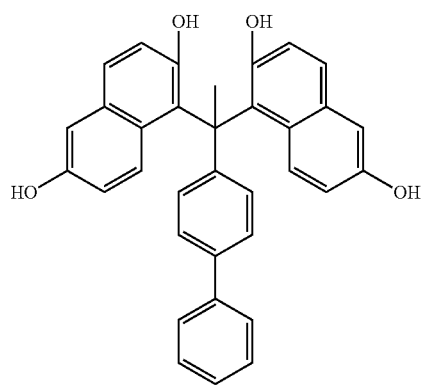
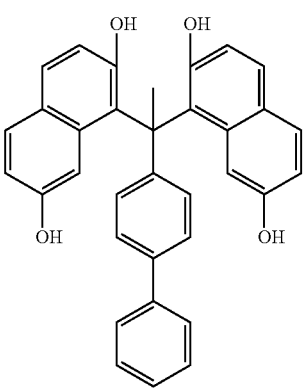
224
-continued
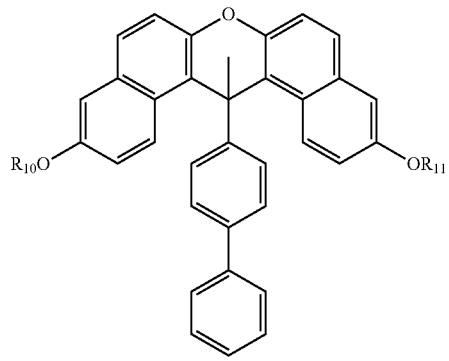
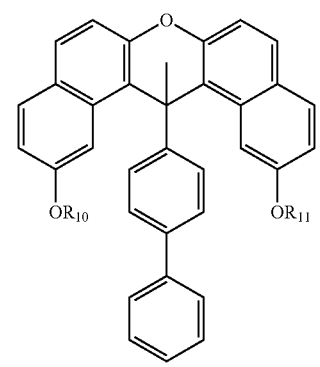
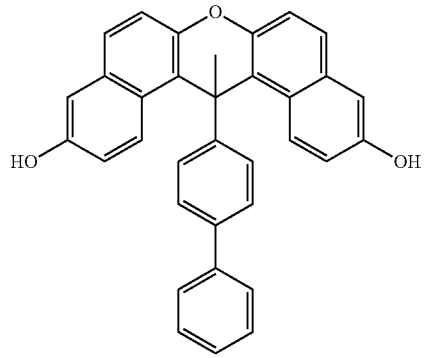
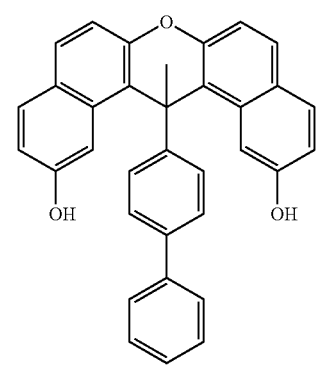

-continued
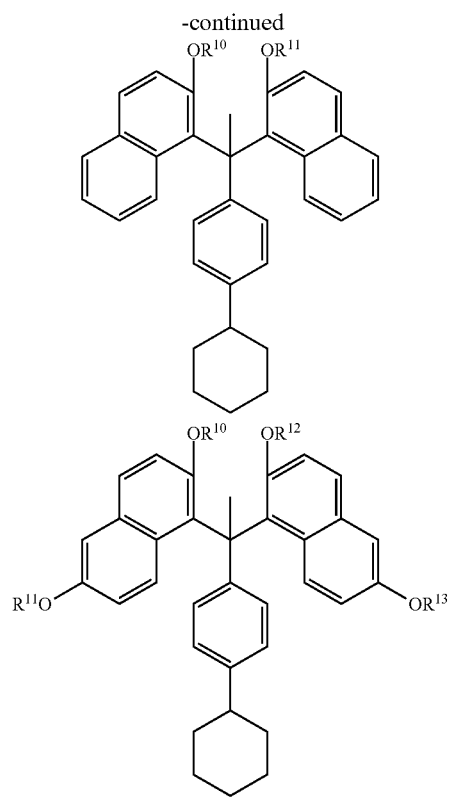
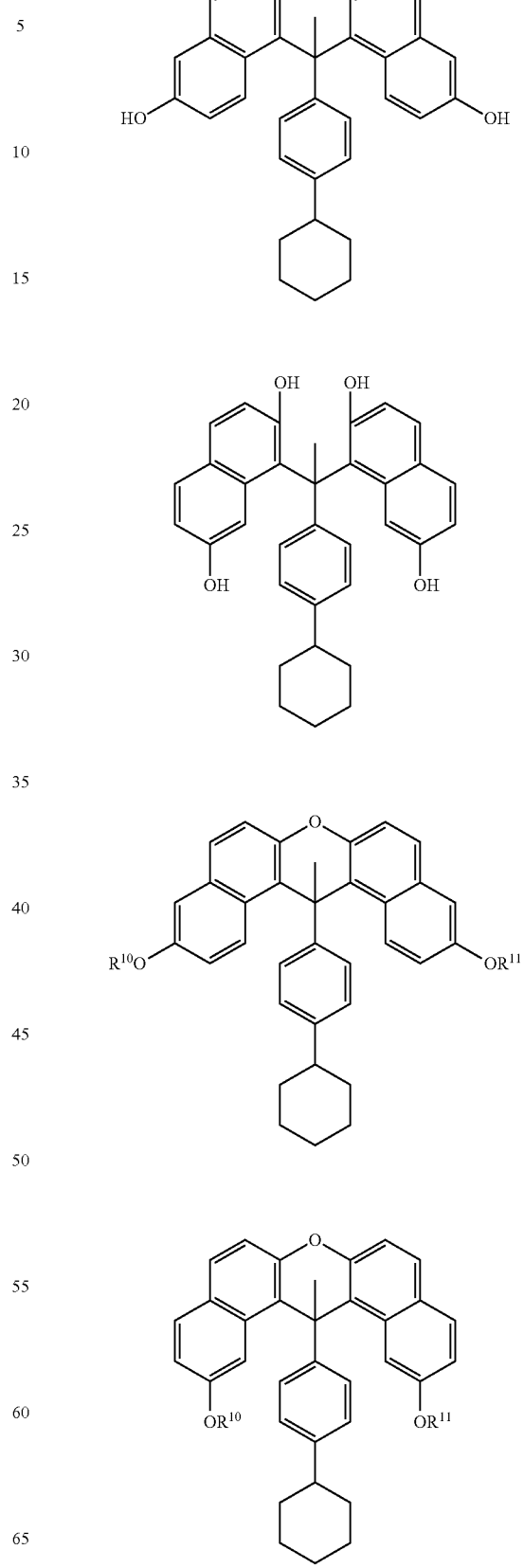

227
-continued
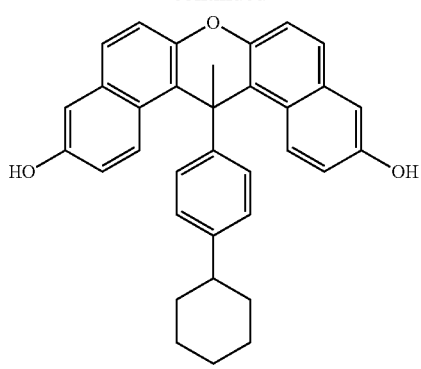
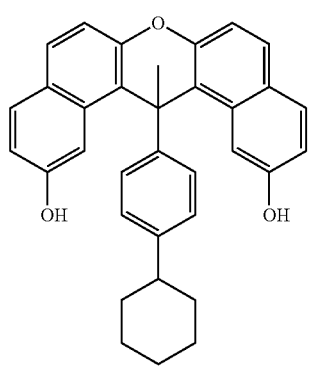
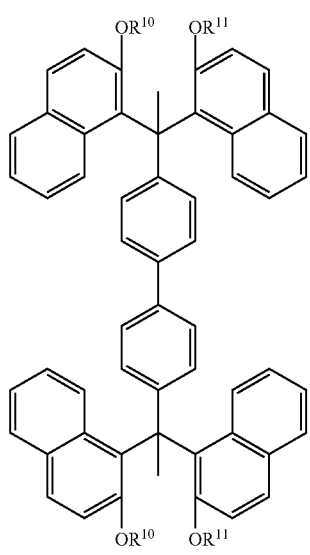
228
-continued
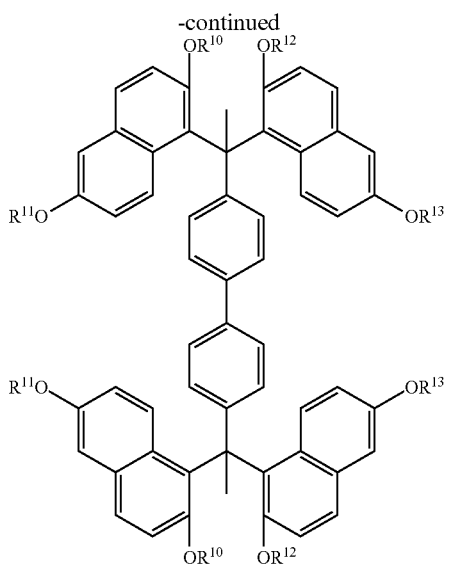
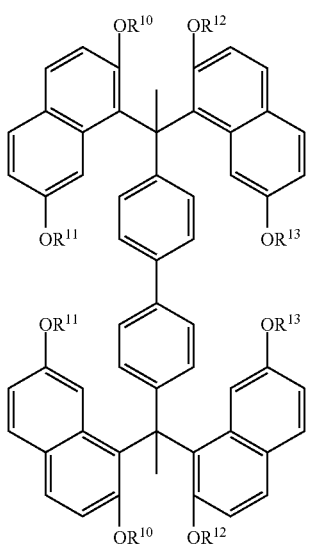
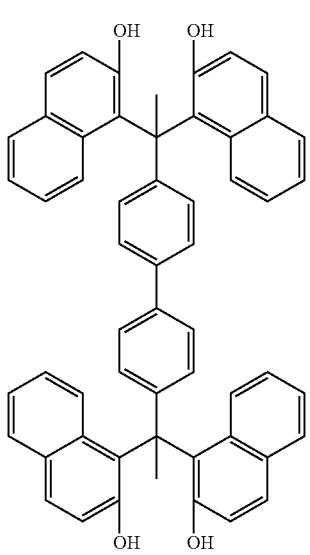

-continued
229
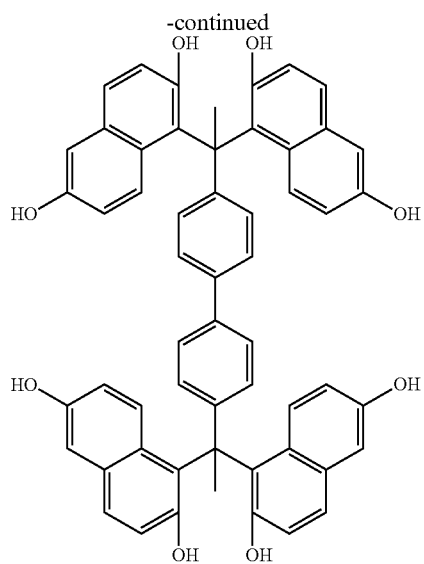
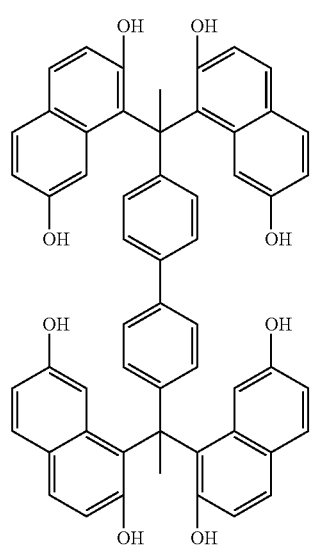
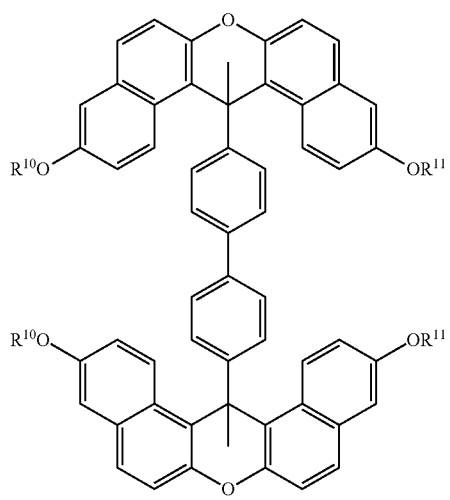
-continued
230
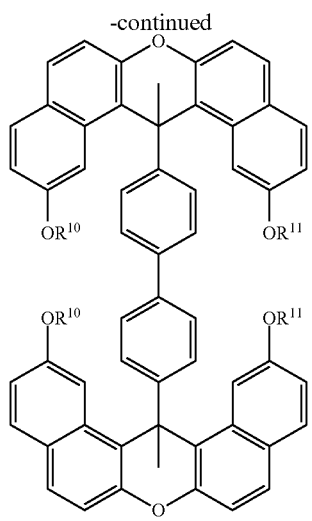
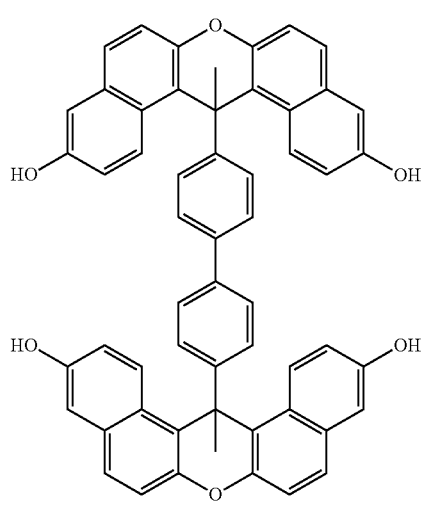
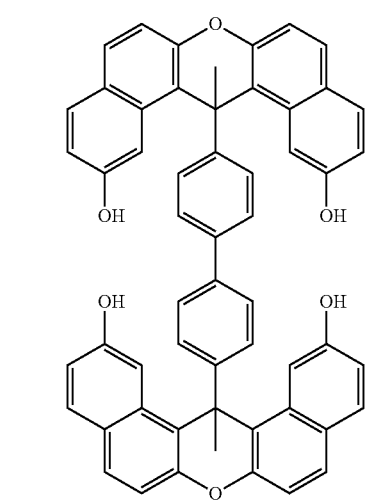

-continued
231
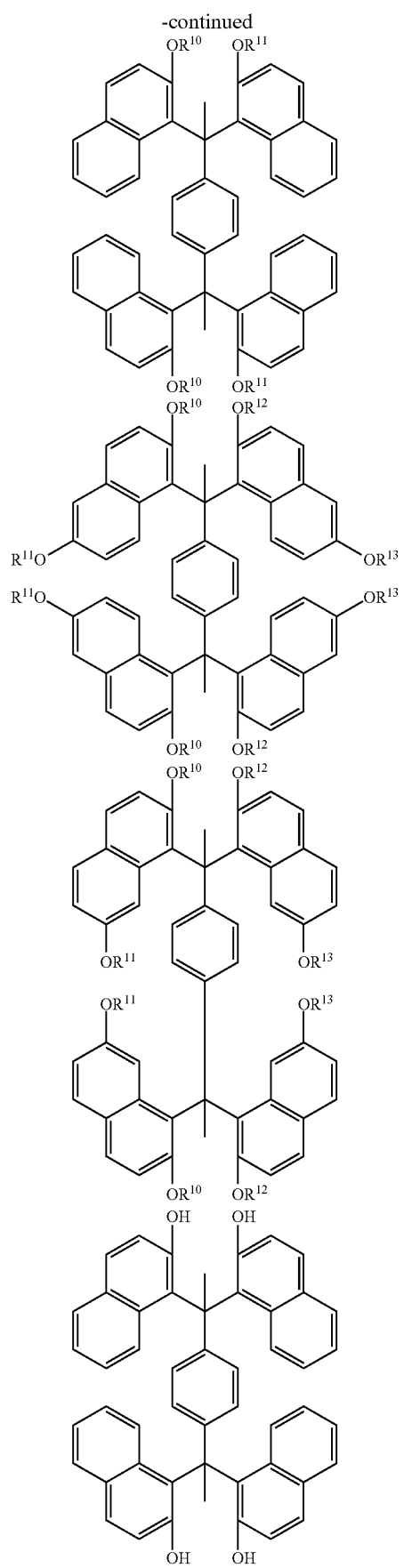
232
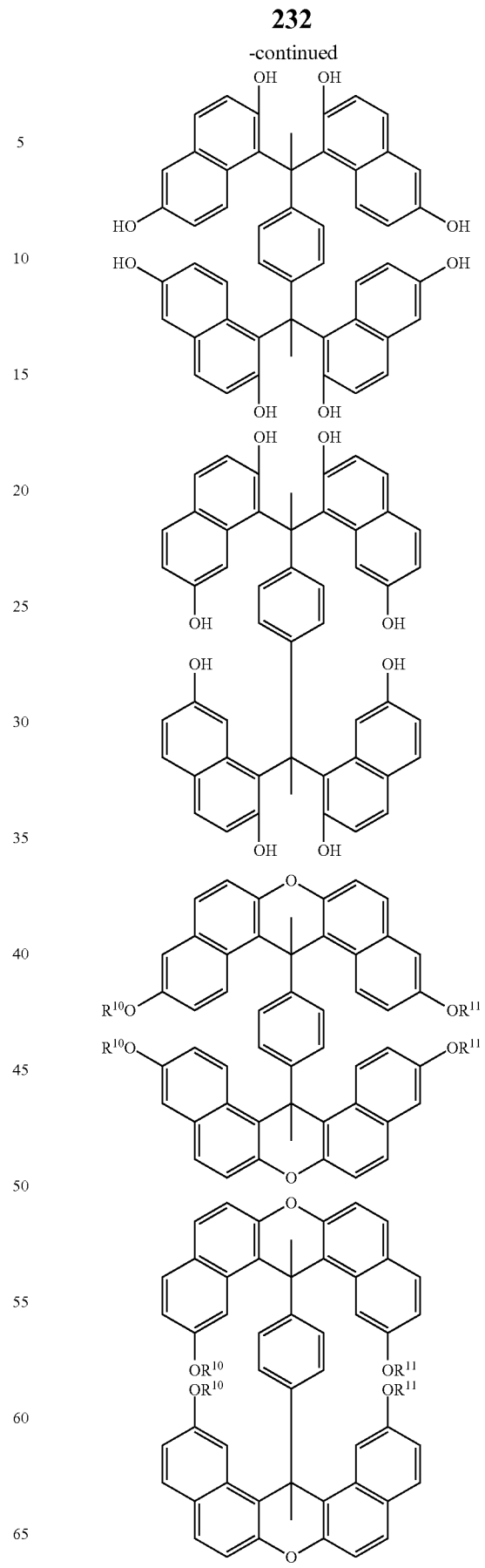

233
-continued
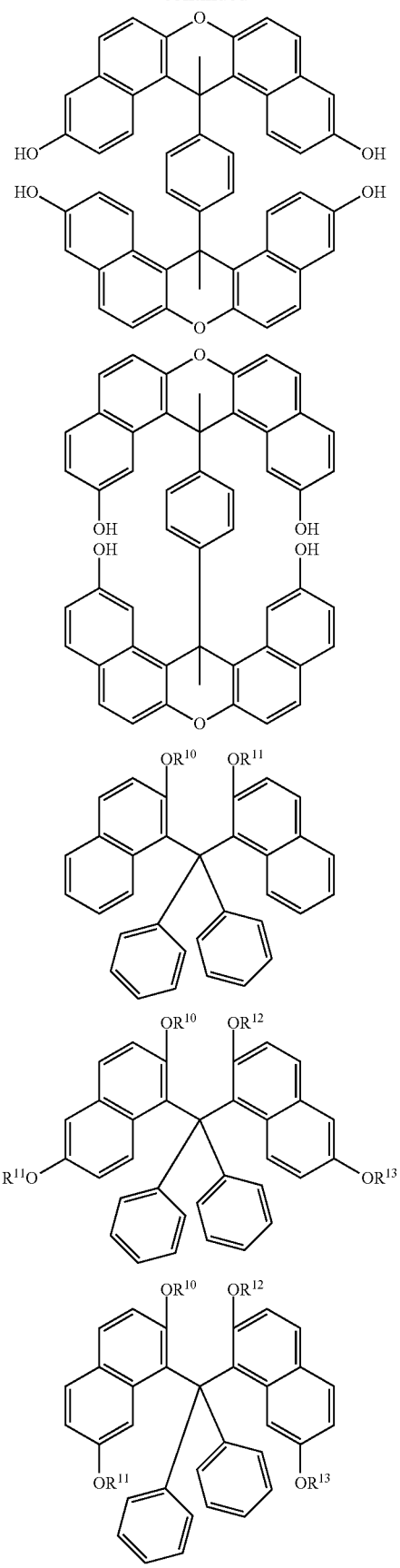
234
-continued
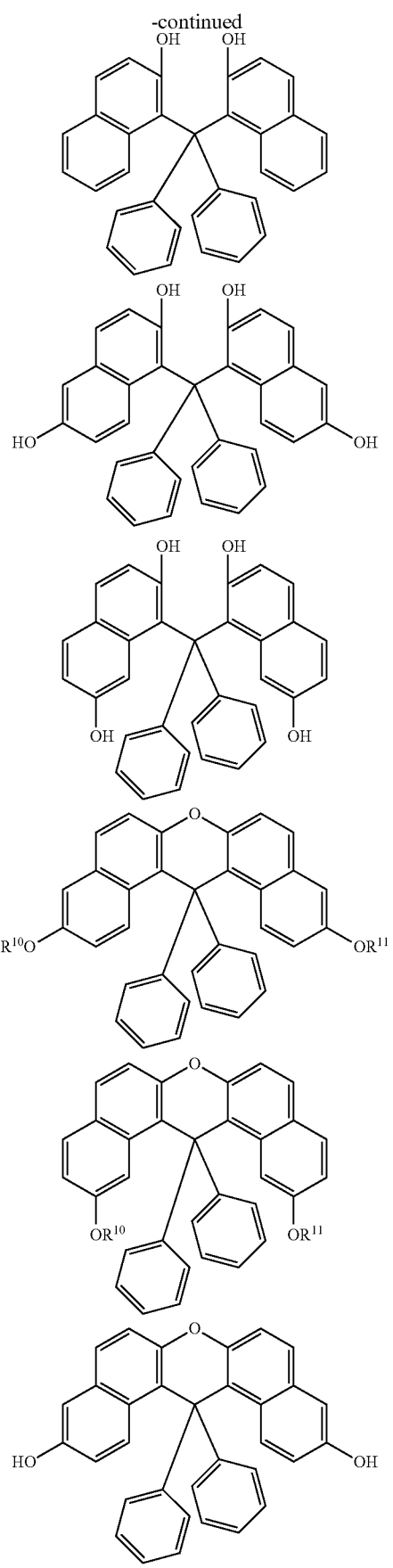

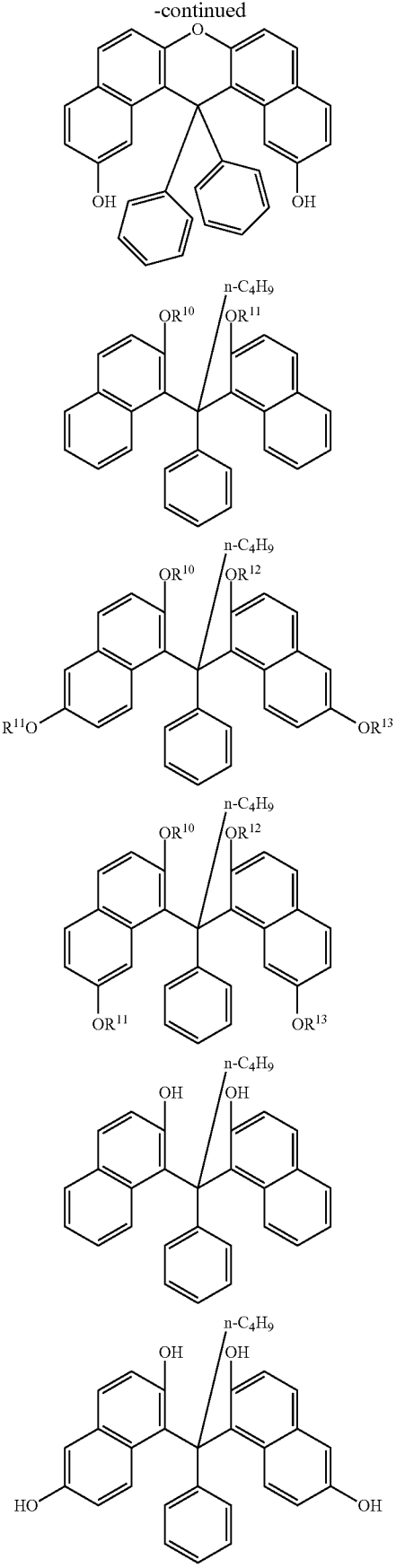
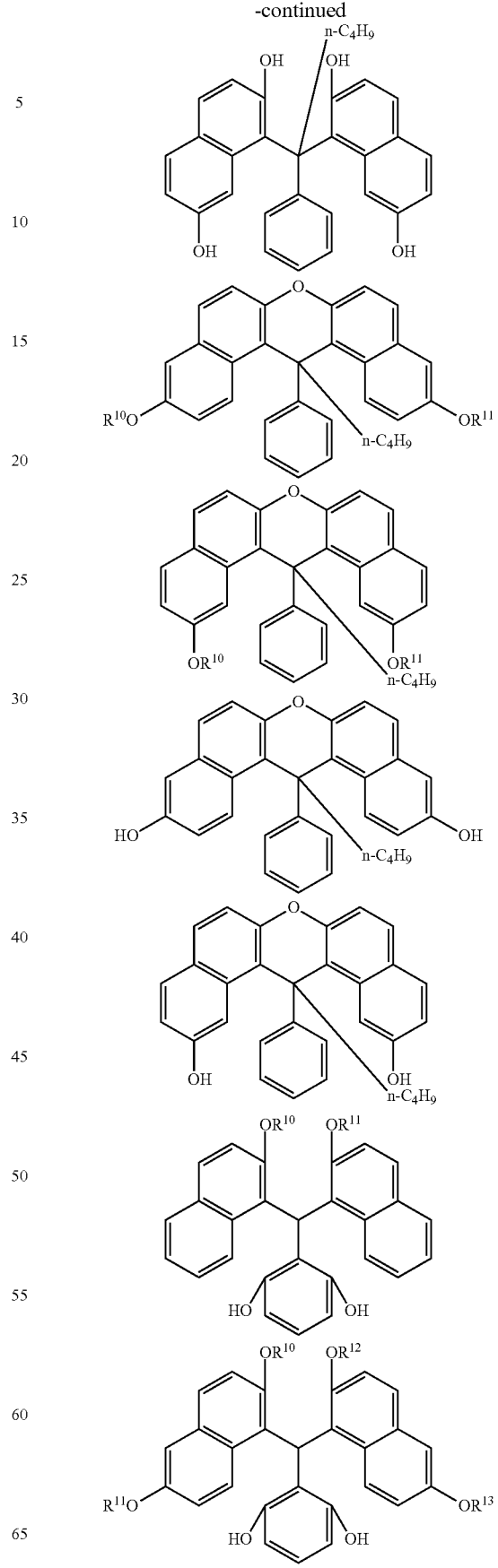

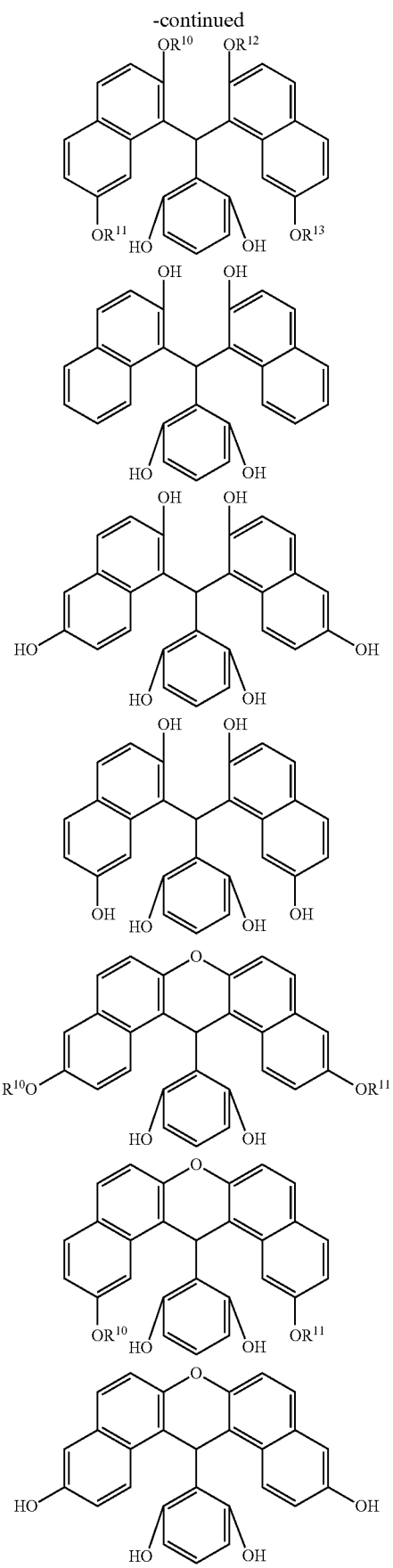
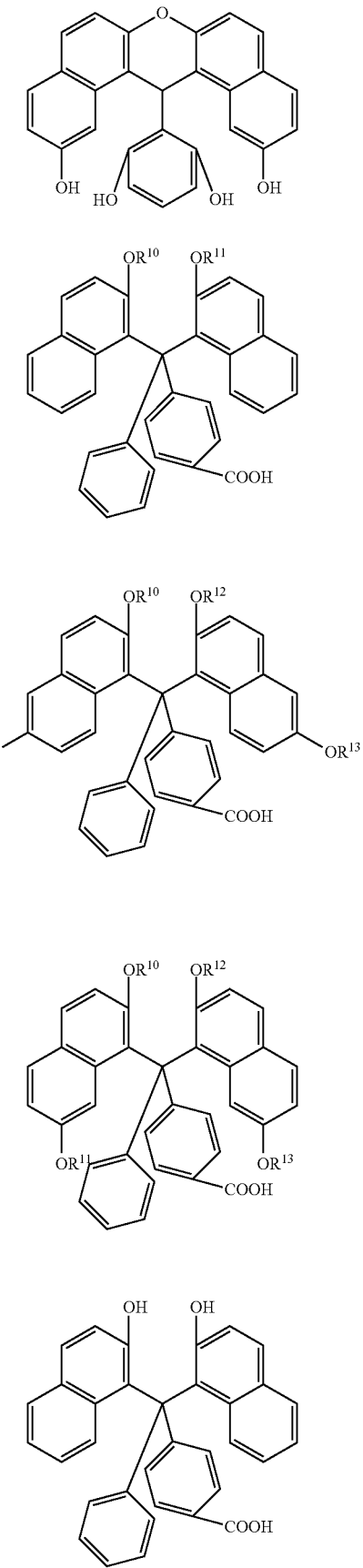

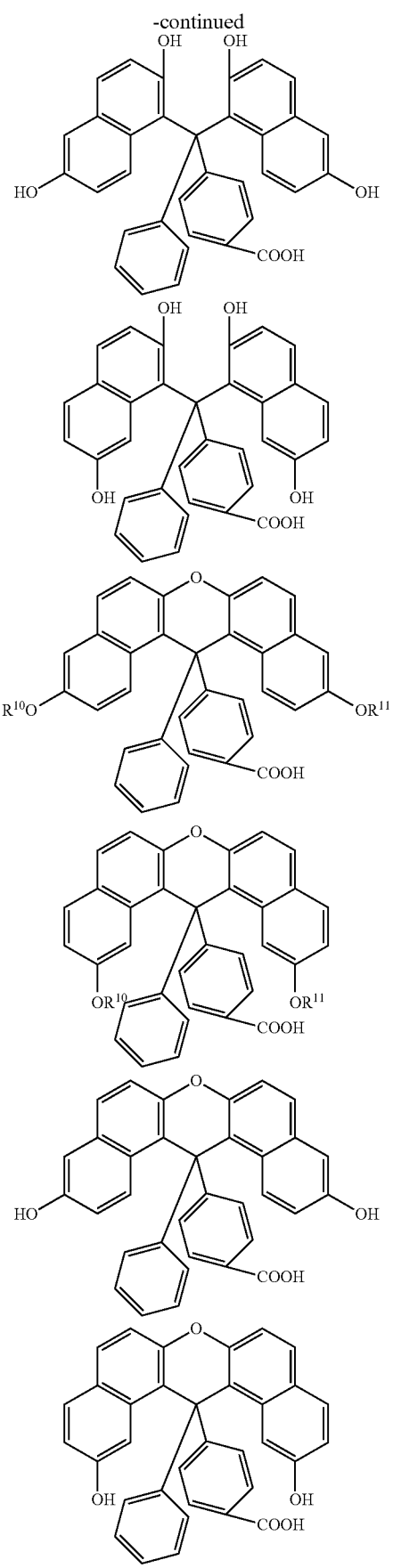
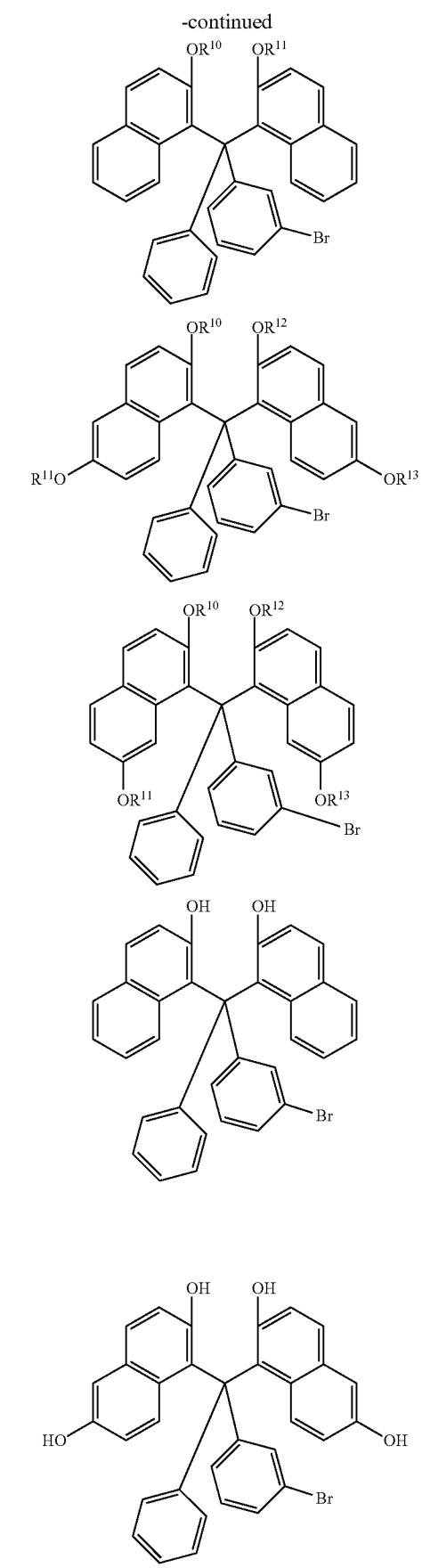

241
-continued
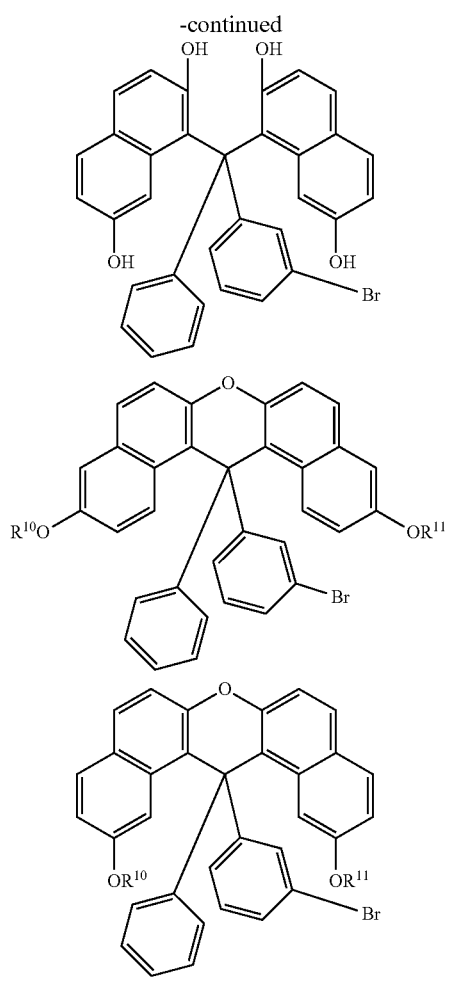
242
-continued
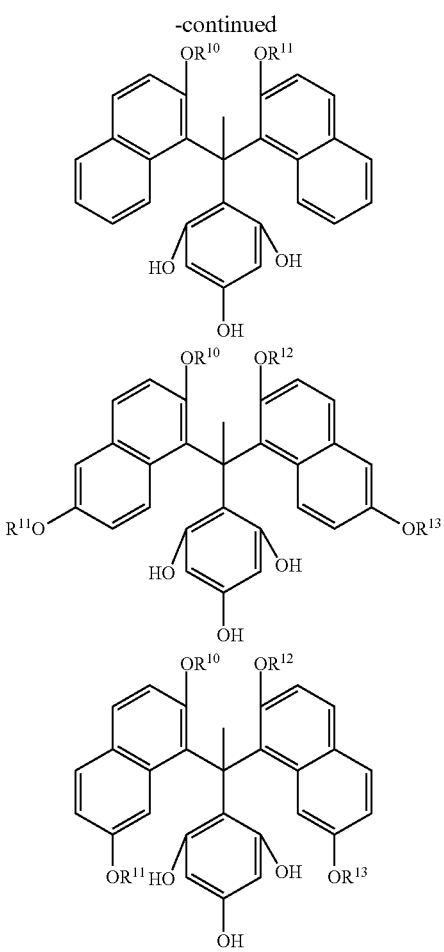
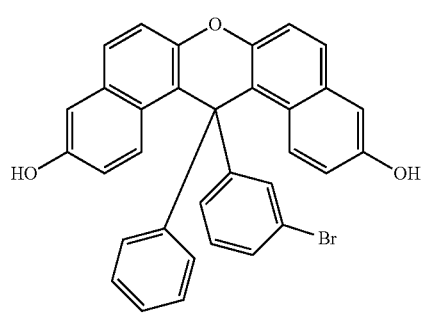
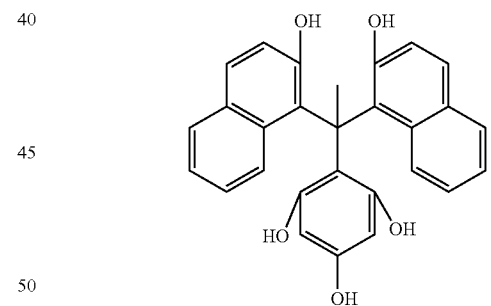
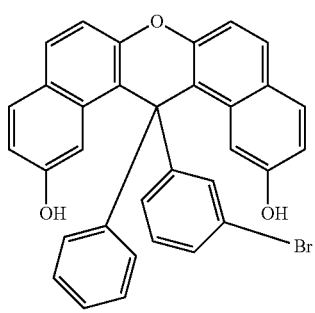
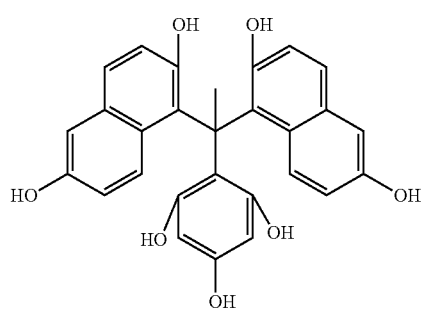

243
-continued
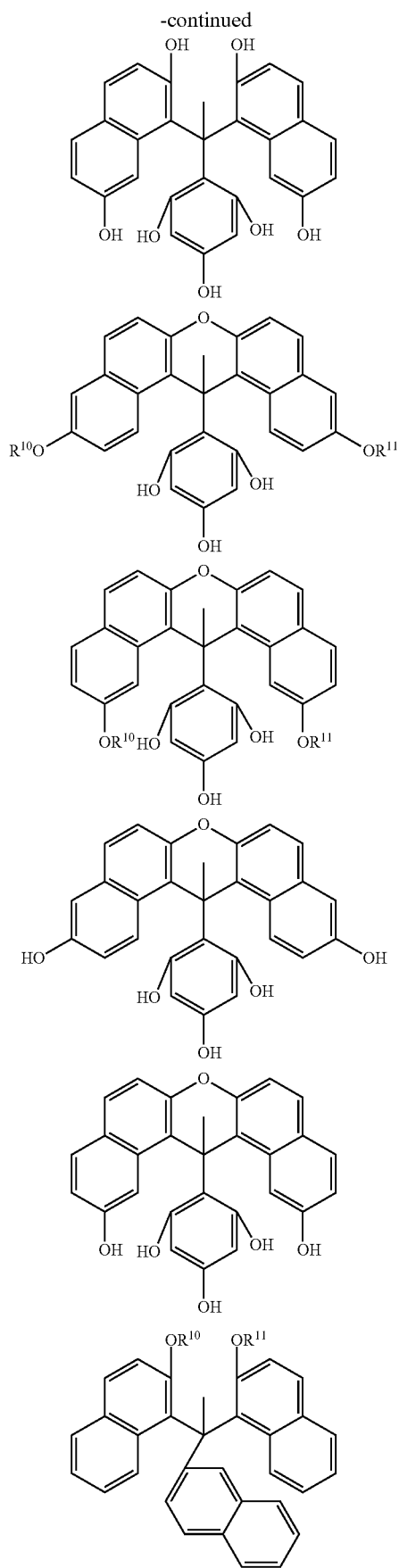
244
-continued
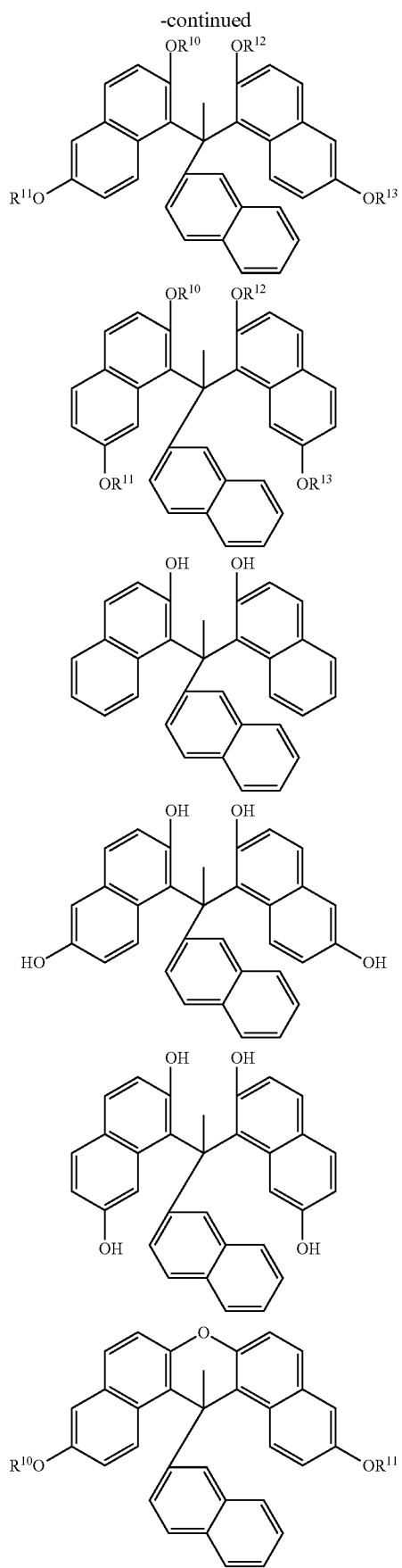

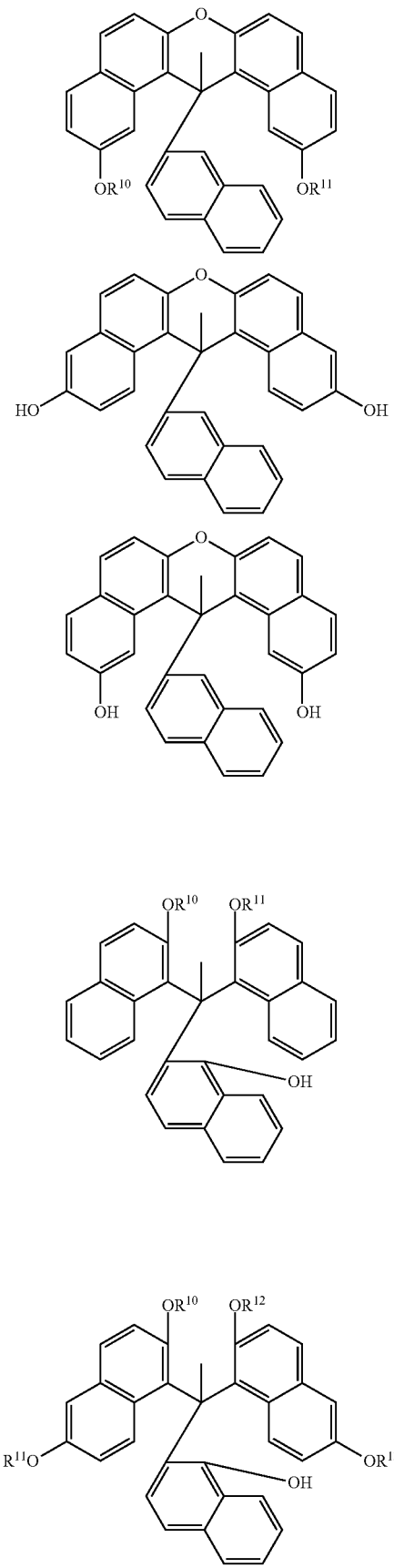

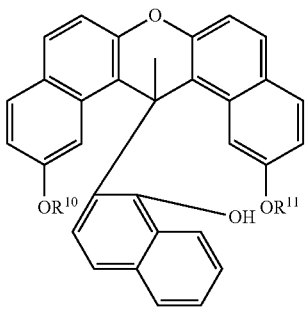
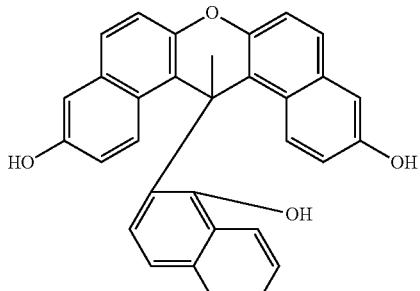
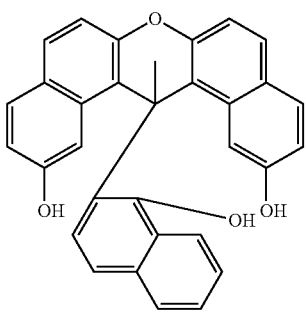
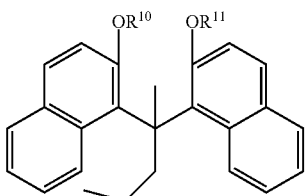
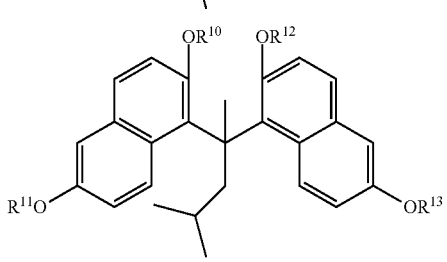
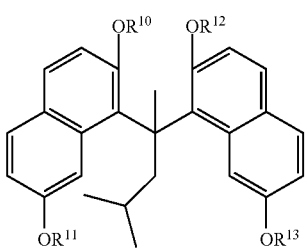
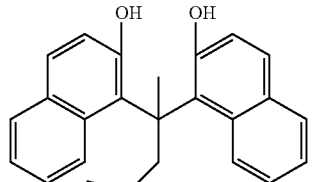
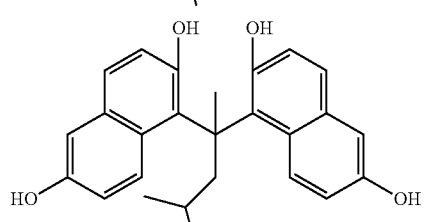
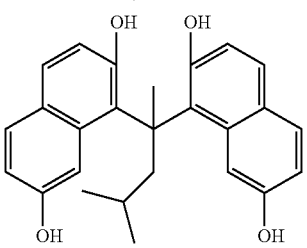
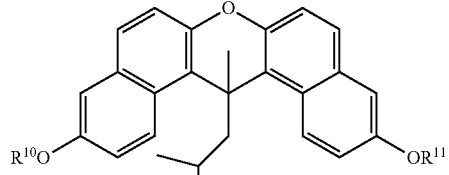
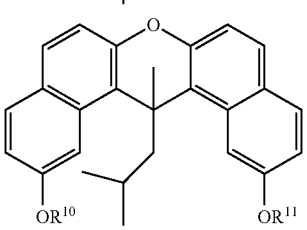
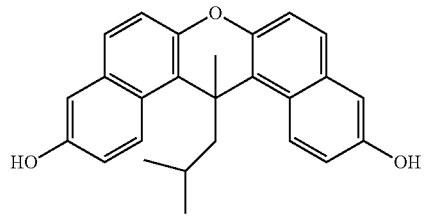
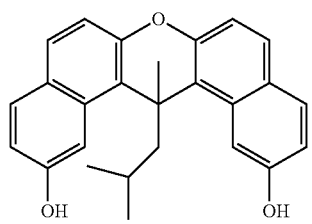

249

-continued

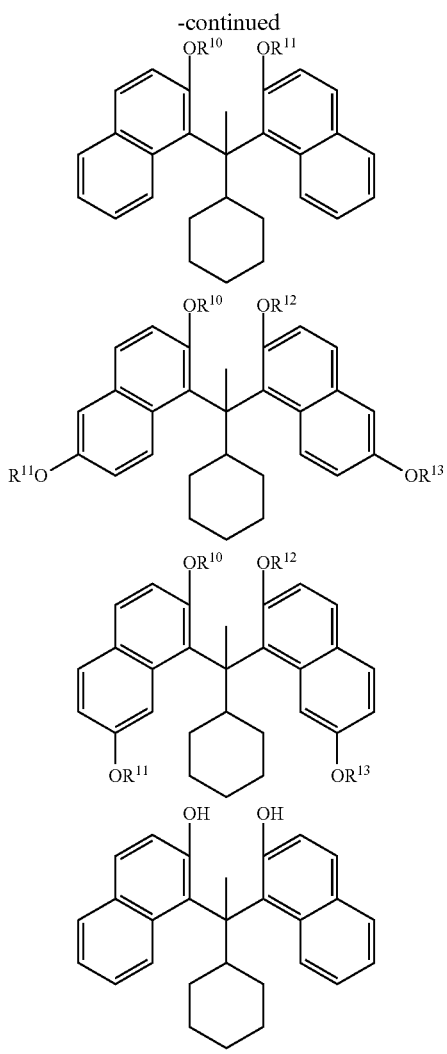

250

-continued

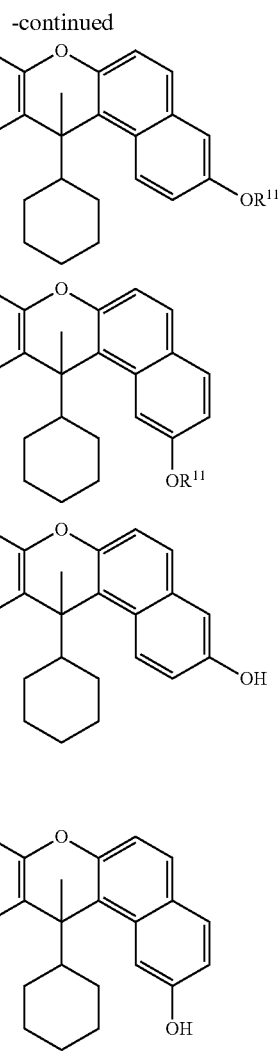

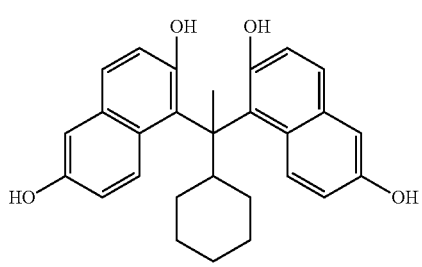

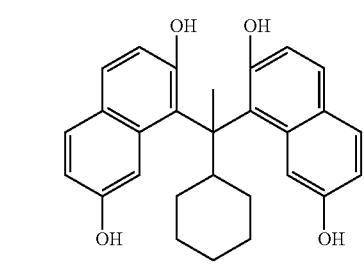

In the above compounds, $R^{10}$ to $R^{13}$ are as defined in the description of the above formula (1-2).

The above compounds preferably have a dibenzoxanthene skeleton from the viewpoint of heat resistance.

Compounds represented by the following formulas, not represented by the above formula (2), are not radiation-sensitive and are thus used as, for example, solubility controlling agents in compositions.

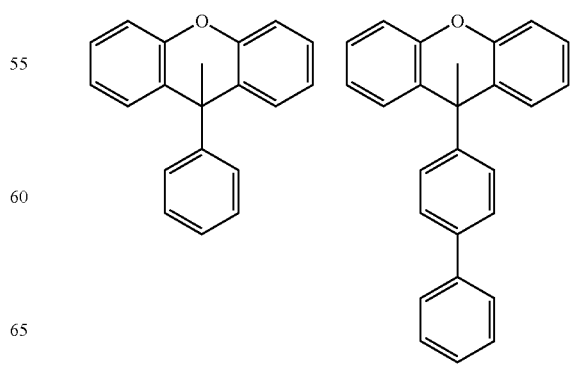

251
-continued
252
-continued
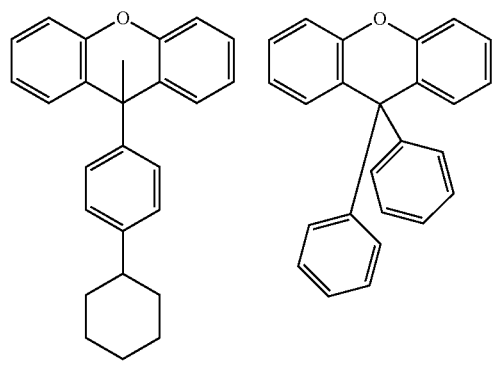
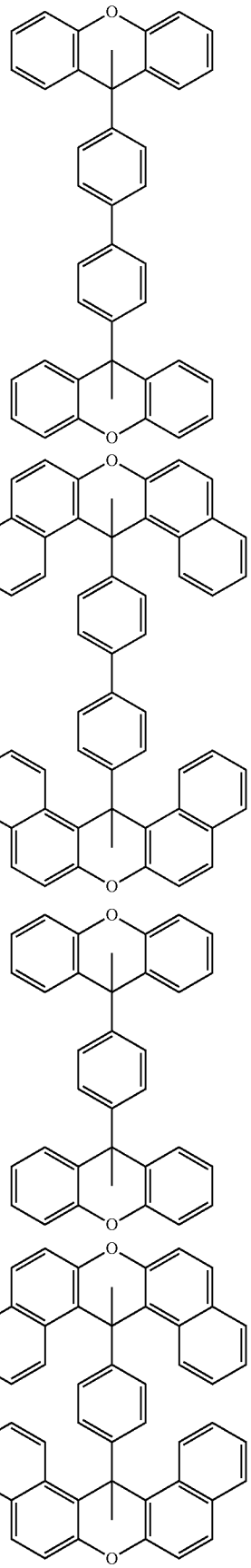

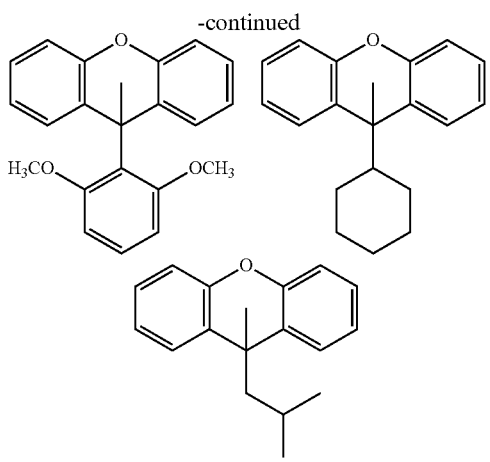

[Method for Producing Compound Represented by Formula (2)]

The compound represented by the formula (2) used in the present embodiment can be arbitrarily synthesized by the application of a publicly known approach, and the synthesis approach is not particularly limited. Examples thereof include (i) a method of subjecting a phenol, a naphthol, or a anthracenol and a corresponding ketone to polycondensation reaction in the presence of an acid catalyst, and (ii) a method of polycondensing a phenol, a naphthol, or a anthracenol with a corresponding aldehyde in the presence of an acid catalyst, followed by the substitution of a methine site of the obtained triarylmethane or xanthene.

Examples of the method (i) of subjecting a phenol, a naphthol, or a anthracenol and a corresponding ketone to polycondensation reaction in the presence of an acid catalyst include (a) a method of performing the reaction in an organic solvent, (b) a method of performing the reaction in a water solvent, and (c) a method of performing the reaction in the absence of a solvent.

In the method (i) (a) of subjecting a phenol, a naphthol, or a anthracenol and a corresponding ketone to polycondensation reaction in the presence of an acid catalyst in an organic solvent, the compound represented by the above formula (2) can be obtained by subjecting a phenol, a naphthol, or a anthracenol and a corresponding ketone to polycondensation reaction in the presence of an acid catalyst at normal pressure. If necessary, this reaction can also be carried out under increased pressure. Also, an acid dissociation group can be introduced to at least one phenolic hydroxy group of the compound by a publicly known method.

In the method (i) of subjecting a phenol, a naphthol, or a anthracenol and a corresponding ketone to polycondensation reaction in the presence of an acid catalyst in a water solvent (method (i)(b)) or in the absence of a solvent (method (i)(c)), the compound represented by the above formula (2) can be obtained by subjecting a phenol, a naphthol, or a anthracenol and a corresponding ketone to polycondensation reaction in the presence of acid and mercapto catalysts. Also, an acid dissociation group can be introduced to at least one phenolic hydroxy group of the compound by a publicly known method. This reaction can be carried out under reduced pressure, at normal pressure, or under increased pressure.

Examples of the naphthol include, but not particularly limited to, naphthol, methylnaphthol, methoxynaphthol, and naphthalenediol. Naphthalenediol is more preferably used from the viewpoint that a xanthene structure can be easily formed.

Examples of the phenol include, but not particularly limited to, phenol, methylphenol, methoxybenzene, catechol, resorcinol, hydroquinone, and trimethylhydroquinone.

Examples of the anthracenol include, but not particularly limited to, anthracenol, methylanthracenol, and methoxyanthracenol. These anthracenols can be used alone as one kind or can be used in combination of two or more kinds. Among them, anthracenol is more preferably used from the viewpoint of increasing a carbon atom concentration and improving heat resistance.

Examples of the ketone include, but not particularly limited to, acetone, methyl ethyl ketone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones can be used alone as one kind or can be used in combination of two or more kinds. Among them, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, or diphenylcarbonylbiphenyl is preferably used from the viewpoint of providing high heat resistance, and acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, or diphenylcarbonylbiphenyl is more preferably used because of high etching resistance.

As the ketone, a ketone having an aromatic ring is preferably used because both high heat resistance and high etching resistance are achieved.

The acid catalyst is not particularly limited and can be arbitrarily selected from well known inorganic acids and organic acids. Examples include inorganic acids such as hydrochloric acid, sulfuric acid, phosphoric acid, hydrobromic acid, and hydrofluoric acid; organic acids such as oxalic acid, formic acid, p-toluenesulfonic acid, methanesulfonic acid, trifluoroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Hydrochloric acid or sulfuric acid is preferably used from the viewpoint of production such as easy availability and handleability. The acid catalyst can be used as one kind or two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

The mercapto catalyst used in the reaction can be arbitrarily selected and used from publicly known catalysts and is not particularly limited. Alkylthiols and mercaptocarboxylic acids are widely known as such acid catalysts. Examples of the alkylthiol include, but not particularly limited to, alkylmercaptans of 1 to 12 carbon atoms, preferably n-octylmercaptan, n-decylmercaptan, and n-dodecylmercaptan, and examples of the mercaptocarboxylic acid include, but not particularly limited to, 2-mercaptopropionic acid and 3-mercaptopropionic acid. Among them, n-octylmercaptan, n-decylmercaptan, or n-dodecylmercaptan is preferable from the viewpoint of production. The mercapto catalysts can be used alone as one kind or can be used in combination of two or more kinds. Also, the amount of the mercapto catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

Upon producing the compound represented by the above formula (2), a reaction solvent may be used. The reaction solvent is not particularly limited as long as the reaction of the ketone used with the naphthol or the like proceeds. For example, water, methanol, ethanol, propanol, butanol, tetrahydrofuran, dioxane, or a mixed solvent thereof can be used. The amount of the solvent is not particularly limited and is, for example, in the range of 0 to 2000 parts by mass based on 100 parts by mass of the reaction raw materials.

Upon producing the polyphenol compound, the reaction temperature is not particularly limited and can be arbitrarily selected according to the reactivity of the reaction raw materials, but is preferably within the range of 10 to 200° C. In order to synthesize the compound represented by the formula (2) of the present embodiment with good selectivity, a lower temperature is more effective, and the range of 10 to 60° C. is more preferable.

The method for producing the compound represented by the above formula (2) is not particularly limited, but there are a method of charging the naphthol or the like, the ketone, and the catalyst in one portion, and a method of dropping the naphthol and the ketone, in the presence of the catalyst. After the polycondensation reaction terminates, the temperature of the reaction vessel is elevated to 130 to 230° C. in order to remove unreacted raw materials, catalyst, etc. present in the system, and volatile portions can be removed at about 1 to 50 mmHg.

The amounts of the raw materials upon producing the compound represented by the above formula (2) are not particularly limited, but the reaction proceeds, for example, by using 2 mol to an excess of the naphthol or the like and 0.001 to 1 mol of the acid catalyst based on 1 mol of the ketone, and reacting them at 20 to 60° C. at normal pressure for about 20 minutes to 100 hours.

Upon producing the compound represented by the above formula (2), the target compound is isolated by a publicly known method after the reaction terminates. Examples of the method for isolating the target compound include, but not particularly limited to, a method of concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the target compound.

In the method (ii) of polycondensing a phenol, a naphthol, or a anthracenol with a corresponding aldehyde in the presence of an acid catalyst, followed by the substitution of a methine site of the obtained triarylmethane or xanthene, compound (A') which replaces a compound represented by the above formula $R^Y$ with a hydrogen atom is obtained by subjecting a phenol, a naphthol, or a anthracenol and a corresponding aldehyde to polycondensation reaction in the presence of an acid catalyst. A hydroxy group of the compound (A') is replaced with a protective group using a protective group introducing agent to prepare compound (B'). Then, an alkyl group corresponding to the $R^Y$ moiety of the compound represented by the above formula (2) is introduced to the compound (B') by reacting a hydrogen atom corresponding to the $R^Y$ moiety of the compound represented by the above formula (2) with an alkylating agent in the presence of a basic catalyst. Then, the compound of the above formula (2) is further obtained by deprotecting the protective group replacing the hydroxy group in the compound (B'). Also, an acid dissociation group can be introduced to at least one phenolic hydroxy group of the compound by a publicly known method. If necessary, this reaction can also be carried out under increased pressure. The alkylating agent can be arbitrarily selected and used from publicly known alkylating agents and is not particularly limited. Examples thereof include alkyl chlorides, alkyl bromides, and alkyl iodides.

In the above production method, the method for introducing an alkyl group corresponding to the $R^Y$ moiety of the compound represented by the above formula (2) to a hydrogen atom corresponding to the $R^Y$ moiety of the compound represented by the above formula (2) in the compound (B') may be performed, instead of the method of reacting the hydrogen atom with an alkylating agent in the presence of a basic catalyst in the production method, by replacing the hydrogen atom corresponding to the $R^Y$ moiety of the compound represented by the above formula (2) with a halogen atom through a reaction of the compound (B') with a halogenating agent, and then reacting the resultant with an alkylating agent to obtain the compound of the above formula (1). The alkylating agent can be arbitrarily selected and used from publicly known alkylating agents and is not particularly limited. Examples thereof include Grignard reagents and alkyllithiums.

Examples of the phenol include, but not particularly limited to, phenol, methylphenol, and methoxyphenol. These phenols can be used alone as one kind or can be used in combination of two or more kinds. Among them, phenol is more preferably used from the viewpoint of the stable supply of raw materials.

Examples of the naphthol include, but not particularly limited to, naphthol, methylnaphthol, and methoxynaphthol. These naphthols can be used alone as one kind or can be used in combination of two or more kinds. Among them, naphthol is more preferably used from the viewpoint of increasing a carbon atom concentration and improving heat resistance.

Examples of the anthracenol include, but not particularly limited to, anthracenol, methylanthracenol, and methoxyanthracenol. These anthracenols can be used alone as one kind or can be used in combination of two or more kinds. Among them, anthracenol is more preferably used from the viewpoint of increasing a carbon atom concentration and improving heat resistance.

Examples of the aldehyde include, but not particularly limited to, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural.

The method for introducing an acid dissociation group to at least one phenolic hydroxy group of a polyphenol compound is publicly known. For example, an acid dissociation group can be introduced to at least one phenolic hydroxy group of the above compound as follows. The compound for introducing the acid dissociation group can be synthesized or easily obtained by a publicly known method. Examples thereof include, but not particularly limited to, acid chlorides, acid anhydrides, active carboxylic acid derivative compounds such as dicarbonate, alkyl halides, vinyl alkyl ethers, dihydropyran, and halocarboxylic acid alkyl esters.

For example, the compound is dissolved or suspended in an aprotic solvent such as acetone, tetrahydrofuran (THF), or propylene glycol monomethyl ether acetate. Subsequently, a vinyl alkyl ether such as ethyl vinyl ether, or dihydropyran is added to the solution or the suspension, and the mixture is reacted at 20 to 60° C. at normal pressure for 6 to 72 hours in the presence of an acid catalyst such as pyridinium p-toluenesulfonate. The reaction solution is neutralized with an alkali compound and added to distilled water to precipitate a white solid. Then, the separated white solid can be washed with distilled water and dried to obtain a compound in which a hydrogen atom of a hydroxy group is replaced with an acid dissociation group.

Alternatively, for example, the above compound having a hydroxy group is dissolved or suspended in an aprotic solvent such as acetone, THF, or propylene glycol monomethyl ether acetate. Subsequently, an alkyl halide such as ethyl chloromethyl ether or a halocarboxylic acid alkyl ester such as methyladamantyl bromoacetate is added to the solution or the suspension, and the mixture is reacted at 20 to 110° C. at normal pressure for 6 to 72 hours in the presence of an alkali catalyst such as potassium carbonate. The reaction solution is neutralized with an acid such as hydrochloric acid and added to distilled water to precipitate a white solid. Then, the separated white solid can be washed with distilled water and dried to obtain a compound in which a hydrogen atom of a hydroxy group is replaced with an acid dissociation group.

As for the timing of introducing an acid dissociation group, the introduction may be carried out after condensation reaction of the binaphthol with the ketone or may be carried out at a stage previous to the condensation reaction. Alternatively, the introduction may be carried out after production of a resin mentioned later.

In the present embodiment, the acid dissociation group refers to a characteristic group that is cleaved in the presence of an acid to form a functional group that changes solubility, such as an alkali soluble group. Examples of the alkali soluble group include a phenolic hydroxy group, a carboxyl group, a sulfonic acid group, and a hexafluoroisopropanol group. A phenolic hydroxy group and a carboxyl group are preferable, and a phenolic hydroxy group is particularly preferable. The acid dissociation group preferably has properties of causing chain cleavage reaction in the presence of an acid in order to enable pattern formation with higher sensitivity and higher resolution.

[Method for Producing Resin Obtained with Compound Represented by Formula (2) as Monomer]

The compound represented by the above formula (2) can be used directly as a film forming composition for lithography. Also, a resin obtained with the compound represented by the above formula (2) as a monomer can be used. For example, a resin obtained by reacting the compound represented by the above formula (2) with a crosslinking compound can also be used.

Examples of the resin obtained with the compound represented by the above formula (2) as a monomer include resins having a structure represented by the following formula (4). That is, the film forming composition for lithography of the present embodiment may contain a resin having a structure represented by the following formula (4)

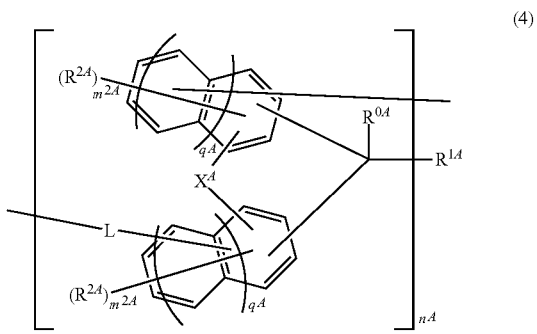

In the formula (4), L is a linear or branched alkylene group of 1 to 30 carbon atoms or a single bond.

$R^{0A}$, $R^{1A}$, $R^{2A}$, $m^{2A}$, $n^A$, $q^A$, and $X^A$ are as defined in the above formula (2).

When $n^A$ is an integer of 2 or larger, $n^A$ structural formulas within the parentheses [ ] may be the same or different.

However, at least one $R^{2A}$ is a hydroxy group or a group in which a hydrogen atom of a hydroxy group is replaced with an acid dissociation group.

The resin of the present embodiment is obtained by reacting the compound represented by the above formula (2) with a crosslinking compound.

As the crosslinking compound, a publicly known compound can be used without particular limitations as long as it can oligomerize or polymerize the compound represented by the above formula (2). Specific examples thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

Specific examples of the resin having the structure represented by the above formula (2) include resins that are made novolac by, for example, a condensation reaction between the compound represented by the above formula (2) with an aldehyde and/or a ketone that is a crosslinking compound.

Herein, examples of the aldehyde used when making the compound represented by the above formula (2) novolac include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural. Examples of the ketone include, but not particularly limited to, acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, anthraquinone, acetophenone, diacetylbenzene, triacetylbenzene, acetonaphthone, diphenylcarbonylnaphthalene, phenylcarbonylbiphenyl, diphenylcarbonylbiphenyl, benzophenone, diphenylcarbonylbenzene, triphenylcarbonylbenzene, benzonaphthone, diphenylcarbonylnaphthalene, phenylcarbonylbiphenyl, and diphenylcarbonylbiphenyl. These ketones can be used alone as one kind or may be used in combination of two or more kinds. Among them, formaldehyde is more preferable. These aldehydes and/or ketones can be used alone as one kind or may be used in combination of two or more kinds. The amount of the above aldehydes and/or ketones used is not particularly limited, but is preferably 0.2 to 5 mol and more preferably 0.5 to 2 mol based on 1 mol of the compound represented by the above formula (2).

A catalyst can also be used in the condensation reaction between the compound represented by the above formula (2) and the aldehyde and/or ketones. The acid catalyst used herein can be arbitrarily selected and used from publicly known catalysts and is not particularly limited. Inorganic acids and organic acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids or solid acids are preferable from the viewpoint of production, and hydrochloric acid or sulfuric acid is preferable from the viewpoint of production such as easy availability and handleability. The acid catalysts can be used alone as one kind, or can be used in combination of two or more kinds. Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials. The aldehyde is not necessarily needed in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, and limonene.

A reaction solvent can also be used in the condensation reaction between the compound represented by the above formula (2) and the aldehyde and/or ketones. The reaction solvent in the polycondensation can be arbitrarily selected and used from publicly known solvents and is not particularly limited, and examples include water, methanol, ethanol, propanol, butanol, tetrahydrofuran, dioxane, or a mixed solvent thereof. The solvents can be used alone as one kind, or can be used in combination of two or more kinds.

Also, the amount of these solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. The reaction method can be arbitrarily selected and used from publicly known approaches and is not particularly limited, and there are a method of charging the compound represented by the above formula (2), the aldehyde and/or ketones, and the catalyst in one portion, and a method of dropping the compound represented by the above formula (2) and the aldehyde and/or ketones in the presence of the catalyst.

After the polycondensation reaction terminates, isolation of the obtained compound can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, a novolac resin that is the target compound can be obtained.

Herein, the resin having the structure represented by the above formula (4) may be a homopolymer of a compound represented by the above formula (2), or may be a copolymer with a further phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

The resin having the structure represented by the above formula (4) may be a copolymer with a polymerizable monomer other than the above-described further phenols. Examples of such a copolymerization monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin having the structure represented by the above formula (2) may be a copolymer of two or more components (for example, a binary to quaternary system) composed of the compound represented by the above formula (2) and the above-described phenol, may be a copolymer of two or more components (for example, a binary to quaternary system) composed of the compound represented by the above formula (2) and the above-described copolymerization monomer, or may be a copolymer of three or more components (for example, a tertiary to quaternary system) composed of the compound represented by the above formula (2), the above-described phenol, and the above-described copolymerization monomer.

The molecular weight of the resin having the structure represented by the above formula (4) is not particularly limited, and the weight average molecular weight (Mw) in terms of polystyrene is preferably 500 to 30,000 and more preferably 750 to 20,000. The resin having the structure represented by the above formula (4) preferably has dispersibility (weight average molecular weight Mw/number average molecular weight Mn) within the range of 1.2 to 7 from the viewpoint of enhancing crosslinking efficiency while suppressing volatile components during baking. The above Mn can be determined by a method described in Examples mentioned later.

The resin having the structure represented by the above formula (4) preferably has high solubility in a solvent from the viewpoint of easier application to a wet process, etc. More specifically, in the case of using 1-methoxy-2-propanol (PGME) and/or propylene glycol monomethyl ether acetate (PGMEA) as a solvent, these compounds and/or resins preferably have a solubility of 10% by mass or more in the solvent. Herein, the solubility in PGME and/or PGMEA is defined as "mass of the resin/(mass of the resin+mass of the solvent)×100 (% by mass)". For example, when 10 g of the resin is dissolved in 90 g of PGMEA, the solubility of the resin in PGMEA is "10% by mass or more";

and when 10 g of the resin is not dissolved in 90 g of PGMEA, the solubility is "less than 10% by mass".

[Method for Purifying Compound and/or Resin]

The method for purifying the compound and/or the resin of the present embodiment comprises the steps of: obtaining a solution (S) by dissolving one or more selected from the compound represented by the above formula (1), the resin obtained with the compound represented by the above formula (1) as a monomer, the compound represented by the above formula (2), and the resin obtained with the compound represented by the above formula (2) as a monomer in a solvent; and extracting impurities in the compound and/or the resin by bringing the obtained solution (S) into contact with an acidic aqueous solution (a first extraction step), wherein the solvent used in the step of obtaining the solution (S) contains an organic solvent that does not inadvertently mix with water.

In the first extraction step, the resin is preferably a resin obtained by a reaction between the compound represented by the above formula (1) and/or the compound represented by the formula (2) and a crosslinking compound. According to the purification method of the present embodiment, the contents of various metals that may be contained as impurities in the compound or the resin having a specific structure described above can be reduced.

More specifically, in the purification method of the present embodiment, the compound and/or the resin is dissolved in an organic solvent that does not inadvertently mix with water to obtain the solution (S), and further, extraction treatment can be carried out by bringing the solution (S) into contact with an acidic aqueous solution. Thereby, metals contained in the solution (S) are transferred to the aqueous phase, then the organic phase and the aqueous phase are separated, and thus the compound and/or the resin having a reduced metal content can be obtained.

The compound and the resin used in the purification method of the present embodiment may be alone, or may be a mixture of two or more kinds. Also, the compound and/or the resin may contain various surfactants, various crosslinking agents, various acid generating agents, various stabilizers, and the like.

The solvent that does not inadvertently mix with water used in the present embodiment is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 times the total mass of the compound and/or the resin to be used.

Specific examples of the solvent that does not inadvertently mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone, cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monomethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the above compound and the resin comprising the compound as a constituent and a relatively low boiling point, and it is thus possible to reduce the load in the case of industrially distilling off the solvent and in the step of removing the solvent by drying. These solvents can be each used alone, and can be used as a mixture of two or more kinds.

The acidic aqueous solution used in the purification method of the present embodiment is arbitrarily selected from among aqueous solutions in which organic compounds or inorganic compounds are dissolved in water, generally known as acidic aqueous solutions. Examples thereof include, but not limited to, aqueous mineral acid solutions in mineral acids such as hydrochloric acid, sulfuric acid, nitric acid, and phosphoric acid are dissolved in water, or aqueous organic acid solutions in organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound or the resin. Normally, the pH range is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (S).

In the purification method of the present embodiment, by bringing an acidic aqueous solution as described above into contact with the solution (S), metals can be extracted from the compound or the resin in the solution (S).

In the purification method of the present embodiment, it is preferable that the solution (S) further contains an organic solvent that inadvertently mixes with water. When an organic solvent that inadvertently mixes with water is contained, there is a tendency that the amount of the above compound and/or the resin charged can be increased, also the fluid separability is improved, and purification can be carried out at a high reaction vessel efficiency. The method for adding the organic solvent that inadvertently mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that inadvertently mixes with water used in the purification method of the present embodiment is not particularly limited, but is preferably an organic solvent that is safely applicable to semiconductor manufacturing processes. The amount of the organic solvent used that inadvertently mixes with water is not particularly limited as long as the solution phase and the aqueous phase separate, but is preferably 0.1 to 100 times, more preferably 0.1 to 50 times, and further preferably 0.1 to 20 times the total mass of the compound and the resin to be used.

Specific examples of the organic solvent used in the purification method of the present embodiment that inadvertently mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

The temperature when extraction treatment is carried out is generally in the range of 20 to 90° C., and preferably 30 to 80° C. The extraction operation is carried out, for example, by thoroughly mixing the solution (S) and the acidic aqueous solution by stirring or the like and then leaving the obtained mixed solution to stand still. Thereby, metals contained in the solution (S) are transferred to the aqueous phase. Also, by this operation, the acidity of the solution is lowered, and the degradation of the compound and/or the resin can be suppressed.

By being left to stand still, the mixed solution is separated into an aqueous phase and a solution phase containing the compound and/or the resin and the solvents, and thus the solution phase is recovered by decantation. The time for leaving the mixed solution to stand still is not particularly limited, but it is preferable to regulate the time for leaving the mixed solution to stand still from the viewpoint of attaining good separation of the solution phase containing the solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step). Specifically, for example, it is preferable that after the above extraction treatment is carried out using an acidic aqueous solution, the solution phase that is extracted and recovered from the aqueous solution and that contains the compound and/or the resin and the solvents is further subjected to extraction treatment with water. The above extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing the compound and/or the resin and the solvents, and thus the solution phase can be recovered by decantation.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing the compound and/or the resin can be easily removed by performing vacuum distillation or a like operation. Also, if required, the concentration of the compound and/or the resin can be regulated to be any concentration by adding a solvent to the solution.

The method for isolating the compound and/or the resin from the obtained solution containing the compound and/or the resin and the solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

[Film Forming Composition for Lithography]

The film forming composition for lithography of the present embodiment contains one or more selected from the group consisting of the compound represented by the above formula (1), the resin obtained with the compound represented by the above formula (1) as a monomer, the compound represented by the above formula (2), and the resin obtained with the compound represented by the above formula (2) as a monomer.

[Film Forming Composition for Lithography for Chemical Amplification Type Resist Purpose]

The film forming composition for lithography for chemical amplification type resist purposes (hereinafter, also referred to as a resist composition) of the present embodiment contains one or more selected from the group consisting of the compound represented by the above formula (1), the resin obtained with the compound represented by the above formula (1) as a monomer, the compound represented by the above formula (2), and the resin obtained with the compound represented by the above formula (2) as a monomer.

It is preferable that the resist composition of the present embodiment should contain a solvent. Examples of the solvent can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate (PGMEA), propylene glycol monoethyl ether acetate, propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the amount of the solid component and the solvent.

The resist composition of the present embodiment may contain at least one selected from the group consisting of an acid generating agent (C), an acid crosslinking agent (G), an acid diffusion controlling agent (E), and a further component (F), as other solid components. In the present specification, the solid components refer to components except for the solvent.

Herein, as the acid generating agent (C), the acid crosslinking agent (G), the acid diffusion controlling agent (E), and the further component (F), publicly known agents can be used, and they are not particularly limited, but those described in International Publication No. WO 2013/024778 are preferable.

[Content Ratio of Each Component]

In the resist composition of the present embodiment, the content of the compound and/or the resin used as a resist base material is not particularly limited, but is preferably 50 to 99.4% by mass of the total mass of the solid components (summation of solid components including the resist base material, and optionally used components such as acid generating agent (C), acid crosslinking agent (G), acid diffusion controlling agent (E), and further component (F) (also referred to as "optional component (F)"), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased.

When both of the compound and the resin are contained as a resist base material, the above content refers to the total amount of these components.

In the resist composition of the present embodiment, the contents of the resist base material (hereinafter, also referred to as a component (A)), the acid generating agent (C), the acid crosslinking agent (G), the acid diffusion controlling agent (E), and the optional component (F) (the component (A)/the acid generating agent (C)/the acid crosslinking agent (G)/the acid diffusion controlling agent (E)/the optional component (F)) are preferably 50 to 99.4/0.001 to 49/0.5 to 49/0.001 to 49/0 to 49, more preferably 55 to 90/1 to 40/0.5 to 40/0.01 to 10/0 to 5, further preferably 60 to 80/3 to 30/1 to 30/0.01 to 5/0 to 1, and particularly preferably 60 to 70/10 to 25/2 to 20/0.01 to 3/0% by mass based on solid matter.

The content ratio of each component is selected from each range so that the summation thereof is 100% by mass. By the above content ratio, performance such as sensitivity, resolution, and developability is excellent.

The resist composition of the present embodiment is generally prepared by dissolving each component in a solvent upon use into a homogeneous solution, and then if required, filtering through a filter or the like with a pore diameter of about 0.2 μm, for example.

The resist composition of the present embodiment can contain an additional resin other than the resin of the present embodiment, within the range not inhibiting the objects of the present invention. Examples of the resin include, but not particularly limited to, a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of the resin is not particularly limited and is arbitrarily adjusted according to the kind of the component (A) to be used, and is preferably 30 parts by mass or less per 100 parts by mass of the component (A), more preferably 10 parts by mass or less, still more preferably 5 parts by mass or less, and particularly preferably 0 part by mass.

[Physical Properties and the Like of Resist Composition]

The resist composition of the present embodiment can form an amorphous film by spin coating. Also, the resist composition of the present embodiment can be applied to a general semiconductor production process. Any of positive type and negative type resist patterns can be individually prepared depending on the type of the compound represented by the above formula (1) and/or (2) or the resin obtained with either of these compounds as a monomer and the kind of a developing solution to be used.

In the case of a positive type resist pattern, the dissolution rate of the amorphous film formed by spin coating with the resist composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the resist composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the unexposed portion being dissolved in a developing solution and the exposed portion not being dissolved in a developing solution is increased. Also, there are effects of reducing LER and defects.

[Film Forming Composition for Lithography for Non-Chemical Amplification Type Resist Purpose]

The component (A) to be contained in the film forming composition for lithography for non-chemical amplification type resist purposes (hereinafter, also referred to as a radiation-sensitive composition) of the present embodiment is used in combination with the optically active diazonaphthoquinone compound (B) mentioned later and is useful as a base material for positive type resists that becomes a compound easily soluble in a developing solution by irradiation with g-ray, h-ray, i-ray, KrF excimer laser, ArF excimer laser, extreme ultraviolet, electron beam, or X-ray. Although the properties of the component (A) are not largely altered by g-ray, h-ray, i-ray, KrF excimer laser, ArF excimer laser, extreme ultraviolet, electron beam, or X-ray, the optically active diazonaphthoquinone compound (B) poorly soluble in a developing solution is converted to an easily soluble compound so that a resist pattern can be formed in a development step.

Since the component (A) to be contained in the radiation-sensitive composition of the present embodiment is a relatively low molecular weight compound, the obtained resist pattern has very small roughness. Also, in the above formula (1), at least one selected from the group consisting of $R^0$ to $R^5$ is preferably a group containing an iodine atom. In the above formula (2), at least one selected from the group consisting of $R^{0A}$, $R^{1A}$, and $R^{2A}$ is preferably a group containing an iodine atom. In the case of applying the component (A) having such a group containing an iodine atom which is a preferable form to the radiation-sensitive composition of the present embodiment, the ability to absorb radiation such as electron beam, extreme ultraviolet (EUV), or X-ray is increased. As a result, this enables the enhancement of the sensitivity, which is preferable.

The glass transition temperature of the component (A) to be contained in the radiation-sensitive composition of the present embodiment is preferably 100° C. or higher, more preferably 120° C. or higher, still more preferably 140° C. or higher, and particularly preferably 150° C. or higher. The upper limit of the glass transition temperature of the component (A) is not particularly limited and is, for example, 400° C. When the glass transition temperature of the component (A) falls within the above range, the resulting radiation-sensitive composition has heat resistance capable of maintaining a pattern shape in a semiconductor lithography process, and improves performance such as high resolution.

The heat of crystallization determined by the differential scanning calorimetry of the glass transition temperature of the component (A) to be contained in the radiation-sensitive composition of the present embodiment is preferably less than 20 J/g. (Crystallization temperature)–(Glass transition temperature) is preferably 70° C. or more, more preferably 80° C. or more, still more preferably 100° C. or more, and particularly preferably 130° C. or more. When the heat of crystallization is less than 20 J/g or (Crystallization temperature)–(Glass transition temperature) falls within the above range, the radiation-sensitive composition easily forms an amorphous film by spin coating, can maintain film formability necessary for a resist over a long period, and can improve resolution.

In the present embodiment, the above heat of crystallization, crystallization temperature, and glass transition temperature can be determined by differential scanning calorimetry using "DSC/TA-50WS" manufactured by Shimadzu Corp. For example, about 10 mg of a sample is placed in an unsealed container made of aluminum, and the temperature is raised to the melting point or more at a temperature increase rate of 20° C./min in a nitrogen gas stream (50 mL/min). After quenching, again the temperature is raised to the melting point or more at a temperature increase rate of 20° C./min in a nitrogen gas stream (30 mL/min). After further quenching, again the temperature is raised to 400° C. at a temperature increase rate of 20° C./min in a nitrogen gas stream (30 mL/min). The temperature at the middle point (where the specific heat is changed into the half) of steps in the baseline shifted in a step-like pattern is defined as the glass transition temperature (Tg). The temperature of the subsequently appearing exothermic peak is defined as the crystallization temperature. The heat is determined from the area of a region surrounded by the exothermic peak and the baseline and defined as the heat of crystallization.

The component (A) to be contained in the radiation-sensitive composition of the present embodiment is preferably low sublimable at 100 or lower, preferably 120° C. or lower, more preferably 130° C. or lower, still more preferably 140° C. or lower, and particularly preferably 150° C. or lower at normal pressure. The low sublimability means that in thermogravimetry, weight reduction when the resist base material is kept at a predetermined temperature for 10 minutes is 10% or less, preferably 5% or less, more preferably 3% or less, still more preferably 1% or less, and particularly preferably 0.1% or less. The low sublimability can prevent an exposure apparatus from being contaminated by outgassing upon exposure. In addition, a good pattern shape with low roughness can be obtained.

The component (A) to be contained in the radiation-sensitive composition of the present embodiment dissolves at preferably 1% by mass or more, more preferably 5% by mass or more, and still more preferably 10% by mass or more at 23° C. in a solvent that is selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate and exhibits the highest ability to dissolve the component (A). Particularly preferably, the component (A) dissolves at 20% by mass or more at 23° C. in a solvent that is selected from PGMEA, PGME, and CHN and exhibits the highest ability to dissolve the component (A). Particularly preferably, the component (A) dissolves at 20% by mass or more at 23° C. in PGMEA. When the above conditions are met, the radiation-sensitive composition is easily used in a semiconductor production process at a full production scale.

[Optically Active Diazonaphthoquinone Compound (B)]

The optically active diazonaphthoquinone compound (B) to be contained in the radiation-sensitive composition of the present embodiment is a diazonaphthoquinone substance including a polymer or non-polymer optically active diazonaphthoquinone compound and is not particularly limited as long as it is generally used as a photosensitive component (sensitizing agent) in positive type resist compositions. One kind or two or more kinds can be optionally selected and used.

Such a sensitizing agent is preferably a compound obtained by reacting naphthoquinonediazide sulfonic acid chloride, benzoquinonediazide sulfonic acid chloride, or the like with a low molecular weight compound or a high molecular weight compound having a functional group condensable with these acid chlorides. Herein, examples of the above functional group condensable with the acid chlorides include, but not particularly limited to, a hydroxyl group and an amino group. Particularly, a hydroxyl group is preferable. Examples of the compound containing a hydroxyl group condensable with the acid chlorides can include, but not particularly limited to, hydroquinone, resorcin, hydroxybenzophenones such as 2,4-dihydroxybenzophenone, 2,3,4-trihydroxybenzophenone, 2,4,6-trihydroxybenzophenone, 2,4,4'-trihydroxybenzophenone, 2,3,4,4'-tetrahydroxybenzophenone, 2,2',4,4'-tetrahydroxybenzophenone, and 2,2',3,4,6'-pentahydroxybenzophenone, hydroxyphenylalkanes such as bis(2,4-dihydroxyphenyl)methane, bis(2,3,4-trihydroxyphenyl)methane, and bis(2,4-dihydroxyphenyl)propane, and hydroxytriphenylmethanes such as 4,4',3",4"-tetrahydroxy-3,5,3',5'-tetramethyltriphenylmethane and 4,4',2",3",4"-pentahydroxy-3,5,3',5'-tetramethyltriphenylmethane.

Preferable examples of the acid chloride such as naphthoquinonediazide sulfonic acid chloride or benzoquinonediazide sulfonic acid chloride include 1,2-naphthoquinonediazide-5-sulfonyl chloride and 1,2-naphthoquinonediazide-4-sulfonyl chloride.

The radiation-sensitive composition of the present embodiment is preferably prepared by, for example, dissolving each component in a solvent upon use into a homogeneous solution, and then if required, filtering through a filter or the like with a pore diameter of about 0.2 μm, for example.

[Properties of Radiation-Sensitive Composition]

The radiation-sensitive composition of the present embodiment can form an amorphous film by spin coating. Also, the radiation-sensitive composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the radiation-sensitive composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the radiation-sensitive composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the compound represented by the above formula (1) and/or the resin comprising the compound as a constituent dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is more suitable for a resist. When the amorphous film has a dissolution rate of 10000 angstrom/sec or less, the resolution may improve. It is presumed that this is because the micro surface portion of the compound represented by the above formula (1) and/or the resin comprising the compound as a constituent dissolves, and LER is reduced. Also, there are effects of reducing defects.

In the case of a negative type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the compound represented by the above formula (1) and/or the resin comprising the compound as a constituent, contrast at the interface between the unexposed portion being dissolved in a developing solution and the exposed portion not being dissolved in a developing solution is increased. Also, there are effects of reducing LER and defects.

[Content Ratio of Each Component]

In the radiation-sensitive composition of the present embodiment, the content of the component (A) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the component (A) falls within the above range, the radiation-sensitive composition of the present embodiment can produce a pattern with high sensitivity and low roughness.

In the radiation-sensitive composition of the present embodiment, the content of the optically active diazonaphthoquinone compound (B) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the optically active diazonaphthoquinone compound (B) falls within the above range, the radiation-sensitive composition of the present embodiment can produce a pattern with high sensitivity and low roughness.

[Further Component (D)]

To the radiation-sensitive composition of the present embodiment, if required, as a component other than the component (A) and the optically active diazonaphthoquinone compound (B), one kind or two kinds or more of various additive agents such as the acid generating agent, acid crosslinking agent, acid diffusion controlling agent, dissolution promoting agent, dissolution controlling agent, sensitizing agent, surfactant, and organic carboxylic acid or oxo acid of phosphor or derivative thereof can be added within the range not inhibiting the objects of the present invention. In the present specification, the further component (D) is also referred to as an optional component (D).

In the radiation-sensitive composition of the present embodiment, the content ratio of each component (the component (A)/the optically active diazonaphthoquinone compound (B)/the optional component (D)) is
preferably 1 to 99/99 to 1/0 to 98,
more preferably 5 to 95/95 to 5/0 to 49,
further preferably 10 to 90/90 to 10/0 to 10,
particularly preferably 20 to 80/80 to 20/0 to 5, and
most preferably 25 to 75/75 to 25/0% by mass based on the solid components.

The content ratio of each component is selected from each range so that the summation thereof is 100% by mass. When the content ratio of each component falls within the above range, the radiation-sensitive composition of the present embodiment is excellent in performance such as sensitivity and resolution, in addition to roughness.

The radiation-sensitive composition of the present embodiment may contain a resin other than the resin of the present embodiment within the range not inhibiting the objects of the present invention. Examples of such a resin include a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of these resins, which is arbitrarily adjusted according to the kind of the component (A) to be used, is preferably 30 parts by mass or less per 100 parts by mass of the component (A), more preferably 10 parts by mass or less, still more preferably 5 parts by mass or less, and particularly preferably 0 part by mass.

[Resist Pattern Formation Method]

The resist pattern formation method of the present embodiment includes the steps of: forming a resist film on a substrate using the above resist composition or radiation-sensitive composition of the present embodiment; exposing the formed resist film; and developing the resist film, thereby forming a resist pattern. The resist pattern according to the present embodiment can also be formed as an upper layer resist in a multilayer process.

Examples of the resist pattern formation method include, but not particularly limited to, the following methods. A resist film is formed by coating a conventionally publicly known substrate with the above resist composition or radiation-sensitive composition of the present embodiment using a coating means such as spin coating, flow casting coating, and roll coating. The conventionally publicly known substrate is not particularly limited. For example, a substrate for electronic components, and the one having a predetermined wiring pattern formed thereon, or the like can be exemplified. More specific examples include a substrate made of a metal such as a silicon wafer, copper, chromium, iron and aluminum, and a glass substrate. Examples of a wiring pattern material include copper, aluminum, nickel, and gold. Also if required, the substrate may be a substrate having an inorganic and/or organic film provided thereon. Examples of the inorganic film include an inorganic antireflection film (inorganic BARC). Examples of the organic film include an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition or radiation-sensitive composition, or the like. In the present embodiment, in order to stably form a fine pattern with a high degree of accuracy in exposure, the resist film is preferably heated after radiation irradiation. The heating conditions vary according to the compounding composition of the resist composition or radiation-sensitive composition, or the like, but are preferably 20 to 250° C., and more preferably 20 to 150° C.

Next, by developing the exposed resist film in a developing solution, a predetermined resist pattern is formed. As the developing solution, a solvent having a solubility parameter (SP value) close to that of the compound represented by the formula (1) or (2) or the resin obtained with the compound represented by the formula (1) or (2) as a monomer to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include dioxane and tetrahydrofuran in addition to the glycol ether-based solvents.

Examples of the amide-based solvent that can be used include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and less than 50% by mass, more preferably less than 30% by mass, and further preferably less than 10% by mass. Particularly preferably, the developing solution is substantially moisture free. That is, the content of the organic solvent in the developing solution is preferably 30% by mass or more and 100% by mass or less based on the total amount of the developing solution, preferably 50% by mass or more and 100% by mass or less, more preferably 70% by mass or more and 100% by mass or less, still more preferably 90% by mass or more and 100% by mass or less, and particularly preferably 95% by mass or more and 100% by mass or less.

Examples of the alkaline aqueous solution include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monomethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant can include the surfactants described in Japanese Patent Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by cross-linking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Still more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development include a linear, branched or cyclic monohydric alcohol. Specific examples which can be used in the rinsing step include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like. Particularly preferable examples of monohydric alcohol having 5 or more carbon atoms which can be used include 1-hexanol, 2-hexanol, 4-methyl-2-pentanol, 1-pentanol, and 3-methyl-1-butanol or the like.

A plurality of these components may be mixed, or the component may be used by mixing the component with an organic solvent other than those described above.

The water content ratio in the rinsing solution is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and most preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the above organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include copper plating, solder plating, nickel plating, and gold plating.

The remaining resist pattern after etching can be peeled by an organic solvent. Examples of the above organic solvent include PGMEA (propylene glycol monomethyl ether acetate), PGME (propylene glycol monomethyl ether), and EL (ethyl lactate). Examples of the above peeling method include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

[Film Forming Composition for Lithography for Underlayer Film Purpose]

The film forming composition for lithography for underlayer film purposes (hereinafter, also referred to as an underlayer film forming material) of the present embodiment contains at least one substance selected from the group consisting of the compound represented by the above formula (1), the resin obtained with the compound represented by the above formula (1) as a monomer, the compound represented by the formula (2), and the resin obtained with the compound represented by the formula (2) as a monomer. In the present embodiment, the content of the substance in the underlayer film forming material is preferably 1 to 100% by mass, more preferably 10 to 100% by mass, still more preferably 50 to 100% by mass, and particularly preferably 100% by mass, from the viewpoint of coatability and quality stability.

The underlayer film forming material of the present embodiment is applicable to a wet process and is excellent in heat resistance and etching resistance. Furthermore, the underlayer film forming material of the present embodiment employs the above substances and can therefore form an underlayer film that is prevented from deteriorating during high temperature baking and is also excellent in etching resistance against oxygen plasma etching or the like. Moreover, the underlayer film forming material of the present embodiment is also excellent in adhesiveness to a resist layer and can therefore produce an excellent resist pattern. The underlayer film forming material of the present embodiment may contain an already known underlayer film forming material for lithography or the like, within the range not deteriorating the effect of the present invention.

[Solvent]

The underlayer film forming material of the present embodiment may contain a solvent. A publicly known solvent can be arbitrarily used as the solvent in the underlayer film forming material of the present embodiment as long as at least the above substances dissolve.

Specific examples of the solvent include, but not particularly limited to: ketone-based solvents such as acetone, methyl ethyl ketone, methyl isobutyl ketone, and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, methyl methoxypropionate, and methyl hydroxyisobutyrate; alcohol-based solvents such as methanol, ethanol, isopropanol, and 1-ethoxy-2-propanol; and aromatic hydrocarbons such as toluene, xylene, and anisole. These solvents can be used alone as one kind or used in combination of two or more kinds.

Among the above solvents, cyclohexanone, propylene glycol monomethyl ether, propylene glycol monomethyl ether acetate, ethyl lactate, methyl hydroxyisobutyrate, or anisole is particularly preferable from the viewpoint of safety.

The content of the solvent is not particularly limited and is preferably 100 to 10,000 parts by mass per 100 parts by mass of the above underlayer film forming material, more preferably 200 to 5,000 parts by mass, and still more preferably 200 to 1,000 parts by mass, from the viewpoint of solubility and film formation.

[Crosslinking Agent]

The underlayer film forming material of the present embodiment may contain a crosslinking agent, if required, from the viewpoint of, for example, suppressing intermixing. The crosslinking agent that may be used in the present embodiment is not particularly limited, but a crosslinking agent described in, for example, International Publication No. WO 2013/024779 can be used.

In the underlayer film forming material of the present embodiment, the content of the crosslinking agent is not particularly limited and is preferably 5 to 50 parts by mass per 100 parts by mass of the underlayer film forming material, and more preferably 10 to 40 parts by mass. By the above preferable range, a mixing event with a resist layer tends to be prevented. Also, an antireflection effect is enhanced, and film formability after crosslinking tends to be enhanced.

[Acid Generating Agent]

The underlayer film forming material of the present embodiment may contain an acid generating agent, if required, from the viewpoint of, for example, further accelerating crosslinking reaction by heat. An acid generating agent that generates an acid by thermal decomposition, an acid generating agent that generates an acid by light irradiation, and the like are known, any of which can be used. For example, International Publication No. WO 2013/024779 can be used.

In the underlayer film forming material of the present embodiment, the content of the acid generating agent is not particularly limited and is preferably 0.1 to 50 parts by mass per 100 parts by mass of the underlayer film forming material, and more preferably 0.5 to 40 parts by mass. By the above preferable range, crosslinking reaction tends to be enhanced by an increased amount of an acid generated. Also, a mixing event with a resist layer tends to be prevented.

[Basic Compound]

The underlayer film forming material of the present embodiment may further contain a basic compound from the viewpoint of, for example, improving storage stability.

The basic compound plays a role as a quencher against acids in order to prevent crosslinking reaction from proceeding due to a trace amount of an acid generated by the acid generating agent. Examples of such a basic compound include, but not particularly limited to, those described in International Publication No. WO 2013/024779.

In the underlayer film forming material according to the present embodiment, the content of the basic compound is not particularly limited and is preferably 0.001 to 2 parts by mass per 100 parts by mass of the underlayer film forming material, and more preferably 0.01 to 1 parts by mass. By the above preferable range, storage stability tends to be enhanced without excessively deteriorating crosslinking reaction.

[Further Additive Agent]

The underlayer film forming material according to the present embodiment may also contain an additional resin and/or compound for the purpose of conferring thermosetting properties or controlling absorbance. Examples of such an additional resin and/or compound include, but not particularly limited to, naphthol resin, naphthol-modified resin of xylene resin, phenol-modified resin of naphthalene resin, polyhydroxystyrene, dicyclopentadiene resin, resins containing (meth)acrylate, dimethacrylate, trimethacrylate, tetramethacrylate, a naphthalene ring such as vinylnaphthalene or polyacenaphthylene, a biphenyl ring such as phenanthrenequinone or fluorene, or a heterocyclic ring having a heteroatom such as thiophene or indene, and resins containing no aromatic ring; and resins or compounds containing an alicyclic structure, such as rosin-based resin, cyclodextrin, adamantine(poly)ol, tricyclodecane(poly)ol, and derivatives thereof. The underlayer film forming material according to the present embodiment may further contain a publicly known additive agent. Examples of the above publicly known additive agent include, but not limited to, ultraviolet absorbers, surfactants, colorants, and nonionic surfactants.

[Underlayer Film for Lithography and Multilayer Resist Pattern Formation Method]

The underlayer film for lithography of the present embodiment is formed from the underlayer film forming material.

The pattern formation method of the present embodiment has the steps of: forming an underlayer film on a substrate using the underlayer film forming material of the present embodiment (step (A-1)); forming at least one photoresist layer on the underlayer film (step (A-2)); and irradiating a predetermined region of the photoresist layer with radiation for development after the second formation step (step (A-3)).

Another pattern formation method of the present embodiment has the steps of: forming an underlayer film on a substrate using the underlayer film forming material of the present embodiment (step (B-1)); forming an intermediate layer film on the underlayer film using a resist intermediate layer film material containing a silicon atom (step (B-2)); forming at least one photoresist layer on the intermediate layer film (step (B-3)); after the step (B-3), irradiating a predetermined region of the photoresist layer with radiation for development, thereby forming a resist pattern (step (B-4)); and after the step (B-4), etching the intermediate layer film with the resist pattern as a mask, etching the underlayer film with the obtained intermediate layer film pattern as an etching mask, and etching the substrate with the obtained underlayer film pattern as an etching mask, thereby forming a pattern on the substrate (step (B-5)).

The underlayer film for lithography of the present embodiment is not particularly limited by its formation method as long as it is formed from the underlayer film forming material of the present embodiment. A publicly known approach can be applied thereto. The underlayer film material can be formed by, for example, applying the underlayer film forming material of the present embodiment onto a substrate by a publicly known coating method or printing method such as spin coating or screen printing, and then removing an organic solvent by volatilization or the like.

It is preferable to perform baking in the formation of the underlayer film, for preventing a mixing event with an upper layer resist while accelerating crosslinking reaction. In this case, the baking temperature is not particularly limited and is preferably in the range of 80 to 450° C., and more preferably 200 to 400° C. The baking time is not particularly limited and is preferably in the range of 10 to 300 seconds. The thickness of the underlayer film can be arbitrarily selected according to required performance and is not particularly limited, but is usually preferably about 30 to 20,000 nm, and more preferably 50 to 15,000 nm.

After preparing the underlayer film, it is preferable to prepare a silicon-containing resist layer or a usual single-layer resist made of hydrocarbon thereon in the case of a two-layer process, and to prepare a silicon-containing intermediate layer thereon and further a silicon-free single-layer resist layer thereon in the case of a three-layer process. In this case, a publicly known photoresist material can be used for forming this resist layer.

After preparing the underlayer film on the substrate, in the case of a two-layer process, a silicon-containing resist layer or a usual single-layer resist made of hydrocarbon can be prepared on the underlayer film. In the case of a three-layer process, a silicon-containing intermediate layer can be prepared on the underlayer film, and a silicon-free single-layer resist layer can be further prepared on the silicon-containing intermediate layer. In these cases, a publicly known photoresist material can be arbitrarily selected and used for forming the resist layer, without particular limitations.

For the silicon-containing resist material for a two-layer process, a silicon atom-containing polymer such as a polysilsesquioxane derivative or a vinylsilane derivative is used as a base polymer, and a positive type photoresist material further containing an organic solvent, an acid generating agent, and if required, a basic compound or the like is preferably used, from the viewpoint of oxygen gas etching resistance. Herein, a publicly known polymer that is used in this kind of resist material can be used as the silicon atom-containing polymer.

A polysilsesquioxane-based intermediate layer is preferably used as the silicon-containing intermediate layer for a three-layer process. By imparting effects as an antireflection film to the intermediate layer, there is a tendency that reflection can be effectively suppressed. For example, use of a material containing a large amount of an aromatic group and having high substrate etching resistance as the underlayer film in a process for exposure at 193 nm tends to increase a k value and enhance substrate reflection. However, the intermediate layer suppresses the reflection so that the substrate reflection can be 0.5% or less. The intermediate layer having such an antireflection effect is not limited, and polysilsesquioxane that crosslinks by an acid or heat in which a light absorbing group having a phenyl group or a silicon-silicon bond is introduced is preferably used for exposure at 193 nm.

Alternatively, an intermediate layer formed by chemical vapour deposition (CVD) may be used. The intermediate layer highly effective as an antireflection film prepared by CVD is not limited, and, for example, a SiON film is known. In general, the formation of an intermediate layer by a wet process such as spin coating or screen printing is more convenient and more advantageous in cost, as compared with CVD. The upper layer resist for a three-layer process may be positive type or negative type, and the same as a single-layer resist generally used can be used.

The underlayer film according to the present embodiment can also be used as an antireflection film for usual single-layer resists or an underlying material for suppression of pattern collapse. The underlayer film of the present embodiment is excellent in etching resistance for an underlying process and can be expected to also function as a hard mask for an underlying process.

In the case of forming a resist layer from the above photoresist material, a wet process such as spin coating or screen printing is preferably used, as in the case of forming the above underlayer film. After coating with the resist material by spin coating or the like, prebaking is generally performed. This prebaking is preferably performed at 80 to 180° C. in the range of 10 to 300 seconds. Then, exposure, post-exposure baking (PEB), and development can be performed according to a conventional method to obtain a resist pattern. The thickness of the resist film is not particularly limited and is generally preferably 30 to 500 nm, and more preferably 50 to 400 nm.

The exposure light can be arbitrarily selected and used according to the photoresist material to be used. General examples thereof can include a high energy ray having a wavelength of 300 nm or less, specifically, excimer laser of 248 nm, 193 nm, or 157 nm, soft x-ray of 3 to 20 nm, electron beam, and X-ray.

In a resist pattern formed by the above method, pattern collapse is suppressed by the underlayer film according to the present embodiment. Therefore, use of the underlayer film according to the present embodiment can produce a finer pattern and can reduce an exposure amount necessary for obtaining the resist pattern.

Next, etching is performed with the obtained resist pattern as a mask. Gas etching is preferably used as the etching of the underlayer film in a two-layer process. The gas etching is preferably etching using oxygen gas. In addition to oxygen gas, an inert gas such as He or Ar, or CO, $CO_2$, $NH_3$, $SO_2$, $N_2$, $NO_2$, or $H_2$ gas may be added. Alternatively, the gas etching may be performed with CO, $CO_2$, $NH_3$, $N_2$, $NO_2$, or $H_2$ gas without the use of oxygen gas. Particularly, the latter gas is preferably used for side wall protection in order to prevent the undercut of pattern side walls.

On the other hand, gas etching is also preferably used as the etching of the intermediate layer in a three-layer process. The same gas etching as described in the above two-layer process is applicable. Particularly, it is preferable to process the intermediate layer in a three-layer process by using chlorofluorocarbon-based gas and using the resist pattern as a mask. Then, as mentioned above, for example, the underlayer film can be processed by oxygen gas etching with the intermediate layer pattern as a mask.

Herein, in the case of forming an inorganic hard mask intermediate layer film as the intermediate layer, a silicon oxide film, a silicon nitride film, or a silicon oxynitride film (SiON film) is formed by CVD, ALD, or the like. A method for forming the nitride film is not limited, and, for example, a method described in Japanese Patent Laid-Open No. 2002-334869 (Patent Literature 6) or WO2004/066377 (Patent Literature 7) can be used. Although a photoresist film can be formed directly on such an intermediate layer film, an organic antireflection film (BARC) may be formed on the intermediate layer film by spin coating and a photoresist film may be formed thereon.

A polysilsesquioxane-based intermediate layer is preferably used as the intermediate layer. By imparting effects as an antireflection film to the resist intermediate layer film, there is a tendency that reflection can be effectively suppressed. A specific material for the polysilsesquioxane-based intermediate layer is not limited, and, for example, a material described in Japanese Patent Laid-Open No. 2007-226170 (Patent Literature 8) or Japanese Patent Laid-Open No. 2007-226204 (Patent Literature 9) can be used.

The subsequent etching of the substrate can also be performed by a conventional method. For example, the substrate made of $SiO_2$ or SiN can be etched mainly using chlorofluorocarbon-based gas, and the substrate made of p-Si, Al, or W can be etched mainly using chlorine- or bromine-based gas. In the case of etching the substrate with chlorofluorocarbon-based gas, the silicon-containing resist of the two-layer resist process or the silicon-containing intermediate layer of the three-layer process is peeled at the same time with substrate processing. On the other hand, in the case of etching the substrate with chlorine- or bromine-based gas, the silicon-containing resist layer or the silicon-containing intermediate layer is separately peeled and in general, peeled by dry etching using chlorofluorocarbon-based gas after substrate processing.

A feature of the underlayer film according to the present embodiment is that it is excellent in etching resistance of these substrates. The substrate can be arbitrarily selected from publicly known ones and used and is not particularly limited. Examples thereof include Si, α-Si, p-Si, $SiO_2$, SiN, SiON, W, TiN, and Al. The substrate may be a laminate having a film to be processed (substrate to be processed) on a base material (support). Examples of such a film to be processed include various low-k films such as Si, $SiO_2$, SiON, SiN, p-Si, α-Si, W, W—Si, Al, Cu, and Al—Si, and stopper films thereof. A material different from that for the base material (support) is generally used. The thickness of the substrate to be processed or the film to be processed is not particularly limited and is generally preferably about 1,000,000 nm, and more preferably 75 to 500,000 nm.

EXAMPLES

The present embodiment will be described in more detail with reference to synthesis examples and examples below. However, the present embodiment is not limited to these examples by any means.

(Carbon Concentration and Oxygen Concentration)

The carbon concentration and the oxygen concentration (% by mass) were measured by organic elemental analysis.

Apparatus: CHN Coder MT-6 (manufactured by Yaic. Yanaco)

(Molecular Weight)

The molecular weight of a compound was measured by LC-MS analysis using Acquity UPLC/MALDI-Synapt HDMS manufactured by Waters Corp.

(Solubility)

A compound was dissolved at 5% by mass in propylene glycol monomethyl ether (PGME) at 23° C. Then, the solution was left to stand still at 5° C. for 30 days. The results were evaluated according to the following criteria.

Evaluation A: No precipitate was visually confirmed.

Evaluation C: Precipitates were visually confirmed.

(Synthesis Example 1) Synthesis of BiN-1

To a container (internal capacity: 300 mL) equipped with a stirrer, a condenser tube, and a burette, after 10 g (69.0 mmol) of 2-naphthol (a reagent manufactured by Sigma-Aldrich) was melted at 120° C., 0.27 g of sulfuric acid was added, and 2.7 g (13.8 mmol) of 4-acetylbiphenyl (a reagent manufactured by Sigma-Aldrich) was added, and the contents were reacted by being stirred at 120° C. for 6 hours to obtain a reaction solution. Next, 100 mL of N-methyl-2-pyrrolidone (manufactured by Kanto Chemical Co., Inc.) and 50 mL of pure water were added to the reaction solution, followed by extraction with ethyl acetate. Next, the mixture was separated until neutral by the addition of pure water, and then concentrated to obtain a solution.

The obtained solution was separated by column chromatography to obtain 1.0 g of the objective compound (BiN-1) represented by the following formula (BiN-1).

As a result of measuring the molecular weight of the obtained compound (BiN-1) by the above method, it was 466. The carbon concentration was 87.5% by mass, and the oxygen concentration was 6.9% by mass.

The following peaks were found by NMR measurement performed on the obtained compound (BiN-1) under the above measurement conditions, and the compound was confirmed to have a chemical structure of the following formula (BiN-1).

δ (ppm) 9.69 (2H, O—H), 7.01-7.67 (21H, Ph-H), 2.28 (3H, C—H)

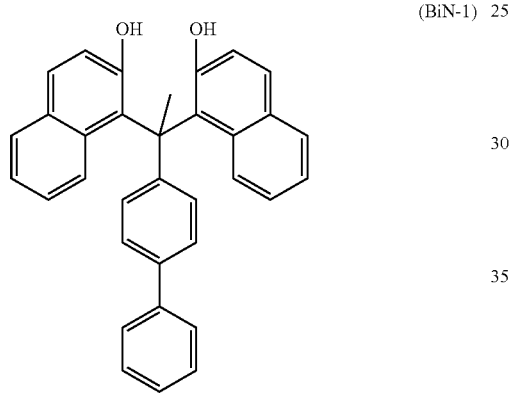

(BiN-1)

(Synthesis Example 2) Synthesis of BiP-1

To a container (internal capacity: 300 mL) equipped with a stirrer, a condenser tube, and a burette, after 12 g (69.0 mmol) of o-phenylphenol (a reagent manufactured by Sigma-Aldrich) was melted at 120° C., 0.27 g of sulfuric acid was added, and 2.7 g (13.8 mmol) of 4-acetylbiphenyl (a reagent manufactured by Sigma-Aldrich) was added, and the contents were reacted by being stirred at 120° C. for 6 hours to obtain a reaction solution. Next, 100 mL of N-methyl-2-pyrrolidone (manufactured by Kanto Chemical Co., Inc.) and 50 mL of pure water were added to the reaction solution, followed by extraction with ethyl acetate. Next, the mixture was separated until neutral by the addition of pure water, and then concentrated to obtain a solution.

The obtained solution was separated by column chromatography to obtain 5.0 g of the objective compound (BiP-1) represented by the following formula (BiP-1).

As a result of measuring the molecular weight of the obtained compound (BiP-1) by the above method, it was 518. The carbon concentration was 88.0% by mass, and the oxygen concentration was 6.2% by mass.

The following peaks were found by NMR measurement performed on the obtained compound (BiP-1) under the above measurement conditions, and the compound was confirmed to have a chemical structure of the following formula (BiP-1).

δ (ppm) 9.48 (2H, O—H), 6.88-7.61 (25H, Ph-H), 3.36 (3H, C—H)

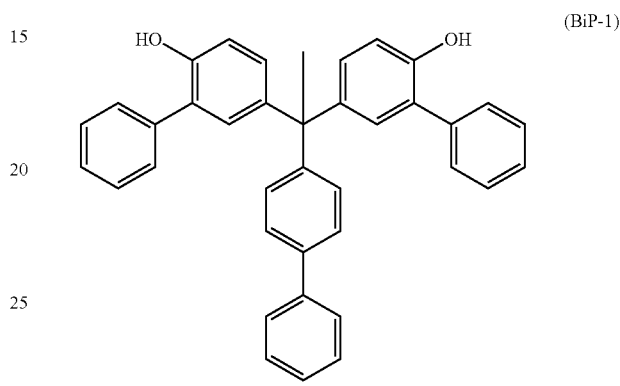

(BiP-1)

Synthesis Examples 3 to 10

The same operations as in Synthesis Example 1 were performed except that 2-naphthol and 4-acetylbiphenyl which were raw materials in Synthesis Example 1 were changed as shown in Table 1 below to obtain each target compound.

Also, the compounds obtained in Synthesis Examples 3 to 10 were each identified by 1H-NMR. The results are shown in Table 2.

TABLE 1

| Synthesis Example | Raw material 1 | Raw material 2 | Product |
|---|---|---|---|
| 1 | 2-Naphthol | 4-Acetylbiphenyl | BiN-1 |
| 2 | o-Phenylphenol | 4-Acetylbiphenyl | BiP-1 |
| 3 | 2,6-Dihydroxynaphthalene | 4-Acetylbiphenyl | BiN-2 |
| 4 | 2,7-Dihydroxynaphthalene | 4-Acetylbiphenyl | BiN-3 |
| 5 | 2,6-Dihydroxynaphthalene | 4'-Cyclohexylacetophenone | BiN-4 |
| 6 | p-Phenylphenol | 4-Acetylbiphenyl | BiP-2 |
| 7 | 2,2'-Dihydroxybiphenyl | 4-Acetylbiphenyl | BiP-3 |
| 8 | 2,2'-Dihydroxybiphenyl | 4'-Cyclohexylacetophenone | BiP-4 |
| 9 | Phenol | 4-Acetylbiphenyl | P-1 |
| 10 | Phenol | 4'-Cyclohexylacetophenone | P-2 |

TABLE 2

| Synthesis Example | Compound Name | 1H-NMR |
|---|---|---|
| 3 | BiN-2 | δ (ppm) 9.2-9.7 (4H, O—H), 6.8-7.9 (19H, Ph—H), 2.5 (3H, C—H$_3$) |
| 4 | BiN-3 | δ (ppm) 9.2-9.7 (4H, O—H), 6.9-7.8 (19H, Ph—H), 2.5 (3H, C—H$_3$) |

TABLE 2-continued
| Synthesis Example | Compound Name | 1H-NMR |
|---|---|---|
| 5 | BiN-4 | δ (ppm) 9.2-9.7 (4H, O—H), 6.8-7.8 (14H, Ph—H), 2.5 (3H, C—H$_3$), 1.4-1.9 (10H, C—H$_2$), 2.7 (1H, C—H) |
| 6 | BiP-2 | δ (ppm) 9.7 (4H, O—H), 6.8-7.8 (23H, Ph—H), 2.3 (3H, C—H$_3$) |
| 7 | BiP-3 | δ (ppm) 9.0 (4H, O—H), 7.0-7.8 (23H, Ph—H), 2.3 (3H, C—H$_3$) |
| 8 | BiP-4 | δ (ppm) 9.0 (4H, O—H), 7.0-7.8 (18H, Ph—H), 2.3 (3H, C—H$_3$), 1.4-1.9 (10H, C—H$_2$), 2.7 (1H, C—H) |
| 9 | P-1 | δ (ppm) 9.1 (2H, O—H), 6.6-7.8 (17H, Ph—H), 2.3 (3H, C—H$_3$) |
| 10 | P-2 | δ (ppm) 9.1 (2H, O—H), 6.6-7.2 (12H, Ph—H), 2.3 (3H, C—H$_3$), 1.4-1.9 (10H, C—H2), 2.7 (1H, C—H) |
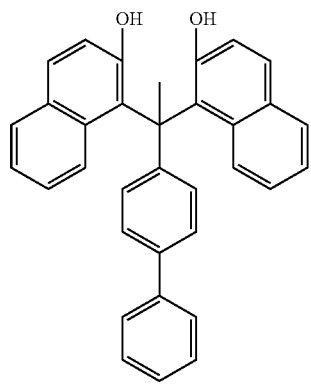
(BiN-1)
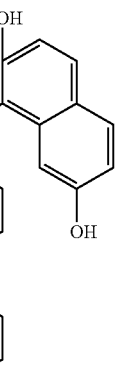
-continued
(BiN-3)
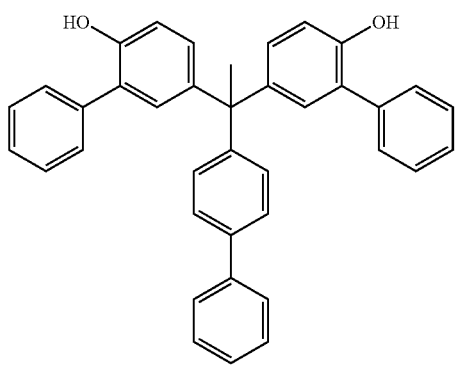
(BiP-1)
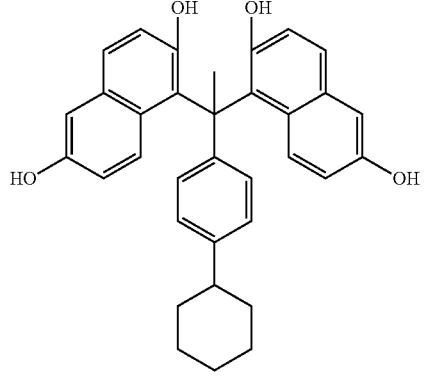
(BiN-4)
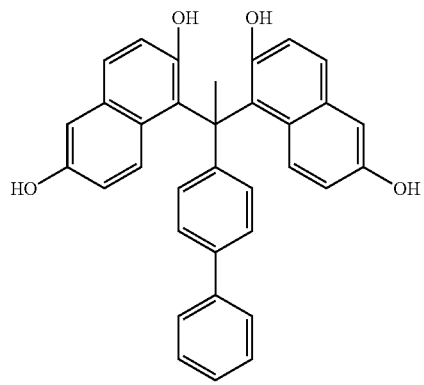
(BiN-2)
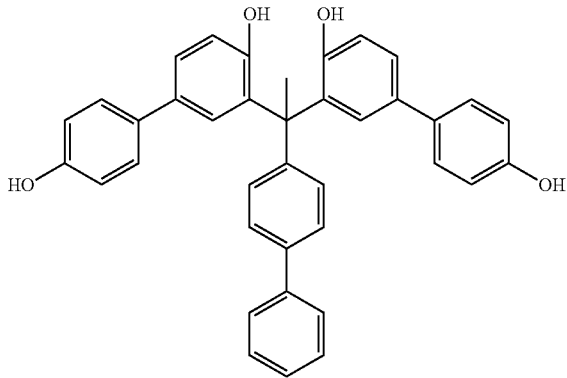
(BiP-2)

(BiP-3)

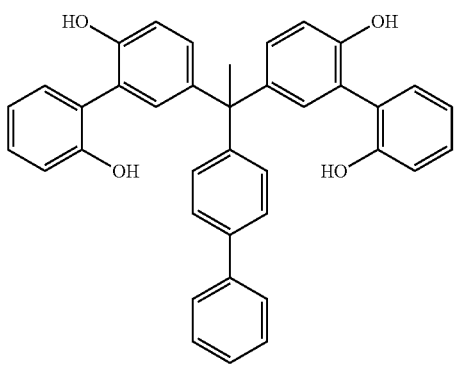

(BiP-4)

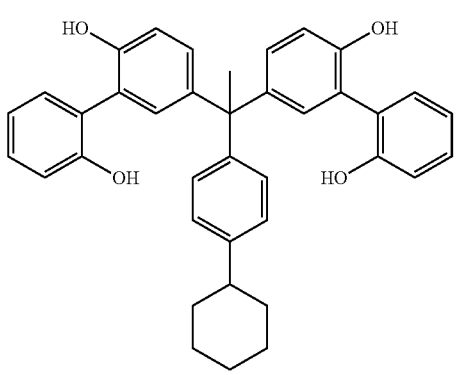

(P-1)

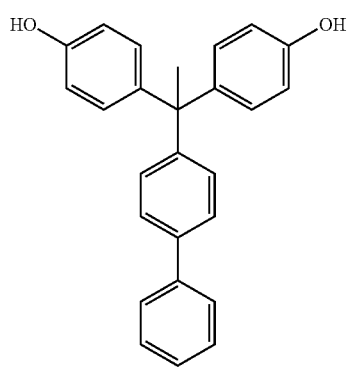

(P-2)

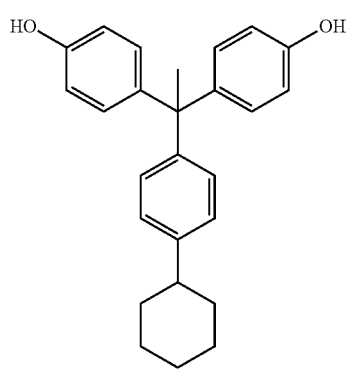

Synthesis Example 11

[Synthesis of BisN-1]

To a container (internal capacity: 100 mL) equipped with a stirrer, a condenser tube, and a burette, 1.60 g (10 mmol) of 2,6-dihydroxynaphthalene (a reagent manufactured by Sigma-Aldrich), 1.82 g (10 mmol) of 4-biphenylaldehyde (manufactured by Mitsubishi Gas Chemical Company Inc.), and 30 mL of methyl isobutyl ketone were added, and 5 mL of 95% sulfuric acid was added. The reaction solution was stirred at 100° C. for 6 hours and reacted. Next, the reaction solution was concentrated. The reaction product was precipitated by the addition of 50 g of pure water. After cooling to room temperature, the precipitates were separated by filtration. The solid matter obtained by filtration was dried and then separated and purified by column chromatography to obtain 3.05 g of the compound (BisN-1) represented by the following formula.

The following peaks were found by $^1$H-NMR, and the compound was confirmed to have a chemical structure of the following formula.

$^1$H-NMR: (d-DMSO, Internal standard TMS)

δ (ppm) 9.7 (2H, O—H), 7.2-8.5 (19H, Ph-H), 6.6 (1H, C—H)

(BisN-1)

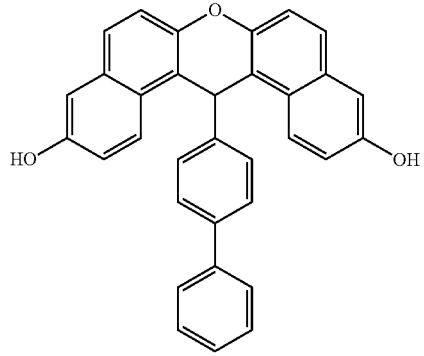

Synthesis of Me-BisN-1

To a container (internal capacity: 200 mL) equipped with a stirrer, a condenser tube, and a burette, 10 g (21.4 mmol) of BisN-1, 7.4 g (53.5 mmol) of potassium carbonate (manufactured by Kanto Chemical Co., Inc.), and 50 mL of N,N-dimethylformamide (manufactured by Kanto Chemical Co., Inc.) were added, and 7.6 g (53.5 mmol) of methyl iodide (manufactured by Kanto Chemical Co., Inc.) was added at 5° C. over 5 minutes. Then, the reaction solution was stirred at room temperature for 6 hours and reacted. Next, the reaction product was precipitated by the addition of 200 mL of pure water to the reaction solution, and separated by filtration. The obtained solid matter was washed and dried to obtain 10 g of the compound (Me-BisN-1) represented by the following formula.

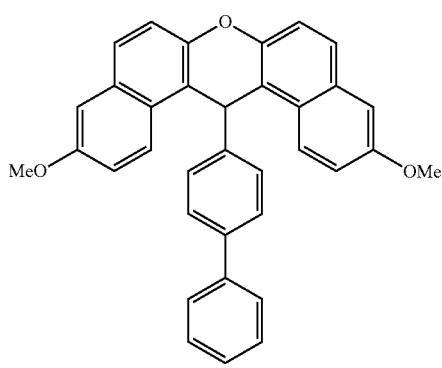

(Me-BisN-1)

Synthesis of Me-XBiN-1

To a container (internal capacity: 200 mL) equipped with a stirrer, a condenser tube, and a burette, 2.5 g (5.1 mmol) of Me-BisN-1 and 50 mL of dimethyl sulfoxide (manufactured by Kanto Chemical Co., Inc.) were added, and 2.2 mL of a 2.6 mol/L solution of n-butyllithium (manufactured by Kanto Chemical Co., Inc.) in n-hexane (5.61 mmol as n-butyllithium) was added. The reaction solution was stirred at room temperature for 30 minutes. Then, 2.1 g (14.5 mmol) of methyl iodide (manufactured by Kanto Chemical Co., Inc.) was added thereto at room temperature, and the reaction solution was stirred at room temperature for 30 minutes and reacted. Next, the reaction product was precipitated by the addition of 200 mL of pure water to the reaction solution, and separated by filtration. The obtained solid matter was washed and dried to obtain 2.2 g of the compound (Me-XBiN-1) represented by the following formula.

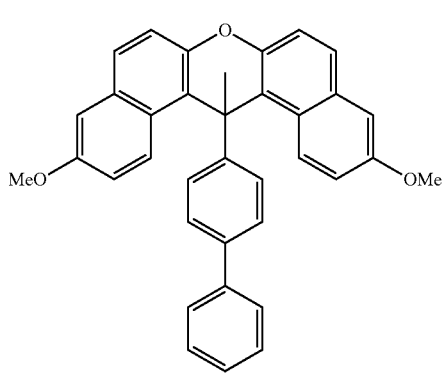

(Me-XBiN-1)

Synthesis of XBiN-1

To a container (internal capacity: 500 mL) equipped with a stirrer, a condenser tube, and a burette, 15 g (29 mmol) of Me-XBiN-1 and 80 g of pyridine hydrochloride (manufactured by Kanto Chemical Co., Inc.) were added, melted at 190° C., then stirred for 2 hours and reacted. After the reaction terminated, the reaction solution was cooled to 90° C., and crystals were precipitated by the addition of 160 mL of pure water of 90° C. The crystals were washed with ethyl acetate/pure water=250 mL/100 mL and subsequently dissolved in 100 mL of ethyl acetate, followed by the addition of ethyl acetate/hexane=150 mL/150 mL to obtain crystals. The obtained crystals were separated and dried to obtain 13 g of the compound (XbiN-1) represented by the following formula.

As a result of measuring the molecular weight of the obtained compound (XbiN-1) by the above method, it was 480. The carbon concentration was 85.0% by mass, and the oxygen concentration was 10.0% by mass.

The following peaks were found by NMR measurement under the above measurement conditions, and the compound was confirmed to have a chemical structure of the following formula (XBiN-1).

δ (ppm) 9.2 (2H, O—H), 6.8-7.9 (19H, Ph-H), 2.5 (3H, C—H)

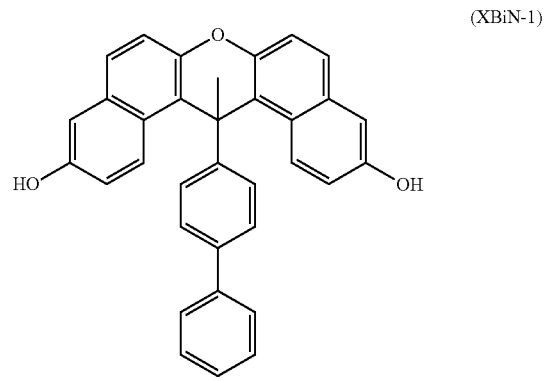

(XBiN-1)

Synthesis Examples 12 and 13

The same operations as in Synthesis Example 1 were performed except that 2,6-dihydroxynaphthalene and 4-biphenylaldehyde which were raw materials in Synthesis Example 11 were changed as shown in Table 3 below to obtain each target compound.

Also, the compounds obtained in Synthesis Examples 12 and 13 were each identified by $^1$H-NMR. The results are shown in Table 4.

TABLE 3

| Synthesis Example | Raw material 1 | Raw material 2 | Product |
|---|---|---|---|
| 11 | 2,6-Dihydroxynaphthalene | 4-Biphenylaldehyde | XBiN-1 |
| 12 | 2,7-Dihydroxynaphthalene | 4-Biphenylaldehyde | XBiN-2 |
| 13 | 2,6-Dihydroxynaphthalene | 4-Cyclohexylbenzaldehyde | XBiN-3 |

TABLE 4

| Synthesis Example | Compound Name | 1H-NMR |
|---|---|---|
| 12 | XBiN-2 | δ (ppm) 9.2 (2H, O—H), 6.9-7.9 (19H, Ph—H), 2.5 (3H, C—H) |
| 13 | XBiN-3 | δ (ppm) 9.2 (2H, O—H), 6.8-7.9 (14H, Ph—H), 2.5 (3H, C—H) 1.4-1.9 (10H, C—H2), 2.7 (1H, C—H) |

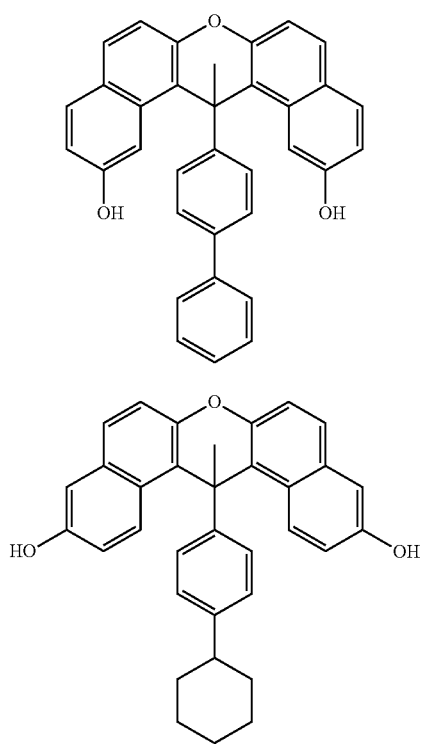

(XBiN-2)

(XBiN-3)

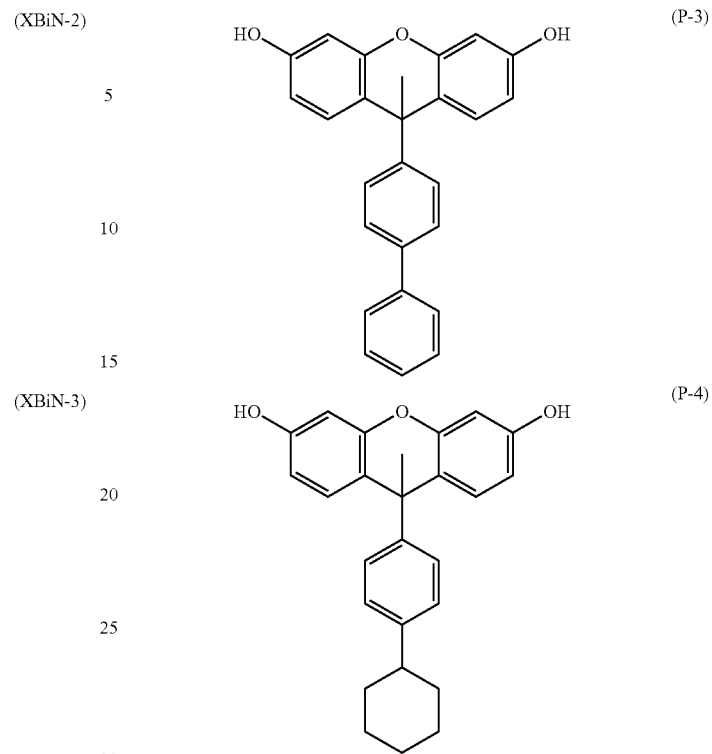

(P-3)

(P-4)

Synthesis Examples 14 and 15

The same operations as in Synthesis Example 1 were performed except that: 2-naphthol and 4-acetylbiphenyl which were raw materials in Synthesis Example 1 were changed as shown in Table 5 below; 1.5 mL of water, 73 mg (0.35 mmol) of dodecylmercaptan, and 2.3 g (22 mmol) of 37% hydrochloric acid were added; and the reaction temperature was changed to 55° C., to obtain each target compound.

Also, the compounds obtained in Synthesis Examples 14 and 15 were each identified by 1H-NMR. The results are shown in Table 6.

TABLE 5

| Synthesis Example | Raw material 1 | Raw material 2 | Product |
|---|---|---|---|
| 1 | 2-Naphthol | 4-Acetylbiphenyl | BiN-1 |
| 14 | Resorcinol | 4-Acetylbiphenyl | P-3 |
| 15 | Resorcinol | 4'-Cyclohexylacetophenone | P-4 |

TABLE 6

| Synthesis Example | Compound Name | 1H-NMR |
|---|---|---|
| 14 | P-3 | δ (ppm) 9.9 (2H, O—H), 6.4-7.8 (15H, Ph—H), 2.3 (3H, C—H) |
| 15 | P-4 | δ (ppm) 9.2 (2H, O—H), 6.4-7.2 (10H, Ph—H), 2.3 (3H, C—H), 1.4-1.9 (10H, C—H2), 2.7 (1H, C—H) |

Synthesis Example 1

A four necked flask (internal capacity: 10 L) equipped with a Dimroth condenser tube, a thermometer, and a stirring blade and having a detachable bottom was prepared. To this four necked flask, 1.09 kg (7 mol) of 1,5-dimethylnaphthalene (manufactured by Mitsubishi Gas Chemical Company, Inc.), 2.1 kg (28 mol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were added in a nitrogen stream, and the mixture was reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a light brown solid dimethylnaphthalene formaldehyde resin.

The molecular weight of the obtained dimethylnaphthalene formaldehyde was Mn: 562.

Subsequently, a four necked flask (internal capacity: 0.5 L) equipped with a Dimroth condenser tube, a thermometer, and a stirring blade was prepared. To this four necked flask, 100 g (0.51 mol) of the dimethylnaphthalene formaldehyde resin obtained as above, and 0.05 g of p-toluenesulfonic acid were added in a nitrogen stream, and the temperature was raised to 190° C. at which the mixture was then heated for 2 hours, followed by stirring. Subsequently, 52.0 g (0.36 mol) of 1-naphthol was added thereto, and the temperature was further raised to 220° C. at which the mixture was reacted for 2 hours. After solvent dilution, neutralization and washing with water were performed, and the solvent was removed under reduced pressure to obtain 126.1 g of a black-brown solid modified resin (CR-1).

The obtained resin (CR-1) had Mn: 885, Mw: 2220, and Mw/Mn: 4.17. The carbon concentration was 89.1% by mass, and the oxygen concentration was 4.5% by mass.

Examples 1 to 15 and Comparative Example 1

Solubility test was conducted using BiN-1, BiP-1, BiN-2, BiN-3, BiN-4, BiP-2, BiP-3, BiP-4, P-1, P-2, XBiN-1, XBiN-2, XBiN-3, P-3, P-4, and CR-1 described above. The results are shown in Table 7.

Underlayer film forming materials for lithography were each prepared according to the composition shown in Table 7. Next, a silicon substrate was spin coated with each of these underlayer film forming materials for lithography, and then baked at 240° C. for 60 seconds and further at 400° C. for 120 seconds to prepare each underlayer film with a film thickness of 200 nm. The following acid generating agent, crosslinking agent, and organic solvent were used.

Acid generating agent: di-tertiary butyl diphenyliodonium nonafluoromethanesulfonate (DTDPI) manufactured by Midori Kagaku Co., Ltd.

Crosslinking agent: NIKALAC MX270 (NIKALAC) (Sanwa Chemical Co., Ltd.)

Organic solvent: propylene glycol monomethyl ether acetate (PGMEA)

Novolac: PSM4357 manufactured by Gunei Chemical Industry Co., Ltd.

Etching test was further conducted under conditions shown below to evaluate etching resistance. The evaluation results are shown in Table 7.

[Etching Test]
Etching apparatus: RIE-10NR manufactured by Samco International, Inc.
Output: 50 W
Pressure: 20 Pa
Time: 2 min
Etching gas
Ar gas flow rate:$CF_4$ gas flow rate:$O_2$ gas flow rate=50:5:5 (sccm)

[Evaluation of Etching Resistance]
The evaluation of etching resistance was conducted by the following procedures.

First, an underlayer film of novolac was prepared under the same conditions as in Example 1 except that novolac (PSM4357 manufactured by Gunei Chemical Industry Co., Ltd.) was used instead of the compound (BiN-1) used in Example 1. Then, this underlayer film of novolac was subjected to the above etching test, and the etching rate was measured.

Next, underlayer films of Examples 1 and Comparative Example 1 were subjected to the above etching test in the same way as above, and the etching rate was measured.

Then, the etching resistance was evaluated according to the following evaluation criteria on the basis of the etching rate of the underlayer film of novolac.

[Evaluation Criteria]
S: The etching rate was less than −15% as compared with the underlayer film of novolac.
A: The etching rate was less than −15% to −10% as compared with the underlayer film of novolac.
B: The etching rate was −10% to +5% as compared with the underlayer film of novolac.
C: The etching rate was more than +5% as compared with the underlayer film of novolac.

TABLE 7

|  | Underlayer film forming material (parts by mass) | Solvent (parts by mass) | Acid generating agent (parts by mass) | Crosslinking agent (parts by mass) | Solubility evaluation | Etching resistance evaluation |
| --- | --- | --- | --- | --- | --- | --- |
| Example 1 | BiN-1 (10) | PGMEA (90) | DTDPI (0.5) | Nikalac (0.5) | A | A |
| Example 2 | BiP-1 (10) | PGMEA (90) | DTDPI (0.5) | Nikalac (0.5) | A | A |
| Example 3 | BiN-2 (10) | PGMEA (90) | DTDPI (0.5) | Nikalac (0.5) | A | A |
| Example 4 | BiN-3 (10) | PGMEA (90) | DTDPI (0.5) | Nikalac (0.5) | A | A |
| Example 5 | BiN-4 (10) | PGMEA (90) | DTDPI (0.5) | Nikalac (0.5) | A | A |
| Example 6 | BiP-2 (10) | PGMEA (90) | DTDPI (0.5) | Nikalac (0.5) | A | A |
| Example 7 | BiP-3 (10) | PGMEA (90) | DTDPI (0.5) | Nikalac (0.5) | A | S |
| Example 8 | BiP-4 (10) | PGMEA (90) | DTDPI (0.5) | Nikalac (0.5) | A | S |
| Example 9 | P-1 (10) | PGMEA (90) | DTDPI (0-5) | Nikalac (0.5) | A | A |
| Example 10 | P-2 (10) | PGMEA (90) | DTDPI (0.5) | Nikalac (0.5) | A | A |
| Example 11 | XBiN-1 (10) | PGMEA (90) | DTDPI (0.5) | Nikalac (0.5) | A | S |
| Example 12 | XBiN-2 (10) | PGMEA (90) | DTDPI (0.5) | Nikalac (05) | A | S |
| Example 13 | XBiN-3 (10) | PGMEA (90) | DTDPI (0.5) | Nikalac (0-5) | A | S |
| Example 14 | P-3 (10) | PGMEA (90) | DTDPI (0.5) | Nikalac (0.5) | A | B |
| Example 15 | P-4 (10) | PGMEA (90) | DTDPI (0.5) | Nikalac (0.5) | A | B |
| Comparative Example 1 | CR-1 (10) | PGMEA (90) | DTDPI (0.5) | Nikalac (0.5) | A | C |

Examples 16 to 30

Next, a SiO$_2$ substrate with a film thickness of 300 nm was coated with each solution of the underlayer film forming material for lithography containing BiN-1, BiP-1, BiN-2, BiN-3, BiN-4, BiP-2, BiP-3, BiP-4, P-1, P-2, XBiN-1, XBiN-2, XBiN-3, P-3, or P-4, and baked at 240° C. for 60 seconds and further at 400° C. for 120 seconds to prepare each underlayer film with a film thickness of 70 nm. This underlayer film was coated with a resist solution for ArF and baked at 130° C. for 60 seconds to form a photoresist layer with a film thickness of 140 nm. The ArF resist solution used was prepared by containing 5 parts by mass of a compound of the formula (11) given below, 1 part by mass of triphenylsulfonium nonafluoromethanesulfonate, 2 parts by mass of tributylamine, and 92 parts by mass of PGMEA.

For the compound of the formula (11), 4.15 g of 2-methyl-2-methacryloyloxyadamantane, 3.00 g of methacryloyloxy-γ-butyrolactone, 2.08 g of 3-hydroxy-1-adamantyl methacrylate, and 0.38 g of azobisisobutyronitrile were dissolved in 80 mL of tetrahydrofuran to prepare a reaction solution. This reaction solution was polymerized for 22 hours with the reaction temperature kept at 63° C. in a nitrogen atmosphere. Then, the reaction solution was added dropwise into 400 mL of n-hexane. The product resin thus obtained was solidified and purified, and the resulting white powder was filtered and dried overnight at 40° C. under reduced pressure to obtain a compound represented by the following formula.

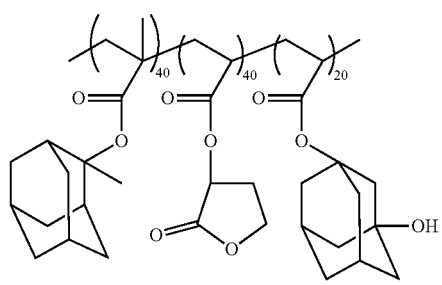

(11)

wherein 40, 40, and 20 represent the ratio of each constituent unit and do not represent a block copolymer.

Subsequently, the photoresist layer was exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a positive type resist pattern.

Results of observing the shape and defects of the obtained resist patterns of 55 nmL/S (1:1) and 80 nmL/S (1:1) are shown in Table 8.

Comparative Example 2

The same operations as in Example 16 were performed except that no underlayer film was formed so that a photoresist layer was formed directly on a SiO$_2$ substrate to obtain a positive type resist pattern. The results are shown in Table 8.

TABLE 8

| Underlayer film forming material | | Resolution (nmL/S) | Sensitivity (μC/cm$^2$) | Resist pattern shape after development |
|---|---|---|---|---|
| Example 16 | As described in Example 1 | 55 | 10 | Good |
| Example 17 | As described in Example 2 | 55 | 10 | Good |
| Example 18 | As described in Example 3 | 55 | 10 | Good |
| Example 19 | As described in Example 4 | 55 | 10 | Good |
| Example 20 | As described in Example 5 | 55 | 10 | Good |
| Example 21 | As escribed in Example 6 | 55 | 10 | Good |
| Example 22 | As described in Example 7 | 55 | 10 | Good |
| Example 23 | As described in Example 8 | 55 | 10 | Good |
| Example 24 | As described in Example 9 | 55 | 10 | Good |
| Example 25 | As described in Example 10 | 55 | 10 | Good |
| Example 26 | As described in Example 11 | 55 | 10 | Good |
| Example 27 | As described in Example 12 | 55 | 10 | Good |
| Example 28 | As described in Example 13 | 55 | 10 | Good |
| Example 29 | As described in Example 14 | 55 | 10 | Good |
| Example 30 | As described in Example 15 | 55 | 10 | Good |
| Comparative Example 2 | None | 80 | 26 | Poor |

As is evident from Table 7, Examples 1 to 15 using BiN-1, BiP-1, BIN-2, BIN-3, BiN-4, BiP-2, BiP-3, BiP-4, P-1, P-2, XBiN-1, XBiN-2, XBiN-3, P-3, and P-4 which were the compounds of the present embodiment were confirmed to be good in terms of both solubility and etching resistance. On the other hand, Comparative Example 1 using CR-1 (phenol-modified dimethylnaphthaleneformaldehyde resin) resulted in poor etching resistance.

In Examples 16 to 30, the resist pattern shape after development was confirmed to be good without any defect. These examples were confirmed to be significantly superior in both resolution and sensitivity to Comparative Example 2 in which underlayer film formation was omitted.

The difference in the resist pattern shapes after development indicated that the underlayer film forming materials for lithography used in Examples 16 to 30 have good adhesiveness to a resist material.

Examples 31 to 45

A SiO$_2$ substrate with a film thickness of 300 nm was coated with the solution of the underlayer film forming material for lithography of each of Examples 1 to 15, and baked at 240° C. for 60 seconds and further at 400° C. for 120 seconds to form each underlayer film with a film thickness of 80 nm. This underlayer film was coated with a silicon-containing intermediate layer material and baked at 200° C. for 60 seconds to form an intermediate layer film with a film thickness of 35 nm. This intermediate layer film was further coated with the above resist solution for ArF and baked at 130° C. for 60 seconds to form a photoresist layer with a film thickness of 150 nm. The silicon-containing intermediate layer material used was the silicon atom-containing polymer described in <Synthesis Example 1> of Japanese Patent Laid-Open No. 2007-226170.

Subsequently, the photoresist layer was mask exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a 55 nm L/S (1:1) positive type resist pattern.

Then, the silicon-containing intermediate layer film (SOG) was dry etched with the obtained resist pattern as a mask using RIE-10NR manufactured by Samco International, Inc. Subsequently, dry etching of the underlayer film with the obtained silicon-containing intermediate layer film pattern as a mask and dry etching of the $SiO_2$ film with the obtained underlayer film pattern as a mask were performed in order.

Respective etching conditions are as shown below.
Conditions for etching of resist intermediate layer film with resist pattern
Output: 50 W
Pressure: 20 Pa
Time: 1 min
Etching gas
Ar gas flow rate:$CF_4$ gas flow rate:$O_2$ gas flow rate=50:8:2 (sccm)
Conditions for etching of resist underlayer film with resist intermediate film pattern
Output: 50 W
Pressure: 20 Pa
Time: 2 min
Etching gas
Ar gas flow rate:$CF_4$ gas flow rate:$O_2$ gas flow rate=50:5:5 (sccm)
Conditions for etching of $SiO_2$ film with resist underlayer film pattern
Output: 50 W
Pressure: 20 Pa
Time: 2 min
Etching gas
Ar gas flow rate:$CsF_{12}$ gas flow rate:$C_2F_6$ gas flow rate:$O_2$ gas flow rate=50:4:3:1 (sccm)
[Evaluation]

The pattern cross section (the shape of the $SiO_2$ film after etching) obtained as described above was observed under an electron microscope manufactured by Hitachi, Ltd. (S-4800). As a result, it was confirmed that the shape of the $SiO_2$ film after etching in a multilayer resist process is a rectangular shape in Examples using the underlayer film of the present embodiment and is good without defects.

Examples 46 to 60

A $SiO_2$ substrate with a film thickness of 300 nm was coated with each optical component forming composition solution having the same composition as in the underlayer film forming materials for lithography of Examples 1 to 15, and baked at 26° C. for 300 seconds to prepare each optical component forming film with a film thickness of 100 nm.

Subsequently, refractive index and transparency tests were conducted at a wavelength of 633 nm using a vacuum ultraviolet variable angle spectroscopic ellipsometer (VUV-VASE) manufactured by J. A. Woollam Co., Inc., and refractive index and transparency were evaluated according to the following criteria.

[Criteria for Evaluating Refractive Index]
A: The refractive index was 1.60 or more.
C: The refractive index was less than 1.60.

[Criteria for Evaluating Transparency]
A: The absorption constant was less than 0.03.
C: The absorption constant was 0.03 or more.

As a result, in all of Examples 46 to 60, the refractive index was evaluated as A, and the transparency was evaluated as A, demonstrating that these optical component forming compositions are useful.

As mentioned above, the present invention is not limited to the above embodiments and examples, and changes or modifications can be arbitrarily made without departing from the spirit of the present invention.

The compound and the resin of the present embodiment have high solubility in a safe solvent and have good heat resistance and etching resistance. The resist composition of the present embodiment imparts a good shape to a resist pattern.

Also, the compound and the resin of the present embodiment are applicable to a wet process and can achieve a compound, a resin, and a film forming composition for lithography useful for forming a photoresist underlayer film excellent in heat resistance and etching resistance. Furthermore, this film forming composition for lithography employs the compound or the resin having high heat resistance and also high solvent solubility and having a specific structure and can therefore form a resist and an underlayer film that is prevented from deteriorating during high temperature baking and is also excellent in etching resistance against oxygen plasma etching or the like. Moreover, the underlayer film thus formed is also excellent in adhesiveness to a resist layer and can therefore form an excellent resist pattern.

Moreover, the composition of the present embodiment has high refractive index and is prevented from being stained by low temperature to high temperature treatments. Therefore, the composition is also useful as various optical component forming compositions.

Accordingly, the present invention is used in for example, electrical insulating materials, resins for resists, encapsulation resins for semiconductors, adhesives for printed circuit boards, electrical laminates mounted in electric equipment, electronic equipment, industrial equipment, and the like, matrix resins of prepregs mounted in electric equipment, electronic equipment, industrial equipment, and the like, buildup laminate materials, resins for fiber-reinforced plastics, resins for encapsulation of liquid crystal display panels, coating materials, various coating agents, adhesives, coating agents for semiconductors, resins for resists for semiconductors, resins for underlayer film formation, and in the form of a film or a sheet, and additionally, can be used widely and effectively in optical components such as plastic lenses (prism lenses, lenticular lenses, microlenses, Fresnel lenses, viewing angle control lenses, contrast improving lenses, etc.), phase difference films, films for electromagnetic wave shielding, prisms, optical fibers, solder resists for flexible printed wiring, plating resists, interlayer insulating films for multilayer printed circuit boards, and photosensitive optical waveguides.

Particularly, the present invention can be effectively used in the fields of resists for lithography, underlayer films for lithography, underlayer films for multilayer resists, and optical components.

The disclosure of Japanese Patent Application No. 2015-254433 filed on Dec. 25, 2015 in the Japan Patent Office is incorporated herein by reference in its entirety.

All literatures, patent applications, and technical standards described herein are incorporated herein by reference to the same extent as if each individual literature, patent application, or technical standard is specifically and individually indicated to be incorporated by reference.

The invention claimed is:

1. A compound represented by formula (1-2), formula (2), or formula (2A):

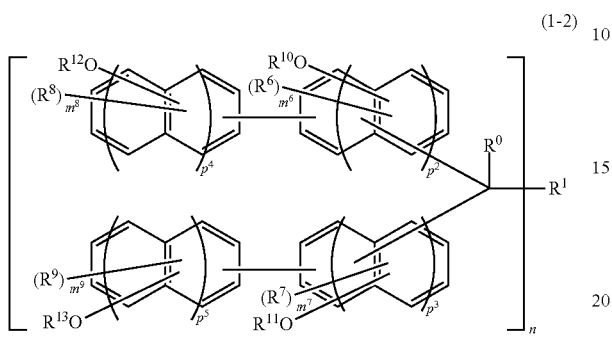

(1-2)

wherein $R^0$ is a methyl group or a phenyl group;

$R^1$ is a biphenyl group or cyclohexyl phenyl group;

$R^6$, $R^7$, $R^8$, and $R^9$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, or a thiol group;

$R^{10}$, $R^{11}$, $R^{12}$, and $R^{13}$ are each independently a hydrogen atom or an acid dissociation group;

$m^6$ and $m^7$ are each independently an integer of 0 to 7;

$m^8$ and $m^9$ are each independently an integer of 0 to 8;

n is an integer of 1 to 2, wherein when n is an integer of 2, n structural formulas within the parentheses [ ] are the same or different; and $p^2$ to $p^5$ are each independently an integer of 0 to 2;

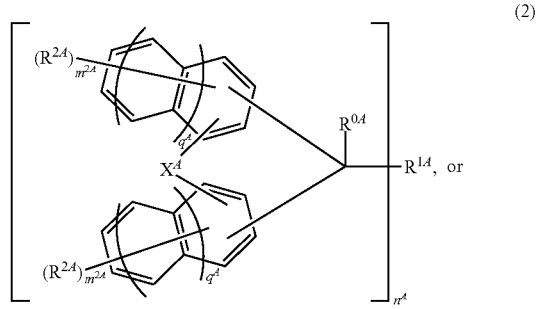

(2)

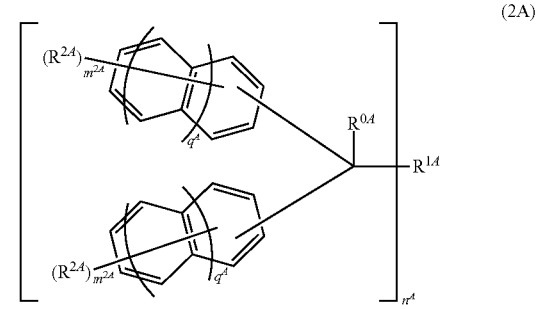

(2A)

wherein $R^{0A}$ is a linear, branched, or cyclic alkyl group of 1 to 30 carbon atoms or an aryl group of 6 to 30 carbon atoms;

in formula (2) each $R^{2A}$ is a hydroxy group;

in formula (2A) each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is defined as an integer of 1 to 4, wherein when $n^A$ is an integer of 2 or larger, $n^A$ structural formulas within the parentheses [ ] are the same or different;

$X^A$ is an oxygen atom or a sulfur atom;

each $m^{2A}$ is independently an integer of 0 to 7, provided that at least one $m^{2A}$ is an integer of 1 to 7;

in formula (2) each $q^A$ is independently 0 or 1, and in formula (2A) each $q^A$ is 1; and $R^{1A}$ is a biphenyl group or cyclohexyl phenyl group.

2. The compound according to claim 1, wherein the compound is the compound represented by formula (1-2).

3. The compound according to claim 1, wherein the compound is the compound represented by formula (2).

4. The compound according to claim 1, wherein $m^6$, $m^7$, $m^8$, and $m^9$ are not 0 at the same time.

5. The compound according to claim 1, wherein the compound represented by the above formula (2) is a compound represented by the following formula (2-1):

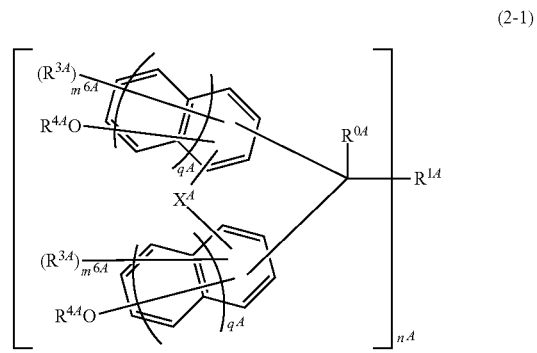

(2-1)

or a compound represented by the above formula (2A) is a compound represented by the following formula (2-1A):

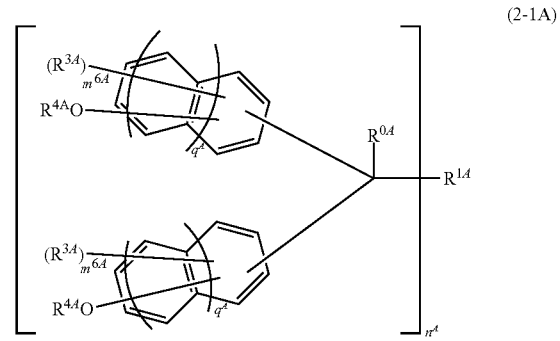

(2-1A)

wherein $R^{0A}$, $R^{1A}$, $n^A$, $q^A$, and $X^A$ are as defined in the description of the above formula (2) and formula (2A);

in formula (2-1) each $R^{3A}$ is a hydroxy group;

in formula (2-1A) each $R^{3A}$ is independently a halogen atom, a linear, branched, or cyclic alkyl group of 1 to 30 carbon atoms, an aryl group of 6 to 30 carbon atoms, or an alkenyl group of 2 to 30 carbon atoms;

in formula (2-1) each $R^{4A}$ is a hydrogen;

in formula (2-1A) each $R^{4A}$ is independently a hydrogen atom or an acid dissociation group; and each $m^{6A}$ is independently an integer of 0 to 5.

6. A resin obtained with the compound according to claim 1 as a monomer.

7. A composition comprising one or more selected from the group consisting of the resin according to claim 6.

8. The compound according to claim 1, wherein the compound is the compound represented by formula (2A).

9. A resin having a structure represented by the following formula (3):

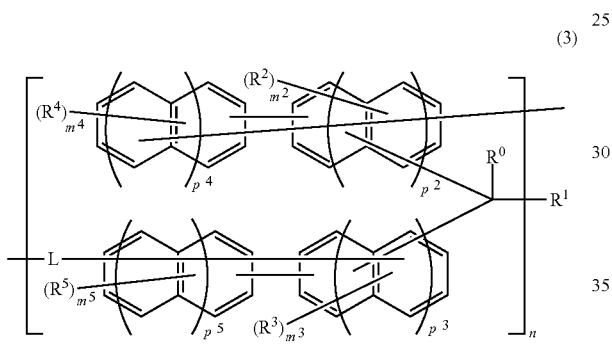

(3)

wherein L is a linear or branched alkylene group of 1 to 30 carbon atoms or a single bond;

$R^0$ is a methyl group or a phenyl group;

$R^1$ a biphenyl group or cyclohexyl phenyl group;

$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;

$m^2$ and $m^3$ are each independently an integer of 0 to 8;

$m^4$ and $m^5$ are each independently an integer of 0 to 9, provided that $m^2$, $m^3$, $m^4$, and $m^5$ are not 0 at the same time;

n is an integer of 1 to 4, wherein when n is an integer of 2 or larger, n structural formulas within the parentheses [ ] are the same or different; and $p^2$ to $p^5$ are each independently an integer of 0 to 2.

10. A resin having a structure represented by the following formula (4) or formula (4A):

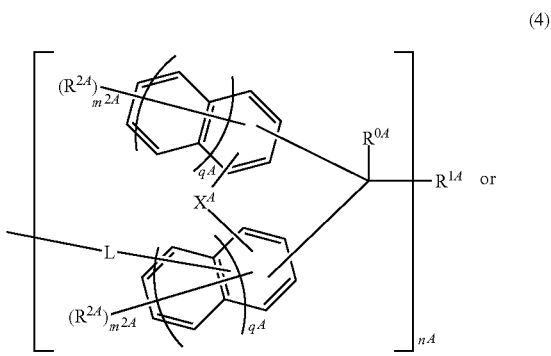

(4)

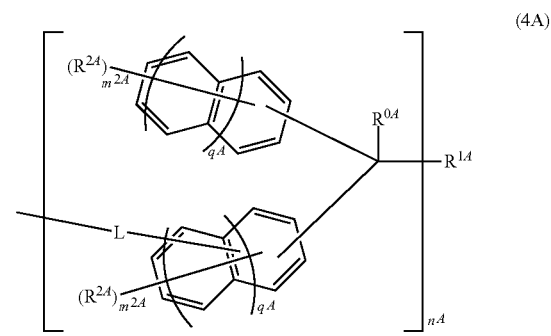

(4A)

wherein L is a linear or branched alkylene group of 1 to 30 carbon atoms or a single bond;

$R^{0A}$ is a linear, branched, or cyclic alkyl group of 1 to 30 carbon atoms or an aryl group of 6 to 30 carbon atoms;

$R^{1A}$ is a biphenyl group or cyclohexyl phenyl group;

each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is defined as an integer of 1 to 4, wherein when $n^A$ is an integer of 2 or larger, $n^A$ structural formulas within the parentheses [ ] are the same or different;

$X^A$ is an oxygen atom or a sulfur atom;

each $m^{2A}$ is independently an integer of 0 to 7, provided that at least one $m^{2A}$ is an integer of 1 to 6; and in formula (2) each $q^A$ is independently 0 or 1, and in formula (2A) each $q^A$ is 1.

11. A composition comprising an acid generating agent and one or more compounds represented by formula (1), formula (2), and formula (2A),

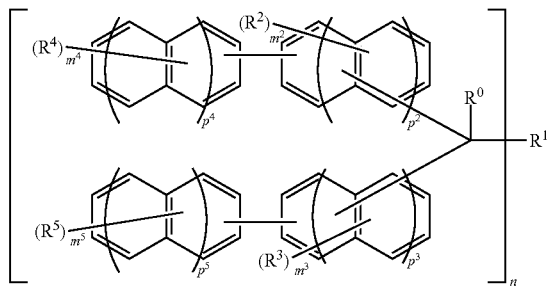

wherein $R^0$ is a methyl group or a phenyl group;
$R^1$ is a biphenyl group or cyclohexyl phenyl group;
$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;
$m^2$ and $m^3$ are each independently an integer of 0 to 8;
$m^4$ and $m^5$ are each independently an integer of 0 to 9, provided that $m^2$, $m^3$, $m^4$, and $m^5$ are not 0 at the same time;
n is an integer of 1 to 2, wherein when n is an integer of 2, n structural formulas within the parentheses [ ] are the same or different; and
$p^2$ to $p^5$ are each independently an integer of 0 to 2;

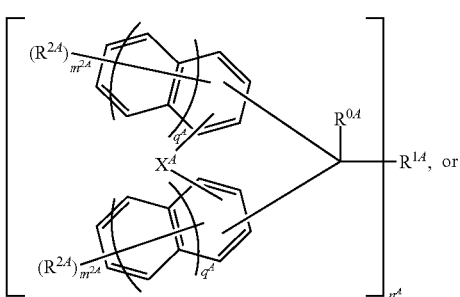

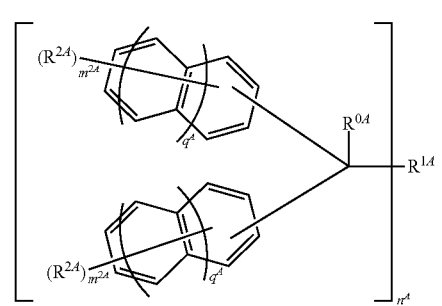

wherein $R^{0A}$ is a linear, branched, or cyclic alkyl group of 1 to 30 carbon atoms or an aryl group of 6 to 30 carbon atoms;
in formula (2) each $R^{2A}$ is a hydroxy group;
in formula (2A) each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;
$n^A$ is defined as an integer of 1 to 4, wherein when $n^A$ is an integer of 2 or larger, $n^A$ structural formulas within the parentheses [ ] are the same or different;
$X^A$ is an oxygen atom or a sulfur atom;
each $m^{2A}$ is independently an integer of 0 to 7, provided that at least one $m^{2A}$ is an integer of 1 to 7;
in formula (2) each $q^A$ is independently 0 or 1, and in formula (2A) each $q^A$ is 1; and
$R^{1A}$ is a biphenyl group or cyclohexyl phenyl group.

12. The composition according to claim 11, further comprising an acid crosslinking agent.

13. A film for lithography produced using the composition of claim 11.

14. An optical component produced using the composition of claim 11.

15. The composition according to claim 11, further comprising a solvent.

16. A method for forming a resist pattern, comprising the steps of:
forming a photoresist layer on a substrate using a film for lithography; and
irradiating a predetermined region of the photoresist layer with radiation for development,
the film for lithography including a composition comprising one or more compounds represented by formula (1), formula (2), or formula (2A):

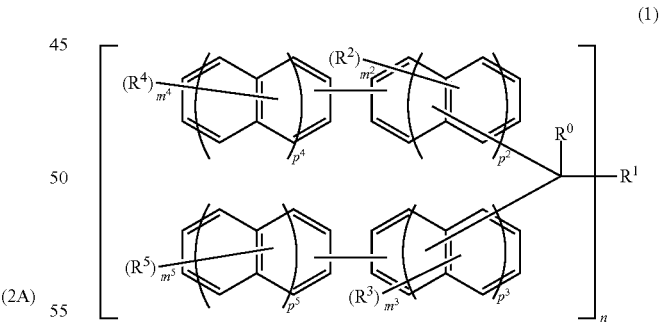

wherein $R^0$ is a methyl group or a phenyl group;
$R^1$ is a biphenyl group or cyclohexyl phenyl group;
$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;

$m^2$ and $m^3$ are each independently an integer of 0 to 8;

$m^4$ and $m^5$ are each independently an integer of 0 to 9, provided that $m^2$, $m^3$, $m^4$, and $m^5$ are not 0 at the same time;

n is an integer of 1 to 2, wherein when n is an integer of 2, n structural formulas within the parentheses [ ] are the same or different; and $p^2$ to $p^5$ are each independently an integer of 0 to 2;

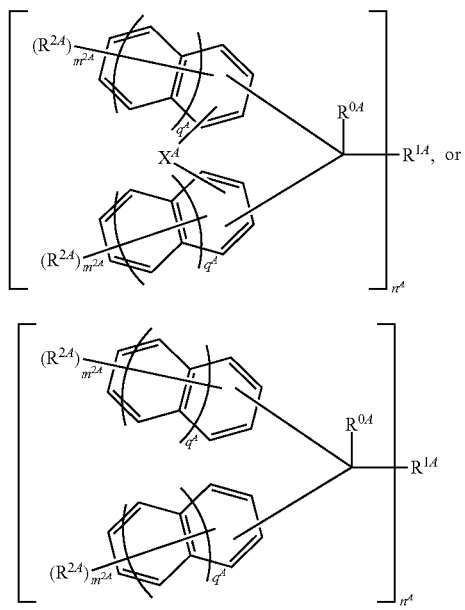

wherein $R^{0A}$ is a linear, branched, or cyclic alkyl group of 1 to 30 carbon atoms or an aryl group of 6 to 30 carbon atoms;

in formula (2) each $R^{2A}$ is a hydroxy group;

in formula (2A) each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is defined as an integer of 1 to 4, wherein when $n^A$ is an integer of 2 or larger, $n^A$ structural formulas within the parentheses [ ] are the same or different;

$X^A$ is an oxygen atom or a sulfur atom;

each $m^{2A}$ is independently an integer of 0 to 7, provided that at least one $m^{2A}$ is an integer of 1 to 7;

each $q^A$ is independently 0 or 1; and $R^{1A}$ is a biphenyl group or cyclohexyl phenyl group.

17. A method for forming a resist pattern, comprising the steps of:

forming an underlayer film on a substrate using a film for lithography;

forming at least one photoresist layer on the underlayer film; and irradiating a predetermined region of the photoresist layer with radiation for development, the film for lithography including a composition comprising one or more compounds represented by formula (1), formula (2), or formula (2A):

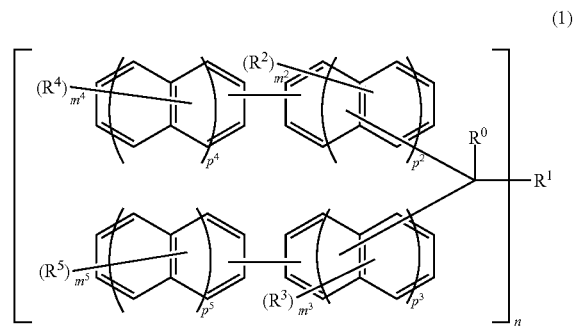

wherein $R^0$ is a methyl group or a phenyl group;

$R^1$ is a biphenyl group or cyclohexyl phenyl group;

$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;

$m^2$ and $m^3$ are each independently an integer of 0 to 8;

$m^4$ and $m^5$ are each independently an integer of 0 to 9, provided that $m^2$, $m^3$, $m^4$, and $m^5$ are not 0 at the same time;

n is an integer of 1 to 2, wherein when n is an integer of 2, n structural formulas within the parentheses [ ] are the same or different; and $p^2$ to $p^5$ are each independently an integer of 0 to 2;

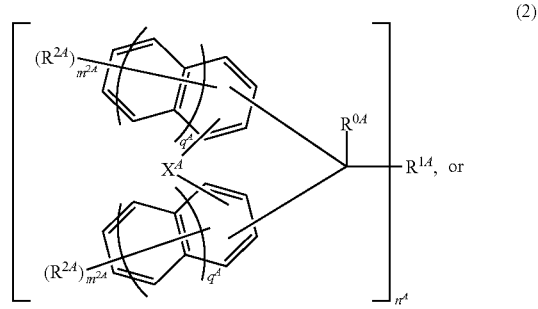

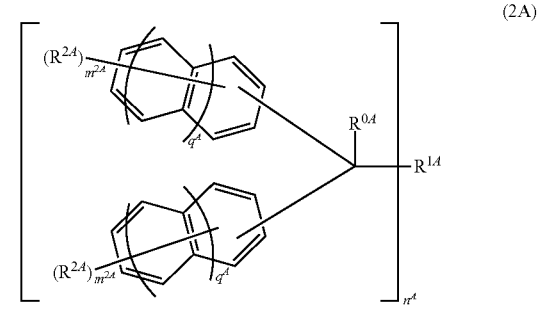

wherein $R^{0A}$ is a linear, branched, or cyclic alkyl group of 1 to 30 carbon atoms or an aryl group of 6 to 30 carbon atoms;

in formula (2) each $R^{2A}$ is a hydroxy group;

in formula (2A) each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is defined as an integer of 1 to 4, wherein when $n^A$ is an integer of 2 or larger, $n^A$ structural formulas within the parentheses [ ] are the same or different;

$X^A$ is an oxygen atom or a sulfur atom;

each $m^{2A}$ is independently an integer of 0 to 7, provided that at least one $m^{2A}$ is an integer of 1 to 7;

each $q^A$ is independently 0 or 1; and $R^{1A}$ is a biphenyl group or cyclohexyl phenyl group.

18. A method for forming a circuit pattern, comprising the steps of:

forming an underlayer film on a substrate using a film for lithography;

forming an intermediate layer film on the underlayer film using a resist intermediate layer film material;

forming at least one photoresist layer on the intermediate layer film;

irradiating a predetermined region of the photoresist layer with radiation for development, thereby forming a resist pattern; and etching the intermediate layer film with the resist pattern as a mask, etching the underlayer film with the obtained intermediate layer film pattern as an etching mask, and etching the substrate with the obtained underlayer film pattern as an etching mask, thereby forming a pattern on the substrate, the film for lithography including a composition comprising one or more compounds represented by formula (1), formula (2), or formula (2A):

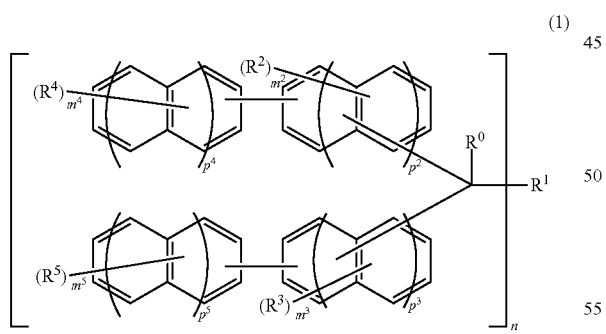

(1)

wherein $R^0$ is a methyl group or a phenyl group;

$R^1$ is a biphenyl group or cyclohexyl phenyl group;

$R^2$ to $R^5$ are each independently a linear, branched, or cyclic alkyl group of 1 to 30 carbon atoms, an aryl group of 6 to 30 carbon atoms, an alkenyl group of 2 to 30 carbon atoms, an alkoxy group of 1 to 30 carbon atoms, a halogen atom, a cyano group, a thiol group, a hydroxy group, or a group in which a hydrogen atom of a hydroxy group is replaced with an acid dissociation group, wherein at least one of $R^2$ to $R^5$ is a hydroxy group or a group in which a hydrogen atom of a hydroxy group is replaced with an acid dissociation group;

$m^2$ and $m^3$ are each independently an integer of 0 to 8;

$m^4$ and $m^5$ are each independently an integer of 0 to 9, provided that $m^2$, $m^3$, $m^4$, and $m^5$ are not 0 at the same time;

n is an integer of 1 to 2, wherein when n is an integer of 2, n structural formulas within the parentheses [ ] are the same or different; and $p^2$ to $p^5$ are each independently an integer of 0 to 2;

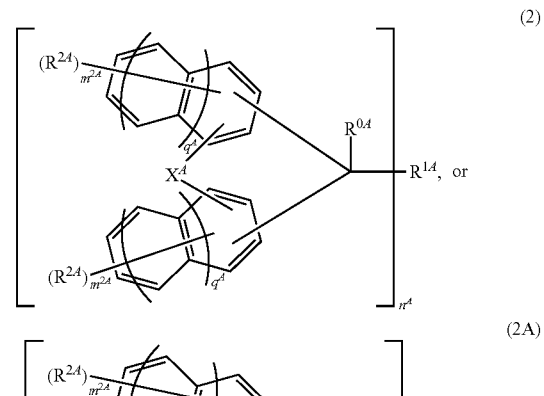

(2)

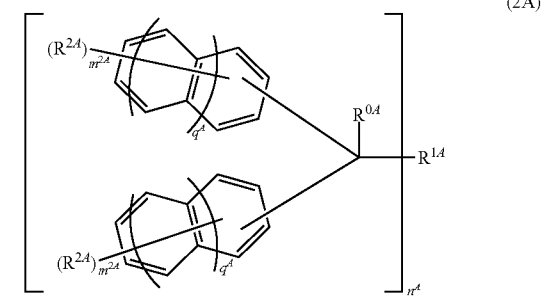

(2A)

wherein $R^{0A}$ is a linear, branched, or cyclic alkyl group of 1 to 30 carbon atoms or an aryl group of 6 to 30 carbon atoms;

each $R^{2A}$ is independently a linear, branched, or cyclic alkyl group of 1 to 30 carbon atoms, an aryl group of 6 to 30 carbon atoms, an alkenyl group of 2 to 30 carbon atoms, a halogen atom, a cyano group, a hydroxy group, or a group in which a hydrogen atom of a hydroxy group is replaced with an acid dissociation group, wherein at least one $R^{2A}$ is a hydroxy group or a group in which a hydrogen atom of a hydroxy group is replaced with an acid dissociation group;

$n^A$ is defined as an integer of 1 to 4, wherein when $n^A$ is an integer of 2 or larger, $n^A$ structural formulas within the parentheses [ ] are the same or different;

$X^A$ is an oxygen atom or a sulfur atom;

each $m^{2A}$ is independently an integer of 0 to 7, provided that at least one $m^{2A}$ is an integer of 1 to 7;

each $q^A$ is independently 0 or 1; and $R^{1A}$ is a biphenyl group or cyclohexyl phenyl group.

\* \* \* \* \*